US 12,060,422 B2
Aug. 13, 2024

(12) United States Patent
Pincetic et al.

(10) Patent No.: US 12,060,422 B2
(45) Date of Patent: Aug. 13, 2024

(54) ANTI-SIRP-BETA1 ANTIBODIES AND METHODS OF USE THEREOF

(71) Applicant: Alector LLC, South San Francisco, CA (US)

(72) Inventors: Andrew Pincetic, San Francisco, CA (US); Patricia Culp, Oakland, CA (US); Arnon Rosenthal, Woodside, CA (US)

(73) Assignee: Alector LLC, South San Francisco, CA (US)

( * ) Notice: Subject to any disclaimer, the term of this patent is extended or adjusted under 35 U.S.C. 154(b) by 663 days.

(21) Appl. No.: 17/256,508

(22) PCT Filed: Jun. 28, 2019

(86) PCT No.: PCT/US2019/039757
§ 371 (c)(1),
(2) Date: Dec. 28, 2020

(87) PCT Pub. No.: WO2020/006374
PCT Pub. Date: Jan. 2, 2020

(65) Prior Publication Data
US 2021/0277113 A1    Sep. 9, 2021

Related U.S. Application Data

(60) Provisional application No. 62/691,913, filed on Jun. 29, 2018.

(51) Int. Cl.
C07K 16/28    (2006.01)
A61K 39/00    (2006.01)
A61P 35/00    (2006.01)

(52) U.S. Cl.
CPC .......... *C07K 16/2803* (2013.01); *A61P 35/00* (2018.01); *A61K 2039/505* (2013.01); *A61K 2039/507* (2013.01); *C07K 2317/31* (2013.01); *C07K 2317/33* (2013.01); *C07K 2317/75* (2013.01); *C07K 2317/92* (2013.01)

(58) Field of Classification Search
CPC ............ C07K 16/2803; C07K 2317/31; C07K 2317/33; C07K 2317/75; C07K 2317/92; C07K 2317/21; C07K 2317/73; C07K 2317/565; A61P 35/00; A61P 25/28; A61P 25/00; A61K 2039/505; A61K 2039/507
See application file for complete search history.

(56) References Cited

U.S. PATENT DOCUMENTS

| | | | |
|---|---|---|---|
| 2003/0054415 A1 | 3/2003 | Buhring et al. | |
| 2005/0244415 A1* | 11/2005 | Matozaki | A61P 31/12 424/146.1 |
| 2009/0285824 A1* | 11/2009 | Calzone | A61P 25/00 536/23.53 |
| 2013/0323249 A1* | 12/2013 | Zhou | A61P 35/00 530/387.3 |
| 2016/0244528 A1* | 8/2016 | Gray | A61P 13/12 |
| 2017/0088620 A1* | 3/2017 | Nioi | C07K 16/2851 |
| 2018/0193496 A1* | 7/2018 | Gualandi | A61K 51/1018 |

FOREIGN PATENT DOCUMENTS

| | | |
|---|---|---|
| CN | 101880324 A | 11/2010 |
| CN | 106456749 A | 2/2017 |
| CN | 108137702 A | 6/2018 |
| WO | 2015138600 A2 | 9/2015 |
| WO | 2017040301 A1 | 3/2017 |
| WO | 2018210793 A2 | 11/2018 |

OTHER PUBLICATIONS

Hatherley D et al. OX130 Monoclonal Antibody Recognizes Human SIRPβ1 but Cross-Reacts on SIRPα from One Allele. (Monoclon Antib Immunodiagn Immunother. Feb. 1, 2016; 35(1): 57-59). (Year: 2016).*
Kharitonenkov A et al. A family of proteins that inhibit signaling through tyrosine kinase receptors. Nature 1997 386, 181-186 (Year: 1997).*
NCBI signal-regulatory protein beta-1 isoform 1 precursor [*Homo sapiens*] https://www.ncbi.nlm.nih.gov/protein/NP_006056.2 (Year: 2023).*
Hayashi A et al. Positive Regulation of Phagocytosis by SIRPβ and Its Signaling Mechanism in Macrophages JBC 2004 279(28) 29450-29460 (Year: 2004).*
Stewart R et al. The role of Fc gamma receptors in the activity of immunomodulatory antibodies for cancer. Journal for ImmunoTherapy of Cancer 2014, 2:29 1-10 (Year: 2014).*
Xenaki KT et al. Antibody or Antibody Fragments: Implications for Molecular Imaging and Targeted Therapy of Solid Tumors. Front. Immunol. 2017 8:1287 1-6 (Year: 2017).*
Gordon SR et al. PD-1 expression by tumor-associated macrophages inhibits phagocytosis and tumor immunity. Nature 2017 545(7655): 495-499 (Year: 2017).*
Dahlén E et al. Bispecific antibodies in cancer immunotherapy. Therapeutic Advances in Vaccines and Immunotherapy 2018 6(1) 3-17 (Year: 2018).*
Ahmad ZA et al. scFv Antibody: Principles and Clinical Application. Clin Dev Immunol. 2012; 2012: 980250 (Year: 2012).*
Almagro JC et al., Progress and Challenges in the Design and Clinical Development of Antibodies for Cancer Therapy Front. Immunol. 2018; 8:1751 (Year: 2018).*
Brown M et al., Tolerance of single, but not multiple, amino acid replacements in antibody VH CDR 2: a means of minimizing B cell wastage from somatic hypermutation? J. Immunol., 1996 156(9):3285-91 (Year: 1996).*
Almagro JC & Fransson J, Humanization of antibodies. Frontiers in Bioscience 2008; 13:1619-33 (Year: 2008).*

(Continued)

*Primary Examiner* — Karen A. Canella
*Assistant Examiner* — John J Skoko, III
(74) *Attorney, Agent, or Firm* — McNeill Baur PLLC

(57) ABSTRACT

The present disclosure is generally directed to compositions that include antibodies, e.g., monoclonal, antibodies, antibody fragments, etc., that specifically bind a SIRPβ1 polypeptide, e.g., a human SIRPβ1, and use of such compositions in preventing, reducing risk, or treating an individual in need thereof.

23 Claims, 23 Drawing Sheets

Specification includes a Sequence Listing.

(56) References Cited

OTHER PUBLICATIONS

Gershoni et al., Epitope Mapping, Biodrugs 2007; 21 (3): 145-156 (Year: 2007).*

Blythe et al., Benchmarking B cell epitope prediction: Underperformance of existing methods, Protein Science (2005), 14:246-248 (Year: 2005).*

Schreiber et al. 3D-Epitope-Explorer (3DEX): Localization of Conformational Epitopes within Three-Dimensional Structures of Proteins, Journal of Computational Chemistry 2005 26(9) 879-887 (Year: 2005).*

Janeway, Immuno Biology The immune system in Health and Disease, 5th edition, 2001, section 7.8 (Year: 2001).*

Lydard et al. Immunology, 2011, in Antibodies: Generation of diversity pp. 76-85 (Year: 2011).*

Biolegend Product Data Sheet: Purified anti-human CD172b (SIRPβ) Antibody, Version 2, 2 pages (Oct. 25, 2016).

Hatherley et al., "OX130 Monoclonal Antibody Recognizes Human SIRPβ1 but Cross-Reacts on SIRPα from One Allele," Monoclonal Antibodies in Immunodiagnosis and Immunotherapy, vol. 35, No. 1, pp. 57-59 (2016).

Hayashi et al., "Positive Regulation of Phagocytosis by SIRP β and Its Signaling Mechanism in Macrphages, " The Journal of Biological Chemistry, vol. 279, No. 28, pp. 29450-29460 (Jul. 9, 2004).

International Search Report and Written Opinion of International Application No. PCT/US2019/039757, dated Jan. 20, 2020 (24 pages).

Invitation to Pay Additional Fees, and Where Applicable, Protest Fee issued in International Application No. PCT/US2019/039757, dated Oct. 21, 2019 (13 pages).

Liu et al., "SIRP[beta]1 is expressed as a disulfide-linked homodimer in leukocytes and positively regulates neutrophil transepithelial migration," J Biol Chem. vol. 280, No. 43, pp. 36132-40 (Oct. 28, 2005).

Supplemental Data: Biolegend Product Data Sheet: Purified anti-human CD172b (SIRPβ) Antibody, Version 2, 4 pages (2016).

Gaikwad et al., "Signal regulatory protein-β1: a Microglial Modulator of Phagocytosis in Alzheimer's Disease", The American Journal of Pathology, Dec. 2009, vol. 175, No. 6, pp. 2528-2539.

Seiffert et al., "Signal-regulatory protein α (SIRPα) but not SIRPβ is involved in T-cell activation, binds to CD47 with high affinity, and is expressed on immature CD34+CD38-hematopoietic cells", Blood, May 1, 2001, vol. 97, No. 9, pp. 2741-2749.

* cited by examiner

SIRPBeta:

| | | | |
|---|---|---|---|
| Isoform 1 | O00241 | 1 | MPVPASWPHLPSPEFLLMTLLGRLTGVAGEDELQVIQPEKSVSVAAGESATLRCAMTSLI | 60 |
| Isoform 3 | Q5TFQ8 | 1 | MPVPASWPHLPSPEFLLMTLLGRLTGVAGEELQVIQPEKSVSVAAGESATLHCTVTSLI | 60 |
| | | | ****************************:***************:*;::**** |
| Isoform 1 | O00241 | 61 | PVGPIMWFRGAGAGRELIYNQKEGHFPRVTTVSELTKRNNLDFSISISNITPADAGTYYC | 120 |
| Isoform 3 | Q5TFQ8 | 61 | PVGPIQWFRGAGPGRELIYNQKEGHFPRVTTVSDLTKRNNWDFSIRISNITPADAGTYYC | 120 |
| | | | ***:*.***************:***:*.;************ |
| Isoform 1 | O00241 | 121 | VKFRKGSPDDVEFKSGAGTELSVRAKPSAPVVSGPAVRATPEHTVSFTCESHGFSPRDIT | 180 |
| Isoform 3 | Q5TFQ8 | 121 | VKFRKGSPDHVEFKSGAGTELSVRAKPSAPVVSGPAARATPQHTVSFTCESNGFSPRDIT | 180 |
| | | | *******.**************************:*****:***** |
| Isoform 1 | O00241 | 181 | LKWFKNGMELSDFQTNVDPAGDSVSYSIHSTARVVLTRGDVHSQVICEIAHITLQGDPLR | 240 |
| Isoform 3 | Q5TFQ8 | 181 | LKWFKNGHELSDFQTNVDPAGDSVSYSIHSTAKVVLTREDVHSQVICEVAHVTLQGDPLR | 240 |
| | | | *****:********************:.:***::******** |
| Isoform 1 | O00241 | 241 | GTAMLSEATRVPPTLEVTQQPMRAENQANVTCQVSNFYPRGLQLTWLENGNVSRTETAST | 300 |
| Isoform 3 | Q5TFQ8 | 241 | GTAMLSETIRVPPTLEVTQQPVRAENQVMTCQVMTCQVRKFYPQALQLTWLENGNVSRTETAST | 300 |
| | | | *****:.*******:*.:  ::..************* |
| Isoform 1 | O00241 | 301 | LTENKDGTYNWMSWLLVNVSAHRDGVVLTCQVEHDGQQAVSKSYALEISAHQKEHGSDIT | 360 |
| Isoform 3 | Q5TFQ8 | 301 | LTENKDGTYNWMSWLLVNVSAHRDGVKLTCQVEHDGQPAVSKSHDLKVSAHPKEQGSNTA | 360 |
| | | | ************************:*****:***::*::*::**:: |
| Isoform 1 | O00241 | 361 | HEAALAPTAPLLVALLLGPKLLLVVGVSAIYICWKQKA | 398 |
| Isoform 3 | Q5TFQ8 | 361 | PGPALASAAPLLIAFLLGPKVLLVVGVSIYVYWKQKA | 398 |
| | | | ..*.:.:*:*::;***** |

FIGURE 1A

SIRPBeta:

```
Isoform 1  O00241    1   MPVPASWPHLPSPFL-LMTLLLGRLTGVAGEDELQVIQPEKSVSVAAGESATLRCAMTSL     59
Isoform 3  P78324    1   MEPAGPAPGRLGPLLCLLLAASCAWSGVAGEEELQVIQPDKSVLVAAGETATLRCTATSL     60
                        *  * .:** ::***   :**:* :: :   .***:*::******;******:*:***

Isoform 1  O00241   60   IPVGPIMWFRGAGAGRELIYNQKEGHFPRVTTVSELTKRNNLQFSISISNITPADAGTYY    119
Isoform 3  P78324   61   IPVGPIQWFRGAGPGRELIYNQKEGHFPRVTTVSDLTKRNNMQFSIRIGNITPADAGTYY    120
                        ****** ******.*******************:*****::**** *.***********

Isoform 1  O00241  120   CVKFRKGSPDDVEEKSGAGTELSVRAKPSAPVVSGPAVRATPEHTVSFTCESHGFSPRDI    179
Isoform 3  P78324  121   CVKFRKGSPDDVEFKSGAGTELSVRAKPSAPVVSGPAARATPQHTVSFTCESHGFSPRDI    180
                        ************* ***********************.****:****************

Isoform 1  O00241  180   TLKWFKNGNELSDFQTNVDPAGDSVSYSIHSTARVVLTRGDVHSQVICEIAHTTLQGGDPL    239
Isoform 3  P78324  181   TLKWFKNGNELSDFQTNVDPVGESVSYSIHSTAKVVLTREDVHSQVICEVAHVTLQGDPL    240
                        ********************.*:*********:****..*********:**.****:**

Isoform 1  O00241  240   RGTANLSEAIRVPPTLEVTQQPMRAENQANVTCQVSNFYPRGLQLTWLENGNVSRTETAS    299
Isoform 3  P78324  241   RGTANLSETIRVPPTLEVTQQPYRAEMQVNVTCQVRKFYPQRLQLTWLENGNVSRTETAS    300
                        ********:************* ***:*.****** :***: *****************

Isoform 1  O00241  300   TLIENKDGTYNWMSWLLVNTCAHRDDVVLTCQVEHDGQQAVSKSYALEISAHQKEHGSDI    359
Isoform 3  P78324  301   TVTENKDGTYNWMSWLLVNVSAHRDDVKLTCQVEHDGQPAVSKSHDLKVSAHPKEQGSNT    360
                        *: ****************.:******.*********.*****: *::*** **:**:

Isoform 1  O00241  360   THEAALAPTAPLLVALLLGPKLLLLVVGVSAITYICWKQKA---------------------   398
Isoform 3  P78324  361   AAEMTGSNERNIYIVVGVVCTLLVALLMAALYLVRIRQKKAQGSTSSTRLHEPEKNAREI    420
                        :   :. :. :::   : .****:****:  :**::****

Isoform 1  O00241  399   -------------------------------------------------------------    398
Isoform 3  P78324  421   TQDTNDITYADLNLPKGKKPAPQAAEPNNHTEYASIQTSPQPASEDTLTYADLDMVHLNR    480

Isoform 1  O00241  399   -----------------------------    398
Isoform 3  P78324  481   TPKQPAPKPEPSFSEYASVQVPRK       504
```

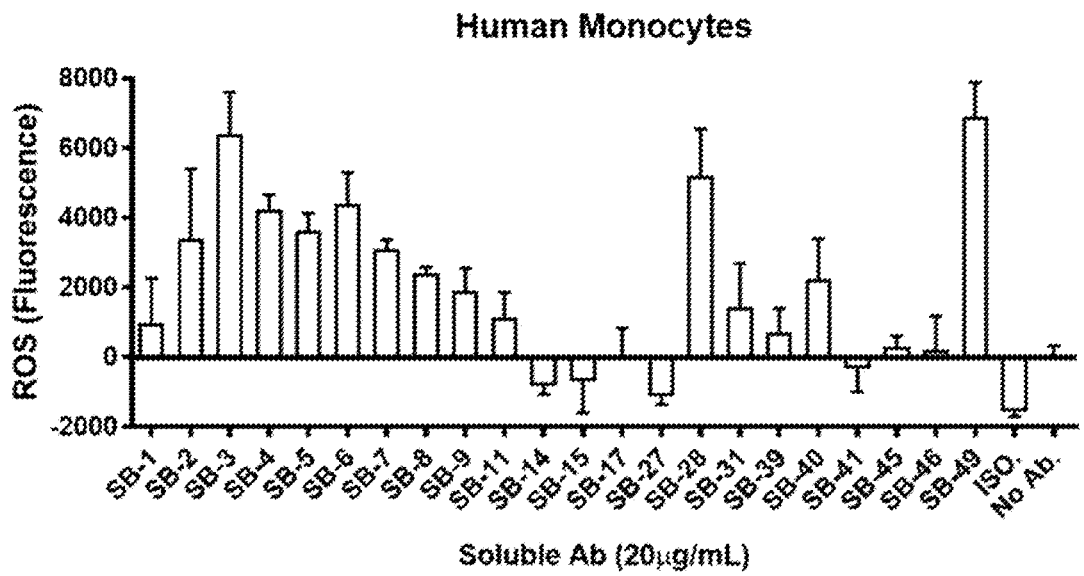
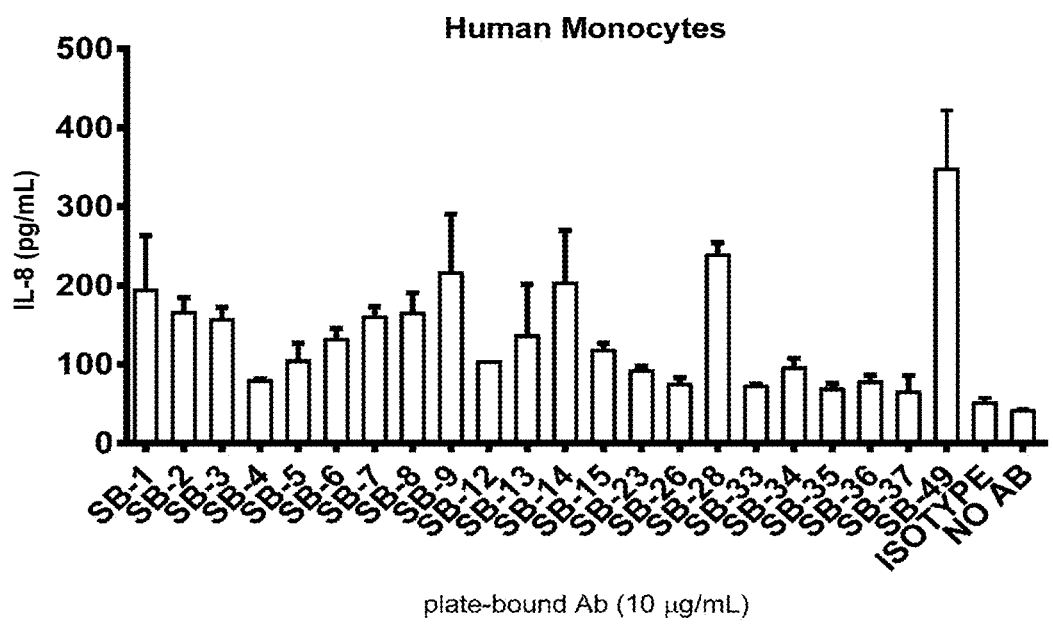
FIGURE 6B

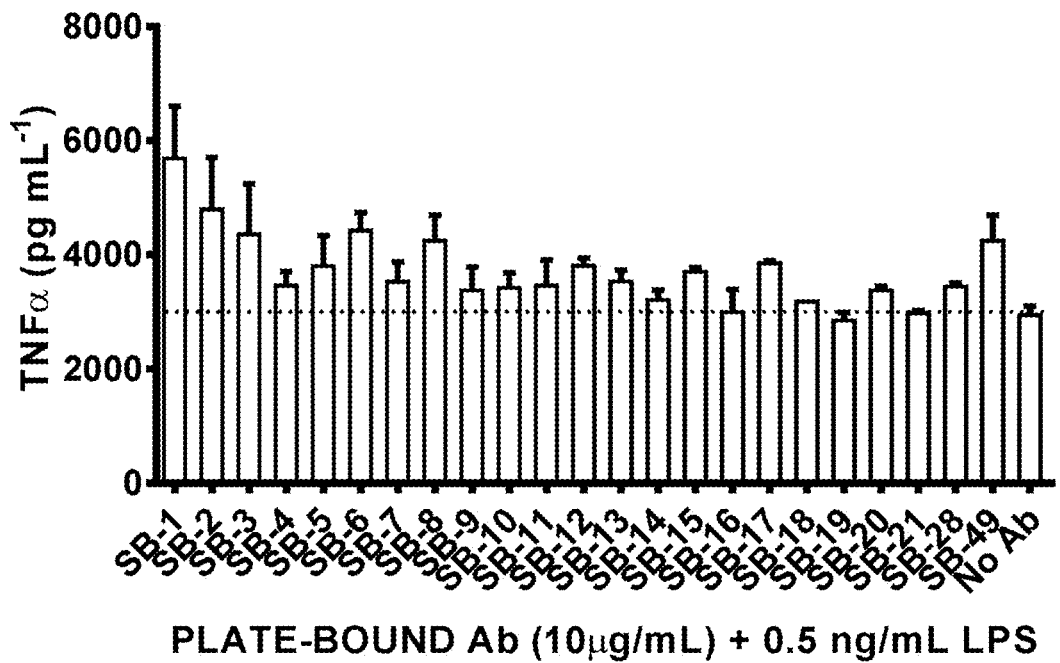
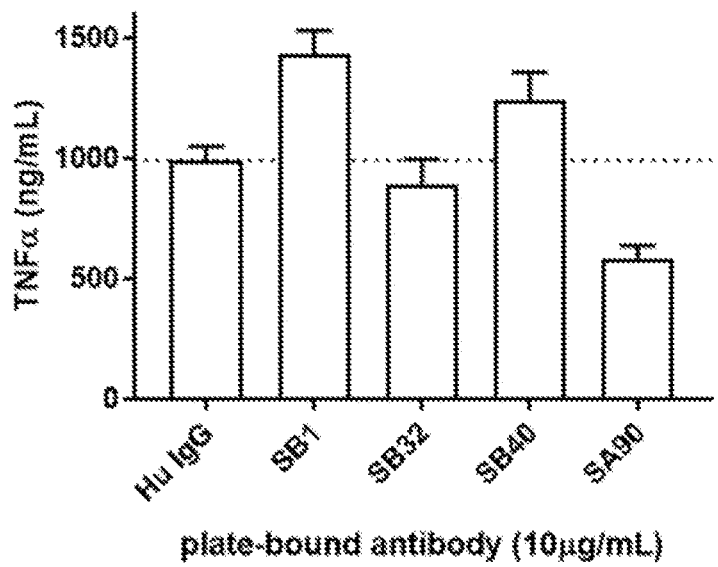
FIGURE 6C

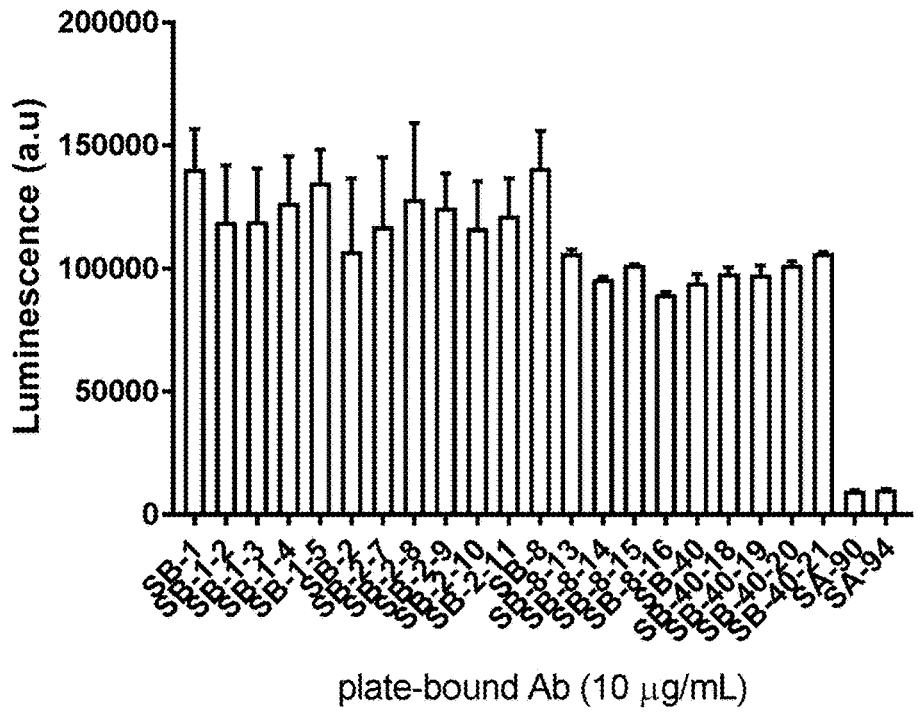
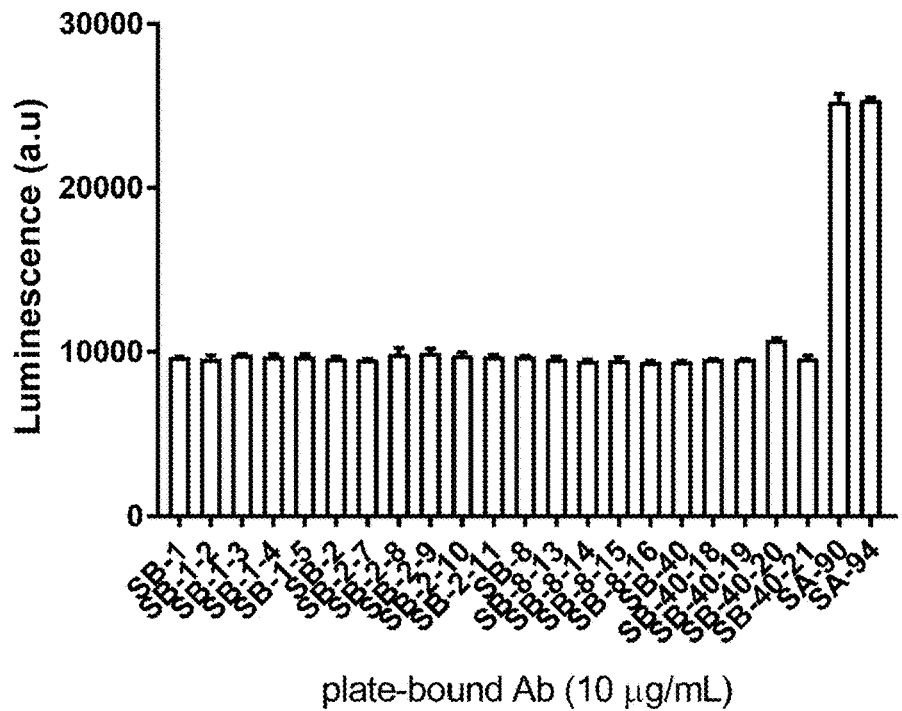
FIGURE 8

SEQUENCE LISTING

<160> NUMBER OF SEQ ID NOS: 388

<210> SEQ ID NO 1
<211> LENGTH: 398
<212> TYPE: PRT
<213> ORGANISM: Homo sapiens

<400> SEQUENCE: 1

Met Pro Val Pro Ala Ser Trp Pro His Leu Pro Ser Pro Phe Leu Leu
1               5                   10                  15

Met Thr Leu Leu Leu Gly Arg Leu Thr Gly Val Ala Gly Glu Asp Glu
            20                  25                  30

Leu Gln Val Ile Gln Pro Glu Lys Ser Val Ser Val Ala Ala Gly Glu
        35                  40                  45

Ser Ala Thr Leu Arg Cys Ala Met Thr Ser Leu Ile Pro Val Gly Pro
    50                  55                  60

Ile Met Trp Phe Arg Gly Ala Gly Ala Gly Arg Glu Leu Ile Tyr Asn
65                  70                  75                  80

Gln Lys Glu Gly His Phe Pro Arg Val Thr Thr Val Ser Glu Leu Thr
                85                  90                  95

Lys Arg Asn Asn Leu Asp Phe Ser Ile Ser Ile Ser Asn Ile Thr Pro
            100                 105                 110

Ala Asp Ala Gly Thr Tyr Tyr Cys Val Lys Phe Arg Lys Gly Ser Pro
        115                 120                 125

Asp Asp Val Glu Phe Lys Ser Gly Ala Gly Thr Glu Leu Ser Val Arg
    130                 135                 140

Ala Lys Pro Ser Ala Pro Val Val Ser Gly Pro Ala Val Arg Ala Thr
145                 150                 155                 160

Pro Glu His Thr Val Ser Phe Thr Cys Glu Ser His Gly Phe Ser Pro
                165                 170                 175

```
Arg Asp Ile Thr Leu Lys Trp Phe Lys Asn Gly Asn Glu Leu Ser Asp
            180                 185                 190

Phe Gln Thr Asn Val Asp Pro Ala Gly Asp Ser Val Ser Tyr Ser Ile
            195                 200                 205

His Ser Thr Ala Arg Val Val Leu Thr Arg Gly Asp Val His Ser Gln
            210                 215                 220

Val Ile Cys Glu Ile Ala His Ile Thr Leu Gln Gly Asp Pro Leu Arg
225                 230                 235                 240

Gly Thr Ala Asn Leu Ser Glu Ala Ile Arg Val Pro Pro Thr Leu Glu
            245                 250                 255

Val Thr Gln Gln Pro Met Arg Ala Glu Asn Gln Ala Asn Val Thr Cys
            260                 265                 270

Gln Val Ser Asn Phe Tyr Pro Arg Gly Leu Gln Leu Thr Trp Leu Glu
            275                 280                 285

Asn Gly Asn Val Ser Arg Thr Glu Thr Ala Ser Thr Leu Ile Glu Asn
            290                 295                 300

Lys Asp Gly Thr Tyr Asn Trp Met Ser Trp Leu Leu Val Asn Thr Cys
305                 310                 315                 320

Ala His Arg Asp Asp Val Val Leu Thr Cys Gln Val Glu His Asp Gly
            325                 330                 335

Gln Gln Ala Val Ser Lys Ser Tyr Ala Leu Glu Ile Ser Ala His Gln
            340                 345                 350

Lys Glu His Gly Ser Asp Ile Thr His Glu Ala Ala Leu Ala Pro Thr
            355                 360                 365

Ala Pro Leu Leu Val Ala Leu Leu Gly Pro Lys Leu Leu Leu Leu Val
            370                 375                 380

Val Gly Val Ser Ala Ile Tyr Ile Cys Trp Lys Gln Lys Ala
385                 390                 395

<210> SEQ ID NO 2
<211> LENGTH: 11
<212> TYPE: PRT
<213> ORGANISM: Artificial sequence
<220> FEATURE:
<223> OTHER INFORMATION: Light chain HVR sequence

<400> SEQUENCE: 2

Arg Ala Ser Gln Ser Val Ser Ser Tyr Leu Ala
1               5                   10

<210> SEQ ID NO 3
<211> LENGTH: 17
<212> TYPE: PRT
<213> ORGANISM: Artificial sequence
<220> FEATURE:
<223> OTHER INFORMATION: Light chain HVR sequence

<400> SEQUENCE: 3

Lys Ser Ser Gln Ser Val Leu Phe Ser Ser Asn Asn Lys Asn Tyr Leu
1               5                   10                  15

Ala

<210> SEQ ID NO 4
<211> LENGTH: 16
<212> TYPE: PRT
<213> ORGANISM: Artificial sequence
<220> FEATURE:
<223> OTHER INFORMATION: Light chain HVR sequence
```

```
<400> SEQUENCE: 4

Arg Ser Ser Gln Ser Leu Leu His Ser Asn Gly Tyr Asn Tyr Leu Asp
1               5                   10                  15

<210> SEQ ID NO 5
<211> LENGTH: 16
<212> TYPE: PRT
<213> ORGANISM: Artificial sequence
<220> FEATURE:
<223> OTHER INFORMATION: Light chain HVR sequence

<400> SEQUENCE: 5

Arg Ser Ser Gln Ser Leu Leu Tyr Ser Asn Gly Tyr Asn Tyr Leu Asp
1               5                   10                  15

<210> SEQ ID NO 6
<211> LENGTH: 11
<212> TYPE: PRT
<213> ORGANISM: Artificial sequence
<220> FEATURE:
<223> OTHER INFORMATION: Light chain HVR sequence

<400> SEQUENCE: 6

Arg Ala Ser Gln Ser Val Ser Ser Asn Leu Ala
1               5                   10

<210> SEQ ID NO 7
<211> LENGTH: 11
<212> TYPE: PRT
<213> ORGANISM: Artificial sequence
<220> FEATURE:
<223> OTHER INFORMATION: Light chain HVR sequence

<400> SEQUENCE: 7

Arg Ala Ser Gln Ser Ile Ser Ser Tyr Leu Asn
1               5                   10

<210> SEQ ID NO 8
<211> LENGTH: 17
<212> TYPE: PRT
<213> ORGANISM: Artificial sequence
<220> FEATURE:
<223> OTHER INFORMATION: Light chain HVR sequence

<400> SEQUENCE: 8

Lys Ser Ser Gln Ser Val Leu Tyr Ser Ser Asn Asn Lys Asn Tyr Leu
1               5                   10                  15

Ala

<210> SEQ ID NO 9
<211> LENGTH: 11
<212> TYPE: PRT
<213> ORGANISM: Artificial sequence
<220> FEATURE:
<223> OTHER INFORMATION: Light chain HVR sequence

<400> SEQUENCE: 9

Arg Ala Ser Gln Gly Ile Ser Ser Trp Leu Ala
1               5                   10

<210> SEQ ID NO 10
<211> LENGTH: 12
<212> TYPE: PRT
<213> ORGANISM: Artificial sequence
<220> FEATURE:
<223> OTHER INFORMATION: Light chain HVR sequence
```

```
<400> SEQUENCE: 10

Arg Ala Ser Gln Ser Val Ser Ser Ser Phe Leu Ala
1               5                   10

<210> SEQ ID NO 11
<211> LENGTH: 11
<212> TYPE: PRT
<213> ORGANISM: Artificial sequence
<220> FEATURE:
<223> OTHER INFORMATION: Light chain HVR sequence

<400> SEQUENCE: 11

Gln Ala Ser Gln Asp Ile Ser Asn Tyr Leu Asn
1               5                   10

<210> SEQ ID NO 12
<211> LENGTH: 11
<212> TYPE: PRT
<213> ORGANISM: Artificial sequence
<220> FEATURE:
<223> OTHER INFORMATION: Light chain HVR sequence

<400> SEQUENCE: 12

Gln Ala Ser Gln Asp Ile Thr Asn Tyr Leu Asn
1               5                   10

<210> SEQ ID NO 13
<211> LENGTH: 11
<212> TYPE: PRT
<213> ORGANISM: Artificial sequence
<220> FEATURE:
<223> OTHER INFORMATION: Light chain HVR sequence

<400> SEQUENCE: 13

Arg Ala Ser Gln Ser Ile Gly Ser Trp Leu Ala
1               5                   10

<210> SEQ ID NO 14
<211> LENGTH: 12
<212> TYPE: PRT
<213> ORGANISM: Artificial sequence
<220> FEATURE:
<223> OTHER INFORMATION: Light chain HVR sequence

<400> SEQUENCE: 14

Arg Ala Ser Gln Ser Val Arg Ser Ser Tyr Leu Ala
1               5                   10

<210> SEQ ID NO 15
<211> LENGTH: 11
<212> TYPE: PRT
<213> ORGANISM: Artificial sequence
<220> FEATURE:
<223> OTHER INFORMATION: Light chain HVR sequence

<400> SEQUENCE: 15

Arg Ala Ser Gln Gly Ile Asp Ser Trp Leu Ala
1               5                   10

<210> SEQ ID NO 16
<211> LENGTH: 7
<212> TYPE: PRT
<213> ORGANISM: Artificial sequence
<220> FEATURE:
<223> OTHER INFORMATION: Light chain HVR sequence
```

```
<400> SEQUENCE: 16

Gly Ala Ser Ser Arg Ala Thr
1               5

<210> SEQ ID NO 17
<211> LENGTH: 7
<212> TYPE: PRT
<213> ORGANISM: Artificial sequence
<220> FEATURE:
<223> OTHER INFORMATION: Light chain HVR sequence

<400> SEQUENCE: 17

Asp Ala Ser Asn Arg Ala Thr
1               5

<210> SEQ ID NO 18
<211> LENGTH: 7
<212> TYPE: PRT
<213> ORGANISM: Artificial sequence
<220> FEATURE:
<223> OTHER INFORMATION: Light chain HVR sequence

<400> SEQUENCE: 18

Trp Ala Ser Thr Arg Glu Ser
1               5

<210> SEQ ID NO 19
<211> LENGTH: 7
<212> TYPE: PRT
<213> ORGANISM: Artificial sequence
<220> FEATURE:
<223> OTHER INFORMATION: Light chain HVR sequence

<400> SEQUENCE: 19

Gly Ala Ser Asn Arg Ala Thr
1               5

<210> SEQ ID NO 20
<211> LENGTH: 7
<212> TYPE: PRT
<213> ORGANISM: Artificial sequence
<220> FEATURE:
<223> OTHER INFORMATION: Light chain HVR sequence

<400> SEQUENCE: 20

Leu Gly Ser Asn Arg Ala Ser
1               5

<210> SEQ ID NO 21
<211> LENGTH: 7
<212> TYPE: PRT
<213> ORGANISM: Artificial sequence
<220> FEATURE:
<223> OTHER INFORMATION: Light chain HVR sequence

<400> SEQUENCE: 21

Ser Ala Ser Thr Arg Ala Thr
1               5

<210> SEQ ID NO 22
<211> LENGTH: 7
<212> TYPE: PRT
<213> ORGANISM: Artificial sequence
<220> FEATURE:
<223> OTHER INFORMATION: Light chain HVR sequence

<400> SEQUENCE: 22
```

Asp Ser Ser Asn Arg Ala Thr
1               5

<210> SEQ ID NO 23
<211> LENGTH: 7
<212> TYPE: PRT
<213> ORGANISM: Artificial sequence
<220> FEATURE:
<223> OTHER INFORMATION: Light chain HVR sequence

<400> SEQUENCE: 23

Ala Ala Ser Ser Leu Gln Ser
1               5

<210> SEQ ID NO 24
<211> LENGTH: 7
<212> TYPE: PRT
<213> ORGANISM: Artificial sequence
<220> FEATURE:
<223> OTHER INFORMATION: Light chain HVR sequence

<400> SEQUENCE: 24

Ala Ala Ser Asn Leu Gln Ser
1               5

<210> SEQ ID NO 25
<211> LENGTH: 7
<212> TYPE: PRT
<213> ORGANISM: Artificial sequence
<220> FEATURE:
<223> OTHER INFORMATION: Light chain HVR sequence

<400> SEQUENCE: 25

Gly Ala Ser Thr Arg Ala Thr
1               5

<210> SEQ ID NO 26
<211> LENGTH: 7
<212> TYPE: PRT
<213> ORGANISM: Artificial sequence
<220> FEATURE:
<223> OTHER INFORMATION: Light chain HVR sequence

<400> SEQUENCE: 26

Asp Ala Ser Asn Leu Glu Thr
1               5

<210> SEQ ID NO 27
<211> LENGTH: 7
<212> TYPE: PRT
<213> ORGANISM: Artificial sequence
<220> FEATURE:
<223> OTHER INFORMATION: Light chain HVR sequence

<400> SEQUENCE: 27

Gly Ala Ser Ser Leu Gln Ser
1               5

<210> SEQ ID NO 28
<211> LENGTH: 7
<212> TYPE: PRT
<213> ORGANISM: Artificial sequence
<220> FEATURE:
<223> OTHER INFORMATION: Light chain HVR sequence

<400> SEQUENCE: 28

Ser Ala Ser Ser Leu Gln Ser
1               5

<210> SEQ ID NO 29
<211> LENGTH: 7
<212> TYPE: PRT
<213> ORGANISM: Artificial sequence
<220> FEATURE:
<223> OTHER INFORMATION: Light chain HVR sequence

<400> SEQUENCE: 29

Asp Ala Ser Lys Arg Ala Thr
1               5

<210> SEQ ID NO 30
<211> LENGTH: 7
<212> TYPE: PRT
<213> ORGANISM: Artificial sequence
<220> FEATURE:
<223> OTHER INFORMATION: Light chain HVR sequence

<400> SEQUENCE: 30

Lys Ala Ser Ser Leu Glu Ser
1               5

<210> SEQ ID NO 31
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 31

Gln Leu Leu Gly Ser Ser Pro Arg Thr
1               5

<210> SEQ ID NO 32
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 32

Gln Gln Ser Ser Ser His Pro Phe Thr
1               5

<210> SEQ ID NO 33
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 33

Gln Gln Arg Leu Phe His Pro Pro Thr
1               5

<210> SEQ ID NO 34
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 34

Gln Gln Tyr Ala Asp Ala Pro Ile Thr

```
1               5

<210> SEQ ID NO 35
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 35

Gln Gln Ser Gly His Leu Pro Ile Thr
1               5

<210> SEQ ID NO 36
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 36

Gln Gln His Tyr Ile Ala Pro Phe Thr
1               5

<210> SEQ ID NO 37
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 37

Gln Gln Val Tyr Ser Ser Pro Tyr Thr
1               5

<210> SEQ ID NO 38
<211> LENGTH: 10
<212> TYPE: PRT
<213> ORGANISM: Artificial sequence
<220> FEATURE:
<223> OTHER INFORMATION: Light chain HVR sequence

<400> SEQUENCE: 38

Gln Gln Tyr His Ser Val Pro Pro Ile Thr
1               5                   10

<210> SEQ ID NO 39
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 39

Met Gln Ala Ile Glu Ser Pro Leu Thr
1               5

<210> SEQ ID NO 40
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 40

Val Gln Ala Leu Gln Thr Pro Leu Thr
1               5
```

```
<210> SEQ ID NO 41
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 41

Gln Gln Leu Asp Asn Leu Pro Tyr Thr
1               5

<210> SEQ ID NO 42
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 42

Met Gln Ala Leu Arg Ser Pro Ile Thr
1               5

<210> SEQ ID NO 43
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 43

Gln Gln Phe Ser Tyr Tyr Pro Ile Thr
1               5

<210> SEQ ID NO 44
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 44

Gln Gln Ala Tyr Ser His Pro Phe Thr
1               5

<210> SEQ ID NO 45
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 45

Gln Gln Leu Phe Ser Thr Pro Phe Thr
1               5

<210> SEQ ID NO 46
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 46

Gln Gln Tyr Tyr Asp Asp Pro Tyr Thr
1               5
```

<210> SEQ ID NO 47
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 47

Leu Gln Ala Leu Gln Thr Pro Ile Thr
1               5

<210> SEQ ID NO 48
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 48

Met Gln Ala Ile Gly Val Pro Pro Thr
1               5

<210> SEQ ID NO 49
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 49

Gln Gln Tyr Tyr Leu Ser Pro Phe Thr
1               5

<210> SEQ ID NO 50
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 50

Met Gln Thr Leu Arg Ile Pro Pro Thr
1               5

<210> SEQ ID NO 51
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 51

Gln Gln Gly Asn Ser Tyr Pro Ile Thr
1               5

<210> SEQ ID NO 52
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 52

Gln Gln Ala Tyr Pro Tyr Pro Leu Thr
1               5

```
<210> SEQ ID NO 53
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 53

Gln Gln Leu Asn Ile His Pro Trp Thr
1               5

<210> SEQ ID NO 54
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 54

Gln Gln Val Asn Ser Phe Pro Trp Thr
1               5

<210> SEQ ID NO 55
<211> LENGTH: 8
<212> TYPE: PRT
<213> ORGANISM: Artificial sequence
<220> FEATURE:
<223> OTHER INFORMATION: Light chain HVR sequence

<400> SEQUENCE: 55

Met Gln Ala Arg Gly Leu Pro Thr
1               5

<210> SEQ ID NO 56
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 56

Gln Gln Ala Val Ser Asp Pro Pro Thr
1               5

<210> SEQ ID NO 57
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 57

Gln Gln Asp Gly Asn Phe Pro Leu Thr
1               5

<210> SEQ ID NO 58
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 58

Met Gln Ala Arg Gly Ser Pro Ile Thr
1               5

<210> SEQ ID NO 59
```

```
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 59

Gln Gln Phe Leu Ser Ser Pro Trp Thr
1               5

<210> SEQ ID NO 60
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 60

Gln Gln Ala Val Ser His Pro Phe Thr
1               5

<210> SEQ ID NO 61
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 61

Gln Gln Asp Phe Leu Thr Pro Ile Thr
1               5

<210> SEQ ID NO 62
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 62

Gln Gln Phe Ala Phe Leu Pro Leu Thr
1               5

<210> SEQ ID NO 63
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 63

Gln Gln Asp Asn Thr Phe Pro Tyr Thr
1               5

<210> SEQ ID NO 64
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 64

Met Gln Thr Leu Gln Val Pro Leu Thr
1               5

<210> SEQ ID NO 65
<211> LENGTH: 8
```

```
<212> TYPE: PRT
<213> ORGANISM: Artificial sequence
<220> FEATURE:
<223> OTHER INFORMATION: Light chain HVR sequence

<400> SEQUENCE: 65

Gln Gln Ala Phe Ser His Arg Thr
1               5

<210> SEQ ID NO 66
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 66

Gln Gln Arg His Thr Tyr Pro Leu Thr
1               5

<210> SEQ ID NO 67
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 67

Gln Gln Ala Val Ser Tyr Pro Ile Thr
1               5

<210> SEQ ID NO 68
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 68

Gln Gln Ser Tyr Asp Phe Pro Leu Thr
1               5

<210> SEQ ID NO 69
<211> LENGTH: 10
<212> TYPE: PRT
<213> ORGANISM: Artificial sequence
<220> FEATURE:
<223> OTHER INFORMATION: Light chain HVR sequence

<400> SEQUENCE: 69

Gln Gln Arg Asp Glu His Pro Pro Trp Thr
1               5                   10

<210> SEQ ID NO 70
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 70

Gln Gln Ala Asp Asn Phe Pro Tyr Thr
1               5

<210> SEQ ID NO 71
<211> LENGTH: 9
<212> TYPE: PRT
```

```
<213> ORGANISM: Artificial sequence
<220> FEATURE:
<223> OTHER INFORMATION: Light chain HVR sequence

<400> SEQUENCE: 71

Gln Gln Gly Asp Ser Phe Pro Ile Thr
1               5

<210> SEQ ID NO 72
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 72

Gln Gln Arg Phe Asp Phe Pro Ile Thr
1               5

<210> SEQ ID NO 73
<211> LENGTH: 8
<212> TYPE: PRT
<213> ORGANISM: Artificial sequence
<220> FEATURE:
<223> OTHER INFORMATION: Light chain HVR sequence

<400> SEQUENCE: 73

Gln Glu Tyr Gly Ser Tyr Arg Thr
1               5

<210> SEQ ID NO 74
<211> LENGTH: 8
<212> TYPE: PRT
<213> ORGANISM: Artificial sequence
<220> FEATURE:
<223> OTHER INFORMATION: Light chain HVR sequence

<400> SEQUENCE: 74

Gln Gln Val Val Ser Val Pro Thr
1               5

<210> SEQ ID NO 75
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 75

Gln Gln Leu Tyr Ser Ser Pro Tyr Thr
1               5

<210> SEQ ID NO 76
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 76

Gln Gln Ala Asp Tyr Phe Pro Ile Thr
1               5

<210> SEQ ID NO 77
<211> LENGTH: 9
<212> TYPE: PRT
<213> ORGANISM: Artificial sequence
```

```
<220> FEATURE:
<223> OTHER INFORMATION: Light chain HVR sequence

<400> SEQUENCE: 77

Gln Gln Ala Ser Asn Phe Pro Ile Thr
1               5

<210> SEQ ID NO 78
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 78

Gln Gln Tyr Phe His Pro Pro Leu Thr
1               5

<210> SEQ ID NO 79
<211> LENGTH: 9
<212> TYPE: PRT
<213> ORGANISM: Artificial sequence
<220> FEATURE:
<223> OTHER INFORMATION: Light chain HVR sequence

<400> SEQUENCE: 79

Gln Gln Phe Leu His Thr Pro Arg Thr
1               5

<210> SEQ ID NO 80
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 80

Ser Tyr Ala Met Ser
1               5

<210> SEQ ID NO 81
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 81

Ser Tyr Gly Met Asn
1               5

<210> SEQ ID NO 82
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 82

Gly Tyr Tyr Met His
1               5

<210> SEQ ID NO 83
<211> LENGTH: 5
<212> TYPE: PRT
<213> ORGANISM: Artificial sequence
<220> FEATURE:
```

-continued

<223> OTHER INFORMATION: Heavy chain HVR sequence

<400> SEQUENCE: 83

Ser Tyr Gly Ile Ser
1               5

<210> SEQ ID NO 84
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 84

Ser Tyr Ala Ile Ser
1               5

<210> SEQ ID NO 85
<211> LENGTH: 6
<212> TYPE: PRT
<213> ORGANISM: Artificial sequence
<220> FEATURE:
<223> OTHER INFORMATION: Heavy chain HVR sequence

<400> SEQUENCE: 85

Ser Gly Tyr Tyr Trp Gly
1               5

<210> SEQ ID NO 86
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 86

Ser Tyr Gly Ile His
1               5

<210> SEQ ID NO 87
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 87

Asn Tyr Ala Ile Ser
1               5

<210> SEQ ID NO 88
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 88

Ser Tyr Tyr Trp Ser
1               5

<210> SEQ ID NO 89
<211> LENGTH: 7
<212> TYPE: PRT
<213> ORGANISM: Artificial sequence
<220> FEATURE:
<223> OTHER INFORMATION: Heavy chain HVR sequence

```
<400> SEQUENCE: 89

Ser Asn Ser Tyr Tyr Trp Gly
1               5

<210> SEQ ID NO 90
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 90

Ser Asn Gly Ile Ser
1               5

<210> SEQ ID NO 91
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 91

Ser Asn Tyr Met Ser
1               5

<210> SEQ ID NO 92
<211> LENGTH: 6
<212> TYPE: PRT
<213> ORGANISM: Artificial sequence
<220> FEATURE:
<223> OTHER INFORMATION: Heavy chain HVR sequence

<400> SEQUENCE: 92

Ser Gly Tyr Tyr Trp Ala
1               5

<210> SEQ ID NO 93
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 93

Ser Leu Ala Ile Ser
1               5

<210> SEQ ID NO 94
<211> LENGTH: 7
<212> TYPE: PRT
<213> ORGANISM: Artificial sequence
<220> FEATURE:
<223> OTHER INFORMATION: Heavy chain HVR sequence

<400> SEQUENCE: 94

Ser Ser Ser Tyr Tyr Trp Gly
1               5

<210> SEQ ID NO 95
<211> LENGTH: 7
<212> TYPE: PRT
<213> ORGANISM: Artificial sequence
<220> FEATURE:
<223> OTHER INFORMATION: Heavy chain HVR sequence
```

```
<400> SEQUENCE: 95

Ser Gly Gly Tyr Tyr Trp Ser
1               5

<210> SEQ ID NO 96
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 96

Ser Tyr Tyr Met His
1               5

<210> SEQ ID NO 97
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 97

Ser Tyr Tyr Met Ser
1               5

<210> SEQ ID NO 98
<211> LENGTH: 7
<212> TYPE: PRT
<213> ORGANISM: Artificial sequence
<220> FEATURE:
<223> OTHER INFORMATION: Heavy chain HVR sequence

<400> SEQUENCE: 98

Ser Ser Ser Tyr Ala Trp Gly
1               5

<210> SEQ ID NO 99
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 99

Ser Tyr Gly Met His
1               5

<210> SEQ ID NO 100
<211> LENGTH: 7
<212> TYPE: PRT
<213> ORGANISM: Artificial sequence
<220> FEATURE:
<223> OTHER INFORMATION: Heavy chain HVR sequence

<400> SEQUENCE: 100

Ser Ser Asp Tyr Tyr Trp Gly
1               5

<210> SEQ ID NO 101
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 101
```

```
Thr Ile Ser Gly Ser Gly Gly Ser Thr Tyr Tyr Ala Asp Ser Val Lys
1               5                   10                  15

Gly

<210> SEQ ID NO 102
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 102

Val Ile Trp Tyr Asp Gly Ser Asn Lys Tyr Tyr Ala Asp Ser Val Lys
1               5                   10                  15

Gly

<210> SEQ ID NO 103
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 103

Trp Ile Asn Pro Ser Ser Gly Gly Thr Asn Tyr Ala Gln Lys Phe Gln
1               5                   10                  15

Gly

<210> SEQ ID NO 104
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 104

Trp Ile Ser Ala Tyr Asn Gly Asn Thr Asn Tyr Ala Gln Lys Leu Gln
1               5                   10                  15

Gly

<210> SEQ ID NO 105
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 105

Trp Ile Asn Pro Asn Ser Gly Gly Thr Asn Tyr Ala Gln Lys Phe Gln
1               5                   10                  15

Gly

<210> SEQ ID NO 106
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 106

Gly Ile Ile Pro Ile Phe Gly Thr Ala Ser Tyr Ala Gln Lys Phe Gln
1               5                   10                  15
```

Gly

<210> SEQ ID NO 107
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 107

Ser Ile Tyr His Ser Gly Ser Thr Tyr Tyr Asn Pro Ser Leu Lys Ser
1               5                   10                  15

<210> SEQ ID NO 108
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 108

Gly Ile Ile Pro Ile Phe Gly Thr Ala Asn Tyr Ala Gln Lys Phe Gln
1               5                   10                  15
Gly

<210> SEQ ID NO 109
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 109

Trp Ile Asn Pro Asn Ser Gly Gly Thr Ser Tyr Ala Gln Lys Phe Gln
1               5                   10                  15
Gly

<210> SEQ ID NO 110
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 110

Ser Ile Tyr Tyr Ser Gly Ser Thr Asn Tyr Asn Pro Ser Leu Lys Ser
1               5                   10                  15

<210> SEQ ID NO 111
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 111

Ser Ile Tyr Tyr Ser Gly Ser Thr Tyr Tyr Asn Pro Ser Leu Lys Ser
1               5                   10                  15

<210> SEQ ID NO 112
<211> LENGTH: 17
<212> TYPE: PRT
<213> ORGANISM: Artificial sequence
<220> FEATURE:
<223> OTHER INFORMATION: Heavy chain HVR sequence

```
<400> SEQUENCE: 112

Ser Ile Ile Pro Ile Phe Gly Thr Ala Asn Tyr Ala Gln Lys Phe Gln
1               5                   10                  15

Gly

<210> SEQ ID NO 113
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 113

Val Ile Tyr Ser Asp Gly Ser Thr Tyr Tyr Ala Asp Ser Val Lys Gly
1               5                   10                  15

<210> SEQ ID NO 114
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 114

Gly Ile Ala Pro Ile Phe Gly Thr Ala Asn Tyr Ala Gln Lys Phe Gln
1               5                   10                  15

Gly

<210> SEQ ID NO 115
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 115

Ser Ile Ser Tyr Ser Gly Ser Thr Tyr Tyr Asn Pro Ser Leu Lys Ser
1               5                   10                  15

<210> SEQ ID NO 116
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 116

Tyr Ile Tyr Tyr Ser Gly Ser Thr Val Tyr Asn Pro Ser Leu Lys Ser
1               5                   10                  15

<210> SEQ ID NO 117
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 117

Ile Ile Asn Pro Gly Gly Gly Ser Thr Ser Tyr Ala Gln Lys Phe Gln
1               5                   10                  15

Gly

<210> SEQ ID NO 118
<211> LENGTH: 16
```

```
<212> TYPE: PRT
<213> ORGANISM: Artificial sequence
<220> FEATURE:
<223> OTHER INFORMATION: Heavy chain HVR sequence

<400> SEQUENCE: 118

Tyr Ile Tyr Ser Ser Gly Ser Thr Asn Tyr Asn Pro Ser Leu Lys Ser
1               5                   10                  15

<210> SEQ ID NO 119
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 119

Val Ile Tyr Ser Gly Gly Ser Thr Tyr Tyr Ala Asp Ser Val Lys Gly
1               5                   10                  15

<210> SEQ ID NO 120
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 120

Trp Ile Asn Pro Asn Ser Gly Gly Thr Lys Tyr Ala Gln Lys Phe Gln
1               5                   10                  15
Gly

<210> SEQ ID NO 121
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 121

Ile Ile Asn Pro Ser Gly Gly Ser Thr Ser Tyr Ala Gln Lys Phe Gln
1               5                   10                  15
Gly

<210> SEQ ID NO 122
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 122

Val Ile Tyr Ser Gly Gly Asp Thr Tyr Tyr Ala Asp Ser Val Lys Gly
1               5                   10                  15

<210> SEQ ID NO 123
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 123

Ala Ile Ser Gly Ser Gly Gly Ser Thr Tyr Tyr Ala Asp Ser Val Lys
1               5                   10                  15
```

Gly

<210> SEQ ID NO 124
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 124

Val Ile Ser Tyr Asp Gly Ser Asn Lys Tyr Tyr Ala Asp Ser Val Lys
1               5                   10                  15

Gly

<210> SEQ ID NO 125
<211> LENGTH: 13
<212> TYPE: PRT
<213> ORGANISM: Artificial sequence
<220> FEATURE:
<223> OTHER INFORMATION: Heavy chain HVR sequence

<400> SEQUENCE: 125

Asp Phe Thr Glu Val Val Gly Trp Leu Gly Met Asp Val
1               5                   10

<210> SEQ ID NO 126
<211> LENGTH: 13
<212> TYPE: PRT
<213> ORGANISM: Artificial sequence
<220> FEATURE:
<223> OTHER INFORMATION: Heavy chain HVR sequence

<400> SEQUENCE: 126

Asp Gln Thr Ala Ala Ala Ala Ile Trp Gly Met Asp Val
1               5                   10

<210> SEQ ID NO 127
<211> LENGTH: 12
<212> TYPE: PRT
<213> ORGANISM: Artificial sequence
<220> FEATURE:
<223> OTHER INFORMATION: Heavy chain HVR sequence

<400> SEQUENCE: 127

Glu Gly Ile Ala Ala Thr Asp Ala Tyr Phe Asp Leu
1               5                   10

<210> SEQ ID NO 128
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 128

Ser Gly Thr His Phe Gly Thr Tyr Ser Tyr Ser Asn Trp Phe Asp Pro
1               5                   10                  15

<210> SEQ ID NO 129
<211> LENGTH: 9
<212> TYPE: PRT
<213> ORGANISM: Artificial sequence
<220> FEATURE:
<223> OTHER INFORMATION: Heavy chain HVR sequence

<400> SEQUENCE: 129

```
Glu Gly Asp Glu Asp Trp Phe Asp Pro
1               5
```

<210> SEQ ID NO 130
<211> LENGTH: 14
<212> TYPE: PRT
<213> ORGANISM: Artificial sequence
<220> FEATURE:
<223> OTHER INFORMATION: Heavy chain HVR sequence

<400> SEQUENCE: 130

```
Glu Thr Arg Gln Asp Ser Ala His Tyr Tyr Gly Met Asp Val
1               5                   10
```

<210> SEQ ID NO 131
<211> LENGTH: 11
<212> TYPE: PRT
<213> ORGANISM: Artificial sequence
<220> FEATURE:
<223> OTHER INFORMATION: Heavy chain HVR sequence

<400> SEQUENCE: 131

```
Gly Gly Ala Met Thr Pro Ala Gly Met Asp Val
1               5                   10
```

<210> SEQ ID NO 132
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 132

```
Asp Gly Leu His Tyr Gly Asp Tyr Ile Val Tyr Tyr Gly Met Asp Val
1               5                   10                  15
```

<210> SEQ ID NO 133
<211> LENGTH: 11
<212> TYPE: PRT
<213> ORGANISM: Artificial sequence
<220> FEATURE:
<223> OTHER INFORMATION: Heavy chain HVR sequence

<400> SEQUENCE: 133

```
Gly Val Pro Arg Gly Asp Leu Gly Met Asp Val
1               5                   10
```

<210> SEQ ID NO 134
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 134

```
Pro Val Asp Ser Ser Ser Tyr Ser Leu Gly Tyr Tyr Tyr Gly Met Asp
1               5                   10                  15

Val
```

<210> SEQ ID NO 135
<211> LENGTH: 11
<212> TYPE: PRT
<213> ORGANISM: Artificial sequence
<220> FEATURE:
<223> OTHER INFORMATION: Heavy chain HVR sequence

<400> SEQUENCE: 135

Asp Thr Tyr Ala Tyr Ser Tyr Gly Met Asp Val
1               5                   10

<210> SEQ ID NO 136
<211> LENGTH: 11
<212> TYPE: PRT
<213> ORGANISM: Artificial sequence
<220> FEATURE:
<223> OTHER INFORMATION: Heavy chain HVR sequence

<400> SEQUENCE: 136

Gly Asp Thr Ser Gly Gly Ala Tyr Phe Asp Leu
1               5                   10

<210> SEQ ID NO 137
<211> LENGTH: 9
<212> TYPE: PRT
<213> ORGANISM: Artificial sequence
<220> FEATURE:
<223> OTHER INFORMATION: Heavy chain HVR sequence

<400> SEQUENCE: 137

Asp Arg Gly Gly Val Gly Phe Asp Tyr
1               5

<210> SEQ ID NO 138
<211> LENGTH: 12
<212> TYPE: PRT
<213> ORGANISM: Artificial sequence
<220> FEATURE:
<223> OTHER INFORMATION: Heavy chain HVR sequence

<400> SEQUENCE: 138

Glu Val Gly Ala Pro Pro Ser Tyr Pro Phe Asp Ile
1               5                   10

<210> SEQ ID NO 139
<211> LENGTH: 14
<212> TYPE: PRT
<213> ORGANISM: Artificial sequence
<220> FEATURE:
<223> OTHER INFORMATION: Heavy chain HVR sequence

<400> SEQUENCE: 139

Ala Asn Tyr Tyr Asp Ser Ser Gly Tyr Ser Gly Leu Asp Leu
1               5                   10

<210> SEQ ID NO 140
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 140

Gly Pro Leu Leu Tyr Gly Asp Tyr His Val Arg Tyr Gly Met Asp Val
1               5                   10                  15

<210> SEQ ID NO 141
<211> LENGTH: 11
<212> TYPE: PRT
<213> ORGANISM: Artificial sequence
<220> FEATURE:
<223> OTHER INFORMATION: Heavy chain HVR sequence

<400> SEQUENCE: 141

Ala Lys Pro Arg Gly Asp Tyr Gly Met Asp Val
1               5                   10

<210> SEQ ID NO 142
<211> LENGTH: 13
<212> TYPE: PRT
<213> ORGANISM: Artificial sequence
<220> FEATURE:
<223> OTHER INFORMATION: Heavy chain HVR sequence

<400> SEQUENCE: 142

Asp Gly Gly Gly Gly Tyr Ala Tyr Glu Tyr Phe Gln His
1               5                   10

<210> SEQ ID NO 143
<211> LENGTH: 14
<212> TYPE: PRT
<213> ORGANISM: Artificial sequence
<220> FEATURE:
<223> OTHER INFORMATION: Heavy chain HVR sequence

<400> SEQUENCE: 143

Asp Gly Arg Glu Tyr Gly Gly His Tyr Tyr Gly Met Asp Val
1               5                   10

<210> SEQ ID NO 144
<211> LENGTH: 11
<212> TYPE: PRT
<213> ORGANISM: Artificial sequence
<220> FEATURE:
<223> OTHER INFORMATION: Heavy chain HVR sequence

<400> SEQUENCE: 144

Val Gly Asn Met Asp Gln Glu Tyr Phe Asp Leu
1               5                   10

<210> SEQ ID NO 145
<211> LENGTH: 13
<212> TYPE: PRT
<213> ORGANISM: Artificial sequence
<220> FEATURE:
<223> OTHER INFORMATION: Heavy chain HVR sequence

<400> SEQUENCE: 145

Pro Thr Arg Tyr Gly Tyr Asp Arg Leu Gly Met Asp Val
1               5                   10

<210> SEQ ID NO 146
<211> LENGTH: 10
<212> TYPE: PRT
<213> ORGANISM: Artificial sequence
<220> FEATURE:
<223> OTHER INFORMATION: Heavy chain HVR sequence

<400> SEQUENCE: 146

Thr Thr Tyr Arg Asp Tyr Tyr Met Asp Val
1               5                   10

<210> SEQ ID NO 147
<211> LENGTH: 13
<212> TYPE: PRT
<213> ORGANISM: Artificial sequence
<220> FEATURE:
<223> OTHER INFORMATION: Heavy chain HVR sequence

<400> SEQUENCE: 147

Asp Arg Ser Arg Gly Tyr Pro Val Tyr Gly Met Asp Val

<210> SEQ ID NO 148
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 148

Ser Gly Gly Asp Tyr Ser Gly Tyr Asp Tyr Ala Ser Gly Met Asp Val
1               5                   10                  15

<210> SEQ ID NO 149
<211> LENGTH: 13
<212> TYPE: PRT
<213> ORGANISM: Artificial sequence
<220> FEATURE:
<223> OTHER INFORMATION: Heavy chain HVR sequence

<400> SEQUENCE: 149

Asp Gly Ser Ala Gly Arg Gln Glu His Gly Met Asp Val
1               5                   10

<210> SEQ ID NO 150
<211> LENGTH: 12
<212> TYPE: PRT
<213> ORGANISM: Artificial sequence
<220> FEATURE:
<223> OTHER INFORMATION: Heavy chain HVR sequence

<400> SEQUENCE: 150

Gln Asp Leu Gly Ser Ser His Trp His Phe Asp Leu
1               5                   10

<210> SEQ ID NO 151
<211> LENGTH: 19
<212> TYPE: PRT
<213> ORGANISM: Artificial sequence
<220> FEATURE:
<223> OTHER INFORMATION: Heavy chain HVR sequence

<400> SEQUENCE: 151

Asp Pro Arg Asp Tyr Ser Ser Gly Ser Gly Gly Trp Gly Tyr
1               5                   10                  15

Phe Asp Leu

<210> SEQ ID NO 152
<211> LENGTH: 14
<212> TYPE: PRT
<213> ORGANISM: Artificial sequence
<220> FEATURE:
<223> OTHER INFORMATION: Heavy chain HVR sequence

<400> SEQUENCE: 152

Ala Pro Tyr Gly Ser Ser Ser Gly Tyr Gly Tyr Phe Asp Leu
1               5                   10

<210> SEQ ID NO 153
<211> LENGTH: 11
<212> TYPE: PRT
<213> ORGANISM: Artificial sequence
<220> FEATURE:
<223> OTHER INFORMATION: Heavy chain HVR sequence

<400> SEQUENCE: 153

```
Glu Gly Pro Gly Tyr Pro Ser Tyr Phe Asp Pro
1               5                   10

<210> SEQ ID NO 154
<211> LENGTH: 12
<212> TYPE: PRT
<213> ORGANISM: Artificial sequence
<220> FEATURE:
<223> OTHER INFORMATION: Heavy chain HVR sequence

<400> SEQUENCE: 154

Glu Gly Leu Tyr Ser Ser Gly Trp Tyr Ile Asp Val
1               5                   10

<210> SEQ ID NO 155
<211> LENGTH: 10
<212> TYPE: PRT
<213> ORGANISM: Artificial sequence
<220> FEATURE:
<223> OTHER INFORMATION: Heavy chain HVR sequence

<400> SEQUENCE: 155

Gly Asp Ser Ser Ser Gly Gly Leu Asp Leu
1               5                   10

<210> SEQ ID NO 156
<211> LENGTH: 9
<212> TYPE: PRT
<213> ORGANISM: Artificial sequence
<220> FEATURE:
<223> OTHER INFORMATION: Heavy chain HVR sequence

<400> SEQUENCE: 156

Gly Gln Tyr Thr Gly Ser Leu Asp Val
1               5

<210> SEQ ID NO 157
<211> LENGTH: 11
<212> TYPE: PRT
<213> ORGANISM: Artificial sequence
<220> FEATURE:
<223> OTHER INFORMATION: Heavy chain HVR sequence

<400> SEQUENCE: 157

Asp Thr Tyr Tyr Thr Pro Tyr Gly Met Asp Val
1               5                   10

<210> SEQ ID NO 158
<211> LENGTH: 12
<212> TYPE: PRT
<213> ORGANISM: Artificial sequence
<220> FEATURE:
<223> OTHER INFORMATION: Heavy chain HVR sequence

<400> SEQUENCE: 158

Gly Arg Pro Gln Ser Glu Ser Tyr Leu Leu Asp Tyr
1               5                   10

<210> SEQ ID NO 159
<211> LENGTH: 11
<212> TYPE: PRT
<213> ORGANISM: Artificial sequence
<220> FEATURE:
<223> OTHER INFORMATION: Heavy chain HVR sequence

<400> SEQUENCE: 159

Glu Gly Pro Glu Gln Leu Trp Tyr Leu Asp Tyr
```

<210> SEQ ID NO 160
<211> LENGTH: 14
<212> TYPE: PRT
<213> ORGANISM: Artificial sequence
<220> FEATURE:
<223> OTHER INFORMATION: Heavy chain HVR sequence

<400> SEQUENCE: 160

Ser Arg Trp Gly Ala Ser Gly Tyr Tyr Tyr Tyr Met Asp Val
1               5                   10

<210> SEQ ID NO 161
<211> LENGTH: 11
<212> TYPE: PRT
<213> ORGANISM: Artificial sequence
<220> FEATURE:
<223> OTHER INFORMATION: Heavy chain HVR sequence

<400> SEQUENCE: 161

Glu Ser Gly Thr Asp Phe Gly Thr Ile Ser Tyr
1               5                   10

<210> SEQ ID NO 162
<211> LENGTH: 13
<212> TYPE: PRT
<213> ORGANISM: Artificial sequence
<220> FEATURE:
<223> OTHER INFORMATION: Heavy chain HVR sequence

<400> SEQUENCE: 162

Gly Gly Ser Asn Tyr Gly Asp Tyr Gly Arg Phe Asp Tyr
1               5                   10

<210> SEQ ID NO 163
<211> LENGTH: 14
<212> TYPE: PRT
<213> ORGANISM: Artificial sequence
<220> FEATURE:
<223> OTHER INFORMATION: Heavy chain HVR sequence

<400> SEQUENCE: 163

Asp Thr Gly Glu Tyr Ser Tyr Ser Pro His Gly Met Asp Val
1               5                   10

<210> SEQ ID NO 164
<211> LENGTH: 11
<212> TYPE: PRT
<213> ORGANISM: Artificial sequence
<220> FEATURE:
<223> OTHER INFORMATION: Heavy chain HVR sequence

<400> SEQUENCE: 164

Val Gly Gln Tyr Pro Ile Tyr Gly Met Asp Val
1               5                   10

<210> SEQ ID NO 165
<211> LENGTH: 12
<212> TYPE: PRT
<213> ORGANISM: Artificial sequence
<220> FEATURE:
<223> OTHER INFORMATION: Heavy chain HVR sequence

<400> SEQUENCE: 165

Gly Pro Gly His Tyr Tyr Val Ala Gly Met Asp Val
1               5                   10

<210> SEQ ID NO 166
<211> LENGTH: 12
<212> TYPE: PRT
<213> ORGANISM: Artificial sequence
<220> FEATURE:
<223> OTHER INFORMATION: Heavy chain HVR sequence

<400> SEQUENCE: 166

Asp Ala Pro Gly Tyr Pro Met Leu Gly Met Asp Val
1               5                   10

<210> SEQ ID NO 167
<211> LENGTH: 18
<212> TYPE: PRT
<213> ORGANISM: Artificial sequence
<220> FEATURE:
<223> OTHER INFORMATION: Heavy chain HVR sequence

<400> SEQUENCE: 167

Glu Gly Ser Ser Phe Trp Ser Gly Ser Ala Val Ser Tyr Tyr Gly Met
1               5                   10                  15

Asp Val

<210> SEQ ID NO 168
<211> LENGTH: 13
<212> TYPE: PRT
<213> ORGANISM: Artificial sequence
<220> FEATURE:
<223> OTHER INFORMATION: Heavy chain HVR sequence

<400> SEQUENCE: 168

Asp Leu Ser Arg Gly Tyr Ala Val Ser Gly Met Asp Val
1               5                   10

<210> SEQ ID NO 169
<211> LENGTH: 8
<212> TYPE: PRT
<213> ORGANISM: Artificial sequence
<220> FEATURE:
<223> OTHER INFORMATION: Heavy chain HVR sequence

<400> SEQUENCE: 169

Ala Ser Pro Trp Glu Leu Asp Val
1               5

<210> SEQ ID NO 170
<211> LENGTH: 20
<212> TYPE: PRT
<213> ORGANISM: Artificial sequence
<220> FEATURE:
<223> OTHER INFORMATION: Heavy chain HVR sequence

<400> SEQUENCE: 170

Asp Leu Gly His Tyr Asp Tyr Trp Ser Gly Ser Arg Asp Tyr Tyr Tyr
1               5                   10                  15

Gly Met Asp Val
            20

<210> SEQ ID NO 171
<211> LENGTH: 16
<212> TYPE: PRT
<213> ORGANISM: Artificial sequence
<220> FEATURE:
<223> OTHER INFORMATION: Heavy chain HVR sequence

```
<400> SEQUENCE: 171

Asp Gly Thr Ile Ala Ala Ala Gly Trp Pro Pro Glu Tyr Phe Gln His
1               5                   10                  15

<210> SEQ ID NO 172
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 172

Gly Pro Thr Gly Tyr Lys Asp Lys Trp Arg Tyr Tyr Tyr Gly Met Asp
1               5                   10                  15

Val

<210> SEQ ID NO 173
<211> LENGTH: 15
<212> TYPE: PRT
<213> ORGANISM: Artificial sequence
<220> FEATURE:
<223> OTHER INFORMATION: Heavy chain HVR sequence

<400> SEQUENCE: 173

Glu Gly Gly Gly His Ala Ser Tyr His Tyr Tyr Gly Met Asp Val
1               5                   10                  15

<210> SEQ ID NO 174
<211> LENGTH: 23
<212> TYPE: PRT
<213> ORGANISM: Artificial sequence
<220> FEATURE:
<223> OTHER INFORMATION: Light chain framework sequence

<400> SEQUENCE: 174

Glu Ile Val Met Thr Gln Ser Pro Gly Thr Leu Ser Leu Ser Pro Gly
1               5                   10                  15

Glu Arg Ala Thr Leu Ser Cys
            20

<210> SEQ ID NO 175
<211> LENGTH: 23
<212> TYPE: PRT
<213> ORGANISM: Artificial sequence
<220> FEATURE:
<223> OTHER INFORMATION: Light chain framework sequence

<400> SEQUENCE: 175

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 176
<211> LENGTH: 23
<212> TYPE: PRT
<213> ORGANISM: Artificial sequence
<220> FEATURE:
<223> OTHER INFORMATION: Light chain framework sequence

<400> SEQUENCE: 176

Glu Ile Val Met Thr Gln Ser Pro Ala Thr Leu Ser Leu Ser Pro Gly
1               5                   10                  15

Glu Arg Ala Thr Leu Ser Cys
```

<210> SEQ ID NO 177
<211> LENGTH: 23
<212> TYPE: PRT
<213> ORGANISM: Artificial sequence
<220> FEATURE:
<223> OTHER INFORMATION: Light chain framework sequence

<400> SEQUENCE: 177

Glu Ile Val Leu Thr Gln Ser Pro Ala Thr Leu Ser Leu Ser Pro Gly
1               5                   10                  15

Glu Arg Ala Thr Ile Thr Cys
            20

<210> SEQ ID NO 178
<211> LENGTH: 23
<212> TYPE: PRT
<213> ORGANISM: Artificial sequence
<220> FEATURE:
<223> OTHER INFORMATION: Light chain framework sequence

<400> SEQUENCE: 178

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 179
<211> LENGTH: 23
<212> TYPE: PRT
<213> ORGANISM: Artificial sequence
<220> FEATURE:
<223> OTHER INFORMATION: Light chain framework sequence

<400> SEQUENCE: 179

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 180
<211> LENGTH: 23
<212> TYPE: PRT
<213> ORGANISM: Artificial sequence
<220> FEATURE:
<223> OTHER INFORMATION: Light chain framework sequence

<400> SEQUENCE: 180

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 181
<211> LENGTH: 23
<212> TYPE: PRT
<213> ORGANISM: Artificial sequence
<220> FEATURE:
<223> OTHER INFORMATION: Light chain framework sequence

<400> SEQUENCE: 181

Asp Ile Gln Met Thr Gln Ser Pro Ser Ser Leu Ser Ala Ser Val Gly
1               5                   10                  15

```
Asp Arg Val Thr Ile Thr Cys
            20

<210> SEQ ID NO 182
<211> LENGTH: 23
<212> TYPE: PRT
<213> ORGANISM: Artificial sequence
<220> FEATURE:
<223> OTHER INFORMATION: Light chain framework sequence

<400> SEQUENCE: 182

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 183
<211> LENGTH: 23
<212> TYPE: PRT
<213> ORGANISM: Artificial sequence
<220> FEATURE:
<223> OTHER INFORMATION: Light chain framework sequence

<400> SEQUENCE: 183

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 184
<211> LENGTH: 23
<212> TYPE: PRT
<213> ORGANISM: Artificial sequence
<220> FEATURE:
<223> OTHER INFORMATION: Light chain framework sequence

<400> SEQUENCE: 184

Glu Ile Val Met Thr Gln Ser Pro Ala Thr Leu Ser Val Ser Pro Gly
1               5                   10                  15

Glu Arg Ala Thr Ile Thr Cys
            20

<210> SEQ ID NO 185
<211> LENGTH: 23
<212> TYPE: PRT
<213> ORGANISM: Artificial sequence
<220> FEATURE:
<223> OTHER INFORMATION: Light chain framework sequence

<400> SEQUENCE: 185

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 186
<211> LENGTH: 15
<212> TYPE: PRT
<213> ORGANISM: Artificial sequence
<220> FEATURE:
<223> OTHER INFORMATION: Light chain framework sequence

<400> SEQUENCE: 186

Trp Tyr Gln Gln Lys Pro Gly Gln Ala Pro Arg Leu Leu Ile Tyr
1               5                   10                  15
```

<210> SEQ ID NO 187
<211> LENGTH: 15
<212> TYPE: PRT
<213> ORGANISM: Artificial sequence
<220> FEATURE:
<223> OTHER INFORMATION: Light chain framework sequence

<400> SEQUENCE: 187

Trp Tyr Gln Gln Lys Pro Gly Gln Pro Pro Lys Leu Leu Ile Tyr
1               5                   10                  15

<210> SEQ ID NO 188
<211> LENGTH: 15
<212> TYPE: PRT
<213> ORGANISM: Artificial sequence
<220> FEATURE:
<223> OTHER INFORMATION: Light chain framework sequence

<400> SEQUENCE: 188

Trp Tyr Leu Gln Lys Pro Gly Gln Ser Pro Gln Leu Leu Ile Tyr
1               5                   10                  15

<210> SEQ ID NO 189
<211> LENGTH: 15
<212> TYPE: PRT
<213> ORGANISM: Artificial sequence
<220> FEATURE:
<223> OTHER INFORMATION: Light chain framework sequence

<400> SEQUENCE: 189

Trp Tyr Leu Gln Lys Pro Gly Gln Ser Pro Gln Val Leu Ile Tyr
1               5                   10                  15

<210> SEQ ID NO 190
<211> LENGTH: 15
<212> TYPE: PRT
<213> ORGANISM: Artificial sequence
<220> FEATURE:
<223> OTHER INFORMATION: Light chain framework sequence

<400> SEQUENCE: 190

Trp Tyr Gln Gln Lys Pro Gly Lys Ala Pro Lys Leu Leu Ile Tyr
1               5                   10                  15

<210> SEQ ID NO 191
<211> LENGTH: 15
<212> TYPE: PRT
<213> ORGANISM: Artificial sequence
<220> FEATURE:
<223> OTHER INFORMATION: Light chain framework sequence

<400> SEQUENCE: 191

Trp Tyr Leu Gln Lys Pro Gly Gln Ser Pro Gln Leu Leu Ile Phe
1               5                   10                  15

<210> SEQ ID NO 192
<211> LENGTH: 32
<212> TYPE: PRT
<213> ORGANISM: Artificial sequence
<220> FEATURE:
<223> OTHER INFORMATION: Light chain framework sequence

<400> SEQUENCE: 192

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 193
<211> LENGTH: 32
<212> TYPE: PRT
<213> ORGANISM: Artificial sequence
<220> FEATURE:
<223> OTHER INFORMATION: Light chain framework sequence

<400> SEQUENCE: 193

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 194
<211> LENGTH: 32
<212> TYPE: PRT
<213> ORGANISM: Artificial sequence
<220> FEATURE:
<223> OTHER INFORMATION: Light chain framework sequence

<400> SEQUENCE: 194

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 195
<211> LENGTH: 32
<212> TYPE: PRT
<213> ORGANISM: Artificial sequence
<220> FEATURE:
<223> OTHER INFORMATION: Light chain framework sequence

<400> SEQUENCE: 195

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 196
<211> LENGTH: 32
<212> TYPE: PRT
<213> ORGANISM: Artificial sequence
<220> FEATURE:
<223> OTHER INFORMATION: Light chain framework sequence

<400> SEQUENCE: 196

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 197
<211> LENGTH: 32
<212> TYPE: PRT
<213> ORGANISM: Artificial sequence
<220> FEATURE:
<223> OTHER INFORMATION: Light chain framework sequence

<400> SEQUENCE: 197

Gly Val Pro Ser Arg Phe Ser Gly Ser Gly Ser Gly Thr Asp Phe Thr
1               5                   10                  15

```
Leu Thr Ile Ser Ser Leu Gln Pro Glu Asp Phe Ala Thr Tyr Tyr Cys
            20                  25                  30

<210> SEQ ID NO 198
<211> LENGTH: 32
<212> TYPE: PRT
<213> ORGANISM: Artificial sequence
<220> FEATURE:
<223> OTHER INFORMATION: Light chain framework sequence

<400> SEQUENCE: 198

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 199
<211> LENGTH: 32
<212> TYPE: PRT
<213> ORGANISM: Artificial sequence
<220> FEATURE:
<223> OTHER INFORMATION: Light chain framework sequence

<400> SEQUENCE: 199

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 200
<211> LENGTH: 10
<212> TYPE: PRT
<213> ORGANISM: Artificial sequence
<220> FEATURE:
<223> OTHER INFORMATION: Light chain framework sequence

<400> SEQUENCE: 200

Phe Gly Gly Gly Thr Lys Val Glu Ile Lys
1               5                   10

<210> SEQ ID NO 201
<211> LENGTH: 30
<212> TYPE: PRT
<213> ORGANISM: Artificial sequence
<220> FEATURE:
<223> OTHER INFORMATION: Heavy chain framework sequence

<400> SEQUENCE: 201

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 202
<211> LENGTH: 30
<212> TYPE: PRT
<213> ORGANISM: Artificial sequence
<220> FEATURE:
<223> OTHER INFORMATION: Heavy chain framework sequence

<400> SEQUENCE: 202

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
```

20                  25                  30

<210> SEQ ID NO 203
<211> LENGTH: 30
<212> TYPE: PRT
<213> ORGANISM: Artificial sequence
<220> FEATURE:
<223> OTHER INFORMATION: Heavy chain framework sequence

<400> SEQUENCE: 203

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 204
<211> LENGTH: 30
<212> TYPE: PRT
<213> ORGANISM: Artificial sequence
<220> FEATURE:
<223> OTHER INFORMATION: Heavy chain framework sequence

<400> SEQUENCE: 204

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 205
<211> LENGTH: 30
<212> TYPE: PRT
<213> ORGANISM: Artificial sequence
<220> FEATURE:
<223> OTHER INFORMATION: Heavy chain framework sequence

<400> SEQUENCE: 205

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser
            20                  25                  30

<210> SEQ ID NO 206
<211> LENGTH: 30
<212> TYPE: PRT
<213> ORGANISM: Artificial sequence
<220> FEATURE:
<223> OTHER INFORMATION: Heavy chain framework sequence

<400> SEQUENCE: 206

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 207
<211> LENGTH: 30
<212> TYPE: PRT
<213> ORGANISM: Artificial sequence
<220> FEATURE:
<223> OTHER INFORMATION: Heavy chain framework sequence

<400> SEQUENCE: 207

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 208
<211> LENGTH: 30
<212> TYPE: PRT
<213> ORGANISM: Artificial sequence
<220> FEATURE:
<223> OTHER INFORMATION: Heavy chain framework sequence

<400> SEQUENCE: 208

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser
            20                  25                  30

<210> SEQ ID NO 209
<211> LENGTH: 30
<212> TYPE: PRT
<213> ORGANISM: Artificial sequence
<220> FEATURE:
<223> OTHER INFORMATION: Heavy chain framework sequence

<400> SEQUENCE: 209

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser
            20                  25                  30

<210> SEQ ID NO 210
<211> LENGTH: 14
<212> TYPE: PRT
<213> ORGANISM: Artificial sequence
<220> FEATURE:
<223> OTHER INFORMATION: Heavy chain framework sequence

<400> SEQUENCE: 210

Trp Val Arg Gln Ala Pro Gly Lys Gly Leu Glu Trp Val Ser
1               5                   10

<210> SEQ ID NO 211
<211> LENGTH: 14
<212> TYPE: PRT
<213> ORGANISM: Artificial sequence
<220> FEATURE:
<223> OTHER INFORMATION: Heavy chain framework sequence

<400> SEQUENCE: 211

Trp Val Arg Gln Ala Pro Gly Lys Gly Leu Glu Trp Val Ala
1               5                   10

<210> SEQ ID NO 212
<211> LENGTH: 14
<212> TYPE: PRT
<213> ORGANISM: Artificial sequence
<220> FEATURE:
<223> OTHER INFORMATION: Heavy chain framework sequence

<400> SEQUENCE: 212

Trp Val Arg Gln Ala Pro Gly Gln Gly Leu Glu Trp Met Gly
1               5                   10

<210> SEQ ID NO 213
<211> LENGTH: 14
<212> TYPE: PRT
<213> ORGANISM: Artificial sequence

```
<220> FEATURE:
<223> OTHER INFORMATION: Heavy chain framework sequence

<400> SEQUENCE: 213

Trp Ile Arg Gln Pro Pro Gly Lys Gly Leu Glu Trp Ile Gly
1               5                   10

<210> SEQ ID NO 214
<211> LENGTH: 14
<212> TYPE: PRT
<213> ORGANISM: Artificial sequence
<220> FEATURE:
<223> OTHER INFORMATION: Heavy chain framework sequence

<400> SEQUENCE: 214

Trp Ile Arg Gln His Pro Gly Lys Gly Leu Glu Trp Ile Gly
1               5                   10

<210> SEQ ID NO 215
<211> LENGTH: 32
<212> TYPE: PRT
<213> ORGANISM: Artificial sequence
<220> FEATURE:
<223> OTHER INFORMATION: Heavy chain framework sequence

<400> SEQUENCE: 215

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 216
<211> LENGTH: 32
<212> TYPE: PRT
<213> ORGANISM: Artificial sequence
<220> FEATURE:
<223> OTHER INFORMATION: Heavy chain framework sequence

<400> SEQUENCE: 216

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 217
<211> LENGTH: 32
<212> TYPE: PRT
<213> ORGANISM: Artificial sequence
<220> FEATURE:
<223> OTHER INFORMATION: Heavy chain framework sequence

<400> SEQUENCE: 217

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 218
<211> LENGTH: 32
<212> TYPE: PRT
<213> ORGANISM: Artificial sequence
<220> FEATURE:
<223> OTHER INFORMATION: Heavy chain framework sequence

<400> SEQUENCE: 218
```

-continued

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 219
<211> LENGTH: 32
<212> TYPE: PRT
<213> ORGANISM: Artificial sequence
<220> FEATURE:
<223> OTHER INFORMATION: Heavy chain framework sequence

<400> SEQUENCE: 219

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 220
<211> LENGTH: 32
<212> TYPE: PRT
<213> ORGANISM: Artificial sequence
<220> FEATURE:
<223> OTHER INFORMATION: Heavy chain framework sequence

<400> SEQUENCE: 220

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 221
<211> LENGTH: 32
<212> TYPE: PRT
<213> ORGANISM: Artificial sequence
<220> FEATURE:
<223> OTHER INFORMATION: Heavy chain framework sequence

<400> SEQUENCE: 221

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 222
<211> LENGTH: 11
<212> TYPE: PRT
<213> ORGANISM: Artificial sequence
<220> FEATURE:
<223> OTHER INFORMATION: Heavy chain framework sequence

<400> SEQUENCE: 222

Trp Gly Gln Gly Thr Thr Val Thr Val Ser Ser
1               5                   10

<210> SEQ ID NO 223
<211> LENGTH: 11
<212> TYPE: PRT
<213> ORGANISM: Artificial sequence
<220> FEATURE:
<223> OTHER INFORMATION: Heavy chain framework sequence

<400> SEQUENCE: 223

Trp Gly Arg Gly Thr Leu Val Thr Val Ser Ser
1               5                   10

```
<210> SEQ ID NO 224
<211> LENGTH: 11
<212> TYPE: PRT
<213> ORGANISM: Artificial sequence
<220> FEATURE:
<223> OTHER INFORMATION: Heavy chain framework sequence

<400> SEQUENCE: 224

Trp Gly Gln Gly Thr Leu Val Thr Val Ser Ser
1               5                   10

<210> SEQ ID NO 225
<211> LENGTH: 11
<212> TYPE: PRT
<213> ORGANISM: Artificial sequence
<220> FEATURE:
<223> OTHER INFORMATION: Heavy chain framework sequence

<400> SEQUENCE: 225

Trp Gly Lys Gly Thr Thr Val Thr Val Ser Ser
1               5                   10

<210> SEQ ID NO 226
<211> LENGTH: 11
<212> TYPE: PRT
<213> ORGANISM: Artificial sequence
<220> FEATURE:
<223> OTHER INFORMATION: Heavy chain framework sequence

<400> SEQUENCE: 226

Trp Gly Gln Gly Thr Met Val Thr Val Ser Ser
1               5                   10

<210> SEQ ID NO 227
<211> LENGTH: 11
<212> TYPE: PRT
<213> ORGANISM: Artificial sequence
<220> FEATURE:
<223> OTHER INFORMATION: Heavy chain framework sequence

<400> SEQUENCE: 227

Trp Gly Gln Gly Thr Thr Val Ser Val Ser Ser
1               5                   10

<210> SEQ ID NO 228
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 228

Ser Phe Gly Met Asn
1               5

<210> SEQ ID NO 229
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 229

Ala Tyr Gly Met Asn
1               5
```

```
<210> SEQ ID NO 230
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 230

Arg Tyr Gly Met His
1               5

<210> SEQ ID NO 231
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 231

Asp Tyr Gly Met His
1               5

<210> SEQ ID NO 232
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 232

Thr Tyr Gly Met His
1               5

<210> SEQ ID NO 233
<211> LENGTH: 6
<212> TYPE: PRT
<213> ORGANISM: Artificial sequence
<220> FEATURE:
<223> OTHER INFORMATION: Heavy chain HVR sequence

<400> SEQUENCE: 233

Ala His Tyr Tyr Trp Gly
1               5

<210> SEQ ID NO 234
<211> LENGTH: 6
<212> TYPE: PRT
<213> ORGANISM: Artificial sequence
<220> FEATURE:
<223> OTHER INFORMATION: Heavy chain HVR sequence

<400> SEQUENCE: 234

Pro His Tyr Tyr Trp Gly
1               5

<210> SEQ ID NO 235
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 235

Ser Tyr Tyr Met Ala
1               5
```

```
<210> SEQ ID NO 236
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 236

Ser Tyr Tyr Met Val
1               5

<210> SEQ ID NO 237
<211> LENGTH: 5
<212> TYPE: PRT
<213> ORGANISM: Artificial sequence
<220> FEATURE:
<223> OTHER INFORMATION: Heavy chain HVR sequence

<400> SEQUENCE: 237

Ser Phe Tyr Ile Ser
1               5

<210> SEQ ID NO 238
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 238

Ala Ile Thr Ala Ser Gly Gly Ser Thr Phe Tyr Ala Asp Ser Val Lys
1               5                   10                  15

Gly

<210> SEQ ID NO 239
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 239

Ala Ile Thr Ser Ser Gly Arg Ser Thr Tyr Tyr Ala Asp Ser Val Lys
1               5                   10                  15

Gly

<210> SEQ ID NO 240
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 240

Ala Ile Arg Ala Ser Gly Gly Ala Thr Tyr Tyr Ala Asp Ser Val Lys
1               5                   10                  15

Gly

<210> SEQ ID NO 241
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 241
```

```
Ala Ile Ser Ala Ser Gly Arg Ser Thr Phe Tyr Ala Asp Ser Val Lys
1               5                   10                  15

Gly

<210> SEQ ID NO 242
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 242

Ala Ile Ser Gly Leu Ala Gly Pro Thr Tyr Ala Asp Ser Val Lys Gly
1               5                   10                  15

<210> SEQ ID NO 243
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 243

Ala Ile Ser Ala Phe Ala Gly Ser Thr Tyr Ala Asp Ser Val Lys Gly
1               5                   10                  15

<210> SEQ ID NO 244
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 244

His Ile Trp Tyr Glu Gly Ser Asn Lys Val Tyr Ala Asp Ser Val Lys
1               5                   10                  15

Gly

<210> SEQ ID NO 245
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 245

Ala Ile Ser Gly Leu Ala Gly Gln Thr Tyr Ala Asp Ser Val Lys Gly
1               5                   10                  15

<210> SEQ ID NO 246
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 246

Ser Ile Phe His Ser Gly His Thr Tyr Tyr Asn Pro Ser Leu Lys Ser
1               5                   10                  15

<210> SEQ ID NO 247
<211> LENGTH: 16
<212> TYPE: PRT
<213> ORGANISM: Artificial sequence
<220> FEATURE:
```

<223> OTHER INFORMATION: Heavy chain HVR sequence

<400> SEQUENCE: 247

Ser Ile Tyr His Ser Gly His Thr Tyr Tyr Asn Pro Ser Leu Lys Ser
1               5                   10                  15

<210> SEQ ID NO 248
<211> LENGTH: 16
<212> TYPE: PRT
<213> ORGANISM: Artificial sequence
<220> FEATURE:
<223> OTHER INFORMATION: Heavy chain HVR sequence

<400> SEQUENCE: 248

Ser Ile Tyr Gln Ser Gly His Thr Tyr Tyr Asn Pro Ser Leu Lys Ser
1               5                   10                  15

<210> SEQ ID NO 249
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 249

Trp Ile Asn Pro Ala Val Gly Ala Thr Ile Tyr Ser Gln Lys Phe Gln
1               5                   10                  15
Gly

<210> SEQ ID NO 250
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 250

Ile Ile Asn Pro Ser Ser Gly Ala Thr Asn Tyr Ala Gln Lys Phe Gln
1               5                   10                  15
Gly

<210> SEQ ID NO 251
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 251

Ile Ile Asn Pro Ser Ser Gly His Thr Asn Tyr Ala Gln Lys Leu Gln
1               5                   10                  15
Gly

<210> SEQ ID NO 252
<211> LENGTH: 17
<212> TYPE: PRT
<213> ORGANISM: Artificial sequence
<220> FEATURE:
<223> OTHER INFORMATION: Heavy chain HVR sequence

<400> SEQUENCE: 252

Ile Ile Asn Pro Ser Ser Gly Asp Thr Asn Tyr Ala Gln Lys Phe Gln
1               5                   10                  15
Gly

<210> SEQ ID NO 253
<211> LENGTH: 13
<212> TYPE: PRT
<213> ORGANISM: Artificial sequence
<220> FEATURE:
<223> OTHER INFORMATION: Heavy chain HVR sequence

<400> SEQUENCE: 253

Asp Gln Thr Ala Ala Trp Gly Ile Trp Gly Met Asp Val
1               5                   10

<210> SEQ ID NO 254
<211> LENGTH: 11
<212> TYPE: PRT
<213> ORGANISM: Artificial sequence
<220> FEATURE:
<223> OTHER INFORMATION: Heavy chain HVR sequence

<400> SEQUENCE: 254

Ala Gly Ala Met Thr Pro Ala Gly Met Asp Val
1               5                   10

<210> SEQ ID NO 255
<211> LENGTH: 23
<212> TYPE: PRT
<213> ORGANISM: Artificial sequence
<220> FEATURE:
<223> OTHER INFORMATION: Light chain FR sequence

<400> SEQUENCE: 255

Glu Val Val Leu Thr Gln Ser Pro Gly Thr Leu Ser Leu Ser Pro Gly
1               5                   10                  15

Glu Arg Ala Thr Leu Ser Cys
            20

<210> SEQ ID NO 256
<211> LENGTH: 30
<212> TYPE: PRT
<213> ORGANISM: Artificial sequence
<220> FEATURE:
<223> OTHER INFORMATION: Heavy chain FR sequence

<400> SEQUENCE: 256

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Gly
            20                  25                  30

<210> SEQ ID NO 257
<211> LENGTH: 30
<212> TYPE: PRT
<213> ORGANISM: Artificial sequence
<220> FEATURE:
<223> OTHER INFORMATION: Light chain FR sequence

<400> SEQUENCE: 257

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 258
<211> LENGTH: 30
<212> TYPE: PRT

```
<213> ORGANISM: Artificial sequence
<220> FEATURE:
<223> OTHER INFORMATION: Light chain FR sequence

<400> SEQUENCE: 258

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser
            20                  25                  30

<210> SEQ ID NO 259
<211> LENGTH: 30
<212> TYPE: PRT
<213> ORGANISM: Artificial sequence
<220> FEATURE:
<223> OTHER INFORMATION: Heavy chain FR sequence

<400> SEQUENCE: 259

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala
            20                  25                  30

<210> SEQ ID NO 260
<211> LENGTH: 30
<212> TYPE: PRT
<213> ORGANISM: Artificial sequence
<220> FEATURE:
<223> OTHER INFORMATION: Heavy chain FR sequence

<400> SEQUENCE: 260

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Leu
            20                  25                  30

<210> SEQ ID NO 261
<211> LENGTH: 30
<212> TYPE: PRT
<213> ORGANISM: Artificial sequence
<220> FEATURE:
<223> OTHER INFORMATION: Heavy chain FR sequence

<400> SEQUENCE: 261

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Lys
            20                  25                  30

<210> SEQ ID NO 262
<211> LENGTH: 30
<212> TYPE: PRT
<213> ORGANISM: Artificial sequence
<220> FEATURE:
<223> OTHER INFORMATION: Heavy chain FR sequence

<400> SEQUENCE: 262

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly
            20                  25                  30

<210> SEQ ID NO 263
<211> LENGTH: 30
```

```
<212> TYPE: PRT
<213> ORGANISM: Artificial sequence
<220> FEATURE:
<223> OTHER INFORMATION: Heavy chain FR sequence

<400> SEQUENCE: 263

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala
            20                  25                  30

<210> SEQ ID NO 264
<211> LENGTH: 14
<212> TYPE: PRT
<213> ORGANISM: Artificial sequence
<220> FEATURE:
<223> OTHER INFORMATION: Heavy chain FR sequence

<400> SEQUENCE: 264

Trp Val Arg Gln Ala Pro Gly Gln Arg Leu Glu Trp Met Gly
1               5                   10

<210> SEQ ID NO 265
<211> LENGTH: 32
<212> TYPE: PRT
<213> ORGANISM: Artificial sequence
<220> FEATURE:
<223> OTHER INFORMATION: Heavy chain FR sequence

<400> SEQUENCE: 265

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 266
<211> LENGTH: 32
<212> TYPE: PRT
<213> ORGANISM: Artificial sequence
<220> FEATURE:
<223> OTHER INFORMATION: Heavy chain FR sequence

<400> SEQUENCE: 266

Arg Val Thr Met Thr Thr Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 267
<211> LENGTH: 108
<212> TYPE: PRT
<213> ORGANISM: Artificial sequence
<220> FEATURE:
<223> OTHER INFORMATION: Light Chain Variable Region

<400> SEQUENCE: 267

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Leu Leu Gly Ser Ser Pro
                85                  90                  95

Arg Thr Phe Gly Gly Gly Thr Lys Val Glu Ile Lys
            100                 105

<210> SEQ ID NO 268
<211> LENGTH: 122
<212> TYPE: PRT
<213> ORGANISM: Artificial sequence
<220> FEATURE:
<223> OTHER INFORMATION: Heavy Chain Variable Region

<400> SEQUENCE: 268

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Thr Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Thr Glu Val Val Gly Trp Leu Gly Met Asp Val Trp
            100                 105                 110

Gly Gln Gly Thr Thr Val Thr Val Ser Ser
            115                 120

<210> SEQ ID NO 269
<211> LENGTH: 108
<212> TYPE: PRT
<213> ORGANISM: Artificial sequence
<220> FEATURE:
<223> OTHER INFORMATION: Light Chain Variable Region

<400> SEQUENCE: 269

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ser His Pro
                85                  90                  95

Phe Thr Phe Gly Gly Gly Thr Lys Val Glu Ile Lys
            100                 105

<210> SEQ ID NO 270
<211> LENGTH: 122
<212> TYPE: PRT

<213> ORGANISM: Artificial sequence
<220> FEATURE:
<223> OTHER INFORMATION: Heavy Chain Variable Region

<400> SEQUENCE: 270

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Asn Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Thr Ala Ala Ala Ile Trp Gly Met Asp Val Trp
            100                 105                 110

Gly Gln Gly Thr Thr Val Thr Val Ser Ser
        115                 120

<210> SEQ ID NO 271
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 271

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Leu Phe His Pro Pro
                85                  90                  95

Thr Phe Gly Gly Gly Thr Lys Val Glu Ile Lys
            100                 105

<210> SEQ ID NO 272
<211> LENGTH: 121
<212> TYPE: PRT
<213> ORGANISM: Artificial sequence
<220> FEATURE:
<223> OTHER INFORMATION: Heavy Chain Variable Region

<400> SEQUENCE: 272

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

```
Gly Trp Ile Asn Pro Ser Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Ile Ala Ala Thr Asp Ala Tyr Phe Asp Leu Trp Gly
                100                 105                 110

Arg Gly Thr Leu Val Thr Val Ser Ser
            115                 120

<210> SEQ ID NO 273
<211> LENGTH: 108
<212> TYPE: PRT
<213> ORGANISM: Artificial sequence
<220> FEATURE:
<223> OTHER INFORMATION: Light Chain Variable Region

<400> SEQUENCE: 273

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ala Pro
                85                  90                  95

Ile Thr Phe Gly Gly Gly Thr Lys Val Glu Ile Lys
                100                 105

<210> SEQ ID NO 274
<211> LENGTH: 125
<212> TYPE: PRT
<213> ORGANISM: Artificial sequence
<220> FEATURE:
<223> OTHER INFORMATION: Heavy Chain Variable Region

<400> SEQUENCE: 274

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Gly Thr His Phe Gly Thr Tyr Ser Tyr Ser Asn Trp Phe
                100                 105                 110

Asp Pro Trp Gly Gln Gly Thr Leu Val Thr Val Ser Ser
```

```
                    115                 120                 125

<210> SEQ ID NO 275
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 275

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Leu Phe His Pro Pro
                85                  90                  95

Thr Phe Gly Gly Gly Thr Lys Val Glu Ile Lys
            100                 105

<210> SEQ ID NO 276
<211> LENGTH: 118
<212> TYPE: PRT
<213> ORGANISM: Artificial sequence
<220> FEATURE:
<223> OTHER INFORMATION: Heavy Chain Variable Region

<400> SEQUENCE: 276

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gly Asp Glu Asp Trp Phe Asp Pro Trp Gly Gln Gly Thr
            100                 105                 110

Leu Val Thr Val Ser Ser
        115

<210> SEQ ID NO 277
<211> LENGTH: 108
<212> TYPE: PRT
<213> ORGANISM: Artificial sequence
<220> FEATURE:
<223> OTHER INFORMATION: Light Chain Variable Region

<400> SEQUENCE: 277

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Gly His Leu Pro
                85                  90                  95

Ile Thr Phe Gly Gly Gly Thr Lys Val Glu Ile Lys
            100                 105
```

<210> SEQ ID NO 278
<211> LENGTH: 113
<212> TYPE: PRT
<213> ORGANISM: Artificial sequence
<220> FEATURE:
<223> OTHER INFORMATION: Light Chain Variable Region

<400> SEQUENCE: 278

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ile Ala Pro Phe Thr Phe Gly Gly Gly Thr Lys Val Glu Ile
            100                 105                 110

Lys
```

<210> SEQ ID NO 279
<211> LENGTH: 123
<212> TYPE: PRT
<213> ORGANISM: Artificial sequence
<220> FEATURE:
<223> OTHER INFORMATION: Heavy Chain Variable Region

<400> SEQUENCE: 279

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Ser Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Glu Thr Arg Gln Asp Ser Ala His Tyr Tyr Gly Met Asp Val
            100                 105                 110

Trp Gly Gln Gly Thr Thr Val Thr Val Ser Ser
        115                 120

<210> SEQ ID NO 280
<211> LENGTH: 108
<212> TYPE: PRT
<213> ORGANISM: Artificial sequence
<220> FEATURE:
<223> OTHER INFORMATION: Light Chain Variable Region

<400> SEQUENCE: 280

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Tyr Ser Ser Pro
                85                  90                  95

Tyr Thr Phe Gly Gly Gly Thr Lys Val Glu Ile Lys
            100                 105

<210> SEQ ID NO 281
<211> LENGTH: 120
<212> TYPE: PRT
<213> ORGANISM: Artificial sequence
<220> FEATURE:
<223> OTHER INFORMATION: Heavy Chain Variable Region

<400> SEQUENCE: 281

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Ala Met Thr Pro Ala Gly Met Asp Val Trp Gly Gln
            100                 105                 110

Gly Thr Thr Val Thr Val Ser Ser
        115                 120

<210> SEQ ID NO 282
<211> LENGTH: 114
<212> TYPE: PRT
<213> ORGANISM: Artificial sequence
<220> FEATURE:
<223> OTHER INFORMATION: Light Chain Variable Region

<400> SEQUENCE: 282

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr His Ser Val Pro Pro Ile Thr Phe Gly Gly Gly Thr Lys Val Glu
            100                 105                 110

Ile Lys

<210> SEQ ID NO 283
<211> LENGTH: 125
<212> TYPE: PRT
<213> ORGANISM: Artificial sequence
<220> FEATURE:
<223> OTHER INFORMATION: Heavy Chain Variable Region

<400> SEQUENCE: 283

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile His Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Leu His Tyr Gly Asp Tyr Ile Val Tyr Tyr Gly Met
            100                 105                 110

Asp Val Trp Gly Gln Gly Thr Thr Val Thr Val Ser Ser
        115                 120                 125

<210> SEQ ID NO 284
<211> LENGTH: 112
<212> TYPE: PRT
<213> ORGANISM: Artificial sequence
<220> FEATURE:
<223> OTHER INFORMATION: Light Chain Variable Region

<400> SEQUENCE: 284

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

```
Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65              70                  75                      80

Ser Arg Val Glu Ala Glu Asp Val Gly Val Tyr Tyr Cys Met Gln Ala
                 85                  90                  95

Ile Glu Ser Pro Leu Thr Phe Gly Gly Gly Thr Lys Val Glu Ile Lys
                100                 105                 110

<210> SEQ ID NO 285
<211> LENGTH: 120
<212> TYPE: PRT
<213> ORGANISM: Artificial sequence
<220> FEATURE:
<223> OTHER INFORMATION: Heavy Chain Variable Region

<400> SEQUENCE: 285

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65              70                  75                      80

Met Glu Leu Ser Ser Leu Arg Ser Glu Asp Thr Ala Val Tyr Tyr Cys
                 85                  90                  95

Ala Arg Gly Val Pro Arg Gly Asp Leu Gly Met Asp Val Trp Gly Gln
                100                 105                 110

Gly Thr Thr Val Thr Val Ser Ser
            115                 120

<210> SEQ ID NO 286
<211> LENGTH: 112
<212> TYPE: PRT
<213> ORGANISM: Artificial sequence
<220> FEATURE:
<223> OTHER INFORMATION: Light Chain Variable Region

<400> SEQUENCE: 286

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Tyr Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65              70                  75                      80

Ser Arg Val Glu Ala Glu Asp Val Gly Val Tyr Tyr Cys Val Gln Ala
                 85                  90                  95

Leu Gln Thr Pro Leu Thr Phe Gly Gly Gly Thr Lys Val Glu Ile Lys
                100                 105                 110

<210> SEQ ID NO 287
```

```
<211> LENGTH: 126
<212> TYPE: PRT
<213> ORGANISM: Artificial sequence
<220> FEATURE:
<223> OTHER INFORMATION: Heavy Chain Variable Region

<400> SEQUENCE: 287

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Val Asp Ser Ser Tyr Ser Leu Gly Tyr Tyr Tyr Gly
            100                 105                 110

Met Asp Val Trp Gly Lys Gly Thr Thr Val Thr Val Ser Ser
        115                 120                 125

<210> SEQ ID NO 288
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 288

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Asp Asn Leu Pro Tyr
                85                  90                  95

Thr Phe Gly Gly Gly Thr Lys Val Glu Ile Lys
            100                 105

<210> SEQ ID NO 289
<211> LENGTH: 120
<212> TYPE: PRT
<213> ORGANISM: Artificial sequence
<220> FEATURE:
<223> OTHER INFORMATION: Heavy Chain Variable Region

<400> SEQUENCE: 289

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30
```

Tyr Met His Trp Val Arg Gln Ala Pro Gly Gln Gly Leu Glu Trp Met
            35                  40                  45

Gly Trp Ile Asn Pro Asn Ser Gly Gly Thr Ser Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Thr Tyr Ala Tyr Ser Tyr Gly Met Asp Val Trp Gly Gln
                100                 105                 110

Gly Thr Thr Val Thr Val Ser Ser
            115                 120

<210> SEQ ID NO 290
<211> LENGTH: 112
<212> TYPE: PRT
<213> ORGANISM: Artificial sequence
<220> FEATURE:
<223> OTHER INFORMATION: Light Chain Variable Region

<400> SEQUENCE: 290

Asp Ile Val Met Thr Gln Ser Pro Leu Ser Leu Pro Val Thr Pro Gly
 1               5                  10                  15

Glu Pro Ala Ser Ile Ser Cys Arg Ser Gln Ser Leu Leu Tyr Ser
            20                  25                  30

Asn Gly Tyr Asn Tyr Leu Asp Trp Tyr Leu Gln Lys Pro Gly Gln Ser
            35                  40                  45

Pro Gln Val Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Arg Ser Pro Ile Thr Phe Gly Gly Gly Thr Lys Val Glu Ile Lys
                100                 105                 110

<210> SEQ ID NO 291
<211> LENGTH: 119
<212> TYPE: PRT
<213> ORGANISM: Artificial sequence
<220> FEATURE:
<223> OTHER INFORMATION: Heavy Chain Variable Region

<400> SEQUENCE: 291

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
            35                  40                  45

Gly Ser Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Asp Thr Ser Gly Gly Ala Tyr Phe Asp Leu Trp Gly Arg Gly
                100                 105                 110

```
Thr Leu Val Thr Val Ser Ser
        115

<210> SEQ ID NO 292
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 292

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Ser Tyr Tyr Pro Ile
                85                  90                  95

Thr Phe Gly Gly Gly Thr Lys Val Glu Ile Lys
            100                 105

<210> SEQ ID NO 293
<211> LENGTH: 118
<212> TYPE: PRT
<213> ORGANISM: Artificial sequence
<220> FEATURE:
<223> OTHER INFORMATION: Heavy Chain Variable Region

<400> SEQUENCE: 293

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Ser Tyr Ala Gln Lys Phe
 50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Gly Val Gly Phe Asp Tyr Trp Gly Gln Gly Thr
            100                 105                 110

Leu Val Thr Val Ser Ser
        115

<210> SEQ ID NO 294
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 294
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser His Pro Phe
                85                  90                  95

Thr Phe Gly Gly Gly Thr Lys Val Glu Ile Lys
            100                 105
```

<210> SEQ ID NO 295
<211> LENGTH: 122
<212> TYPE: PRT
<213> ORGANISM: Artificial sequence
<220> FEATURE:
<223> OTHER INFORMATION: Heavy Chain Variable Region

<400> SEQUENCE: 295

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Asn
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Val Gly Ala Pro Pro Ser Tyr Pro Phe Asp Ile Trp
            100                 105                 110

Gly Gln Gly Thr Met Val Thr Val Ser Ser
        115                 120
```

<210> SEQ ID NO 296
<211> LENGTH: 113
<212> TYPE: PRT
<213> ORGANISM: Artificial sequence
<220> FEATURE:
<223> OTHER INFORMATION: Light Chain Variable Region

<400> SEQUENCE: 296

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Val Tyr Tyr Cys Gln Gln
                85                  90                  95

Leu Phe Ser Thr Pro Phe Thr Phe Gly Gly Thr Lys Val Glu Ile
            100                 105                 110

Lys

<210> SEQ ID NO 297
<211> LENGTH: 123
<212> TYPE: PRT
<213> ORGANISM: Artificial sequence
<220> FEATURE:
<223> OTHER INFORMATION: Heavy Chain Variable Region

<400> SEQUENCE: 297

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Ser Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Asn Tyr Tyr Asp Ser Ser Gly Tyr Ser Gly Leu Asp Leu
            100                 105                 110

Trp Gly Arg Gly Thr Leu Val Thr Val Ser Ser
        115                 120

<210> SEQ ID NO 298
<211> LENGTH: 113
<212> TYPE: PRT
<213> ORGANISM: Artificial sequence
<220> FEATURE:
<223> OTHER INFORMATION: Light Chain Variable Region

<400> SEQUENCE: 298

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asp Asp Pro Tyr Thr Phe Gly Gly Thr Lys Val Glu Ile
            100                 105                 110

Lys

<210> SEQ ID NO 299
<211> LENGTH: 125
```

<212> TYPE: PRT
<213> ORGANISM: Artificial sequence
<220> FEATURE:
<223> OTHER INFORMATION: Heavy Chain Variable Region

<400> SEQUENCE: 299

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Pro Leu Leu Tyr Gly Asp Tyr His Val Arg Tyr Gly Met
            100                 105                 110

Asp Val Trp Gly Gln Gly Thr Thr Val Thr Val Ser Ser
        115                 120                 125

<210> SEQ ID NO 300
<211> LENGTH: 112
<212> TYPE: PRT
<213> ORGANISM: Artificial sequence
<220> FEATURE:
<223> OTHER INFORMATION: Light Chain Variable Region

<400> SEQUENCE: 300

Glu Ile Val Leu Thr Gln Ser Pro Ala Thr Leu Ser Leu Ser Pro Gly
1               5                   10                  15

Glu Arg Ala Thr Leu Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Leu Gln Thr Pro Ile Thr Phe Gly Gly Gly Thr Lys Val Glu Ile Lys
            100                 105                 110

<210> SEQ ID NO 301
<211> LENGTH: 120
<212> TYPE: PRT
<213> ORGANISM: Artificial sequence
<220> FEATURE:
<223> OTHER INFORMATION: Heavy Chain Variable Region

<400> SEQUENCE: 301

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met

```
                    35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ala Lys Pro Arg Gly Asp Tyr Gly Met Asp Val Trp Gly Gln
            100                 105                 110

Gly Thr Thr Val Thr Val Ser Ser
        115                 120

<210> SEQ ID NO 302
<211> LENGTH: 112
<212> TYPE: PRT
<213> ORGANISM: Artificial sequence
<220> FEATURE:
<223> OTHER INFORMATION: Light Chain Variable Region

<400> SEQUENCE: 302

Asp Ile Val Met Thr Gln Ser Pro Leu Ser Leu Pro Val Thr Pro Gly
  1               5                  10                  15

Glu Pro Ala Ser Ile Ser Cys Arg Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Ile Gly Val Pro Pro Thr Phe Gly Gly Gly Thr Lys Val Glu Ile Lys
            100                 105                 110

<210> SEQ ID NO 303
<211> LENGTH: 122
<212> TYPE: PRT
<213> ORGANISM: Artificial sequence
<220> FEATURE:
<223> OTHER INFORMATION: Heavy Chain Variable Region

<400> SEQUENCE: 303

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Gly Gly Gly Tyr Ala Tyr Glu Tyr Phe Gln His Trp
            100                 105                 110
```

-continued

Gly Gln Gly Thr Leu Val Thr Val Ser Ser
        115                 120

<210> SEQ ID NO 304
<211> LENGTH: 113
<212> TYPE: PRT
<213> ORGANISM: Artificial sequence
<220> FEATURE:
<223> OTHER INFORMATION: Light Chain Variable Region

<400> SEQUENCE: 304

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Leu Ser Pro Phe Thr Phe Gly Gly Gly Thr Lys Val Glu Ile
            100                 105                 110

Lys

<210> SEQ ID NO 305
<211> LENGTH: 123
<212> TYPE: PRT
<213> ORGANISM: Artificial sequence
<220> FEATURE:
<223> OTHER INFORMATION: Heavy Chain Variable Region

<400> SEQUENCE: 305

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Arg Glu Tyr Gly Gly His Tyr Tyr Gly Met Asp Val
            100                 105                 110

Trp Gly Gln Gly Thr Thr Val Thr Val Ser Ser
        115                 120

<210> SEQ ID NO 306
<211> LENGTH: 112
<212> TYPE: PRT
<213> ORGANISM: Artificial sequence
<220> FEATURE:
<223> OTHER INFORMATION: Light Chain Variable Region

<400> SEQUENCE: 306

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Thr
                85                  90                  95

Leu Arg Ile Pro Pro Thr Phe Gly Gly Gly Thr Lys Val Glu Ile Lys
            100                 105                 110

<210> SEQ ID NO 307
<211> LENGTH: 120
<212> TYPE: PRT
<213> ORGANISM: Artificial sequence
<220> FEATURE:
<223> OTHER INFORMATION: Heavy Chain Variable Region

<400> SEQUENCE: 307

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Asn
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65              70                  75                  80

Met Glu Leu Arg Ser Leu Arg Ser Asp Asp Thr Ala Val Tyr Tyr Cys
                85                  90                  95

Ala Arg Val Gly Asn Met Asp Gln Glu Tyr Phe Asp Leu Trp Gly Arg
            100                 105                 110

Gly Thr Leu Val Thr Val Ser Ser
        115                 120

<210> SEQ ID NO 308
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 308

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Gly Asn Ser Tyr Pro Ile
                    85                  90                  95

Thr Phe Gly Gly Gly Thr Lys Val Glu Ile Lys
                100                 105
```

<210> SEQ ID NO 309
<211> LENGTH: 121
<212> TYPE: PRT
<213> ORGANISM: Artificial sequence
<220> FEATURE:
<223> OTHER INFORMATION: Heavy Chain Variable Region

<400> SEQUENCE: 309

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
                20                  25                  30

Tyr Met Ser Trp Val Arg Gln Ala Pro Gly Lys Gly Leu Glu Trp Val
            35                  40                  45

Ser Val Ile Tyr Ser Asp Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Pro Thr Arg Tyr Gly Tyr Asp Arg Leu Gly Met Asp Val Trp Gly
                100                 105                 110

Gln Gly Thr Thr Val Thr Val Ser Ser
            115                 120
```

<210> SEQ ID NO 310
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 310

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Pro Tyr Pro Leu
                85                  90                  95

Thr Phe Gly Gly Gly Thr Lys Val Glu Ile Lys
                100                 105
```

<210> SEQ ID NO 311
<211> LENGTH: 119
<212> TYPE: PRT
<213> ORGANISM: Artificial sequence
<220> FEATURE:

<223> OTHER INFORMATION: Heavy Chain Variable Region

<400> SEQUENCE: 311

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ala Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Thr Thr Tyr Arg Asp Tyr Tyr Met Asp Val Trp Gly Lys Gly
            100                 105                 110
Thr Thr Val Thr Val Ser Ser
            115
```

<210> SEQ ID NO 312
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 312

```
Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Leu Asn Ile His Pro Trp
                85                  90                  95
Thr Phe Gly Gly Gly Thr Lys Val Glu Ile Lys
            100                 105
```

<210> SEQ ID NO 313
<211> LENGTH: 122
<212> TYPE: PRT
<213> ORGANISM: Artificial sequence
<220> FEATURE:
<223> OTHER INFORMATION: Heavy Chain Variable Region

<400> SEQUENCE: 313

```
Gln Val Gln Leu Gln Glu Ser Gly Pro Gly Leu Val Lys Pro Ser Glu
1               5                   10                  15
Thr Leu Ser Leu Thr Cys Ala Val Ser Gly Tyr Ser Ile Ser Ser Gly
            20                  25                  30
Tyr Tyr Trp Ala Trp Ile Arg Gln Pro Pro Gly Lys Gly Leu Glu Trp
        35                  40                  45
Ile Gly Ser Ile Tyr His Ser Gly Ser Thr Tyr Tyr Asn Pro Ser Leu
```

```
                    50                  55                  60
Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                     85                  90                  95

Ala Arg Asp Arg Ser Arg Gly Tyr Pro Val Tyr Gly Met Asp Val Trp
                100                 105                 110

Gly Gln Gly Thr Thr Val Thr Val Ser Ser
            115                 120

<210> SEQ ID NO 314
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 314

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Asn Ser Phe Pro Trp
                 85                  90                  95

Thr Phe Gly Gly Gly Thr Lys Val Glu Ile Lys
                100                 105

<210> SEQ ID NO 315
<211> LENGTH: 125
<212> TYPE: PRT
<213> ORGANISM: Artificial sequence
<220> FEATURE:
<223> OTHER INFORMATION: Heavy Chain Variable Region

<400> SEQUENCE: 315

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Leu
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Gly Gly Asp Tyr Ser Gly Tyr Asp Tyr Ala Ser Gly Met
                100                 105                 110

Asp Val Trp Gly Gln Gly Thr Thr Val Thr Val Ser Ser
            115                 120                 125
```

```
<210> SEQ ID NO 316
<211> LENGTH: 111
<212> TYPE: PRT
<213> ORGANISM: Artificial sequence
<220> FEATURE:
<223> OTHER INFORMATION: Light Chain Variable Region

<400> SEQUENCE: 316

Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gly Leu Pro Thr Phe Gly Gly Thr Lys Val Glu Ile Lys
            100                 105                 110

<210> SEQ ID NO 317
<211> LENGTH: 122
<212> TYPE: PRT
<213> ORGANISM: Artificial sequence
<220> FEATURE:
<223> OTHER INFORMATION: Heavy Chain Variable Region

<400> SEQUENCE: 317

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Ser Ala Gly Arg Gln Glu His Gly Met Asp Val Trp
            100                 105                 110

Gly Gln Gly Thr Thr Val Thr Val Ser Ser
        115                 120

<210> SEQ ID NO 318
<211> LENGTH: 113
<212> TYPE: PRT
<213> ORGANISM: Artificial sequence
<220> FEATURE:
<223> OTHER INFORMATION: Light Chain Variable Region

<400> SEQUENCE: 318

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
```

```
                20                  25                  30
Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ala Val Ser Asp Pro Pro Thr Phe Gly Gly Gly Thr Lys Val Glu Ile
            100                 105                 110

Lys
```

<210> SEQ ID NO 319
<211> LENGTH: 121
<212> TYPE: PRT
<213> ORGANISM: Artificial sequence
<220> FEATURE:
<223> OTHER INFORMATION: Heavy Chain Variable Region

<400> SEQUENCE: 319

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Asp Leu Gly Ser Ser His Trp His Phe Asp Leu Trp Gly
            100                 105                 110

Arg Gly Thr Leu Val Thr Val Ser Ser
        115                 120
```

<210> SEQ ID NO 320
<211> LENGTH: 108
<212> TYPE: PRT
<213> ORGANISM: Artificial sequence
<220> FEATURE:
<223> OTHER INFORMATION: Light Chain Variable Region

<400> SEQUENCE: 320

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Gly Asn Phe Pro
```

```
                85                  90                  95
Leu Thr Phe Gly Gly Gly Thr Lys Val Glu Ile Lys
            100                 105

<210> SEQ ID NO 321
<211> LENGTH: 129
<212> TYPE: PRT
<213> ORGANISM: Artificial sequence
<220> FEATURE:
<223> OTHER INFORMATION: Heavy Chain Variable Region

<400> SEQUENCE: 321

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Pro Arg Asp Tyr Ser Gly Ser Ser Gly Gly Gly
            100                 105                 110

Trp Gly Tyr Phe Asp Leu Trp Gly Arg Gly Thr Leu Val Thr Val Ser
        115                 120                 125

Ser

<210> SEQ ID NO 322
<211> LENGTH: 112
<212> TYPE: PRT
<213> ORGANISM: Artificial sequence
<220> FEATURE:
<223> OTHER INFORMATION: Light Chain Variable Region

<400> SEQUENCE: 322

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Phe Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gly Ser Pro Ile Thr Phe Gly Gly Gly Thr Lys Val Glu Ile Lys
            100                 105                 110

<210> SEQ ID NO 323
<211> LENGTH: 123
<212> TYPE: PRT
<213> ORGANISM: Artificial sequence
<220> FEATURE:
<223> OTHER INFORMATION: Heavy Chain Variable Region
```

```
<400> SEQUENCE: 323

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Tyr Gly Ser Ser Gly Tyr Gly Tyr Phe Asp Leu
            100                 105                 110

Trp Gly Arg Gly Thr Leu Val Thr Val Ser Ser
        115                 120

<210> SEQ ID NO 324
<211> LENGTH: 108
<212> TYPE: PRT
<213> ORGANISM: Artificial sequence
<220> FEATURE:
<223> OTHER INFORMATION: Light Chain Variable Region

<400> SEQUENCE: 324

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Leu Ser Ser Pro
                85                  90                  95

Trp Thr Phe Gly Gly Gly Thr Lys Val Glu Asn Gln
            100                 105

<210> SEQ ID NO 325
<211> LENGTH: 121
<212> TYPE: PRT
<213> ORGANISM: Artificial sequence
<220> FEATURE:
<223> OTHER INFORMATION: Heavy Chain Variable Region

<400> SEQUENCE: 325

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Val Tyr Asn Pro Ser
50                  55                  60
```

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Pro Gly Tyr Pro Ser Tyr Phe Asp Pro Trp Gly
            100                 105                 110

Gln Gly Thr Leu Val Thr Val Ser Ser
            115                 120

<210> SEQ ID NO 326
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 326

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Val Ser His Pro Phe
                85                  90                  95

Thr Phe Gly Gly Gly Thr Lys Val Glu Ile Lys
            100                 105

<210> SEQ ID NO 327
<211> LENGTH: 121
<212> TYPE: PRT
<213> ORGANISM: Artificial sequence
<220> FEATURE:
<223> OTHER INFORMATION: Heavy Chain Variable Region

<400> SEQUENCE: 327

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Gly Gly Gly Ser Thr Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Leu Tyr Ser Ser Gly Trp Tyr Ile Asp Val Trp Gly
            100                 105                 110

Gln Gly Thr Leu Val Thr Val Ser Ser
            115                 120

```
<210> SEQ ID NO 328
<211> LENGTH: 113
<212> TYPE: PRT
<213> ORGANISM: Artificial sequence
<220> FEATURE:
<223> OTHER INFORMATION: Light Chain Variable Region

<400> SEQUENCE: 328

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Asp Phe Leu Thr Pro Ile Thr Phe Gly Gly Gly Thr Lys Val Glu Ile
            100                 105                 110

Lys

<210> SEQ ID NO 329
<211> LENGTH: 118
<212> TYPE: PRT
<213> ORGANISM: Artificial sequence
<220> FEATURE:
<223> OTHER INFORMATION: Heavy Chain Variable Region

<400> SEQUENCE: 329

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Ser Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Asp Ser Ser Ser Gly Gly Leu Asp Leu Trp Gly Arg Gly Thr
            100                 105                 110

Leu Val Thr Val Ser Ser
        115

<210> SEQ ID NO 330
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 330

Asp Ile Gln Met Thr Gln Ser Pro Ser Ser Leu Ser Ala Ser Val Gly
1               5                   10                  15
```

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
         35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Phe Ala Phe Leu Pro Leu
                 85                  90                  95

Thr Phe Gly Gly Gly Thr Lys Val Glu Asn Gln
                100                 105

<210> SEQ ID NO 331
<211> LENGTH: 117
<212> TYPE: PRT
<213> ORGANISM: Artificial sequence
<220> FEATURE:
<223> OTHER INFORMATION: Heavy Chain Variable Region

<400> SEQUENCE: 331

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
         35                  40                  45

Ser Val Ile Tyr Ser Gly Gly Ser Thr Tyr Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Gln Tyr Thr Gly Ser Leu Asp Val Trp Gly Gln Gly Thr Met
                100                 105                 110

Val Thr Val Ser Ser
        115

<210> SEQ ID NO 332
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 332

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Asp Asn Thr Phe Pro Tyr
                 85                  90                  95

```
Thr Phe Gly Gly Gly Thr Lys Val Glu Ile Lys
            100                 105
```

<210> SEQ ID NO 333
<211> LENGTH: 120
<212> TYPE: PRT
<213> ORGANISM: Artificial sequence
<220> FEATURE:
<223> OTHER INFORMATION: Heavy Chain Variable Region

<400> SEQUENCE: 333

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Lys Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Tyr Tyr Thr Pro Tyr Gly Met Asp Val Trp Gly Gln
            100                 105                 110

Gly Thr Thr Val Thr Val Ser Ser
        115                 120
```

<210> SEQ ID NO 334
<211> LENGTH: 112
<212> TYPE: PRT
<213> ORGANISM: Artificial sequence
<220> FEATURE:
<223> OTHER INFORMATION: Light Chain Variable Region

<400> SEQUENCE: 334

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Val Pro Leu Thr Phe Gly Gly Gly Thr Lys Val Glu Ile Lys
            100                 105                 110
```

<210> SEQ ID NO 335
<211> LENGTH: 121
<212> TYPE: PRT
<213> ORGANISM: Artificial sequence
<220> FEATURE:
<223> OTHER INFORMATION: Heavy Chain Variable Region

<400> SEQUENCE: 335

-continued

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Arg Pro Gln Ser Glu Ser Tyr Leu Leu Asp Tyr Trp Gly
        100                 105                 110

Gln Gly Thr Leu Val Thr Val Ser Ser
            115                 120

<210> SEQ ID NO 336
<211> LENGTH: 106
<212> TYPE: PRT
<213> ORGANISM: Artificial sequence
<220> FEATURE:
<223> OTHER INFORMATION: Light Chain Variable Region

<400> SEQUENCE: 336

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe Ser His Arg Thr
            85                  90                  95

Phe Gly Gly Gly Thr Lys Val Glu Ile Lys
        100                 105

<210> SEQ ID NO 337
<211> LENGTH: 120
<212> TYPE: PRT
<213> ORGANISM: Artificial sequence
<220> FEATURE:
<223> OTHER INFORMATION: Heavy Chain Variable Region

<400> SEQUENCE: 337

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

-continued

Met Glu Leu Ser Ser Leu Arg Ser Glu Asp Thr Ala Val Tyr Tyr Cys
                85                  90                  95

Ala Arg Glu Gly Pro Glu Gln Leu Trp Tyr Leu Asp Tyr Trp Gly Gln
            100                 105                 110

Gly Thr Leu Val Thr Val Ser Ser
        115                 120

<210> SEQ ID NO 338
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 338

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg His Thr Tyr Pro Leu
                85                  90                  95

Thr Phe Gly Gly Gly Thr Lys Val Glu Ile Lys
            100                 105

<210> SEQ ID NO 339
<211> LENGTH: 123
<212> TYPE: PRT
<213> ORGANISM: Artificial sequence
<220> FEATURE:
<223> OTHER INFORMATION: Heavy Chain Variable Region

<400> SEQUENCE: 339

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Trp Gly Ala Ser Gly Tyr Tyr Tyr Met Asp Val
            100                 105                 110

Trp Gly Gln Gly Thr Met Val Thr Val Ser Ser
        115                 120

<210> SEQ ID NO 340
<211> LENGTH: 107
<212> TYPE: PRT

```
<213> ORGANISM: Artificial sequence
<220> FEATURE:
<223> OTHER INFORMATION: Light Chain Variable Region

<400> SEQUENCE: 340

Asp Ile Gln Met Thr Gln Ser Pro Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Val Ser Tyr Pro Ile
                85                  90                  95

Thr Phe Gly Gly Gly Thr Lys Val Glu Ile Lys
            100                 105

<210> SEQ ID NO 341
<211> LENGTH: 120
<212> TYPE: PRT
<213> ORGANISM: Artificial sequence
<220> FEATURE:
<223> OTHER INFORMATION: Heavy Chain Variable Region

<400> SEQUENCE: 341

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Gly Thr Asp Phe Gly Thr Ile Ser Tyr Trp Gly Gln
            100                 105                 110

Gly Thr Leu Val Thr Val Ser Ser
        115                 120

<210> SEQ ID NO 342
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 342

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asp Phe Pro Leu
                85                  90                  95

Thr Phe Gly Gly Gly Thr Lys Val Glu Ile Lys
                100                 105

<210> SEQ ID NO 343
<211> LENGTH: 122
<212> TYPE: PRT
<213> ORGANISM: Artificial sequence
<220> FEATURE:
<223> OTHER INFORMATION: Heavy Chain Variable Region

<400> SEQUENCE: 343

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Ala Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Ser Asn Tyr Gly Asp Tyr Gly Arg Phe Asp Tyr Trp
                100                 105                 110

Gly Gln Gly Thr Leu Val Thr Val Ser Ser
            115                 120

<210> SEQ ID NO 344
<211> LENGTH: 108
<212> TYPE: PRT
<213> ORGANISM: Artificial sequence
<220> FEATURE:
<223> OTHER INFORMATION: Light Chain Variable Region

<400> SEQUENCE: 344

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asp Glu His Pro Pro
                85                  90                  95

Trp Thr Phe Gly Gly Gly Thr Lys Val Glu Ile Lys
                100                 105
```

```
<210> SEQ ID NO 345
<211> LENGTH: 123
<212> TYPE: PRT
<213> ORGANISM: Artificial sequence
<220> FEATURE:
<223> OTHER INFORMATION: Heavy Chain Variable Region

<400> SEQUENCE: 345

Gln Val Gln Leu Val Gln Ser Gly Ala Glu Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Ser Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Thr Gly Glu Tyr Ser Tyr Ser Pro His Gly Met Asp Val
            100                 105                 110

Trp Gly Gln Gly Thr Thr Val Thr Val Ser Ser
        115                 120

<210> SEQ ID NO 346
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 346

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asp Asn Phe Pro Tyr
                85                  90                  95

Thr Phe Gly Gly Gly Thr Lys Val Glu Ile Lys
            100                 105

<210> SEQ ID NO 347
<211> LENGTH: 121
<212> TYPE: PRT
<213> ORGANISM: Artificial sequence
<220> FEATURE:
<223> OTHER INFORMATION: Heavy Chain Variable Region

<400> SEQUENCE: 347

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30
```

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Gly Gln Tyr Pro Ile Tyr Gly Met Asp Val Trp Gly
            100                 105                 110

Gln Gly Thr Thr Val Thr Val Ser Ser
        115                 120

<210> SEQ ID NO 348
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 348

Glu Ile Val Met Thr Gln Ser Pro Ala Thr Leu Ser Val Ser Pro Gly
1               5                   10                  15

Glu Arg Ala Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ser Phe Pro Ile
                85                  90                  95

Thr Phe Gly Gly Gly Thr Lys Val Glu Ile Lys
            100                 105

<210> SEQ ID NO 349
<211> LENGTH: 121
<212> TYPE: PRT
<213> ORGANISM: Artificial sequence
<220> FEATURE:
<223> OTHER INFORMATION: Heavy Chain Variable Region

<400> SEQUENCE: 349

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Pro Gly His Tyr Tyr Val Ala Gly Met Asp Val Trp Gly

```
                100             105             110
Gln Gly Thr Thr Val Thr Val Ser Ser
            115                 120

<210> SEQ ID NO 350
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 350

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Phe Asp Phe Pro Ile
                85                  90                  95

Thr Phe Gly Gly Gly Thr Lys Val Glu Ile Lys
            100                 105

<210> SEQ ID NO 351
<211> LENGTH: 121
<212> TYPE: PRT
<213> ORGANISM: Artificial sequence
<220> FEATURE:
<223> OTHER INFORMATION: Heavy Chain Variable Region

<400> SEQUENCE: 351

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Ala Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ala Pro Gly Tyr Pro Met Leu Gly Met Asp Val Trp Gly
            100                 105                 110

Gln Gly Thr Thr Val Ser Val Ser Ser
            115                 120

<210> SEQ ID NO 352
<211> LENGTH: 106
<212> TYPE: PRT
<213> ORGANISM: Artificial sequence
<220> FEATURE:
<223> OTHER INFORMATION: Light Chain Variable Region

<400> SEQUENCE: 352
```

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu Tyr Gly Ser Tyr Arg Thr
                85                  90                  95

Phe Gly Gly Gly Thr Lys Val Glu Ile Lys
            100                 105

<210> SEQ ID NO 353
<211> LENGTH: 126
<212> TYPE: PRT
<213> ORGANISM: Artificial sequence
<220> FEATURE:
<223> OTHER INFORMATION: Heavy Chain Variable Region

<400> SEQUENCE: 353

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Asp Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Gly Ser Ser Phe Trp Ser Gly Ser Ala Val Ser Tyr Tyr Gly
            100                 105                 110

Met Asp Val Trp Gly Gln Gly Thr Thr Val Thr Val Ser Ser
        115                 120                 125

<210> SEQ ID NO 354
<211> LENGTH: 105
<212> TYPE: PRT
<213> ORGANISM: Artificial sequence
<220> FEATURE:
<223> OTHER INFORMATION: Light Chain Variable Region

<400> SEQUENCE: 354

Val Leu Thr Gln Ser Pro Gly Thr Leu Ser Leu Ser Pro Gly Glu Arg
1               5                   10                  15

Ala Thr Leu Ser Cys Arg Ala Ser Gln Ser Val Ser Ser Ser Phe Leu
            20                  25                  30

Ala Trp Tyr Gln Gln Lys Pro Gly Gln Ala Pro Arg Leu Leu Ile Tyr
        35                  40                  45

Gly Ala Ser Ser Arg Ala Thr Gly Ile Pro Asp Arg Phe Ser Gly Ser
50                  55                  60

Gly Ser Gly Thr Asp Phe Thr Leu Thr Ile Ser Arg Leu Glu Pro Glu
```

```
                65                  70                  75                  80
Asp Phe Ala Val Tyr Tyr Cys Gln Gln Val Val Ser Val Pro Thr Phe
                    85                  90                  95

Gly Gly Gly Thr Lys Val Glu Ile Lys
            100                 105

<210> SEQ ID NO 355
<211> LENGTH: 122
<212> TYPE: PRT
<213> ORGANISM: Artificial sequence
<220> FEATURE:
<223> OTHER INFORMATION: Heavy Chain Variable Region

<400> SEQUENCE: 355

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Ala Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Leu Ser Arg Gly Tyr Ala Val Ser Gly Met Asp Val Trp
            100                 105                 110

Gly Gln Gly Thr Thr Val Thr Val Ser Ser
        115                 120

<210> SEQ ID NO 356
<211> LENGTH: 108
<212> TYPE: PRT
<213> ORGANISM: Artificial sequence
<220> FEATURE:
<223> OTHER INFORMATION: Light Chain Variable Region

<400> SEQUENCE: 356

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Tyr Ser Ser Pro
                85                  90                  95

Tyr Thr Phe Gly Gly Gly Thr Lys Val Glu Ile Lys
            100                 105

<210> SEQ ID NO 357
<211> LENGTH: 117
<212> TYPE: PRT
<213> ORGANISM: Artificial sequence
<220> FEATURE:
```

<223> OTHER INFORMATION: Heavy Chain Variable Region

<400> SEQUENCE: 357

```
Glu Val Gln Leu Leu Glu Ser Gly Gly Gly Leu Val Gln Pro Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ser Pro Trp Glu Leu Asp Val Trp Gly Gln Gly Thr Met
            100                 105                 110

Val Thr Val Ser Ser
            115
```

<210> SEQ ID NO 358
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 358

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ala Asp Tyr Phe Pro Ile
                85                  90                  95

Thr Phe Gly Gly Gly Thr Lys Val Glu Ile Lys
            100                 105
```

<210> SEQ ID NO 359
<211> LENGTH: 130
<212> TYPE: PRT
<213> ORGANISM: Artificial sequence
<220> FEATURE:
<223> OTHER INFORMATION: Heavy Chain Variable Region

<400> SEQUENCE: 359

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Ala Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
```

```
                    50                  55                  60
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Leu Gly His Tyr Asp Tyr Trp Ser Gly Ser Arg Asp
            100                 105                 110

Tyr Tyr Tyr Gly Met Asp Val Trp Gly Gln Gly Thr Thr Val Thr Val
        115                 120                 125

Ser Ser
130

<210> SEQ ID NO 360
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 360

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Asp Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Ser Asn Phe Pro Ile
                 85                  90                  95

Thr Phe Gly Gly Gly Thr Lys Val Glu Ile Lys
            100                 105

<210> SEQ ID NO 361
<211> LENGTH: 125
<212> TYPE: PRT
<213> ORGANISM: Artificial sequence
<220> FEATURE:
<223> OTHER INFORMATION: Heavy Chain Variable Region

<400> SEQUENCE: 361

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Thr Ile Ala Ala Gly Trp Pro Pro Glu Tyr Phe
            100                 105                 110
```

```
Gln His Trp Gly Gln Gly Thr Leu Val Thr Val Ser Ser
        115                 120                 125

<210> SEQ ID NO 362
<211> LENGTH: 107
<212> TYPE: PRT
<213> ORGANISM: Artificial sequence
<220> FEATURE:
<223> OTHER INFORMATION: Light Chain Variable Region

<400> SEQUENCE: 362

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Phe His Pro Pro Leu
                85                  90                  95

Thr Phe Gly Gly Gly Thr Lys Val Glu Ile Lys
            100                 105

<210> SEQ ID NO 363
<211> LENGTH: 127
<212> TYPE: PRT
<213> ORGANISM: Artificial sequence
<220> FEATURE:
<223> OTHER INFORMATION: Heavy Chain Variable Region

<400> SEQUENCE: 363

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Pro Thr Gly Tyr Lys Asp Lys Trp Arg Tyr Tyr Tyr
            100                 105                 110

Gly Met Asp Val Trp Gly Gln Gly Thr Thr Val Thr Val Ser Ser
        115                 120                 125

<210> SEQ ID NO 364
<211> LENGTH: 113
<212> TYPE: PRT
<213> ORGANISM: Artificial sequence
<220> FEATURE:
<223> OTHER INFORMATION: Light Chain Variable Region

<400> SEQUENCE: 364

Asp Ile Val Met Thr Gln Ser Pro Asp Ser Leu Ala Val Ser Leu Gly
```

```
              1               5                  10                  15
            Glu Arg Ala Thr Ile Asn Cys Lys Ser Ser Gln Ser Val Leu Phe Ser
                            20                  25                  30

Ser Asn Asn Lys Asn Tyr Leu Ala Trp Tyr Gln Gln Lys Pro Gly Gln
                        35                  40                  45

Pro Pro Lys Leu Leu Ile Tyr Trp Ala Ser Thr Arg Glu Ser Gly Val
                    50                  55                  60

Pro Asp Arg Phe Ser Gly Ser Gly Ser Gly Thr Asp Phe Thr Leu Thr
            65                  70                  75                  80

Ile Ser Ser Leu Gln Ala Glu Asp Val Ala Val Tyr Tyr Cys Gln Gln
                            85                  90                  95

Phe Leu His Thr Pro Arg Thr Phe Gly Gly Gly Thr Lys Val Glu Ile
                            100                 105                 110

Lys

<210> SEQ ID NO 365
<211> LENGTH: 124
<212> TYPE: PRT
<213> ORGANISM: Artificial sequence
<220> FEATURE:
<223> OTHER INFORMATION: Heavy Chain Variable Region

<400> SEQUENCE: 365

Gln Val Gln Leu Val Gln Ser Gly Ala Glu Val Lys Lys Pro Gly Ser
            1               5                   10                  15

Ser Val Lys Val Ser Cys Lys Ala Ser Gly Gly Thr Phe Ser Ser Tyr
                            20                  25                  30

Ala Ile Ser Trp Val Arg Gln Ala Pro Gly Gln Gly Leu Glu Trp Met
                        35                  40                  45

Gly Gly Ile Ile Pro Ile Phe Gly Thr Ala Asn Tyr Ala Gln Lys Phe
                    50                  55                  60

Gln Gly Arg Val Thr Ile Thr Ala Asp Glu Ser Thr Ser Thr Ala Tyr
            65                  70                  75                  80

Met Glu Leu Ser Ser Leu Arg Ser Glu Asp Thr Ala Val Tyr Tyr Cys
                            85                  90                  95

Ala Arg Glu Gly Gly His Ala Ser Tyr His Tyr Tyr Gly Met Asp
                            100                 105                 110

Val Trp Gly Gln Gly Thr Thr Val Thr Val Ser Ser
                        115                 120

<210> SEQ ID NO 366
<211> LENGTH: 122
<212> TYPE: PRT
<213> ORGANISM: Artificial sequence
<220> FEATURE:
<223> OTHER INFORMATION: Heavy Chain Variable Region

<400> SEQUENCE: 366

Gln Val Gln Leu Val Glu Ser Gly Gly Gly Val Val Gln Pro Gly Arg
            1               5                   10                  15

Ser Leu Arg Leu Ser Cys Ala Ala Ser Gly Phe Thr Phe Gly Ser Phe
                            20                  25                  30

Gly Met Asn Trp Val Arg Gln Ala Pro Gly Lys Gly Leu Glu Trp Val
                        35                  40                  45

Ser Ala Ile Thr Ala Ser Gly Gly Ser Thr Tyr Ala Asp Ser Val
                    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Lys Asp Phe Thr Glu Val Val Gly Trp Leu Gly Met Asp Val Trp
                100                 105                 110

Gly Gln Gly Thr Thr Val Thr Val Ser Ser
                115                 120

<210> SEQ ID NO 367
<211> LENGTH: 122
<212> TYPE: PRT
<213> ORGANISM: Artificial sequence
<220> FEATURE:
<223> OTHER INFORMATION: Heavy Chain Variable Region

<400> SEQUENCE: 367

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
                20                  25                  30

Gly Met Asn Trp Val Arg Gln Ala Pro Gly Lys Gly Leu Glu Trp Val
            35                  40                  45

Ser Ala Ile Thr Ser Ser Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Lys Asp Phe Thr Glu Val Val Gly Trp Leu Gly Met Asp Val Trp
                100                 105                 110

Gly Gln Gly Thr Thr Val Thr Val Ser Ser
                115                 120

<210> SEQ ID NO 368
<211> LENGTH: 122
<212> TYPE: PRT
<213> ORGANISM: Artificial sequence
<220> FEATURE:
<223> OTHER INFORMATION: Heavy Chain Variable Region

<400> SEQUENCE: 368

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ala Tyr
                20                  25                  30

Gly Met Asn Trp Val Arg Gln Ala Pro Gly Lys Gly Leu Glu Trp Val
            35                  40                  45

Ser Ala Ile Arg Ala Ser Gly Gly Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Lys Asp Phe Thr Glu Val Val Gly Trp Leu Gly Met Asp Val Trp
                100                 105                 110

Gly Gln Gly Thr Thr Val Thr Val Ser Ser
                115                 120
```

```
<210> SEQ ID NO 369
<211> LENGTH: 122
<212> TYPE: PRT
<213> ORGANISM: Artificial sequence
<220> FEATURE:
<223> OTHER INFORMATION: Heavy Chain Variable Region

<400> SEQUENCE: 369

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ala Tyr
                20                  25                  30

Gly Met Asn Trp Val Arg Gln Ala Pro Gly Lys Gly Leu Glu Trp Val
            35                  40                  45

Ser Ala Ile Ser Ala Ser Gly Arg Ser Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Thr Glu Val Val Gly Trp Leu Gly Met Asp Val Trp
            100                 105                 110

Gly Gln Gly Thr Thr Val Thr Val Ser Ser
        115                 120

<210> SEQ ID NO 370
<211> LENGTH: 108
<212> TYPE: PRT
<213> ORGANISM: Artificial sequence
<220> FEATURE:
<223> OTHER INFORMATION: Light Chain Variable Region

<400> SEQUENCE: 370

Glu Val Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Ser Ser His Pro
                85                  90                  95

Phe Thr Phe Gly Gly Gly Thr Lys Val Glu Ile Lys
            100                 105

<210> SEQ ID NO 371
<211> LENGTH: 121
<212> TYPE: PRT
<213> ORGANISM: Artificial sequence
<220> FEATURE:
<223> OTHER INFORMATION: Heavy Chain Variable Region

<400> SEQUENCE: 371

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Arg Tyr
```

```
                 20                  25                  30
Gly Met His Trp Val Arg Gln Ala Pro Gly Lys Gly Leu Glu Trp Val
             35                  40                  45

Ser Ala Ile Ser Gly Leu Ala Gly Pro Thr Tyr Ala Asp Ser Val Lys
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Gln Thr Ala Ala Ala Ile Trp Gly Met Asp Val Trp Gly
             100                 105                 110

Gln Gly Thr Thr Val Thr Val Ser Ser
         115                 120

<210> SEQ ID NO 372
<211> LENGTH: 121
<212> TYPE: PRT
<213> ORGANISM: Artificial sequence
<220> FEATURE:
<223> OTHER INFORMATION: Heavy Chain Variable Region

<400> SEQUENCE: 372

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Leu Asp Tyr
                 20                  25                  30

Gly Met His Trp Val Arg Gln Ala Pro Gly Lys Gly Leu Glu Trp Val
             35                  40                  45

Ser Ala Ile Ser Ala Phe Ala Gly Ser Thr Tyr Ala Asp Ser Val Lys
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Gln Thr Ala Ala Ala Ile Trp Gly Met Asp Val Trp Gly
             100                 105                 110

Gln Gly Thr Thr Val Thr Val Ser Ser
         115                 120

<210> SEQ ID NO 373
<211> LENGTH: 122
<212> TYPE: PRT
<213> ORGANISM: Artificial sequence
<220> FEATURE:
<223> OTHER INFORMATION: Heavy Chain Variable Region

<400> SEQUENCE: 373

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Lys Thr Tyr
                 20                  25                  30

Gly Met His Trp Val Arg Gln Ala Pro Gly Lys Gly Leu Glu Trp Val
             35                  40                  45

Ala His Ile Trp Tyr Glu Gly Ser Asn Lys Val Tyr Ala Asp Ser Val
         50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Arg Asp Gln Thr Ala Ala Ala Ile Trp Gly Met Asp Val Trp
            100                 105                 110

Gly Gln Gly Thr Thr Val Thr Val Ser Ser
            115                 120

<210> SEQ ID NO 374
<211> LENGTH: 121
<212> TYPE: PRT
<213> ORGANISM: Artificial sequence
<220> FEATURE:
<223> OTHER INFORMATION: Heavy Chain Variable Region

<400> SEQUENCE: 374

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ser Ala Ile Ser Gly Leu Ala Gly Gln Thr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gln Thr Ala Ala Ala Ala Ile Trp Gly Met Asp Val Trp Gly
            100                 105                 110

Gln Gly Thr Thr Val Thr Val Ser Ser
        115                 120

<210> SEQ ID NO 375
<211> LENGTH: 121
<212> TYPE: PRT
<213> ORGANISM: Artificial sequence
<220> FEATURE:
<223> OTHER INFORMATION: Heavy Chain Variable Region

<400> SEQUENCE: 375

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala Arg Tyr
            20                  25                  30

Gly Met His Trp Val Arg Gln Ala Pro Gly Lys Gly Leu Glu Trp Val
        35                  40                  45

Ser Ala Ile Ser Gly Leu Ala Gly Pro Thr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gln Thr Ala Ala Trp Gly Ile Trp Gly Met Asp Val Trp Gly
            100                 105                 110

Gln Gly Thr Thr Val Thr Val Ser Ser
        115                 120

<210> SEQ ID NO 376
```

```
<211> LENGTH: 120
<212> TYPE: PRT
<213> ORGANISM: Artificial sequence
<220> FEATURE:
<223> OTHER INFORMATION: Heavy Chain Variable Region

<400> SEQUENCE: 376

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ala His
            20                  25                  30

Tyr Tyr Trp Gly Trp Ile Arg Gln Pro Pro Gly Lys Gly Leu Glu Trp
        35                  40                  45

Ile Gly Ser Ile Phe His Ser Gly His Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Ala Met Thr Pro Ala Gly Met Asp Val Trp Gly Gln
            100                 105                 110

Gly Thr Thr Val Thr Val Ser Ser
        115                 120

<210> SEQ ID NO 377
<211> LENGTH: 120
<212> TYPE: PRT
<213> ORGANISM: Artificial sequence
<220> FEATURE:
<223> OTHER INFORMATION: Heavy Chain Variable Region

<400> SEQUENCE: 377

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Pro His
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly His Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Ala Met Thr Pro Ala Gly Met Asp Val Trp Gly Gln
            100                 105                 110

Gly Thr Thr Val Thr Val Ser Ser
        115                 120

<210> SEQ ID NO 378
<211> LENGTH: 120
<212> TYPE: PRT
<213> ORGANISM: Artificial sequence
<220> FEATURE:
<223> OTHER INFORMATION: Heavy Chain Variable Region

<400> SEQUENCE: 378

Gln Val Gln Leu Gln Glu Ser Gly Pro Gly Leu Val Lys Pro Ser Glu
1               5                   10                  15
```

Thr Leu Ser Leu Thr Cys Ala Val Ser Gly Tyr Ser Ile Ser Ala His
            20                  25                  30

Tyr Tyr Trp Gly Trp Ile Arg Gln Pro Pro Gly Lys Gly Leu Glu Trp
            35                  40                  45

Ile Gly Ser Ile Phe His Ser Gly His Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Gly Ala Met Thr Pro Ala Gly Met Asp Val Trp Gly Gln
            100                 105                 110

Gly Thr Thr Val Thr Val Ser Ser
            115                 120

<210> SEQ ID NO 379
<211> LENGTH: 123
<212> TYPE: PRT
<213> ORGANISM: Artificial sequence
<220> FEATURE:
<223> OTHER INFORMATION: Heavy Chain Variable Region

<400> SEQUENCE: 379

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Ala Trp Val Arg Gln Ala Pro Gly Gln Arg Leu Glu Trp Met
            35                  40                  45

Gly Trp Ile Asn Pro Ala Val Gly Ala Thr Ile Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Gly Glu Tyr Ser Tyr Ser Pro His Gly Met Asp Val
            100                 105                 110

Trp Gly Gln Gly Thr Thr Val Thr Val Ser Ser
            115                 120

<210> SEQ ID NO 380
<211> LENGTH: 123
<212> TYPE: PRT
<213> ORGANISM: Artificial sequence
<220> FEATURE:
<223> OTHER INFORMATION: Heavy Chain Variable Region

<400> SEQUENCE: 380

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Val Trp Val Arg Gln Ala Pro Gly Gln Gly Leu Glu Trp Met
            35                  40                  45

Gly Ile Ile Asn Pro Ser Ser Gly Ala Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

```
Met Glu Leu Arg Ser Leu Arg Ser Asp Asp Thr Ala Val Tyr Tyr Cys
                85                  90                  95

Ala Arg Asp Thr Gly Glu Tyr Ser Tyr Ser Pro His Gly Met Asp Val
            100                 105                 110

Trp Gly Gln Gly Thr Thr Val Thr Val Ser Ser
        115                 120

<210> SEQ ID NO 381
<211> LENGTH: 123
<212> TYPE: PRT
<213> ORGANISM: Artificial sequence
<220> FEATURE:
<223> OTHER INFORMATION: Heavy Chain Variable Region

<400> SEQUENCE: 381

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Tyr Ile Ser Trp Val Arg Gln Ala Pro Gly Gln Gly Leu Glu Trp Met
        35                  40                  45

Gly Ile Ile Asn Pro Ser Ser Gly His Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Gly Glu Tyr Ser Tyr Ser Pro His Gly Met Asp Val
            100                 105                 110

Trp Gly Gln Gly Thr Thr Val Thr Val Ser Ser
        115                 120

<210> SEQ ID NO 382
<211> LENGTH: 123
<212> TYPE: PRT
<213> ORGANISM: Artificial sequence
<220> FEATURE:
<223> OTHER INFORMATION: Heavy Chain Variable Region

<400> SEQUENCE: 382

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Val Trp Val Arg Gln Ala Pro Gly Gln Gly Leu Glu Trp Met
        35                  40                  45

Gly Ile Ile Asn Pro Ser Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Tyr Ser Tyr Ser Pro His Gly Met Asp Val
            100                 105                 110

Trp Gly Gln Gly Thr Thr Val Thr Val Ser Ser
        115                 120
```

```
<210> SEQ ID NO 383
<211> LENGTH: 12
<212> TYPE: PRT
<213> ORGANISM: Artificial sequence
<220> FEATURE:
<223> OTHER INFORMATION: Light chain HVR sequence

<400> SEQUENCE: 383

Arg Ala Ser Gln Ser Val Ser Ser Tyr Leu Ala
1               5                   10

<210> SEQ ID NO 384
<211> LENGTH: 398
<212> TYPE: PRT
<213> ORGANISM: Homo sapiens

<400> SEQUENCE: 384

Met Pro Val Pro Ala Ser Trp Pro His Leu Pro Ser Pro Phe Leu Leu
1               5                   10                  15

Met Thr Leu Leu Leu Gly Arg Leu Thr Gly Val Ala Gly Glu Glu Glu
                20                  25                  30

Leu Gln Val Ile Gln Pro Asp Lys Ser Ile Ser Val Ala Ala Gly Glu
            35                  40                  45

Ser Ala Thr Leu His Cys Thr Val Thr Ser Leu Ile Pro Val Gly Pro
    50                  55                  60

Ile Gln Trp Phe Arg Gly Ala Gly Pro Gly Arg Glu Leu Ile Tyr Asn
65                  70                  75                  80

Gln Lys Glu Gly His Phe Pro Arg Val Thr Thr Val Ser Asp Leu Thr
                85                  90                  95

Lys Arg Asn Asn Met Asp Phe Ser Ile Arg Ile Ser Asn Ile Thr Pro
            100                 105                 110

Ala Asp Ala Gly Thr Tyr Tyr Cys Val Lys Phe Arg Lys Gly Ser Pro
        115                 120                 125

Asp His Val Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Ala Gly Asp Ser Val Ser Tyr Ser Ile
        195                 200                 205

His Ser Thr Ala Lys Val Val Leu Thr Arg Glu Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
            260                 265                 270

Gln Val Arg Lys Phe Tyr Pro Gln Arg Leu Gln Leu Thr Trp Leu Glu
        275                 280                 285

Asn Gly Asn Val Ser Arg Thr Glu Thr Ala Ser Thr Leu Thr Glu Asn
    290                 295                 300

Lys Asp Gly Thr Tyr Asn Trp Met Ser Trp Leu Leu Val Asn Val Ser
305                 310                 315                 320
```

```
Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
            340                 345                 350

Lys Glu Gln Gly Ser Asn Thr Ala Pro Gly Pro Ala Leu Ala Ser Ala
        355                 360                 365

Ala Pro Leu Leu Ile Ala Phe Leu Leu Gly Pro Lys Val Leu Leu Val
    370                 375                 380

Val Gly Val Ser Val Ile Tyr Val Tyr Trp Lys Gln Lys Ala
385                 390                 395

<210> SEQ ID NO 385
<211> LENGTH: 504
<212> TYPE: PRT
<213> ORGANISM: Homo sapiens

<400> SEQUENCE: 385

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
```

```
            290                 295                 300
Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
                340                 345                 350

Pro Lys Glu Gln Gly Ser Asn Thr Ala Ala Glu Asn Thr Gly Ser Asn
                355                 360                 365

Glu Arg Asn Ile Tyr Ile Val Val Gly Val Val Cys Thr Leu Leu Val
            370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
                420                 425                 430

Asn Leu Pro Lys Gly Lys Lys Pro Ala Pro Gln Ala Ala Glu Pro Asn
            435                 440                 445

Asn His Thr Glu Tyr Ala Ser Ile Gln Thr Ser Pro Gln Pro Ala Ser
            450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
                500

<210> SEQ ID NO 386
<211> LENGTH: 397
<212> TYPE: PRT
<213> ORGANISM: Mus musculus

<400> SEQUENCE: 386

Met Leu Leu Leu Asp Ala Trp Thr His Ile Pro His Cys Val Leu Leu
1               5                   10                  15

Leu Ile Leu Leu Leu Gly Leu Lys Gly Ala Ala Val Arg Glu Leu Lys
                20                  25                  30

Val Ile Gln Pro Val Lys Ser Phe Phe Val Gly Ala Gly Gly Ser Ala
                35                  40                  45

Thr Leu Asn Cys Thr Val Thr Tyr Leu Leu Pro Val Gly Pro Ile Lys
            50                  55                  60

Trp Tyr Arg Gly Val Gly Gln Ser Arg Leu Leu Ile Tyr Pro Phe Thr
65                  70                  75                  80

Gly Glu Tyr Phe Pro Arg Ile Thr Ser Val Ser Asp Val Lys Lys Arg
                85                  90                  95

Ser Asn Leu Asp Phe Ser Ile Arg Ile Ser Asn Val Thr Pro Ala Asp
                100                 105                 110

Ser Gly Thr Tyr Tyr Cys Val Lys Phe Gln Arg Gly Ser Ser Glu Pro
            115                 120                 125

Asp Ile Glu Ile Gln Ser Gly Gly Thr Glu Leu Ser Val Phe Ala
            130                 135                 140

Lys Pro Ser Ser Pro Met Val Ser Gly Pro Ala Ala Arg Ala Val Pro
145                 150                 155                 160
```

Gln Gln Thr Val Thr Phe Thr Cys Arg Ser His Gly Phe Pro Gln
                165                 170                 175

Asn Leu Thr Leu Lys Trp Phe Lys Asn Gly Asn Glu Ile Ser His Leu
            180                 185                 190

Glu Thr Ser Val Glu Pro Glu Thr Ser Val Ser Tyr Arg Val Ser
        195                 200                 205

Ser Thr Val Gln Val Val Leu Glu Pro Arg Asp Val Arg Ser Gln Ile
210                 215                 220

Ile Cys Glu Val Asp His Val Thr Leu Asp Arg Ala Pro Leu Arg Gly
225                 230                 235                 240

Ile Ala His Ile Ser Glu Ile Ile Gln Val Pro Pro Thr Leu Glu Ile
                245                 250                 255

Ser Gln Gln Pro Thr Met Val Trp Asn Val Ile Asn Val Thr Cys Gln
            260                 265                 270

Ile Gln Lys Phe Tyr Pro Arg Arg Phe Gln Val Thr Trp Leu Glu Asn
        275                 280                 285

Gly Asn Ile Ser Arg Arg Glu Val Pro Phe Thr His Ile Val Asn Lys
    290                 295                 300

Asp Gly Thr Tyr Asn Trp Ile Ser Trp Leu Leu Val Asn Ile Ser Ala
305                 310                 315                 320

Leu Glu Glu Asn Met Val Val Thr Cys Gln Val Glu His Asp Gly Gln
                325                 330                 335

Ala Glu Val Ile Glu Thr His Thr Val Val Thr Glu His Gln Arg
            340                 345                 350

Val Lys Gly Thr Ser Thr Met Ser Glu Leu Lys Thr Ala Gly Ile Ala
            355                 360                 365

Lys Ile Pro Val Ala Val Leu Leu Gly Ser Lys Ile Leu Leu Leu Ile
370                 375                 380

Ala Ala Thr Val Ile Tyr Met Arg Lys Lys Gln Asn Ala
385                 390                 395

<210> SEQ ID NO 387
<211> LENGTH: 118
<212> TYPE: PRT
<213> ORGANISM: Artificial sequence
<220> FEATURE:
<223> OTHER INFORMATION: SIRPalpha domain 1 (IgV domain)

<400> SEQUENCE: 387

Glu Glu Leu Gln Val Ile Gln Pro Asp Lys Ser Val Leu Val Ala Ala
1               5                   10                  15

Gly Glu Thr Ala Thr Leu Arg Cys Thr Ala Thr Ser Leu Ile Pro Val
            20                  25                  30

Gly Pro Ile Gln Trp Phe Arg Gly Ala Gly Pro Gly Arg Glu Leu Ile
        35                  40                  45

Tyr Asn Gln Lys Glu Gly His Phe Pro Arg Val Thr Thr Val Ser Asp
    50                  55                  60

Leu Thr Lys Arg Asn Asn Met Asp Phe Ser Ile Arg Ile Gly Asn Ile
65                  70                  75                  80

Thr Pro Ala Asp Ala Gly Thr Tyr Tyr Cys Val Lys Phe Arg Lys Gly
                85                  90                  95

Ser Pro Asp Asp Val Glu Phe Lys Ser Gly Ala Gly Thr Glu Leu Ser
            100                 105                 110

Val Arg Ala Lys Pro Ser
        115

```
<210> SEQ ID NO 388
<211> LENGTH: 119
<212> TYPE: PRT
<213> ORGANISM: Artificial sequence
<220> FEATURE:
<223> OTHER INFORMATION: SIRPbeta1 domain 1 (IgV domain)

<400> SEQUENCE: 388

Glu Asp Glu Leu Gln Val Ile Gln Pro Glu Lys Ser Val Ser Val Ala
1               5                   10                  15

Ala Gly Glu Ser Ala Thr Leu Arg Cys Ala Met Thr Ser Leu Ile Pro
            20                  25                  30

Val Gly Pro Ile Met Trp Phe Arg Gly Ala Gly Ala Gly Arg Glu Leu
        35                  40                  45

Ile Tyr Asn Gln Lys Glu Gly His Phe Pro Arg Val Thr Thr Val Ser
    50                  55                  60

Glu Leu Thr Lys Arg Asn Asn Leu Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115
```

ANTI-SIRP-BETA1 ANTIBODIES AND METHODS OF USE THEREOF

CROSS-REFERENCE TO RELATED APPLICATIONS

This application is a national phase entry pursuant to 35 U.S.C. § 371 of International Application No. PCT/US2019/039757, filed Jun. 28, 2019, which claims the benefit of priority of U.S. Provisional Application No. 62/691,913, filed Jun. 29, 2018, both of which are incorporated by reference herein in their entirety for any purpose.

FIELD OF THE PRESENT DISCLOSURE

The present disclosure relates to anti-SIRPβ1 antibodies and therapeutic uses of such antibodies.

BACKGROUND OF THE PRESENT DISCLOSURE

Signal regulatory protein beta (SIRPβ) belongs to the SIRP family of transmembrane receptors, which are expressed within the myeloid cell lineage (including monocytes, macrophages, granulocytes, and dendritic cells) and in neuronal cells. The SIRP family of proteins is characterized by an extracellular region containing 2 membrane-proximal IgC domains and a distal IgV domain. Unlike SIRPα receptors, SIRPβ proteins contain short cytoplasmic domains that lack cytoplasmic sequence motifs capable of recruiting protein tyrosine phosphatase SHP-2 and SHP-1. SIRPβ1 isoform 1 associates with the adaptor protein DAP12, which contains a single cytoplasmic immunoreceptor tyrosine-based activating (ITAM) motif See, e.g., Dietrich et al. 2000, J Immunol 164:9-12; Liu et al. 2005 J Biol Chem 280: 36132-36140. SIRPβ has been shown to be a microglial modulator of phagocytosis in Alzheimer's disease. See, e.g., Gaikwad et at. 2009 Am J Pathol 175:2528-2539.

Accordingly, there is a need for therapeutic anti-SIRPβ1 antibodies to treat disease, disorders, and conditions associated with SIRPβ1 activity.

SUMMARY OF THE PRESENT DISCLOSURE

In some embodiments, an isolated antibody that binds to human SIRPβ1 is provided, wherein the antibody has at least one, at least two at least three, at least four, or at least five properties selected from:
a) binds to human SIRPβ1 isoform 1, but does not bind to human SIRPα;
b) binds to human SIRPβ1 isoform 1, but does not bind to human SIRPγ;
c) binds to human SIRPβ1 isoform 1, but does not bind to human SIRPβ1 isoform 3;
d) binds to human SIRPβ1 isoform 1, but does not bind to mouse SIRPβ1;
e) binds to human SIRPβ1 isoform 1, but does not bind to cynomolgus monkey SIRPβ1 isoform 1;
f) agonizes SIRPβ1 activity on CD14-positive monocytes in vitro and/or in vivo;
g) induces or increases respiratory burst in immune cells, such as neutrophils and/or monocytes in vitro and/or in vivo;
h) induces or increases IL-8 expression in monocytes in vitro and/or in vivo;
i) induces or increases TNFα expression in macrophages and/or dendritic cells in vitro and/or in vivo;
j) induces neutrophil-mediated phagocytosis, for example, of tumor cells in vitro and/or in vivo;
k) increases neutrophil-mediated tumor cell clearance in vivo;
l) increases TREM2 expression on macrophages in vitro and/or in vivo;
m) increases viability of macrophages in vitro and/or in vivo, alone and/or in combination with an agonist anti-TREM2 antibody; and
n) increases viability of dendritic cells in vitro and/or in vivo.

In some embodiments, the antibody binds to human SIRPβ1 isoform 1, but does not bind to human SIRPα or human SIRPβ1 isoform 3. In some embodiments, the antibody binds to human SIRPβ1 isoform 1, but does not bind to human SIRPα, SIRPγ, or human SIRPβ1 isoform 3. In some embodiments, the antibody has at least one, at least two, or at least three properties selected from:
a) agonizes SIRPβ1 activity on CD14-positive monocytes in vitro and/or in vivo;
b) induces or increases respiratory burst in immune cells, such as neutrophils and/or monocytes in vitro and/or in vivo;
c) induces or increases IL-8 expression in monocytes in vitro and/or in vivo;
d) induces or increases TNFα expression in macrophages and/or dendritic cells in vitro and/or in vivo;
e) induces neutrophil-mediated phagocytosis, for example, of tumor cells in vitro and/or in vivo;
o) increases neutrophil-mediated tumor cell clearance in vivo;
p) increases TREM2 expression on macrophages in vitro and/or in vivo;
q) increases viability of macrophages in vitro and/or in vivo, alone and/or in combination with an agonist anti-TREM2 antibody; and
f) increases viability of dendritic cells in vitro and/or in vivo.

In some embodiments, an isolated antibody that binds to human SIRPβ1 is provided, wherein the antibody comprises a heavy chain variable region and a light chain variable region, wherein the heavy chain variable region comprises (a) HVR-H1 comprising an amino acid sequence of an HVR-H1 shown in Table 4 and/or Table 9; (b) HVR-H2 comprising an amino acid sequence of an HVR-H2 shown in Table 4 and/or Table 9; (c) HVR-H3 comprising an amino acid sequence of an HVR-H3 shown in Table 4 and/or Table 9; (d) HVR-L1 comprising an amino acid sequence of an HVR-L1 shown in Table 3 and/or Table 8; (e) HVR-L2 comprising an amino acid sequence of an HVR-L2 shown in Table 3 and/or Table 8; and (f) HVR-L3 comprising an amino acid sequence of an HVR-L3 shown in Table 3 and/or Table 8. In some embodiments, the heavy chain variable region comprises one, two, three or four framework regions selected from VH FR1, VH FR2, VH FR3, and VH FR4 shown in Table 6. In some embodiments, the light chain variable region comprises one, two, three or four framework regions selected from VL FR1, VL FR2, VL FR3, and VL FR4 shown in Table 5.

In some embodiments, the antibody comprises HVR-H1, HVR-H2, HVR-H2, HVR-L1, HVR-L2, and HVR-L3 of an antibody selected from SB-1, SB-2, SB-3, SB-4, SB-5, SB-6, SB-7, SB-8, SB-9, SB-10, SB-11, SB-12, SB-13, SB-14, SB-15, SB-16, SB-17, SB-18, SB-19, SB-20, SB-21, SB-22, SB-23, SB-24, SB-25, SB-26, SB-27, SB-28, SB-29, SB-30, SB-31, SB-32, SB-33, SB-34, SB-35, SB-36, SB-37, SB-38, SB-39, SB-40, SB-41, SB-42, SB-43, SB-44, SB-45, SB-46, SB-47, SB-48, SB-49, SB-50, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Tables 3, 4, 8, and 9). In some embodiments, the antibody comprises a heavy chain variable region comprising an amino acid sequence at least 90%, at least 95%, at least 97%, or at least 99% identical to a sequence selected from SEQ ID NOs: 268, 270, 272, 274, 276, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 366, 367, 368, 369, 371, 372, 373, 374, 375, 376, 377, 378, 379, 380, 381, or 382. In some embodiments, the antibody comprises a heavy chain variable region selected from SEQ ID NOs: 268, 270, 272, 274, 276, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 366, 367, 368, 369, 371, 372, 373, 374, 375, 376, 377, 378, 379, 380, 381, or 382. In some embodiments, the antibody comprises a light chain variable region comprising an amino acid sequence at least 90%, at least 95%, at least 97%, or at least 99% identical to a sequence selected from SEQ ID NOs: 267, 269, 271, 273, 275, 277, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, or 370. In some embodiments, the antibody comprises a light chain variable region selected from SEQ ID NOs: 267, 269, 271, 273, 275, 277, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, or 370. In some embodiments, the antibody comprises a heavy chain variable region that is at least 90%, at least 95%, at least 97%, or at least 99% identical to the heavy chain variable region, and a light chain variable region 90%, at least 95%, at least 97%, or at least 99% identical to the light chain variable region, of an antibody selected from SB-1, SB-2, SB-3, SB-4, SB-5, SB-6, SB-7, SB-8, SB-9, SB-10, SB-11, SB-12, SB-13, SB-14, SB-15, SB-16, SB-17, SB-18, SB-19, SB-20, SB-21, SB-22, SB-23, SB-24, SB-25, SB-26, SB-27, SB-28, SB-29, SB-30, SB-31, SB-32, SB-33, SB-34, SB-35, SB-36, SB-37, SB-38, SB-39, SB-40, SB-41, SB-42, SB-43, SB-44, SB-45, SB-46, SB-47, SB-48, SB-49, SB-50, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody comprises a heavy chain variable region and a light chain variable region of an antibody selected from SB-1, SB-2, SB-3, SB-4, SB-5, SB-6, SB-7, SB-8, SB-9, SB-10, SB-11, SB-12, SB-13, SB-14, SB-15, SB-16, SB-17, SB-18, SB-19, SB-20, SB-21, SB-22, SB-23, SB-24, SB-25, SB-26, SB-27, SB-28, SB-29, SB-30, SB-31, SB-32, SB-33, SB-34, SB-35, SB-36, SB-37, SB-38, SB-39, SB-40, SB-41, SB-42, SB-43, SB-44, SB-45, SB-46, SB-47, SB-48, SB-49, SB-50, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21.

In some embodiments, the antibody comprises HVR-H1, HVR-H2, HVR-H2, HVR-L1, HVR-L2, and HVR-L3 of an antibody selected from SB-1, SB-2, SB-3, SB-4, SB-5, SB-6, SB-7, SB-8, SB-9, SB-14, SB-28, SB-39, SB-40, SB-49, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Tables 3, 4, 8, and 9). In some embodiments, the antibody comprises a heavy chain variable region that is at least 90%, at least 95%, at least 97%, or at least 99% identical to the heavy chain variable region of an antibody selected from SB-1, SB-2, SB-3, SB-4, SB-5, SB-6, SB-7, SB-8, SB-9, SB-14, SB-28, SB-39, SB-40, SB-49, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody comprises a heavy chain variable region of an antibody selected from SB-1, SB-2, SB-3, SB-4, SB-5, SB-6, SB-7, SB-8, SB-9, SB-14, SB-28, SB-39, SB-40, SB-49, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody comprises a light chain variable region that is at least 90%, at least 95%, at least 97%, or at least 99% identical to the light chain variable region of an antibody selected from SB-1, SB-2, SB-3, SB-4, SB-5, SB-6, SB-7, SB-8, SB-9, SB-14, SB-28, SB-39, SB-40, SB-49, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody comprises a light chain variable region of an antibody selected from SB-1, SB-2, SB-3, SB-4, SB-5, SB-6, SB-7, SB-8, SB-9, SB-14, SB-28, SB-39, SB-40, SB-49, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody comprises a heavy chain variable region that is at least 90%, at least 95%, at least 97%, or at least 99% identical to the heavy chain variable region, and a light chain variable region 90%, at least 95%, at least 97%, or at least 99% identical to the light chain variable region, of an antibody selected from SB-1, SB-2, SB-3, SB-4, SB-5, SB-6, SB-7, SB-8, SB-9, SB-14, SB-28, SB-39, SB-40, SB-49, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody comprises a heavy chain variable region and a light chain variable region of an antibody selected from SB-1, SB-2, SB-3, SB-4, SB-5, SB-6, SB-7, SB-8, SB-9, SB-14, SB-28, SB-39, SB-40, SB-49, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21.

In some embodiments, the antibody comprises HVR-H1, HVR-H2, HVR-H2, HVR-L1, HVR-L2, and HVR-L3 of an antibody selected from SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Tables 8 and 9). In some embodiments, the antibody comprises a heavy chain variable region that is at least 90%, at least 95%, at least 97%, or at least 99% identical to the heavy chain variable region of an antibody selected from SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody comprises a heavy chain variable region of an antibody selected from SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody comprises a light chain variable region that is at least 90%, at least 95%, at least 97%, or at least 99% identical to the light chain variable region of an antibody selected from SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody comprises a light chain variable region of an antibody selected from SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody comprises a heavy chain variable region that is at least 90%, at least 95%, at least 97%, or at least 99% identical to the heavy chain variable region, and a light chain variable region 90%, at least 95%, at least 97%, or at least 99% identical to the light chain variable region, of an antibody selected from SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody comprises a heavy chain variable region and a light chain variable region of an antibody selected from SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21.

In some embodiments, the antibody comprises (a) HVR-H1 comprising the amino acid sequence of SEQ ID NO: 80, 228, or 229; (b) HVR-H2 comprising the amino acid sequence of SEQ ID NO: 101, 239, 239, 240, or 241; (c) HVR-H3 comprising the amino acid sequence of SEQ ID NO: 125; (d) HVR-L1 comprising the amino acid sequence of SEQ ID NO: 383; (e) HVR-L2 comprising the amino acid sequence of SEQ ID NO: 16; and (f) HVR-L3 comprising the amino acid sequence of SEQ ID NO: 31. In some embodiments, the antibody comprises a heavy chain variable region that is at least 90%, at least 95%, at least 97%, or at least 99% identical to the amino acid sequence of SEQ ID NO: 366, 367, 368, or 369. In some embodiments, the antibody comprises a light chain variable region that is at least 90%, at least 95%, at least 97%, or at least 99% identical to the amino acid sequence of SEQ ID NO: 267. In some embodiments, the antibody comprises a heavy chain variable region comprising the amino acid sequence of SEQ ID NO: 366, 367, 368, or 369. In some embodiments, the antibody comprises a light chain variable region comprising the amino acid sequence of SEQ ID NO: 267.

In some embodiments, the antibody comprises (a) HVR-H1 comprising the amino acid sequence of SEQ ID NO: 81, 99, 230, 231, or 232; (b) HVR-H2 comprising the amino acid sequence of SEQ ID NO: 102, 242, 243, 244, or 245; (c) HVR-H3 comprising the amino acid sequence of SEQ ID NO: 126 or 253; (d) HVR-L1 comprising the amino acid sequence of SEQ ID NO: 383; (e) HVR-L2 comprising the amino acid sequence of SEQ ID NO: 16; and (f) HVR-L3 comprising the amino acid sequence of SEQ ID NO: 32. In some embodiments, the antibody comprises a heavy chain variable region that is at least 90%, at least 95%, at least 97%, or at least 99% identical to the amino acid sequence of SEQ ID NO: 371, 372, 373, 374, or 375. In some embodiments, the antibody comprises a light chain variable region that is at least 90%, at least 95%, at least 97%, or at least 99% identical to the amino acid sequence of SEQ ID NO: 269 or 370. In some embodiments, the antibody comprises a heavy chain variable region comprising the amino acid sequence of SEQ ID NO: 371, 372, 373, 374, or 375. In some embodiments, the antibody comprises a light chain variable region comprising the amino acid sequence of SEQ ID NO: 269 or 370. In some embodiments, the antibody comprises a heavy chain variable region comprising the amino acid sequence of SEQ ID NO: 371, 372, or 373 and a light chain variable region comprising the amino acid sequence of SEQ ID NO: 370; or a heavy chain variable region comprising the amino acid sequence of SEQ ID NO: 374 or 375 and a light chain variable region comprising the amino acid sequence of SEQ ID NO: 269.

In some embodiments, the antibody comprises (a) HVR-H1 comprising the amino acid sequence of SEQ ID NO: 85, 233, or 234; (b) HVR-H2 comprising the amino acid sequence of SEQ ID NO: 107, 246, 247, or 248; (c) HVR-H3 comprising the amino acid sequence of SEQ ID NO: 131 or 254; (d) HVR-L1 comprising the amino acid sequence of SEQ ID NO: 383; (e) HVR-L2 comprising the amino acid sequence of SEQ ID NO: 19; and (f) HVR-L3 comprising the amino acid sequence of SEQ ID NO: 37. In some embodiments, the antibody comprises a heavy chain variable region that is at least 90%, at least 95%, at least 97%, or at least 99% identical to the amino acid sequence of SEQ ID NO: 376, 377, or 378. In some embodiments, the antibody comprises a light chain variable region that is at least 90%, at least 95%, at least 97%, or at least 99% identical to the amino acid sequence of SEQ ID NO: 280. In some embodiments, the antibody comprises a heavy chain variable region comprising the amino acid sequence of SEQ ID NO: 376, 377, or 378. In some embodiments, the antibody comprises a light chain variable region comprising the amino acid sequence of SEQ ID NO: 280.

In some embodiments, the antibody comprises (a) HVR-H1 comprising the amino acid sequence of SEQ ID NO: 97, 235, 236, or 237; (b) HVR-H2 comprising the amino acid sequence of SEQ ID NO: 121, 249, 250, 251, or 252; (c) HVR-H3 comprising the amino acid sequence of SEQ ID NO: 163; (d) HVR-L1 comprising the amino acid sequence of SEQ ID NO: 2; (e) HVR-L2 comprising the amino acid sequence of SEQ ID NO: 22; and (f) HVR-L3 comprising the amino acid sequence of SEQ ID NO: 69. In some embodiments, the antibody comprises a heavy chain variable region that is at least 90%, at least 95%, at least 97%, or at least 99% identical to the amino acid sequence of SEQ ID NO: 379, 380, 381, or 382. In some embodiments, the antibody comprises a light chain variable region that is at least 90%, at least 95%, at least 97%, or at least 99% identical to the amino acid sequence of SEQ ID NO: 344. In some embodiments, the antibody comprises a heavy chain variable region comprising the amino acid sequence of SEQ ID NO: 379, 380, 381, or 382. In some embodiments, the antibody comprises a light chain variable region comprising the amino acid sequence of SEQ ID NO: 344.

In some embodiments, the antibody comprises (a) HVR-H1 comprising the amino acid sequence of SEQ ID NO: 229; (b) HVR-H2 comprising the amino acid sequence of SEQ ID NO: 239; (c) HVR-H3 comprising the amino acid sequence of SEQ ID NO: 125; (d) HVR-L1 comprising the amino acid sequence of SEQ ID NO: 383; (e) HVR-L2 comprising the amino acid sequence of SEQ ID NO: 16; and (f) HVR-L3 comprising the amino acid sequence of SEQ ID NO: 31. In some embodiments, the antibody comprises a heavy chain variable region that is at least 90%, at least 95%, at least 97%, or at least 99% identical to the amino acid sequence of SEQ ID NO: 367. In some embodiments, the antibody comprises a light chain variable region that is at least 90%, at least 95%, at least 97%, or at least 99% identical to the amino acid sequence of SEQ ID NO: 267. In some embodiments, the antibody comprises a heavy chain variable region comprising the amino acid sequence of SEQ ID NO: 367. In some embodiments, the antibody comprises a light chain variable region comprising the amino acid sequence of SEQ ID NO: 267.

In some embodiments, the antibody comprises (a) HVR-H1 comprising the amino acid sequence of SEQ ID NO: 231; (b) HVR-H2 comprising the amino acid sequence of SEQ ID NO: 243; (c) HVR-H3 comprising the amino acid sequence of SEQ ID NO: 126; (d) HVR-L1 comprising the amino acid sequence of SEQ ID NO: 383; (e) HVR-L2 comprising the amino acid sequence of SEQ ID NO: 16; and (f) HVR-L3 comprising the amino acid sequence of SEQ ID NO: 32. In some embodiments, the antibody comprises a heavy chain variable region that is at least 90%, at least 95%, at least 97%, or at least 99% identical to the amino acid sequence of SEQ ID NO: 372. In some embodiments, the antibody comprises a light chain variable region that is at least 90%, at least 95%, at least 97%, or at least 99% identical to the amino acid sequence of SEQ ID NO: 370. In some embodiments, the antibody comprises a heavy chain variable region comprising the amino acid sequence of SEQ ID NO: 372. In some embodiments, the antibody comprises a light chain variable region comprising the amino acid sequence of SEQ ID NO: 270.

In some embodiments, the antibody comprises (a) HVR-H1 comprising the amino acid sequence of SEQ ID NO: 233; (b) HVR-H2 comprising the amino acid sequence of SEQ ID NO: 246; (c) HVR-H3 comprising the amino acid sequence of SEQ ID NO: 131; (d) HVR-L1 comprising the amino acid sequence of SEQ ID NO: 383; (e) HVR-L2 comprising the amino acid sequence of SEQ ID NO: 19; and (f) HVR-L3 comprising the amino acid sequence of SEQ ID NO: 37. In some embodiments, the antibody comprises a heavy chain variable region that is at least 90%, at least 95%, at least 97%, or at least 99% identical to the amino acid sequence of SEQ ID NO: 376. In some embodiments, the antibody comprises a light chain variable region that is at least 90%, at least 95%, at least 97%, or at least 99% identical to the amino acid sequence of SEQ ID NO: 280. In some embodiments, the antibody comprises a heavy chain variable region comprising the amino acid sequence of SEQ ID NO: 376. In some embodiments, the antibody comprises a light chain variable region comprising the amino acid sequence of SEQ ID NO: 280.

In some embodiments, the antibody is a monoclonal antibody. In some embodiments, the antibody is of the IgG class, the IgM class, or the IgA class. In some embodiments, the antibody is of the IgG class and has an IgG1, IgG2, or IgG4 isotype. In some embodiments, the antibody has an IgG1 isotype. In some embodiments, the antibody comprises a E430G substitution and a P331S substitution according to EU numbering.

In some embodiments, the antibody is an antibody fragment. In some embodiments, the fragment is a Fab, Fab', Fab'-SH, F(ab')$_2$, Fv or scFv fragment.

In some embodiments, the antibody has an affinity ($K_D$) for human SIRPβ1 isoform 1 of 0.1 nM to 50 nM, or 0.5 nM to 10 nM, or 0.5 nM to 5 nM. In some embodiments, affinity is measured using a ForteBio Octet® system.

In some embodiments, the antibody recognizes a first and a second antigen, wherein the first antigen is SIRPβ1 and the second antigen is:
  (a) an antigen facilitating transport across the blood-brain-barrier;
  (b) an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), and diphtheria toxin receptor;
  (c) a disease-causing agent selected from the group consisting of disease-causing peptides or proteins or disease-causing nucleic acids, wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein A1, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides;
  (d) ligands and/or proteins expressed on immune cells, wherein the ligands and/or proteins selected from the group consisting of CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; and
  (e) a protein, lipid, polysaccharide, or glycolipid expressed on one or more tumor cells.

In some embodiments, an isolated antibody that binds to human SIRPβ1 is provided, wherein the antibody competes with one or more antibodies provided herein for binding to human SIRPβ1 isoform 1. In some embodiments, an isolated antibody that binds to human SIRPβ1 is provided, wherein the antibody binds essentially the same or overlapping SIRPβ1 isoform 1 epitope as one or more antibodies provided herein.

In some embodiments, an isolated nucleic acid is provided, comprising a nucleic acid sequence encoding an anti-SIRPβ1 antibody provided herein. In some embodiments, a vector comprising the nucleic acid is provided. In some embodiments, an isolated host cell is provided, comprising the vector. In some embodiments, an isolated host cell is provided that expresses an anti-SIRPβ1 antibody provided herein. In some embodiments, methods of producing an antibody that binds to human SIRPβ1 are provided, comprising culturing a host cell that expresses an anti-SIRPβ1 antibody provided herein so that the antibody is produced. In some embodiments, the method further comprises recovering the antibody produced by the cell.

In some embodiments, a pharmaceutical composition is provided, comprising an anti-SIRPβ1 antibody provided herein and a pharmaceutically acceptable carrier.

In some embodiments, a method of treating cancer is provided, comprising administering to an individual in need thereof a therapeutically effective amount of an anti-SIRPβ1 antibody provided herein. In some embodiments, the cancer is selected from selected from sarcoma, bladder cancer, brain cancer, breast cancer, colon cancer, rectal cancer, endometrial cancer, kidney cancer, renal pelvis cancer, leukemia, lung cancer, small cell lung cancer, melanoma, lymphoma, pancreatic cancer, prostate cancer, ovarian cancer, and fibrosarcoma, glioblastoma multiforme; renal clear cell carcinoma; adrenocortical carcinoma; bladder urothelial carcinoma, diffuse large B-cell lymphoma, lung adenocarcinoma; pancreatic adenocarcinoma, renal cell cancer, Hodgkin's lymphoma, non-Hodgkin's lymphoma, indolent B cell lymphoma, aggressive B cell lymphoma, T cell lymphoma, acute lymphoblastic leukemia (ALL), acute myeloid leukemia (AML), chronic lymphocytic leukemia (CLL), chronic myeloid leukemia (CML), multiple myeloma, myelodysplastic syndromes, myeloproliferative neoplasms, breast invasive carcinoma, cervical squamous cell carcinoma, endocervical adenocarcinoma, cholangiocarcinoma, colon adenocarcinoma, diffuse large B-cell lymphoma, esophageal carcinoma, head and neck squamous cell carcinoma, kidney chromophobe, renal papillary cell carcinoma, lower grade glioma, hepatocellular carcinoma, lung squamous cell carcinoa, mesothelioma, ovarian serous cystadenomcarcinoma, pancreatic adenocarcinoma, pheochromocytoma and paraganglioma, prostate adenocarconimo, rectal adenocarcinoma, cutaneous melanoma, stomach adenocarcinoma, testicular germ cell tumors, thyroid carcinoma, thyumoma, uterine corpus endometrial carcinoma, uternine carcinosarcoma, and uveal melanoma.

In some embodiments, a method of treatment further comprises administering a therapeutic agent that inhibits or agonizes PD1, PDL1, CD40, OX40, ICOS, CD28, CD137/4-1BB, CD27, GITR, CTLA4, PD-L2, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, or CD73. In some embodiments, a method of treatment further comprises administering to the individual at least one antibody that specifically binds to an inhibitory checkpoint molecule, and/or one or more standard or investigational anti-cancer therapies.

In some embodiments, a method of treatment further comprises administering at least one antibody that specifically binds to an inhibitory checkpoint molecule in combination with the anti-SIRPA antibody. In some embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM-1 antibody, an anti-TIM3 antibody, an anti-TIM-4 antibody, an anti-A2AR antibody, an anti-CD39 antibody, an anti-CD73 antibody, an anti-LAG-3 antibody, an anti-phosphatidylserine antibody, an anti-CD27 antibody, an anti-CD30 antibody, an anti-TNFα antibody, an anti-CD33 antibody, an anti-Siglec-5 antibody, an anti-Siglec-7 antibody, an anti-Siglec-9 antibody, an anti-Siglec-11 antibody, an antagonistic anti-TREM1 antibody, an antagonistic anti-TREM2 antibody, an anti-TIGIT antibody, an anti-VISTA antibody, an anti-CD2 antibody, an anti-CD5 antibody, and any combination thereof.

In some embodiments, a method of treatment further comprises administering one or more standard or investigational anti-cancer therapies selected from radiotherapy, cytotoxic chemotherapy, targeted therapy, imatinib therapy, trastuzumab therapy, etanercept therapy, adoptive cell transfer (ACT) therapy, chimeric antigen receptor T cell transfer (CAR-T) therapy, vaccine therapy, and cytokine therapy.

In some embodiments, a method of treatment further comprises administering to the individual at least one antibody that specifically binds to an inhibitory cytokine. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, a method of treatment further comprises administering to the individual at least one agonistic antibody that specifically binds to a stimulatory checkpoint protein. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, an agonist anti-CD30 antibody, an agonist anti-BTLA antibody, an agonist anti-HVEM antibody, an agonist anti-CD2 antibody, an agonist anti-CD5 antibody, and any combination thereof.

In some embodiments, a method of treatment further comprises administering to the individual at least one stimulatory cytokine. In some embodiments, the at least one stimulatory cytokine is selected from IFN-α4, IFN-β, IL-10, TNF-α, IL-6, IL-8, CRP, IL-20 family members, LIF, IFN-γ, OSM, CNTF, GM-CSF, IL-11, IL-12, IL-15, IL-17, IL-18, IL-23, CXCL10, IL-33, MCP-1, MIP-1-beta, and any combination thereof.

In some embodiments, use of an anti-SIRPβ1 antibody provided herein for the preparation of a medicament is provided. In some embodiments, the medicament is for treating cancer. In some embodiments, an anti-SIRPβ1 antibody provided herein is provided for treating cancer.

In some embodiments, a method of treating a neurodegenerative disease or disorder is provided, comprising administering to an individual in need thereof a therapeutically effective amount of an anti-SIRPβ1 antibody provided herein. In some embodiments, the neurodegenerative disease or disorder is selected from dementia, frontotemporal dementia, progressive supranuclear palsy, Alzheimer's disease, vascular dementia, Nasu-Hakola disease, cognitive deficit, memory loss, seizures, retinal dystrophy, amyotrophic lateral sclerosis, traumatic brain injury, a spinal cord injury, stroke, Parkinson's disease, acute disseminated encephalomyelitis, retinal degeneration, age related macular degeneration, glaucoma, multiple sclerosis.

In some embodiments, use of an anti-SIRPβ1 antibody provided herein for the preparation of a medicament for treating a neurodegenerative disease or disorder is provided. In some embodiments, the neurodegenerative disease or disorder is selected from dementia, frontotemporal dementia, progressive supranuclear palsy, Alzheimer's disease, vascular dementia, Nasu-Hakola disease, cognitive deficit, memory loss, seizures, retinal dystrophy, amyotrophic lateral sclerosis, traumatic brain injury, a spinal cord injury, stroke, Parkinson's disease, acute disseminated encephalomyelitis, retinal degeneration, age related macular degeneration, glaucoma, multiple sclerosis. In some embodiments, an anti-SIRPβ1 antibody provided herein for use in treating a neurodegenerative disease or disorder is provided. In some embodiments, the neurodegenerative disease or disorder is selected from dementia, frontotemporal dementia, progressive supranuclear palsy, Alzheimer's disease, vascular dementia, Nasu-Hakola disease, cognitive deficit, memory loss, seizures, retinal dystrophy, amyotrophic lateral sclerosis, traumatic brain injury, a spinal cord injury, stroke, Parkinson's disease, acute disseminated encephalomyelitis, retinal degeneration, age related macular degeneration, glaucoma, multiple sclerosis.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 1A shows an alignment of the amino acid sequences of SIRPβ1 isoform 1 (SEQ ID NO: 1; Uniprot Accession No. 000241) and SIRPβ1 isoform 3 (SEQ ID NO: 384; Uniprot Accession No. Q5TFQ8). FIG. 1B shows an alignment of the amino acid sequences of SIRPβ1 isoform 1 (SEQ ID NO: 1) with SIRPα (SEQ ID NO: 385; Uniprot Accession No. P78324), which shows high homology within the extracellular domains.

FIG. 2 shows an alignment of the amino acid sequences of human SIRPβ1 isoform 1 (SEQ ID NO: 1) and mouse SIRPβ1 (SEQ ID NO: 386; Uniprot Accession No. Q8BFX8).

FIG. 6B shows SIRPβ1-mediated respiratory burst (top panel) or IL-8 release (bottom panel) from primary human monocytes. FIG. 6C shows SIRPβ11-mediated TNFα cytokine release from primary human macrophages or dendritic cells (DCs).

FIG. 8 shows induction of human SIRPβ1-dependent luciferase expression in a cell-based reporter assay by affinity matured antibodies. Results presented are raw luminescence values. The background level is set to 10,000 on y-axis.

FIG. 15A and FIG. 15B show titration curves of various anti-SIRP receptor antibodies binding BW5147.G.1.4 cells overexpressing recombinant human SIRPβ1 or recombinant human SIRPα, respectively. FIG. 15C shows titration curves of antibodies binding Jurkat cells, an immortalized human T cell line that endogenously expresses SIRPγ. Positive control antibodies were anti-SIRPα/β clone 18D5, anti-SIRPα/β/γ clone KWAR23, and anti-SIRPγ clone LSB2.20.

DETAILED DESCRIPTION

Figure 3A:
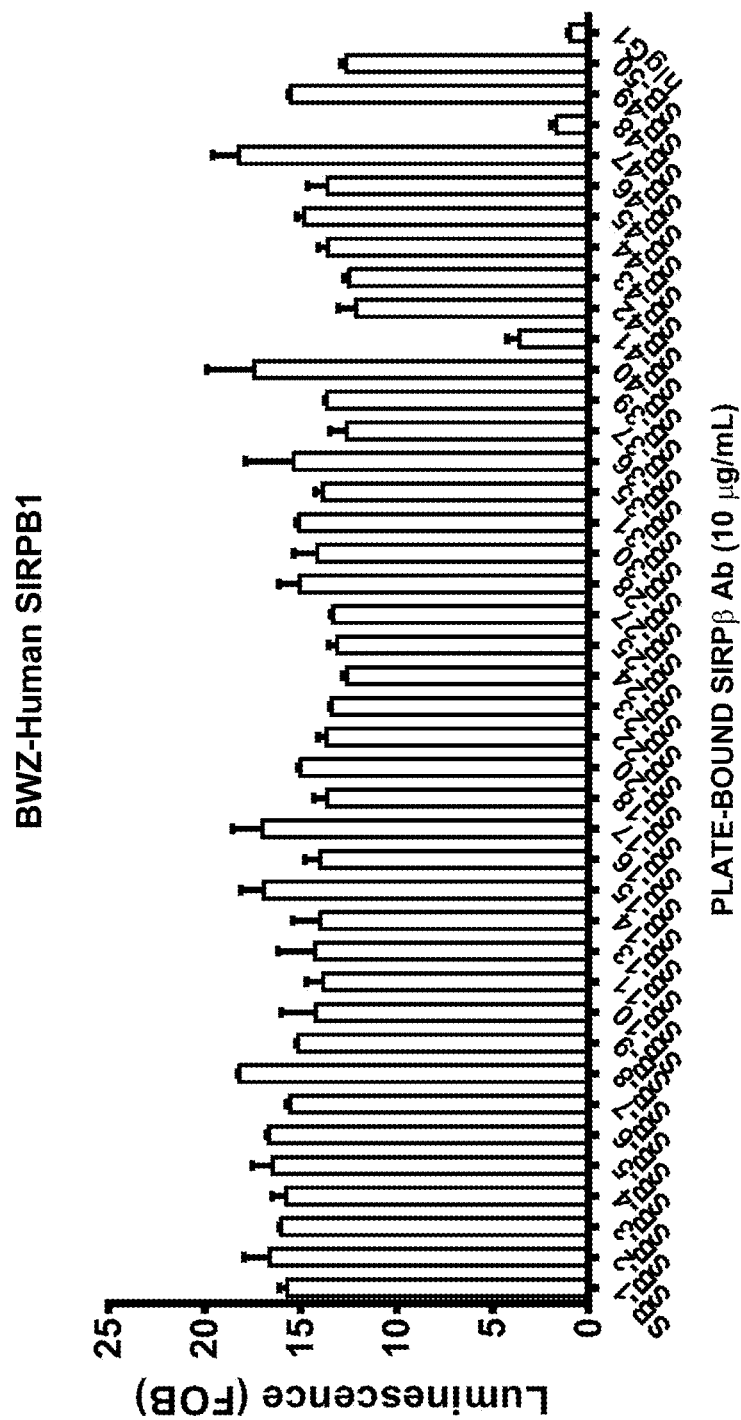
FIG. 3A-3B shows induction of human SIRPβ1-dependent luciferase expression in a cell-based reporter assay. Cells were stimulated with plate-bound anti-SIRPβ1 antibodies (3A) or anti-SIRPα (SA-9C2) (3B) or human IgG1 isotype control. Results are expressed as fold over background. The background level is set to 1 on y-axis.

The present disclosure relates to anti-SIRPβ1 antibodies (e.g., monoclonal antibodies); methods of making and using such antibodies; pharmaceutical compositions comprising such antibodies; nucleic acids encoding such antibodies; and host cells comprising nucleic acids encoding such antibodies.

The techniques and procedures described or referenced herein are generally well understood and commonly employed using conventional methodology by those skilled in the art, such as, for example, the widely utilized methodologies such as those described in Sambrook et al. *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003); *Monoclonal Antibodies: A Practical Approach* (P. Shepherd and C. Dean, eds., Oxford University Press, 2000).

All references cited herein, including patent applications and publications, are hereby incorporated by reference in their entirety.

I. Definitions

The terms "Signal-Regulatory Protein β1," "SIRPβ1," and "SIRPβ1 polypeptide" are used interchangeably herein refer herein to any native SIRPβ1 from any vertebrate source, including mammals such as primates (e.g., humans and cynos) and rodents (e.g., mice and rats), unless otherwise indicated. In some embodiments, the term encompasses both wild-type sequences and naturally occurring variant sequences, e.g., splice variants or allelic variants. In some embodiments, the term encompasses "full-length," unprocessed SIRPβ1 as well as any form of SIRPβ1 that results from processing in the cell. In some embodiments, the SIRPβ1 is human SIRPβ1. In some embodiments, the amino acid sequence of an exemplary SIRPβ1 isoform 1 is Uniprot Accession No. O00241 as of Feb. 28, 2018. In some embodiments, the amino acid sequence of an exemplary human SIRPβ1 is SEQ ID NO: 1. In some embodiments, the amino acid sequence of an exemplary SIRPβ1 isoform 3 is Uniprot Accession No. Q5TFQ8 as of Jan. 31, 2018. In some embodiments, the amino acid sequence of an exemplary human SIRPβ1 isoform 3 is SEQ ID NO: 384. Unless specifically indicated otherwise, "SIRPβ1" as used herein refers to SIRPβ1 isoform 1.

The terms "anti-SIRPβ1 antibody," an "antibody that binds to SIRPβ1," and "antibody that specifically binds SIRPβ1" refer to an antibody that is capable of binding SIRPβ1 with sufficient affinity such that the antibody is useful as a diagnostic and/or therapeutic agent in targeting SIRPβ1. In one embodiment, the extent of binding of an anti-SIRPβ 1 antibody to an unrelated, non-SIRPβ 1 polypeptide is less than about 10% of the binding of the antibody to SIRPβ1 as measured, e.g., by a radioimmunoassay (RIA). In certain embodiments, an antibody that binds to SIRPβ1 has a dissociation constant ($K_D$) of <1 μM, <100 nM, <10 nM, <1 nM, <0.1 nM, <0.01 nM, or <0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-SIRPβ1 antibody binds to an epitope of SIRPβ1 that is conserved among SIRPβ1 polypeptides from different species.

With regard to the binding of an antibody to a target molecule, the term "specific binding" or "specifically binds" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a $K_D$ for the target of about any of $10^{-4}$ M or lower, $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, $10^{-12}$ M or lower or a $K_D$ in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and $K_D$ values are inversely related. A high affinity for an antigen is measured by a low $K_D$ value. In one embodiment, the term "specific binding" refers to binding where a molecule binds to a particular polypeptide or epitope on a particular polypeptide without substantially binding to any other polypeptide or polypeptide epitope.

The term "immunoglobulin" (Ig) is used interchangeably with "antibody" herein. The term "antibody" herein is used in the broadest sense and specially covers monoclonal antibodies, polyclonal antibodies, multispecific antibodies (e.g., bispecific antibodies) including those formed from at least two intact antibodies, and antibody fragments so long as they exhibit the desired biological activity.

"Native antibodies" are usually heterotetrameric glycoproteins of about 150,000 Daltons, composed of two identical Light ("L") chains and two identical heavy ("H") chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

For the structure and properties of the different classes of antibodies, see, e.g., *Basic and Clinical Immunology*, 8th Ed., Daniel P. Stites, Abba I. Terr and Tristram G. Parslow (eds.), Appleton & Lange, Norwalk, C T, 1994, page 71 and Chapter 6.

The light chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("a"), delta ("δ"), epsilon ("ε"), gamma ("γ"), and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three-dimensional configurations of different classes of immunoglobulins are well known and described generally in, for example, Abbas et al., Cellular and Molecular Immunology, 4$^{th}$ ed. (W.B. Saunders Co., 2000).

The "variable region" or "variable domain" of an antibody, such as an anti-SIRPβ1 antibody of the present disclosure, refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-SIRPβ1 antibodies of the present disclosure. The variable domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Immunological Interest*, Fifth Edition, National Institute of Health, Bethesda, MD (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as a monoclonal anti-SIRPβ1 antibody of the present disclosure, obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method, recombinant DNA methods, and technologies for producing human or human-like antibodies in animals that have parts or all of the human immunoglobulin loci or genes encoding human immunoglobulin sequences.

The terms "full-length antibody," "intact antibody" or "whole antibody" are used interchangeably to refer to an antibody, such as an anti-SIRPβ1 antibody of the present disclosure, in its substantially intact form, as opposed to an antibody fragment. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" refers to a molecule other than an intact antibody that comprises a portion of an intact antibody that binds the antigen to which the intact antibody binds. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-SIRPβ1 antibodies of the present disclosure, produces two identical antigen-binding fragments, called "Fab" fragments, and a residual "Fc" fragment, a designation reflecting the ability to crystallize readily. The Fab fragment consists of an entire light chain along with the variable region domain of the heavy chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both heavy chains held together by disulfides. The effector functions of antibodies are determined by sequences in the Fc region, the region which is also recognized by Fc receptors (FcR) found on certain types of cells.

"Functional fragments" of antibodies, such as anti-SIRPβ1 antibodies of the present disclosure, comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the variable domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains.

As used herein, a "chimeric antibody" refers to an antibody (immunoglobulin), such as a chimeric anti-SIRPβ1 antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as humanized forms of anti-SIRPβ1 antibodies of the present disclosure, are chimeric antibodies comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one that possesses an amino-acid sequence corresponding to that of an antibody, such as an anti-SIRPβ1 antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries and yeast-based platform technologies. Human antibodies can be prepared by administering the antigen to a transgenic animal that has been modified to produce such antibodies in response to antigenic challenge, but whose endogenous loci have been disabled, e.g., immunized xenomice as well as generated via a human B-cell hybridoma technology.

The term "hypervariable region" or "HVR," when used herein refers to the regions of an antibody-variable domain, such as that of an anti-SIRPβ1 antibody of the present disclosure, that are hypervariable in sequence and/or form structurally defined loops. Generally, antibodies comprise six HVRs; three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. Naturally occurring camelid antibodies consisting of a heavy chain only are functional and stable in the absence of light chain.

A number of HVR delineations are in use and are encompassed herein. In some embodiments, the HVRs may be Kabat complementarity-determining regions (CDRs) based on sequence variability and are the most commonly used (Kabat et al., supra). In some embodiments, the HVRs may be Chothia CDRs. Chothia refers instead to the location of the structural loops (Chothia and Lesk *J. Mol. Biol.* 196: 901-917 (1987)). In some embodiments, the HVRs may be AbM HVRs. The AbM HVRs represent a compromise between the Kabat CDRs and Chothia structural loops, and are used by Oxford Molecular's AbM antibody-modeling software. In some embodiments, the HVRs may be "contact" HVRs. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

An "acceptor human framework" as used herein is a framework comprising the amino acid sequence of a $V_L$ or $V_H$ framework derived from a human immunoglobulin framework or a human consensus framework. An acceptor human framework "derived from" a human immunoglobulin framework or a human consensus framework may comprise the same amino acid sequence thereof, or it may comprise pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the VL human immunoglobulin framework sequence or human consensus framework sequence.

A "human consensus framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest*, 5th Ed. Public Health Service, National Institutes of Health, Bethesda, MD (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al., supra.

An "amino-acid modification" at a specified position, e.g., of an anti-SIRPβ1 antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an affinity matured anti-SIRPβ1 antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al. *Bio/Technology* 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155: 1994-2004 (1995); Jackson et al. *J. Immunol.* 154(7):3310-9 (1995); and Hawkins et al, *J. Mol. Biol.* 226:889-896 (1992).

"Fv" is the minimum antibody fragment which comprises a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains, which enables the sFv to form the desired structure for antigen binding.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. Other FcRs, including those to be identified in the future, are encompassed by the term "FcR" herein. FcRs can also increase the serum half-life of antibodies.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared.

The term "compete" when used in the context of antibodies (e.g., neutralizing antibodies) that compete for the same epitope means competition between antibody as determined by an assay in which the antibody being tested prevents or inhibits (e.g., reduces) specific binding of a reference molecule (e.g., a ligand, or a reference antibody) to a common antigen (e.g., SIRPβ1 or a fragment thereof). Numerous types of competitive binding assays can be used to determine if antibody competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antibody and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the examples herein. Usually, when a competing antibody is present in excess, it will inhibit (e.g., reduce) specific binding of a reference antibody to a common antigen by at least 20%, 30%, 40%, 50%, 60%, 70%, 80%, 85%, 90%, 95%, 97.5%, and/or near 100%.

As used herein, an "interaction" between a SIRPβ1 polypeptide and a second polypeptide encompasses, without limitation, protein-protein interaction, a physical interaction, a chemical interaction, binding, covalent binding, and ionic binding. As used herein, an antibody "inhibits interaction" between two polypeptides when the antibody disrupts, reduces, or completely eliminates an interaction between the two polypeptides. An antibody of the present disclosure, thereof, "inhibits interaction" between two polypeptides when the antibody thereof binds to one of the two polypeptides. In some embodiments, the interaction can be inhibited by at least about any of 20%, 30%, 40%, 50%, 60%, 70%, 80%, 85%, 90%, 95%, 97.5%, and/or near 100%.

The term "epitope" includes any determinant capable of being bound by an antibody. An epitope is a region of an antigen that is bound by an antibody that targets that antigen, and when the antigen is a polypeptide, includes specific amino acids that directly contact the antibody. Most often, epitopes reside on polypeptides, but in some instances, can reside on other kinds of molecules, such as nucleic acids. Epitope determinants can include chemically active surface groupings of molecules such as amino acids, sugar side chains, phosphoryl or sulfonyl groups, and can have specific three-dimensional structural characteristics, and/or specific charge characteristics. Generally, antibodies specific for a particular target antigen will preferentially recognize an epitope on the target antigen in a complex mixture of polypeptides and/or macromolecules.

An "agonist" antibody or an "activating" antibody is an antibody that induces (e.g., increases) one or more activities or functions of the antigen after the antibody binds the antigen.

An "antagonist" antibody or a "blocking" antibody or an "inhibitory" antibody is an antibody that reduces, inhibits, and/or eliminates (e.g., decreases) antigen binding to one or more ligand after the antibody binds the antigen, and/or that reduces, inhibits, and/or eliminates (e.g., decreases) one or more activities or functions of the antigen after the antibody binds the antigen. In some embodiments, antagonist antibodies, or blocking antibodies, or inhibitory antibodies substantially or completely inhibit antigen binding to one or more ligand and/or one or more activities or functions of the antigen.

An "isolated" antibody, such as an isolated anti-SIRPβ1 antibody of the present disclosure, is one that has been identified, separated and/or recovered from a component of its production environment (e.g., naturally or recombinantly). Preferably, the isolated antibody is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the antibody will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

An "isolated" nucleic acid molecule encoding an antibody, such as an anti-SIRPβ1 antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

"Carriers" as used herein include pharmaceutically acceptable carriers, excipients, or stabilizers that are nontoxic to the cell or mammal being exposed thereto at the dosages and concentrations employed.

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration. In some embodiments, administration in conjunction is administration as a part of the same treatment regimen.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

I. Anti-SIRPβ1 Antibodies

Provided herein are anti-SIRPβ1 antibodies. Antibodies provided are useful, e.g., for the diagnosis or treatment of the SIRPβ1 mediated disorders.

In some embodiments, an anti-SIRPβ1 antibody of the present disclosure is an agonist of SIRPβ1 activity. In some embodiments, an anti-SIRPβ1 antibody is provided that binds to human SIRPβ1 isoform 1 but does not bind to human SIRPα. In some embodiments, an anti-SIRPβ1 antibody is provided that binds to human SIRPβ1 isoform 1 but does not bind to human SIRPγ. In some embodiments, an anti-SIRPβ1 antibody is provided that binds to human SIRPβ1 isoform 1 but does not bind to human SIRPβ1 isoform 3. In some embodiments, an anti-SIRPβ1 antibody is provided that binds to human SIRPβ1 isoform 1 but does not bind to mouse SIRPβ1 and/or cynomolgus monkey SIRPβ1. In some embodiments, an anti-SIRPβ1 antibody of the present disclosure agonizes SIRPβ1 activity on CD14-positive monocytes. In some embodiments, an anti-SIRPβ1 antibody of the present disclosure induces respiratory burst in immune cells, such as neutrophils, monocytes, and/or macrophages. In some embodiments, an anti-SIRPβ1 antibody of the present disclosure induces or increases IL-8 expression in monocytes. In some embodiments, an anti-SIRPβ1 antibody of the present disclosure induces or increases TNFα expression in macrophages and/or dendritic cells. In some embodiments, an anti-SIRPβ1 antibody of the present disclosure induces neutrophil-mediated phagocytosis, for example, of tumor cells. In some embodiments, an anti-SIRPβ1 antibody of the present disclosure increases neutrophil-mediated tumor cell clearance. In some embodiments, an anti-SIRPβ1 antibody of the present disclosure increases or enhances anti-tumor properties or activity of neutrophils.

In some embodiments, an anti-SIRPβ1 antibody of the present disclosure recruits immune cells. In some embodiments, an anti-SIRPβ1 antibody of the present disclosure induces syk phosphorylation. In some embodiments, an anti-SIRPβ1 antibody of the present disclosure induces syk phosphorylation when clustered by adjacent cells expressing Fc gamma receptors.

In some embodiments, SIRPβ1 antibody of the present disclosure downregulates SIRPβ1 expression on the surface of a cell. In some embodiments, SIRPβ1 antibody of the present disclosure does not downregulate SIRPβ1 expression on the surface of a cell. In some embodiments, SIRPβ1 antibody of the present disclosure blocks binding of a ligand to SIRPβ1. In some embodiments, SIRPβ1 antibody of the present disclosure does not block binding of a ligand to SIRPβ1.

In some embodiments, an anti-SIRPβ1 antibody is provided that has one or more properties selected from:
  a) binds to human SIRPβ1 isoform 1, but does not bind to human SIRPα;
  b) binds to human SIRPβ1 isoform 1, but does not bind to human SIRPγ;
  c) binds to human SIRPβ1 isoform 1, but does not bind to human SIRPβ1 isoform 3;
  d) binds to human SIRPβ1 isoform 1, but does not bind to mouse SIRPβ1;
  e) binds to human SIRPβ1 isoform 1, but does not bind to cynomolgus monkey SIRPβ1;
  f) agonizes SIRPβ1 activity on CD14-positive monocytes in vitro and/or in vivo;
  g) induces or increases respiratory burst in immune cells, such as neutrophils and/or monocytes in vitro and/or in vivo;
  h) induces or increases IL-8 expression in monocytes in vitro and/or in vivo;
  i) induces or increases TNFα expression in macrophages and/or dendritic cells in vitro and/or in vivo;
  j) induces or increases neutrophil-mediated phagocytosis, for example, of tumor cells in vitro and/or in vivo;
  k) induces or increases neutrophil-mediated tumor cell clearance in vivo;
  l) upregulates TREM2 expression on macrophages in vitro and/or in vivo;
  m) increases viability of macrophages in vitro and/or in vivo, alone and/or in combination with an agonist anti-TREM2 antibody; and
  n) increases viability of dendritic cells in vitro and/or in vivo.

In some embodiments, an anti-SIRPβ1 antibody is provided that has the following properties:
  a) binds to human SIRPβ1 isoform 1, but does not bind to human SIRPα;
  b) binds to human SIRPβ1 isoform 1, but does not bind to human SIRPγ;
  c) binds to human SIRPβ1 isoform 1, but does not bind to human SIRPβ1 isoform 3;
  d) binds to human SIRPβ1 isoform 1, but does not bind to mouse SIRPβ1;
  e) binds to human SIRPβ1 isoform 1, but does not bind to cynomolgus monkey SIRPβ1;
  f) agonizes SIRPβ1 activity on CD14-positive monocytes in vitro and/or in vivo;
  g) induces or increases respiratory burst in immune cells, such as neutrophils and/or monocytes in vitro and/or in vivo;
  h) induces or increases IL-8 expression in monocytes in vitro and/or in vivo;
  i) induces or increases TNFα expression in macrophages and/or dendritic cells in vitro and/or in vivo;
  j) induces or increases neutrophil-mediated phagocytosis, for example, of tumor cells in vitro and/or in vivo;
  o) induces or increases neutrophil-mediated tumor cell clearance in vivo;
  p) upregulates TREM2 expression on macrophages in vitro and/or in vivo;
  q) increases viability of macrophages in vitro and/or in vivo, alone and/or in combination with an agonist anti-TREM2 antibody; and
  k) increases viability of dendritic cells in vitro and/or in vivo.

A. Exemplary Antibodies and Certain Other Antibody Embodiments

In some embodiments, provided herein are anti-SIRPβ1 antibodies comprising at least one, two, three, four, five, or six HVRs selected from (a) HVR-H1 comprising an amino acid sequence of an HVR-H1 shown in Table 4 and/or Table 9; (b) HVR-H2 comprising an amino acid sequence of an HVR-H1 shown in Table 4 and/or Table 9; (c) HVR-H3 comprising an amino acid sequence of an HVR-H1 shown in Table 4 and/or Table 9; (d) HVR-L1 comprising an amino acid sequence of an HVR-H1 shown in Table 3 and/or Table 8; (e) HVR-L2 comprising an amino acid sequence of an HVR-H1 shown in Table 3 and/or Table 8; and (f) HVR-L3 comprising an amino acid sequence of an HVR-H1 shown in Table 3 and/or Table 8.

In some embodiments, provided herein are anti-SIRPβ1 antibodies comprising HVR-H1, HVR-H2, HVR-H3, HVR-L1, HVR-L2, and HVR-L3, wherein: (a) HVR-H1 comprising an amino acid sequence of an HVR-H1 shown in Table 4 and/or Table 9; (b) HVR-H2 comprising an amino acid sequence of an HVR-H2 shown in Table 4 and/or Table 9; (c) HVR-H3 comprising an amino acid sequence of an HVR-H3 shown in Table 4 and/or Table 9; (d) HVR-L1 comprising an amino acid sequence of an HVR-L1 shown in Table 3 and/or Table 8; (e) HVR-L2 comprising an amino acid sequence of an HVR-L2 shown in Table 3 and/or Table 8; and (f) HVR-L3 comprising an amino acid sequence of an HVR-L3 shown in Table 3 and/or Table 8.

In some embodiments, provided herein are anti-SIRPβ1 antibodies comprising six HVRs of an antibody selected from SB-1, SB-2, SB-3, SB-4, SB-5, SB-6, SB-7, SB-8, SB-9, SB-10, SB-11, SB-12, SB-13, SB-14, SB-15, SB-16, SB-17, SB-18, SB-19, SB-20, SB-21, SB-22, SB-23, SB-24, SB-25, SB-26, SB-27, SB-28, SB-29, SB-30, SB-31, SB-32, SB-33, SB-34, SB-35, SB-36, SB-37, SB-38, SB-39, SB-40, SB-41, SB-42, SB-43, SB-44, SB-45, SB-46, SB-47, SB-48, SB-49, SB-50, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Tables 3, 4, 8, and 9).

In some embodiments, provided herein are anti-SIRPβ1 antibodies comprising six HVRs of an antibody selected from SB-1, SB-2, SB-3, SB-4, SB-5, SB-6, SB-7, SB-8, SB-9, SB-14, SB-28, SB-39, SB-40, SB-49, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Tables 3, 4, 8, and 9).

In some embodiments, provided herein are anti-SIRPβ1 antibodies comprising six HVRs of an antibody selected from SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Tables 8 and 9).

In some embodiments, provided herein are anti-SIRPβ1 antibodies comprising six HVRs of an antibody selected from SB-1-3, SB-2-8, and SB-8-13 (shown in Tables 8 and 9).

In some embodiments, provided herein are anti-SIRPβ1 antibodies comprising (a) HVR-H1 comprising the amino acid sequence of SEQ ID NO: 228; (b) HVR-H2 comprising the amino acid sequence of SEQ ID NO: 238; (c) HVR-H3 comprising the amino acid sequence of SEQ ID NO: 125; (d) HVR-L1 comprising the amino acid sequence of SEQ ID NO: 383; (e) HVR-L2 comprising the amino acid sequence of SEQ ID NO: 16; and (f) HVR-L3 comprising the amino acid sequence of SEQ ID NO: 31.

In some embodiments, provided herein are anti-SIRPβ1 antibodies comprising (a) HVR-H1 comprising the amino acid sequence of SEQ ID NO: 229; (b) HVR-H2 comprising the amino acid sequence of SEQ ID NO: 239; (c) HVR-H3 comprising the amino acid sequence of SEQ ID NO: 125; (d) HVR-L1 comprising the amino acid sequence of SEQ ID NO: 383; (e) HVR-L2 comprising the amino acid sequence of SEQ ID NO: 16; and (f) HVR-L3 comprising the amino acid sequence of SEQ ID NO: 31.

In some embodiments, provided herein are anti-SIRPβ1 antibodies comprising (a) HVR-H1 comprising the amino acid sequence of SEQ ID NO: 229; (b) HVR-H2 comprising the amino acid sequence of SEQ ID NO: 240; (c) HVR-H3 comprising the amino acid sequence of SEQ ID NO: 125; (d) HVR-L1 comprising the amino acid sequence of SEQ ID NO: 383; (e) HVR-L2 comprising the amino acid sequence of SEQ ID NO: 16; and (f) HVR-L3 comprising the amino acid sequence of SEQ ID NO: 31.

In some embodiments, provided herein are anti-SIRPβ1 antibodies comprising (a) HVR-H1 comprising the amino acid sequence of SEQ ID NO: 229; (b) HVR-H2 comprising the amino acid sequence of SEQ ID NO: 241; (c) HVR-H3 comprising the amino acid sequence of SEQ ID NO: 125; (d) HVR-L1 comprising the amino acid sequence of SEQ ID NO: 383; (e) HVR-L2 comprising the amino acid sequence of SEQ ID NO: 16; and (f) HVR-L3 comprising the amino acid sequence of SEQ ID NO: 31.

In some embodiments, provided herein are anti-SIRPβ1 antibodies comprising (a) HVR-H1 comprising the amino acid sequence of SEQ ID NO: 230; (b) HVR-H2 comprising the amino acid sequence of SEQ ID NO: 242; (c) HVR-H3 comprising the amino acid sequence of SEQ ID NO: 126; (d) HVR-L1 comprising the amino acid sequence of SEQ ID NO: 383; (e) HVR-L2 comprising the amino acid sequence of SEQ ID NO: 16; and (f) HVR-L3 comprising the amino acid sequence of SEQ ID NO: 32.

In some embodiments, provided herein are anti-SIRPβ1 antibodies comprising (a) HVR-H1 comprising the amino acid sequence of SEQ ID NO: 231; (b) HVR-H2 comprising the amino acid sequence of SEQ ID NO: 243; (c) HVR-H3 comprising the amino acid sequence of SEQ ID NO: 126; (d) HVR-L1 comprising the amino acid sequence of SEQ ID NO: 383; (e) HVR-L2 comprising the amino acid sequence of SEQ ID NO: 16; and (f) HVR-L3 comprising the amino acid sequence of SEQ ID NO: 32.

In some embodiments, provided herein are anti-SIRPβ1 antibodies comprising (a) HVR-H1 comprising the amino acid sequence of SEQ ID NO: 232; (b) HVR-H2 comprising the amino acid sequence of SEQ ID NO: 244; (c) HVR-H3 comprising the amino acid sequence of SEQ ID NO: 126; (d) HVR-L1 comprising the amino acid sequence of SEQ ID NO: 383; (e) HVR-L2 comprising the amino acid sequence of SEQ ID NO: 16; and (f) HVR-L3 comprising the amino acid sequence of SEQ ID NO: 32.

In some embodiments, provided herein are anti-SIRPβ1 antibodies comprising (a) HVR-H1 comprising the amino acid sequence of SEQ ID NO: 99; (b) HVR-H2 comprising the amino acid sequence of SEQ ID NO: 245; (c) HVR-H3 comprising the amino acid sequence of SEQ ID NO: 126; (d) HVR-L1 comprising the amino acid sequence of SEQ ID NO: 383; (e) HVR-L2 comprising the amino acid sequence of SEQ ID NO: 16; and (f) HVR-L3 comprising the amino acid sequence of SEQ ID NO: 32.

In some embodiments, provided herein are anti-SIRPβ1 antibodies comprising (a) HVR-H1 comprising the amino acid sequence of SEQ ID NO: 230; (b) HVR-H2 comprising the amino acid sequence of SEQ ID NO: 242; (c) HVR-H3 comprising the amino acid sequence of SEQ ID NO: 253; (d) HVR-L1 comprising the amino acid sequence of SEQ ID NO: 383; (e) HVR-L2 comprising the amino acid sequence of SEQ ID NO: 16; and (f) HVR-L3 comprising the amino acid sequence of SEQ ID NO: 32.

In some embodiments, provided herein are anti-SIRPβ1 antibodies comprising (a) HVR-H1 comprising the amino acid sequence of SEQ ID NO: 233; (b) HVR-H2 comprising the amino acid sequence of SEQ ID NO: 246; (c) HVR-H3 comprising the amino acid sequence of SEQ ID NO: 131; (d) HVR-L1 comprising the amino acid sequence of SEQ ID NO: 383; (e) HVR-L2 comprising the amino acid sequence of SEQ ID NO: 19; and (f) HVR-L3 comprising the amino acid sequence of SEQ ID NO: 37.

In some embodiments, provided herein are anti-SIRPβ1 antibodies comprising (a) HVR-H1 comprising the amino acid sequence of SEQ ID NO: 234; (b) HVR-H2 comprising the amino acid sequence of SEQ ID NO: 247; (c) HVR-H3 comprising the amino acid sequence of SEQ ID NO: 131; (d) HVR-L1 comprising the amino acid sequence of SEQ ID NO: 383; (e) HVR-L2 comprising the amino acid sequence of SEQ ID NO: 19; and (f) HVR-L3 comprising the amino acid sequence of SEQ ID NO: 37.

In some embodiments, provided herein are anti-SIRPβ1 antibodies comprising (a) HVR-H1 comprising the amino acid sequence of SEQ ID NO: 233; (b) HVR-H2 comprising the amino acid sequence of SEQ ID NO: 248; (c) HVR-H3 comprising the amino acid sequence of SEQ ID NO: 131; (d) HVR-L1 comprising the amino acid sequence of SEQ ID NO: 383; (e) HVR-L2 comprising the amino acid sequence of SEQ ID NO: 19; and (f) HVR-L3 comprising the amino acid sequence of SEQ ID NO: 37.

In some embodiments, provided herein are anti-SIRPβ1 antibodies comprising (a) HVR-H1 comprising the amino acid sequence of SEQ ID NO: 233; (b) HVR-H2 comprising the amino acid sequence of SEQ ID NO: 246; (c) HVR-H3 comprising the amino acid sequence of SEQ ID NO: 254; (d) HVR-L1 comprising the amino acid sequence of SEQ ID NO: 383; (e) HVR-L2 comprising the amino acid sequence of SEQ ID NO: 19; and (f) HVR-L3 comprising the amino acid sequence of SEQ ID NO: 37.

In some embodiments, provided herein are anti-SIRPβ1 antibodies comprising (a) HVR-H1 comprising the amino acid sequence of SEQ ID NO: 235; (b) HVR-H2 comprising the amino acid sequence of SEQ ID NO: 249; (c) HVR-H3 comprising the amino acid sequence of SEQ ID NO: 163; (d) HVR-L1 comprising the amino acid sequence of SEQ ID NO: 2; (e) HVR-L2 comprising the amino acid sequence of SEQ ID NO: 22; and (f) HVR-L3 comprising the amino acid sequence of SEQ ID NO: 69.

In some embodiments, provided herein are anti-SIRPβ1 antibodies comprising (a) HVR-H1 comprising the amino acid sequence of SEQ ID NO: 236; (b) HVR-H2 comprising the amino acid sequence of SEQ ID NO: 250; (c) HVR-H3 comprising the amino acid sequence of SEQ ID NO: 163; (d) HVR-L1 comprising the amino acid sequence of SEQ ID NO: 2; (e) HVR-L2 comprising the amino acid sequence of SEQ ID NO: 22; and (f) HVR-L3 comprising the amino acid sequence of SEQ ID NO: 69.

In some embodiments, provided herein are anti-SIRPβ1 antibodies comprising (a) HVR-H1 comprising the amino acid sequence of SEQ ID NO: 237; (b) HVR-H2 comprising the amino acid sequence of SEQ ID NO: 251; (c) HVR-H3 comprising the amino acid sequence of SEQ ID NO: 163; (d) HVR-L1 comprising the amino acid sequence of SEQ ID NO: 2; (e) HVR-L2 comprising the amino acid sequence of SEQ ID NO: 22; and (f) HVR-L3 comprising the amino acid sequence of SEQ ID NO: 69.

In some embodiments, provided herein are anti-SIRPβ1 antibodies comprising (a) HVR-H1 comprising the amino acid sequence of SEQ ID NO: 236; (b) HVR-H2 comprising the amino acid sequence of SEQ ID NO: 252; (c) HVR-H3 comprising the amino acid sequence of SEQ ID NO: 163; (d) HVR-L1 comprising the amino acid sequence of SEQ ID NO: 2; (e) HVR-L2 comprising the amino acid sequence of SEQ ID NO: 22; and (f) HVR-L3 comprising the amino acid sequence of SEQ ID NO: 69.

In some embodiments, provided herein are anti-SIRPβ1 antibodies comprising at least one, at least two, or all three $V_H$ HVR sequences selected from (a) HVR-H1 comprising an amino acid sequence of an HVR-H1 shown in Table 4 and/or Table 9; (b) HVR-H2 comprising an amino acid sequence of an HVR-H2 shown in Table 4 and/or Table 9; (c) HVR-H3 comprising an amino acid sequence of an HVR-H3 shown in Table 4 and/or Table 9. In some embodiments, an anti-SIRPβ1 antibody comprises HVR-H1, HVR, H2, and HVR-H3 of an antibody selected from SB-1, SB-2, SB-3, SB-4, SB-5, SB-6, SB-7, SB-8, SB-9, SB-10, SB-11, SB-12, SB-13, SB-14, SB-15, SB-16, SB-17, SB-18, SB-19, SB-20, SB-21, SB-22, SB-23, SB-24, SB-25, SB-26, SB-27, SB-28, SB-29, SB-30, SB-31, SB-32, SB-33, SB-34, SB-35, SB-36, SB-37, SB-38, SB-39, SB-40, SB-41, SB-42, SB-43, SB-44, SB-45, SB-46, SB-47, SB-48, SB-49, SB-50, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Tables 4 and 9). In some embodiments, an anti-SIRPβ1 antibody comprises HVR-H1, HVR, H2, and HVR-H3 of an antibody selected from SB-1, SB-2, SB-3, SB-4, SB-5, SB-6, SB-7, SB-8, SB-9, SB-14, SB-28, SB-39, SB-40, SB-49, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Tables 4 and 9). In some embodiments, an anti-SIRPβ1 antibody comprises HVR-H1, HVR, H2, and HVR-H3 of an antibody selected from SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Table 9). In some embodiments, an anti-SIRPβ1 antibody comprises HVR-H1, HVR, H2, and HVR-H3 of an antibody selected from SB-1-3, SB-2-8, and SB-8-13 (shown in Table 9). In some embodiments, an anti-SIRP 1 antibody comprises (a) HVR-H1 comprising the amino acid sequence of SEQ ID NO: 229; (b) HVR-H2 comprising the amino acid sequence of SEQ ID NO: 239; and (c) HVR-H3 comprising the amino acid sequence of SEQ ID NO: 125. In some embodiments, an anti-SIRPβ1 antibody comprises (a) HVR-H1 comprising the amino acid sequence of SEQ ID NO: 231; (b) HVR-H2 comprising the amino acid sequence of SEQ ID NO: 243; and (c) HVR-H3 comprising the amino acid sequence of SEQ ID NO: 126. In some embodiments, an anti-SIRPβ1 antibody comprises (a) HVR-H1 comprising the amino acid sequence of SEQ ID NO: 233; (b) HVR-H2 comprising the amino acid sequence of SEQ ID NO: 246; and (c) HVR-H3 comprising the amino acid sequence of SEQ ID NO: 131.

In some embodiments, provided herein are anti-SIRPβ1 antibodies comprising at least one, at least two, or all three $V_L$ HVR sequences selected from (a) HVR-L1 comprising an amino acid sequence of an HVR-L1 shown in Table 3 and/or Table 8; (b) HVR-L2 comprising an amino acid sequence of an HVR-L2 shown in Table 3 and/or Table 8; (c) HVR-L3 comprising an amino acid sequence of an HVR-L3 shown in Table 3 and/or Table 8. In some embodiments, an anti-SIRPβ1 antibody comprises HVR-L1, HVR, L2, and HVR-L3 of an antibody selected from SB-1, SB-2, SB-3, SB-4, SB-5, SB-6, SB-7, SB-8, SB-9, SB-10, SB-11, SB-12, SB-13, SB-14, SB-15, SB-16, SB-17, SB-18, SB-19, SB-20, SB-21, SB-22, SB-23, SB-24, SB-25, SB-26, SB-27, SB-28, SB-29, SB-30, SB-31, SB-32, SB-33, SB-34, SB-35, SB-36, SB-37, SB-38, SB-39, SB-40, SB-41, SB-42, SB-43, SB-44, SB-45, SB-46, SB-47, SB-48, SB-49, SB-50, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Tables 3 and 8). In some embodiments, an anti-SIRPβ1 antibody comprises HVR-L1, HVR, L2, and HVR-L3 of an antibody selected from SB-1, SB-2, SB-3, SB-4, SB-5, SB-6, SB-7, SB-8, SB-9, SB-14, SB-28, SB-39, SB-40, SB-49, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Tables 3 and 8). In some embodiments, an anti-SIRPβ1 antibody comprises HVR-L1, HVR, L2, and HVR-L3 of an antibody selected from SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Table 8). In some embodiments, an anti-SIRPβ1 antibody comprises HVR-L1, HVR, L2, and HVR-L3 of an antibody selected from SB-1-3, SB-2-8, and SB-8-13 (shown in Table 8). In some embodiments, an anti-SIRPβ1 antibody comprises (a) HVR-L1 comprising the amino acid sequence of SEQ ID NO: 383; (b) HVR-L2 comprising the amino acid sequence of SEQ ID NO: 16; and (c) HVR-L3 comprising the amino acid sequence of SEQ ID NO: 31. In some embodiments, an anti-SIRPβ1 antibody comprises (a) HVR-L1 comprising the amino acid sequence of SEQ ID NO: 383; (b) HVR-L2 comprising the amino acid sequence of SEQ ID NO: 16; and (c) HVR-L3 comprising the amino acid sequence of SEQ ID NO: 32. In some embodiments, an anti-SIRPβ1 antibody comprises (a) HVR-L1 comprising the amino acid sequence of SEQ ID NO: 383; (b) HVR-L2 comprising the amino acid sequence of SEQ ID NO: 19; and (c) HVR-L3 comprising the amino acid sequence of SEQ ID NO: 37.

In some embodiments, provided herein are anti-SIRPβ1 antibodies comprising (a) a $V_H$ domain comprising at least one, at least two, or all three $V_H$ HVR sequences selected from (i) HVR-H1 comprising an amino acid sequence of an HVR-H1 shown in Table 4 and/or Table 9, (ii) HVR-H2 comprising an amino acid sequence of an HVR-H1 shown in Table 4 and/or Table 9, and (iii) HVR-H3 comprising an amino acid sequence of an HVR-H1 shown in Table 4 and/or Table 9; and (b) a $V_L$ domain comprising at least one, at least two, or all three $V_L$ HVR sequences selected from (i) HVR-L1 comprising an amino acid sequence of an HVR-H1 shown in Table 3 and/or Table 8, (ii) HVR-L2 comprising an amino acid sequence of an HVR-H1 shown in Table 3 and/or Table 8, and (iii) HVR-L3 comprising an amino acid sequence of an HVR-H1 shown in Table 3 and/or Table 8.

In some embodiments, provided herein are anti-SIRPβ1 antibodies comprising (a) a $V_H$ domain comprising (i) HVR-H1 comprising an amino acid sequence of an HVR-H1 shown in Table 4 and/or Table 9, (ii) HVR-H2 comprising an amino acid sequence of an HVR-H1 shown in Table 4 and/or Table 9, and (iii) HVR-H3 comprising an amino acid sequence of an HVR-H1 shown in Table 4 and/or Table 9; and (b) a $V_L$ domain comprising (i) HVR-L1 comprising an amino acid sequence of an HVR-H1 shown in Table 3 and/or Table 8, (ii) HVR-L2 comprising an amino acid sequence of an HVR-H1 shown in Table 3 and/or Table 8, and (iii) HVR-L3 comprising an amino acid sequence of an HVR-H1 shown in Table 3 and/or Table 8.

In some embodiments, provided herein are anti-SIRPβ1 antibodies comprising a $V_H$ domain comprising HVR-H1, HVR-H2, and HVR-H2, and a $V_L$ domain comprising HVR-L1, HVR-L2, and HVR-L3, wherein HVR-H1, HVR-H2, HVR-H2, HVR-L1, HVR-L2, and HVR-L3 are the HVRs of an antibody selected from SB-1, SB-2, SB-3, SB-4, SB-5, SB-6, SB-7, SB-8, SB-9, SB-10, SB-11, SB-12, SB-13, SB-14, SB-15, SB-16, SB-17, SB-18, SB-19, SB-20, SB-21, SB-22, SB-23, SB-24, SB-25, SB-26, SB-27, SB-28, SB-29, SB-30, SB-31, SB-32, SB-33, SB-34, SB-35, SB-36, SB-37, SB-38, SB-39, SB-40, SB-41, SB-42, SB-43, SB-44, SB-45, SB-46, SB-47, SB-48, SB-49, SB-50, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Tables 3, 4, 8, and 9).

In some embodiments, provided herein are anti-SIRPβ1 antibodies comprising a $V_H$ domain comprising HVR-H1, HVR-H2, and HVR-H2, and a $V_L$ domain comprising HVR-L1, HVR-L2, and HVR-L3, wherein HVR-H1, HVR-H2, HVR-H2, HVR-L1, HVR-L2, and HVR-L3 are the HVRs of an antibody selected from SB-1, SB-2, SB-3, SB-4, SB-5, SB-6, SB-7, SB-8, SB-9, SB-14, SB-28, SB-39, SB-40, SB-49, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Tables 3, 4, 8, and 9).

In some embodiments, provided herein are anti-SIRPβ1 antibodies comprising a $V_H$ domain comprising HVR-H1, HVR-H2, and HVR-H2, and a $V_L$ domain comprising HVR-L1, HVR-L2, and HVR-L3, wherein HVR-H1, HVR-H2, HVR-H2, HVR-L1, HVR-L2, and HVR-L3 are the HVRs of an antibody selected from SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21 (shown in Tables 8 and 9).

In some embodiments, provided herein are anti-SIRPβ1 antibodies comprising a $V_H$ domain comprising HVR-H1, HVR-H2, and HVR-H2, and a $V_L$ domain comprising HVR-L1, HVR-L2, and HVR-L3, wherein HVR-H1, HVR-H2, HVR-L1, HVR-L2, and HVR-L3 are the HVRs of an antibody selected from SB-1-3, SB-2-8, and SB-8-13 (shown in Tables 8 and 9).

In some embodiments, provided herein are anti-SIRPβ1 antibodies comprising (a) a $V_H$ domain comprising (i) HVR-H1 comprising the amino acid sequence of SEQ ID NO: 229; (ii) HVR-H2 comprising the amino acid sequence of SEQ ID NO: 239; (iii) HVR-H3 comprising the amino acid sequence of SEQ ID NO: 125; and (b) a $V_L$ domain comprising (iv) HVR-L1 comprising the amino acid sequence of SEQ ID NO: 383; (v) HVR-L2 comprising the amino acid sequence of SEQ ID NO: 16; and (vi) HVR-L3 comprising the amino acid sequence of SEQ ID NO: 31.

In some embodiments, provided herein are anti-SIRPβ1 antibodies comprising (a) a $V_H$ domain comprising (i) HVR-H1 comprising the amino acid sequence of SEQ ID NO: 231; (ii) HVR-H2 comprising the amino acid sequence of SEQ ID NO: 243; (iii) HVR-H3 comprising the amino acid sequence of SEQ ID NO: 126; and (b) a $V_L$ domain comprising (iv) HVR-L1 comprising the amino acid sequence of SEQ ID NO: 383; (v) HVR-L2 comprising the amino acid sequence of SEQ ID NO: 16; and (vi) HVR-L3 comprising the amino acid sequence of SEQ ID NO: 32.

In some embodiments, provided herein are anti-SIRPβ1 antibodies comprising (a) a $V_H$ domain comprising (i) HVR-H1 comprising the amino acid sequence of SEQ ID NO: 233; (ii) HVR-H2 comprising the amino acid sequence of SEQ ID NO: 246; (iii) HVR-H3 comprising the amino acid sequence of SEQ ID NO: 131; and (b) a $V_L$ domain comprising (iv) HVR-L1 comprising the amino acid sequence of SEQ ID NO: 383; (v) HVR-L2 comprising the amino acid sequence of SEQ ID NO: 19; and (vi) HVR-L3 comprising the amino acid sequence of SEQ ID NO: 37.

In another aspect, an anti-SIRPβ1 antibody comprises a heavy chain variable domain ($V_H$) sequence having at least 90%, 91%, 92%, 93%, 94%, 95%, 96%, 97%, 98%, 99%, or 100% sequence identity to the amino acid sequence of SEQ ID NO: 268, 270, 272, 274, 276, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 366, 367, 368, 369, 371, 372, 373, 374, 375, 376, 377, 378, 379, 380, 381, or 382. In certain embodiments, a $V_H$ sequence having at least 90%, 91%, 92%, 93%, 94%, 95%, 96%, 97%, 98%, or 99% identity to the amino acid sequence of SEQ ID NO: 268, 270, 272, 274, 276, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, or 365 contains substitutions (e.g., conservative substitutions), insertions, or deletions relative to the reference sequence, but an anti-SIRPβ1 antibody comprising that sequence retains the ability to bind to SIRPβ1. In certain embodiments, a total of 1 to 10 amino acids have been substituted, inserted, and/or deleted in SEQ ID NO: 268, 270, 272, 274, 276, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 366, 367, 368, 369, 371, 372, 373, 374, 375, 376, 377, 378, 379, 380, 381, or 382. In certain embodiments, a total of 1 to 5 amino acids have been substituted, inserted and/or deleted in SEQ ID NO: 268, 270, 272, 274, 276, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 366, 367, 368, 369, 371, 372, 373, 374, 375, 376, 377, 378, 379, 380, 381, or 382. In certain embodiments, substitutions, insertions, or deletions occur in regions outside the HVRs (i.e., in the FRs). Optionally, the anti-SIRPβ1 antibody comprises the $V_H$ sequence of SEQ ID NO: 268, 270, 272, 274, 276, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 366, 367, 368, 369, 371, 372, 373, 374, 375, 376, 377, 378, 379, 380, 381, or 382, including post-translational modifications of that sequence. In a particular embodiment, the $V_H$ comprises one, two or three HVRs selected from: (a) HVR-H1 comprising an amino acid sequence of an HVR-H1 shown in Table 4 and/or Table 9; (b) HVR-H2 comprising an amino acid sequence of an HVR-H1 shown in Table 4 and/or Table 9; (c) HVR-H3 comprising an amino acid sequence of an HVR-H1 shown in Table 4 and/or Table 9.

In another aspect, an anti-SIRPβ1 antibody is provided, wherein the antibody comprises a light chain variable domain ($V_L$) having at least 90%, 91%, 92%, 93%, 94%, 95%, 96%, 97%, 98%, 99%, or 100% sequence identity to the amino acid sequence of SEQ ID NO: 267, 269, 271, 273, 275, 277, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, or 370. In certain embodiments, a $V_L$ sequence having at least 90%, 91%, 92%, 93%, 94%, 95%, 96%, 97%, 98%, or 99% identity to the amino acid sequence of SEQ ID NO: 267, 269, 271, 273, 275, 277, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, or 370 contains substitutions (e.g., conservative substitutions), insertions, or deletions relative to the reference sequence, but an anti-SIRPβ1 antibody comprising that sequence retains the ability to bind to SIRPβ1. In some embodiments, a total of 1 to 10 amino acids have been substituted, inserted and/or deleted in SEQ ID NO: 267, 269, 271, 273, 275, 277, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, or 370. In certain embodiments, a total of 1 to 5 amino acids have been substituted, inserted and/or deleted in SEQ ID NO: 267, 269, 271, 273, 275, 277, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, or 370. In certain embodiments, the substitutions, insertions, or deletions occur in regions outside the HVRs (i.e., in the FRs). Optionally, the anti-SIRPβ1 antibody comprises the $V_L$ sequence of SEQ ID NO: 267, 269, 271, 273, 275, 277, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, or 370, including post-translational modifications of that sequence. In a particular embodiment, the $V_L$ comprises one, two or three HVRs selected from (a) HVR-L1 comprising an amino acid sequence of an HVR-H1 shown in Table 3 and/or Table 8; (b) HVR-L2 comprising an amino acid sequence of an HVR-H1 shown in Table 3 and/or Table 8; and (c) HVR-L3 comprising an amino acid sequence of an HVR-H1 shown in Table 3 and/or Table 8.

In some embodiments, the anti-SIRPβ1 antibody is provided, wherein the antibody comprises a $V_H$ as in any of the embodiments provided above, and a $V_L$ as in any of the embodiments provided above. In some embodiments, provided herein are anti-SIRPβ1 antibodies, wherein the antibody comprises a $V_H$ as in any of the embodiments provided above, and a $V_L$ as in any of the embodiments provided above. In one embodiment, the antibody comprises a $V_H$ sequence selected from SEQ ID NO: 268, 270, 272, 274, 276, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 366, 367, 368, 369, 371, 372, 373, 374, 375, 376, 377, 378, 379, 380, 381, and 382; and $V_L$ sequence selected from SEQ ID NO: 267, 269, 271, 273, 275, 277, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, and 370, including post-translational modifications of those sequences. In some embodiments, the antibody comprises the $V_H$ sequence and $V_L$ sequence of an antibody selected from SB-1, SB-2, SB-3, SB-4, SB-5, SB-6, SB-7, SB-8, SB-9, SB-10, SB-11, SB-12, SB-13, SB-14, SB-15, SB-16, SB-17, SB-18, SB-19, SB-20, SB-21, SB-22, SB-23, SB-24, SB-25, SB-26, SB-27, SB-28, SB-29, SB-30, SB-31, SB-32, SB-33, SB-34, SB-35, SB-36, SB-37, SB-38, SB-39, SB-40, SB-41, SB-42, SB-43, SB-44, SB-45, SB-46, SB-47, SB-48, SB-49, SB-50, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody comprises the $V_H$ sequence and $V_L$ sequence of an antibody selected from SB-1, SB-2, SB-3, SB-4, SB-5, SB-6, SB-7, SB-8, SB-9, SB-14, SB-28, SB-39, SB-40, SB-49, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody comprises the $V_H$ sequence and $V_L$ sequence of an antibody selected from SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody comprises the $V_H$ sequence and $V_L$ sequence of an antibody selected from SB-1-3, SB-2-8, and SB-8-13. In some embodiments, the antibody comprises the $V_H$ sequence of SEQ ID NO: 367 and $V_L$ sequence of SEQ ID NO: 267. In some embodiments, the antibody comprises the $V_H$ sequence of SEQ ID NO: 372 and $V_L$ sequence of SEQ ID NO: 370. In some embodiments, the antibody comprises the $V_H$ sequence of SEQ ID NO: 376 and $V_L$ sequence of SEQ ID NO: 280.

In some embodiments, an anti-SIRPβ1 antibody competes for binding with an antibody comprising a $V_H$ sequence selected from SEQ ID NO: 268, 270, 272, 274, 276, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 366, 367, 368, 369, 371, 372, 373, 374, 375, 376, 377, 378, 379, 380, 381, and 382, and a $V_L$ sequence selected from SEQ ID NO: 267, 269, 271, 273, 275, 277, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, and 370. In some embodiments, an anti-SIRPβ1 antibody competes for binding with an antibody selected from SB-1, SB-2, SB-3, SB-4, SB-5, SB-6, SB-7, SB-8, SB-9, SB-10, SB-11, SB-12, SB-13, SB-14, SB-15, SB-16, SB-17, SB-18, SB-19, SB-20, SB-21, SB-22, SB-23, SB-24, SB-25, SB-26, SB-27, SB-28, SB-29, SB-30, SB-31, SB-32, SB-33, SB-34, SB-35, SB-36, SB-37, SB-38, SB-39, SB-40, SB-41, SB-42, SB-43, SB-44, SB-45, SB-46, SB-47, SB-48, SB-49, SB-50, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, an anti-SIRPβ1 antibody competes for binding with an antibody selected from SB-1, SB-2, SB-3, SB-4, SB-5, SB-6, SB-7, SB-8, SB-9, SB-14, SB-28, SB-39, SB-40, SB-49, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, an anti-SIRPβ1 antibody competes for binding with an antibody selected from SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, an anti-SIRPβ1 antibody competes for binding with an antibody selected from SB-1-3, SB-2-8, and SB-8-13. In some embodiments, an anti-SIRPβ1 antibody competes for binding with an antibody comprising the $V_H$ sequence of SEQ ID NO: 367 and $V_L$ sequence of SEQ ID NO: 267. In some embodiments, an anti-SIRPβ1 antibody competes for binding with an antibody comprising the $V_H$ sequence of SEQ ID NO: 372 and $V_L$ sequence of SEQ ID NO: 370. In some embodiments, an anti-SIRPβ1 antibody competes for binding with an antibody comprising the $V_H$ sequence of SEQ ID NO: 376 and $V_L$ sequence of SEQ ID NO: 280.

In some embodiments, the antibody binds to an epitope of human SIRPβ1 that is the same as or overlaps with the epitope bound by an anti-SIRPβ1 antibody comprising a $V_H$ sequence selected from SEQ ID NO: 268, 270, 272, 274, 276, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 366, 367, 368, 369, 371, 372, 373, 374, 375, 376, 377, 378, 379, 380, 381, and 382, and a $V_L$ sequence selected from SEQ ID NO: 267, 269, 271, 273, 275, 277, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, and 370. In some embodiments, the antibody binds to an epitope of human SIRPβ1 that is the same as or overlaps with the epitope bound by an anti-SIRPβ1 antibody selected from SB-1, SB-2, SB-3, SB-4, SB-5, SB-6, SB-7, SB-8, SB-9, SB-10, SB-11, SB-12, SB-13, SB-14, SB-15, SB-16, SB-17, SB-18, SB-19, SB-20, SB-21, SB-22, SB-23, SB-24, SB-25, SB-26, SB-27, SB-28, SB-29, SB-30, SB-31, SB-32, SB-33, SB-34, SB-35, SB-36, SB-37, SB-38, SB-39, SB-40, SB-41, SB-42, SB-43, SB-44, SB-45, SB-46, SB-47, SB-48, SB-49, SB-50, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21.

In some embodiments, the antibody binds to an epitope of human SIRPβ1 that is the same as or overlaps with the epitope bound by an anti-SIRPβ1 antibody selected from SB-1, SB-2, SB-3, SB-4, SB-5, SB-6, SB-7, SB-8, SB-9, SB-14, SB-28, SB-39, SB-40, SB-49, SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody binds to an epitope of human SIRPβ1 that is the same as or overlaps with the epitope bound by an anti-SIRPβ1 antibody selected from SB-1-2, SB-1-3, SB-1-4, SB-1-5, SB-2-7, SB-2-8, SB-2-9, SB-2-10, SB-2-11, SB-8-13, SB-8-14, SB-8-15, SB-8-16, SB-40-18, SB-40-19, SB-40-20, and SB-40-21. In some embodiments, the antibody binds to an epitope of human SIRPβ1 that is the same as or overlaps with the epitope bound by an anti-SIRPβ1 antibody selected from SB-1-3, SB-2-8, and SB-8-13. In some embodiments, an anti-SIRPβ1 antibody binds to an epitope of human SIRPβ1 that is the same as or overlaps with the epitope bound by an anti-SIRPβ1 antibody comprising the $V_H$ sequence of SEQ ID NO: 367 and $V_L$ sequence of SEQ ID NO: 267. In some embodiments, an anti-SIRPβ1 antibody binds to an epitope of human SIRPβ1 that is the same as or overlaps with the epitope bound by an anti-SIRPβ1 antibody comprising the $V_H$ sequence of SEQ ID NO: 372 and $V_L$ sequence of SEQ ID NO: 370. In some embodiments, an anti-SIRPβ1 antibody binds to an epitope of human SIRPβ1 that is the same as or overlaps with the epitope bound by an anti-SIRPβ1 antibody comprising the $V_H$ sequence of SEQ ID NO: 376 and $V_L$ sequence of SEQ ID NO: 280. In some embodiments, the epitope of human SIRPβ1 is the same epitope as bound by an anti-SIRPβ1 antibody.

In some embodiments, an anti-SIRPβ1 antibody binds to an epitope within amino acids 30 to 148 of SEQ ID NO: 1. In some embodiments, an anti-SIRPβ1 antibody binds to an epitope within amino acids 30 to 136 of SEQ ID NO: 1. In some embodiments, an anti-SIRPβ1 antibody binds to an epitope within amino acids 30 to 80 of SEQ ID NO: 1. In some embodiments, an anti-SIRPβ1 antibody binds to an epitope within amino acids 40 to 90 of SEQ ID NO: 1. In some embodiments, an anti-SIRPβ1 antibody binds to an epitope within amino acids 50 to 100 of SEQ ID NO: 1. In some embodiments, an anti-SIRPβ1 antibody binds to an epitope within amino acids 60 to 110 of SEQ ID NO: 1. In some embodiments, an anti-SIRPβ1 antibody binds to an epitope within amino acids 70 to 120 of SEQ ID NO: 1. In some embodiments, an anti-SIRPβ1 antibody binds to an epitope within amino acids 80 to 130 of SEQ ID NO: 1. In some embodiments, an anti-SIRPβ1 antibody binds to an epitope within amino acids 90 to 140 of SEQ ID NO: 1.

In some embodiments, the anti-SIRPβ1 antibody according to any of the above embodiments is a monoclonal antibody, including a humanized and/or human antibody. In some embodiments, the anti-SIRPβ1 antibody is an antibody fragment, e.g., a Fv, Fab, Fab', scFv, diabody, or F(ab')$_2$ fragment. In some embodiments, the anti-SIRPβ1 antibody is a substantially full-length antibody, e.g., an IgG1 antibody, IgG2a antibody or other antibody class or isotype as defined herein.

In some embodiments, an anti-SIRPβ1 antibody according to any of the above embodiments may incorporate any of the features, singly or in combination, as described in Sections 1-7 below:

(1) Anti-SIRPβ1 Antibody Binding Affinity

In some embodiments of any of the antibodies provided herein, the antibody has a dissociation constant ($K_D$) of <1 μM, <100 nM, <10 nM, <1 nM, <0.1 nM, <0.01 nM, or <0.001 nM (e.g., $10^{-8}$ M or less, e.g., from $10^{-8}$ M to $10^{-13}$ M, e.g., from $10^{-9}$ M to $10^{-13}$ M). Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. In one embodiment, $K_D$ is measured by a radiolabeled antigen binding assay (RIA). In some embodiments, an RIA is performed with the Fab version of an antibody of interest and its antigen, for example as described in Chen et al. J. Mol. Biol. 293:865-881(1999)). In some embodiments, $K_D$ is measured using a BIACORE surface plasmon resonance assay, for example, an assay using a BIACORE-2000 or a BIACORE-3000 (BIAcore, Inc., Piscataway, NJ) is performed at 25° C. with immobilized antigen CM5 chips at ~10 response units (RU). In some embodiments, $K_D$ is measured using a ForteBio Octet® Red384 system (ForteBio, Menlo Park, CA), for example, as discussed in the examples herein.

In some embodiments, the $K_D$ is determined using a monovalent antibody (e.g., a Fab) or a full-length antibody. In some embodiments, the $K_D$ is determined using a full-length antibody in a monovalent form.

(2) Antibody Fragments

In some embodiments of any of the antibodies provided herein, the antibody antibodies is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. Nat. Med. 9:129-134 (2003). For a review of scFv fragments, see, e.g., WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP404097; WO 1993/01161; Hudson et al. Nat. Med. 9:129-134 (2003). Triabodies and tetrabodies are also described in Hudson et al. Nat. Med. 9:129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

(3) Chimeric and Humanized Antibodies

In some embodiments of any of the antibodies provided herein, the antibody is a chimeric antibody. Certain chimeric antibodies are described, e.g., in U.S. Pat. No. 4,816,567. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments of any of the antibodies provided herein, the antibody is a humanized antibody. Typically, a non-human antibody is humanized to reduce immunogenicity to humans, while retaining the specificity and affinity of the parental non-human antibody. In certain embodiments, a humanized antibody is substantially non-immunogenic in humans. In certain embodiments, a humanized antibody has substantially the same affinity for a target as an antibody from another species from which the humanized antibody is derived. See, e.g., U.S. Pat. Nos. 5,530,101, 5,693,761; 5,693,762; and 5,585,089. In certain embodiments, amino acids of an antibody variable domain that can be modified without diminishing the native affinity of the antigen binding domain while reducing its immunogenicity are identified. See, e.g., U.S. Pat. Nos. 5,766,886 and 5,869,619. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. Front. Biosci. 13:161 9-1633 (2008), and are further described, e.g., in U.S. Pat. Nos. 5,821,337, 7,527,791, 6,982,321, and 7,087,409. Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA 89:4285 (1992); and Presta et al., J. Immunol. 151:2623 (1993)); human mature (somatically mutated) framework regions or human germline framework regions (see, e.g., Almagro and Fransson Front. Biosci. 13:1619-1633 (2008)); and framework regions derived from screening FR libraries (see, e.g., Baca et al. J. Biol. Chem. 272:10678-10684 (1997) and Rosok et al. J. Biol. Chem. 271:22611-22618 (1996)).

(4) Human Antibodies

In some embodiments of any of the antibodies provided herein, the antibody is a human antibody. Human antibodies can be produced using various techniques known in the art. Human antibodies are described generally in van Dijk et al. Curr. Opin. Pharmacol. 5:368-74 (2001) and Lonberg Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human MAbs with the desired specificity can be produced and selected. Certain exemplary methods are described in U.S. Pat. No. 5,545,807, EP 546073, and EP 546073. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.* 133:3001 (1984) and Boerner et al. *J. Immunol.* 147:86 (1991)). Human antibodies generated via human B-cell hybridoma technology are also described in Li et al. *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers et al. *Histology and Histopathology* 20(3):927-937 (2005) and Vollmers et al. *Methods and Findings in Experimental and Clinical Pharmacology* 27(3): 185-91 (2005). Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

In some embodiments of any of the antibodies provided herein, the antibody is a human antibody isolated by in vitro methods and/or screening combinatorial libraries for antibodies with the desired activity or activities. Suitable examples include but are not limited to phage display (CAT, Morphosys, Dyax, Biosite/Medarex, Xoma, Symphogen, Alexion (formerly Proliferon), Affimed) ribosome display (CAT), yeast-based platform technology (Adimab), and the like. In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.* 12: 433-455 (1994). For example, a variety of methods are known in the art for generating phage display libraries and screening such libraries for antibodies possessing the desired binding characteristics. See also Sidhu et al. *J. Mol. Biol.* 338(2): 299-310, 2004; Lee et al. *J. Mol. Biol.* 340(5): 1073-1093, 2004; Fellouse *Proc. Natl. Acad. Sci. USA* 101(34):12467-12472 (2004); and Lee et al. *J. Immunol. Methods* 284(-2): 119-132 (2004). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al. EMBO J. 12: 725-734 (1993). Finally, naive libraries can also be made synthetically by cloning unrearranged V-gene segments from stem cells, and using PCR primers comprising random sequence to encode the highly variable HVR3 regions and to accomplish rearrangement in vitro, as described by Hoogenboom et al. *J. Mol. Biol.,* 227: 381-388, 1992. Patent publications describing human antibody phage libraries include, for example: U.S. Pat. No. 5,750,373, and US Patent Publication Nos. 2007/0292936 and 2009/0002360. Antibodies isolated from human antibody libraries are considered human antibodies or human antibody fragments herein.

(5) Constant Regions Including Fc Regions

In some embodiments of any of the antibodies provided herein, the antibody comprises an Fc. In some embodiments, the Fc is a human IgG1, IgG2, IgG3, and/or IgG4 isotype. In some embodiments, the antibody is of the IgG class, the IgM class, or the IgA class.

In certain embodiments of any of the antibodies provided herein, the antibody has an IgG2 isotype. In some embodiments, the antibody contains a human IgG2 constant region. In some embodiments, the human IgG2 constant region includes an Fc region. In some embodiments, the antibody induces the one or more SIRPβ1 activities or independently of binding to an Fc receptor. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG4 isotype. In some embodiments, the antibody contains a human IgG4 constant region. In some embodiments, the human IgG4 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has a hybrid IgG2/4 isotype. In some embodiments, the antibody includes an amino acid sequence comprising amino acids 118 to 260 according to EU numbering of human IgG2 and amino acids 261-447 according to EU numbering of human IgG4 (WO 1997/11971; WO 2007/106585).

In some embodiments, the Fc region increases clustering without activating complement as compared to a corresponding antibody comprising an Fc region that does not comprise the amino acid substitutions. In some embodiments, the antibody induces one or more activities of a target specifically bound by the antibody. In some embodiments, the antibody binds to SIRPβ1.

It may also be desirable to modify an anti-SIRPβ1 antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII to reduce Antibody-dependent cell-mediated cytotoxicity. In some embodiments, the effector function is impaired by removing N-glycosylation of the Fc region (e.g., in the $C_H2$ domain of IgG) of the antibody. In some embodiments, the effector function is impaired by modifying regions such as 233-236, 297, and/or 327-331 of human IgG as described in WO 99/58572 and Armour et al. *Molecular Immunology* 40: 585-593 (2003); Reddy et al. *J. Immunology* 164:1925-1933 (2000). In other embodiments, it may also be desirable to modify an anti-SIRPβ1 antibody of the present disclosure to modify effector function to increase finding selectivity toward the ITIM-containing FcγRIIb (CD32b) to increase clustering of SIRPβ1 antibodies on adjacent cells without activating humoral responses including Antibody-dependent cell-mediated cytotoxicity and antibody-dependent cellular phagocytosis.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule. Other amino acid sequence modifications.

(6) Multispecific Antibodies

Multispecific are antibodies that have binding specificities for at least two different epitopes, including those on the same or another polypeptide (e.g., one or more SIRPβ1 polypeptides of the present disclosure). In some embodiments, the multispecific antibody is a bispecific antibody. In some embodiments, the multispecific antibody is a trispecific antibody. In some embodiments, the multispecific antibody is a tetraspecific antibody. Such antibodies can be derived from full-length antibodies or antibody fragments (e.g., F(ab')$_2$ bispecific antibodies). In some embodiments, the multispecific antibody comprises a first antigen binding region which binds to first site on SIRPβ1 and comprises a second antigen binding region which binds to a second site on SIRPβ1. In some embodiment, the multispecific antibodies comprises a first antigen binding region which binds to SIRPβ1 and a second antigen binding region that binds to a second polypeptide.

Provided herein are multispecific antibodies comprises a first antigen binding region, wherein the first antigen binding region comprises the six HVRs of an antibody described herein, which binds to SIRPβ1 and a second antigen binding region that binds to a second polypeptide. In some embodiments, the first antigen binding region comprises the V$_H$ or V$_L$ of an antibody described herein.

In some embodiments of any of the multispecific antibodies, the second polypeptide is an antigen facilitating transport across the blood-brain-barrier. In some embodiments, and antibody herein is conjugated to a peptide that facilitates transport across the blood-brain barrier. Numerous antigens and peptides are known in the art that facilitate transport across the blood-brain barrier (see, e.g., Gabathuler R. *Neurobiol. Dis.* 37:48-57 (2010)). Such second antigens and peptides include, without limitation, transferrin receptor (TR), insulin receptor (HIR), insulin-like growth factor receptor (IGFR), low-density lipoprotein receptor related proteins 1 and 2 (LPR-1 and 2), diphtheria toxin receptor, including CRM197 (a non-toxic mutant of diphtheria toxin), TMEM 30(A) (Flippase), protein transduction domains such as TAT, Syn-B, or penetratin, poly-arginine or generally positively charged peptides, Angiopep peptides such as ANG1005 (see, e.g., Gabathuler, 2010), and other cell surface proteins that are enriched on blood-brain barrier endothelial cells (see, e.g., Daneman et al. *PLoS One* 5(10): e13741 (2010)). In some embodiments, the second polypeptide is transferrin.

In some embodiments of any of the multispecific antibodies, the second polypeptide is a disease-causing protein selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein A1, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides. In some embodiments, the second polypeptide is Tau. In some embodiments, the second polypeptide is Aβ. In some embodiments, the second polypeptide is TREM2. In some embodiments, the second polypeptide is α-synuclein.

In some embodiments of any of the multispecific antibodies, the second polypeptide is a ligand and/or protein expressed on immune cells, wherein the ligand and/or protein is selected from CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine.

In some embodiments of any of the multispecific antibodies, the second polypeptide is a protein, lipid, polysaccharide, or glycolipid expressed on one or more tumor cells and any combination thereof.

In some embodiments of any of the multispecific antibodies, the second polypeptide is an immunoglobulin-like receptor, such as TREM2. In some embodiments of any of the multispecific antibodies, the second polypeptide is an immunoglobulin-like receptor expressed on myeloid lineage cells.

The multivalent antibody contains at least one polypeptide chain (and preferably two polypeptide chains), wherein the polypeptide chain or chains comprise two or more variable domains. For instance, the polypeptide chain or chains may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise V$_H$-C$_H$1-flexible linker-V$_H$-C$_H$1-Fc region chain; or V$_H$-C$_H$1-V$_H$-C$_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Techniques for making multispecific antibodies include, but are not limited to, recombinant co-expression of two immunoglobulin heavy chain-light chain pairs having different specificities (see Milstein and Cuello *Nature* 305: 537 (1983), WO 93/08829, and Traunecker et al. *EMBO J.* 10:3655 (1991)), and "knob-in-hole" engineering (see, e.g., U.S. Pat. No. 5,731,168). See also WO 2013/026833 (CrossMab). Multi-specific antibodies may also be made by engineering electrostatic steering effects for making antibody Fc-heterodimeric molecules (WO 2009/089004A1); cross-linking two or more antibodies (see, e.g., U.S. Pat. No. 4,676,980); using leucine; using "diabody" technology for making bispecific antibody fragments (see, e.g., Hollinger et al. *Proc. Natl. Acad. Sci. USA* 90:6444-6448 (1993)); and using single-chain Fv (scFv) dimers (see, e.g., Gruber et al. *J Immunol.* 152:5368 (1994)); and preparing trispecific antibodies as described, e.g., in Tutt et al. *J Immunol.* 147: 60 (1991).

Engineered antibodies with three or more functional antigen binding sites, including "Octopus antibodies," are also included herein (see, e.g., US 2006/0025576). The antibody herein also includes a "Dual Acting FAb" or "DAF" comprising an antigen binding site that binds to multiple SIRPβ1 (see, US 2008/0069820, for example).

(7) Antibody Variants

In some embodiments of any of the antibodies provided herein, amino acid sequence variants of the antibodies are contemplated. For example, it may be desirable to improve the binding affinity and/or other biological properties of the antibody.

(i) Substitution, Insertion, and Deletion Variants

In some embodiments of any of the antibodies provided herein, antibody variants having one or more amino acid substitutions are provided. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody.

TABLE 1

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the polypeptide or antibody described herein, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al. *J. Mol. Biol.,* 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0+1); aspartate (+3.0+1); glutamate (+3.0+1); serine (+0.3); asparagine (+0.2); glutamine (+0.2); glycine (0); threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within +2 is included, in certain embodiments, those which are within +1 are included, and in certain embodiments, those within +0.5 are included. One can also identify epitopes from primary amino acid sequences on the basis of hydrophilicity. These regions are also referred to as "epitopic core regions".

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

Amino acid sequence insertions include amino- and/or carboxyl-terminal fusions ranging in length from one residue to polypeptides comprising a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

(ii) Glycosylation Variants

In some embodiments of any of the antibodies provided herein, the antibody is altered to increase or decrease the extent to which the antibody is glycosylated. Addition or deletion of glycosylation sites to an antibody may be conveniently accomplished by altering the amino acid sequence such that one or more glycosylation sites is created or removed.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 according to Kabat numbering of the CH2 domain of the Fc region. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. See, e.g., US Patent Publication Nos. 2003/0157108 and 2004/0093621. Examples of publications related to "defucosylated" or "fucose-deficient" antibody variants include: US 2003/0157108; US 2003/0115614; US 2002/0164328; US 2004/0093621; US 2004/0132140; US 2004/0110704; US 2004/0110282; US 2004/0109865; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Led 3 CHO cells deficient in protein fucosylation (Ripka et al. *Arch. Biochem. Biophys.* 249:533-545 (1986); US 2003/0157108), and knockout cell lines, such as alpha-1,6-fucosyltransferase gene, FUT8, knockout CHO cells (see, e.g., Yamane-Ohnuki et al. *Biotech. Bioeng.* 87: 614 (2004) and Kanda et al. *Biotechnol. Bioeng.* 94(4):680-688 (2006)).

(iii) Modified Constant Regions

In some embodiments of any of the antibodies provided herein, the antibody Fe is an antibody Fe isotype and/or modification. In some embodiments, the antibody Fe isotype and/or modification is capable of binding to Fe gamma receptor.

In some embodiments of any of the antibodies provided herein, the modified antibody Fe is an IgG1 modified Fc. In some embodiments, the IgG1 modified Fc comprises one or more modifications. For example, in some embodiments, the IgG1 modified Fc comprises one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) *R. J Biol. Chem.* 276, 6591-6604), L234A, L235A (Hutchins et al. (1995) *Proc Natl Acad Sci USA*, 92:11980-11984; Alegre et al., (1994) *Transplantation* 57:1537-1543. 31; Xu et al., (2000) *Cell Immunol,* 200:16-26), G237A (Alegre et al. (1994) *Transplantation* 57:1537-1543. 31; Xu et al. (2000) *Cell Immunol,* 200:16-26), C226S, C229S, E233P, L234V, L234F, L235E (McEarchern et al., (2007) *Blood,* 109:1185-1192), P331S (Sazinsky et al., (2008) *Proc Natl Acad Sci USA* 2008, 105:20167-20172), S267E, L328F, A330L, M252Y, S254T, and/or T256E, where the amino acid position is according to the EU numbering convention.

In some embodiments of any of the IgG1 modified Fe, the Fc comprises N297A mutation according to EU numbering. In some embodiments of any of the IgG1 modified Fe, the Fc comprises D265A and N297A mutations according to EU numbering. In some embodiments of any of the IgG1 modified Fe, the Fc comprises D270A mutations according to EU numbering. In some embodiments, the IgG1 modified Fc comprises L234A and L235A mutations according to EU numbering. In some embodiments of any of the IgG1 modified Fe, the Fc comprises L234A and G237A mutations according to EU numbering. In some embodiments of any of the IgG1 modified Fe, the Fc comprises L234A, L235A and G237A mutations according to EU numbering. In some embodiments of any of the IgG1 modified Fe, the Fc comprises one or more (including all) of P238D, L328E, E233, G237D, H268D, P271G and A330R mutations according to EU numbering. In some embodiments of any of the IgG1 modified Fe, the Fc comprises one or more of S267E/L328F mutations according to EU numbering. In some embodiments of any of the IgG1 modified Fe, the Fc comprises P238D, L328E, E233D, G237D, H268D, P271G and A330R mutations according to EU numbering. In some embodiments of any of the IgG1 modified Fe, the Fc comprises P238D, L328E, G237D, H268D, P271G and A330R mutations according to EU numbering. In some embodiments of any of the IgG1 modified Fe, the Fc comprises P238D, S267E, L328E, E233D, G237D, H268D, P271G and A330R mutations according to EU numbering. In some embodiments of any of the IgG1 modified Fe, the Fc comprises P238D, S267E, L328E, G237D, H268D, P271G and A330R mutations according to EU numbering. In some embodiments of any of the IgG1 modified Fe, the Fc comprises C226S, C229S, E233P, L234V, and L235A mutations according to EU numbering. In some embodiments of any of the IgG1 modified Fe, the Fc comprises L234F, L235E, and P331S mutations according to EU numbering. In some embodiments of any of the IgG1 modified Fe, the Fc comprises S267E and L328F mutations according to EU numbering. In some embodiments of any of the IgG1 modified Fc, the Fc comprises S267E mutations according to EU numbering. In some embodiments of any of the IgG1 modified Fc, the Fc comprises a substitute of the constant heavy 1 (CH1) and hinge region of IgG1 with CH1 and hinge region of IgG2 (amino acids 118-230 of IgG2 according to EU numbering) with a Kappa light chain.

In some embodiments of any of the IgG1 modified Fc, the Fc includes two or more amino acid substitutions that increase antibody clustering without activating complement as compared to a corresponding antibody having an Fc region that does not include the two or more amino acid substitutions. Accordingly, in some embodiments of any of the IgG1 modified Fc, the IgG1 modified Fc is an antibody comprising an Fc region, where the antibody comprises an amino acid substitution at position E430G and one or more amino acid substitutions in the Fc region at a residue position selected from: L234F, L235A, L235E, S267E, K322A, L328F, A330S, P331S, and any combination thereof according to EU numbering. In some embodiments, the IgG1 modified Fc comprises an amino acid substitution at positions E430G, L243A, L235A, and P331S according to EU numbering. In some embodiments, the IgG1 modified Fc comprises an amino acid substitution at positions E430G and P331S according to EU numbering. In some embodiments, the IgG1 modified Fc comprises an amino acid substitution at positions E430G and K322A according to EU numbering. In some embodiments, the IgG1 modified Fc comprises an amino acid substitution at positions E430G, A330S, and P331S according to EU numbering. In some embodiments, the IgG1 modified Fc comprises an amino acid substitution at positions E430G, K322A, A330S, and P331S according to EU numbering. In some embodiments, the IgG1 modified Fc comprises an amino acid substitution at positions E430G, K322A, and A330S according to EU numbering. In some embodiments, the IgG1 modified Fc comprises an amino acid substitution at positions E430G, K322A, and P331S according to EU numbering.

In some embodiments of any of the IgG1 modified Fc, the IgG1 modified Fc may further comprise herein may be combined with an A330L mutation (Lazar et al. *Proc Natl Acad Sci USA*, 103:4005-4010 (2006)), or one or more of L234F, L235E, and/or P331S mutations (Sazinsky et al. Proc Natl Acad Sci USA, 105:20167-20172 (2008)), according to the EU numbering convention, to eliminate complement activation. In some embodiments of any of the IgG1 modified Fc, the IgG1 modified Fc may further comprise one or more of A330L, A330S, L234F, L235E, and/or P331S according to EU numbering. In some embodiments of any of the IgG1 modified Fc, the IgG1 modified Fc may further comprise one or more mutations to enhance the antibody half-life in human serum (e.g., one or more (including all) of M252Y, S254T, and T256E mutations according to the EU numbering convention). In some embodiments of any of the IgG1 modified Fc, the IgG1 modified Fc may further comprise one or more of E430G, E430S, E430F, E430T, E345K, E345Q, E345R, E345Y, S440Y, and/or S440W according to EU numbering.

Other aspects of the present disclosure relate to antibodies having modified constant regions (i.e., Fc regions). An antibody dependent on binding to FcγR receptor to activate targeted receptors may lose its agonist activity if engineered to eliminate FcγR binding (see, e.g., Wilson et al. *Cancer Cell* 19:101-113 (2011); Armour et al. *Immunology* 40:585-593 (2003); and White et al. *Cancer Cell* 27:138-148 (2015)). As such, it is thought that an anti-SIRPβ1 antibody of the present disclosure with the correct epitope specificity can activate the target antigen, with minimal adverse effects, when the antibody has an Fc domain from a human IgG2 isotype (CH1 and hinge region) or another type of Fc domain that is capable of preferentially binding the inhibitory FcγRIIB receptors, or a variation thereof.

In some embodiments of any of the antibodies provided herein, the modified antibody Fc is an IgG2 modified Fc. In some embodiments, the IgG2 modified Fc comprises one or more modifications. For example, in some embodiments, the IgG2 modified Fc comprises one or more amino acid substitutions (e.g., relative to a wild-type Fc region of the same isotype). In some embodiments of any of the IgG2 modified Fc, the one or more amino acid substitutions are selected from V234A (Alegre et al. *Transplantation* 57:1537-1543 (1994); Xu et al. *Cell Immunol*, 200:16-26 (2000)); G237A (Cole et al. *Transplantation*, 68:563-571 (1999)); H268Q, V309L, A330S, P331S (US 2007/0148167; Armour et al. *Eur J Immunol* 29: 2613-2624 (1999); Armour et al. *The Haematology Journal* 1(Suppl. 1):27 (2000); Armour et al. *The Haematology Journal* 1(Suppl. 1):27 (2000)), C219S, and/or C220S (White et al. *Cancer Cell* 27, 138-148 (2015)); S267E, L328F (Chu et al. *Mol Immunol*, 45:3926-3933 (2008)); and M252Y, S254T, and/or T256E according to the EU numbering convention. In some embodiments of any of the IgG2 modified Fc, the Fc comprises an amino acid substitution at positions V234A and G237A according to EU numbering. In some embodiments of any of the IgG2 modified Fc, the Fc comprises an amino acid substitution at positions C219S or C220S according to EU numbering. In some embodiments of any of the IgG2 modified Fc, the Fc comprises an amino acid substitution at positions A330S and P331S according to EU numbering. In some embodiments of any of the IgG2 modified Fc, the Fc comprises an amino acid substitution at positions S267E and L328F according to EU numbering.

In some embodiments of any of the IgG2 modified Fc, the Fc comprises a C127S amino acid substitution according to the EU numbering convention (White et al., (2015) *Cancer Cell* 27, 138-148; Lightle et al. *Protein Sci.* 19:753-762 (2010); and WO 2008/079246). In some embodiments of any of the IgG2 modified Fc, the antibody has an IgG2 isotype with a Kappa light chain constant domain that comprises a C214S amino acid substitution according to the EU numbering convention (White et al. *Cancer Cell* 27:138-148 (2015); Lightle et al. *Protein Sci.* 19:753-762 (2010); and WO 2008/079246).

In some embodiments of any of the IgG2 modified Fc, the Fc comprises a C220S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc comprises a C219S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc includes an IgG2 isotype heavy chain constant domain 1(CH1) and hinge region (White et al. *Cancer Cell* 27:138-148 (2015)). In certain embodiments of any of the IgG2 modified Fc, the IgG2 isotype CH1 and hinge region comprise the amino acid sequence of 118-230 according to EU numbering. In some embodiments of any of the IgG2 modified Fc, the antibody Fc region comprises a S267E amino acid substitution, a L328F amino acid substitution, or both, and/or a N297A or N297Q amino acid substitution according to the EU numbering convention.

In some embodiments of any of the IgG2 modified Fc, the Fc further comprises one or more amino acid substitution at positions E430G, E430S, E430F, E430T, E345K, E345Q, E345R, E345Y, S440Y, and S440W according to EU numbering. In some embodiments of any of the IgG2 modified Fc, the Fc may further comprise one or more mutations to enhance the antibody half-life in human serum (e.g., one or more (including all) of M252Y, S254T, and T256E mutations according to the EU numbering convention). In some embodiments of any of the IgG2 modified Fc, the Fc may further comprise A330S and P331S.

In some embodiments of any of the IgG2 modified Fc, the Fc is an IgG2/4 hybrid Fc. In some embodiments, the IgG2/4 hybrid Fc comprises IgG2 aa 118 to 260 and IgG4 aa 261 to 447. In some embodiments of any IgG2 modified Fc, the Fc comprises one or more amino acid substitutions at positions H268Q, V309L, A330S, and P331S according to EU numbering.

In some embodiments of any of the IgG1 and/or IgG2 modified Fc, the Fc comprises one or more additional amino acid substitutions selected from A330L, L234F; L235E, or P331S according to EU numbering; and any combination thereof.

In certain embodiments of any of the IgG1 and/or IgG2 modified Fc, the Fc comprises one or more amino acid substitutions at a residue position selected from C127S, L234A, L234F, L235A, L235E, S267E, K322A, L328F, A330S, P331S, E345R, E430G, S440Y, and any combination thereof according to EU numbering. In some embodiments of any of the IgG1 and/or IgG2 modified Fc, the Fc comprises an amino acid substitution at positions E430G, L243A, L235A, and P331S according to EU numbering. In some embodiments of any of the IgG1 and/or IgG2 modified Fc, the Fc comprises an amino acid substitution at positions E430G and P331S according to EU numbering. In some embodiments of any of the IgG1 and/or IgG2 modified Fc, the Fc comprises an amino acid substitution at positions E430G and K322A according to EU numbering. In some embodiments of any of the IgG1 and/or IgG2 modified Fc, the Fc comprises an amino acid substitution at positions E430G, A330S, and P331S according to EU numbering. In some embodiments of any of the IgG1 and/or IgG2 modified Fc, the Fc comprises an amino acid substitution at positions E430G, K322A, A330S, and P331S according to EU numbering. In some embodiments of any of the IgG1 and/or IgG2 modified Fc, the Fc comprises an amino acid substitution at positions E430G, K322A, and A330S according to EU numbering. In some embodiments of any of the IgG1 and/or IgG2 modified Fc, the Fc comprises an amino acid substitution at positions E430G, K322A, and P331S according to EU numbering. In some embodiments of any of the IgG1 and/or IgG2 modified Fc, the Fc comprises an amino acid substitution at positions S267E and L328F according to EU numbering. In some embodiments of any of the IgG1 and/or IgG2 modified Fc, the Fc comprises an amino acid substitution at position C127S according to EU numbering. In some embodiments of any of the IgG1 and/or IgG2 modified Fc, the Fc comprises an amino acid substitution at positions E345R, E430G and S440Y according to EU numbering.

In some embodiments of any of the antibodies provided herein, the modified antibody Fc is an IgG4 modified Fc. In some embodiments, the IgG4 modified Fc comprises one or more modifications. For example, in some embodiments, the IgG4 modified Fc comprises one or more amino acid substitutions (e.g., relative to a wild-type Fc region of the same isotype). In some embodiments of any of the IgG4 modified Fc, the one or more amino acid substitutions are selected from L235A, G237A, S229P, L236E (Reddy et al. J Immunol 164:1925-1933(2000)), S267E, E318A, L328F, M252Y, S254T, and/or T256E according to the EU numbering convention. In some embodiments of any of the IgG4 modified Fc, the Fc may further comprise L235A, G237A, and E318A according to the EU numbering convention. In some embodiments of any of the IgG4 modified Fc, the Fc may further comprise S228P and L235E according to the EU numbering convention. In some embodiments of any of the IgG4 modified Fc, the IgG4 modified Fc may further comprise S267E and L328F according to the EU numbering convention.

In some embodiments of any of the IgG4 modified Fc, the IgG4 modified Fc comprises may be combined with an S228P mutation according to the EU numbering convention (Angal et al. *Mol Immunol.* 30:105-108 (1993)) and/or with one or more mutations described in (Peters et al. *J Biol Chem.* 287(29):24525-33 (2012)) to enhance antibody stabilization.

In some embodiments of any of the IgG4 modified Fc, the IgG4 modified Fc may further comprise one or more mutations to enhance the antibody half-life in human serum (e.g., one or more (including all) of M252Y, S254T, and T256E mutations according to the EU numbering convention).

In some embodiments of any of the IgG4 modified Fc, the Fc comprises L235E according to EU numbering. In certain embodiments of any of the IgG4 modified Fc, the Fc comprises one or more amino acid substitutions at a residue position selected from C127S, F234A, L235A, L235E, S267E, K322A, L328F, E345R, E430G, S440Y, and any combination thereof, according to EU numbering. In some embodiments of any of the IgG4 modified Fc, the Fc comprises an amino acid substitution at positions E430G, L243A, L235A, and P331S according to EU numbering. In some embodiments of any of the IgG4 modified Fc, the Fc comprises an amino acid substitution at positions E430G and P331S according to EU numbering. In some embodiments of any of the IgG4 modified Fc, the Fc comprises an amino acid substitution at positions E430G and K322A according to EU numbering. In some embodiments of any of the IgG4 modified Fc, the Fc comprises an amino acid substitution at position E430 according to EU numbering. In some embodiments of any of the IgG4 modified Fc, the Fc region comprises an amino acid substitution at positions E430G and K322A according to EU numbering. In some embodiments of any of the IgG4 modified Fc, the Fc comprises an amino acid substitution at positions S267E and L328F according to EU numbering. In some embodiments of any of the IgG4 modified Fc, the Fc comprises an amino acid substitution at position C127S according to EU numbering. In some embodiments of any of the IgG4 modified Fc, the Fc comprises an amino acid substitution at positions E345R, E430G and S440Y according to EU numbering.

(8) Other Antibody Modifications

In some embodiments of any of the antibodies, the antibody is a derivative. The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding protein can have a greater circulating half-life than an antigen binding protein that is not chemically modified. In certain embodiments, a chemically modified antigen binding protein can have improved targeting capacity for desired cells, tissues, and/or organs. In some embodiments, a derivative antigen binding protein is covalently modified to include one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative antigen binding protein comprises one or more polymer, including, but not limited to, monomethoxy-polyethylene glycol, dextran, cellulose, copolymers of ethylene glycol/propylene glycol, carboxymethylcellulose, polyvinyl pyrrolidone, poly-1, 3-dioxolane, poly-1,3,6-trioxane, ethylene/maleic anhydride copolymer, polyaminoacids (either homopolymers or random copolymers), poly-(N-vinyl pyrrolidone)-polyethylene glycol, propylene glycol homopolymers, a polypropylene oxide/ethylene oxide copolymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, *J. Adv. Drug Res.*, 15:29 (1986); and Evans et al. J Med. Chem., 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —CH$_2$NH—, —CH$_2$S—, —CH$_2$—CH$_2$—, —CH=CH- (cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo and Gierasch *Ann. Rev. Biochem.*, 61:387 (1992), incorporated herein by reference for any purpose); for example, by adding internal cysteine residues capable of forming intramolecular disulfide bridges which cyclize the peptide.

Drug conjugation involves coupling of a biological active cytotoxic (anticancer) payload or drug to an antibody that specifically targets a certain tumor marker (e.g. a polypeptide that, ideally, is only to be found in or on tumor cells). Anti bodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue OncLive Jul. 5, 2012; ADC Review on antibody-drug conjugates; and Ducry et al. *Bioconjugate Chemistry* 21 (1):5-13 (2010).

II. Antibody Activities

In some embodiments, an anti-SIRPβ1 antibody is provided that binds to human SIRPβ1 isoform 1, but does not bind to human SIRPα. In some embodiments, an anti-SIRPβ1 antibody is provided that binds to human SIRPβ1 isoform 1, but does not bind to human SIRPγ. In some embodiments, an anti-SIRPβ1 antibody is provided that binds to human SIRPβ1 isoform 1, but does not bind to human SIRPβ1 isoform 3. In some embodiments, an anti-SIRPβ1 antibody is provided that binds to human SIRPβ1 isoform 1, but does not bind to mouse SIRPβ1. In some embodiments, an anti-SIRPβ1 antibody is provided that binds to human SIRPβ1 isoform 1, but does not bind to cynomolgus monkey SIRPβ1. In some embodiments, an anti-SIRPβ1 antibody is provided that binds to human SIRPβ1 isoform 1, but does not bind to cynomolgus monkey SIRPβ1 isoform 1.

In some embodiments, binding of an anti-SIRPβ1 antibody to an antigen may be determined using a ForteBio Octet® Red384 system (ForteBio, Menlo Park, CA), for example, at described in Example 1. Antibody binding may be determined using, for example, a Fab fragment of the antibody (for monovalent binding) or a full-length antibody such as an IgG (for bivalent binding, or avidity). An exemplary binding assay for full-length antibodies using a ForteBio Octet® Red384 system is as follows. Antibodies are loaded onto AHQ sensors. The loaded antibodies are then exposed to antigen, and the off-rate measured in assay buffer at various time intervals (such as 3 minutes). Kinetics data may then be fit using a binding model in the data analysis software provided with the system. For antibody Fab fragment affinity measurements, in some embodiments, an antigen-Fc may be loaded onto AHQ sensors and then exposed to the antibody Fab fragment. The off-rate is measured as above, and the data analyzed using the software provided with the system.

In some embodiments, and anti-SIRPβ1 antibody is provided that agonizes SIRPβ1 activity on CD14-positive monocytes in vitro and/or in vivo. In some embodiments, and anti-SIRPβ1 antibody is provided that agonizes SIRPβ1 activity on CD14-positive monocytes in vitro. In some embodiments, and anti-SIRPβ1 antibody is provided that agonizes SIRPβ1 activity on CD14-positive monocytes in vivo. In some embodiments, the anti-SIRPβ1 antibody agonizes SIRPβ1 activity on CD14-positive monocytes in vitro in an assay in which the anti-SIRPβ1 antibody is immobilized on a solid support, such as a culture plate, or bound by a secondary anti-IgG antibody, or bound by Fc gamma receptor on an accessory cell. In some embodiments, and anti-SIRPβ1 antibody is provided that agonizes SIRPβ1 activity on CD14-positive monocytes in vivo. A nonlimiting exemplary assay for determining whether an anti-SIRPβ1 antibody agonizes SIRPβ1 activity on CD14-positive monocytes in vitro is described in Examples 3 and 4. For example, isolated monocytes are starved for a period of time, such as 4 hours, and then incubated with anti-SIRPβ1 antibody, e.g., in the presence of anti-IgG antibody. Following incubation, cells are lysed and phosphorylation of one or more of Syk, ERK, AKT, SIRPβ1, and/or DAP12 is measured, for example, using an anti-phosphotyrosine and/or anti-phosphoserine antibody. An increase in phosphorylation of one or more of Syk, ERK, AKT, SIRPβ1, and/or DAP12 is indicative of an increase in SIRPβ1 activity (i.e., agonist of SIRPβ1 activity). As another example, monocytes may be incubated with anti-SRPβ1 antibody in the presence of accessory cells that express Fc gamma receptors, such as B cells. Following incubation, cells are lysed and phosphorylation of one or more of Syk, ERK, AKT, SIRPβ1, and/or DAP12 is determined as above. An increase in phosphorylation of one or more of Syk, ERK, AKT, SIRPβ1, and/or DAP12 is indicative of an increase in SIRPβ1 activity (i.e., that the anti-SIRPβ1 antibody is an agonist of SIRP 1 activity). A nonlimiting exemplary assay to determine whether an anti-SIRPβ1 antibody agonizes SIRPβ 1 activity on CD14-positive monocytes in vivo comprises administering the anti-SIRP 1 antibody to a human STRβ1 BAC transgenic C57BL/6 mouse, and isolating CD14-positive monocytes, e.g., by FACS. The monocytes are then lysed and phosphorylation of one or more of Syk, ERK, AKT, SIRPβ1, and/or DAP12 is measured as described above. An increase in phosphorylation of one or more of Syk, ERK, AKT, SIRPβ1, and/or DAP12 is indicative of an increase in SIRPβ1 activity (i.e., agonist of SIRPβ1 activity).

In some embodiments, an anti-SIRPβ1 antibody is provided that induces or increases respiratory burst in immune cells, such as neutrophils and/or monocytes in vitro and/or in vivo. In some embodiments, an anti-SIRPβ1 antibody is provided that induces or increases respiratory burst in immune cells, such as neutrophils and/or monocytes in vitro. In some embodiments, an anti-SIRPβ1 antibody is provided that induces or increases respiratory burst in immune cells, such as neutrophils and/or monocytes in vivo. Nonlimiting exemplary in vitro assays for determining whether an anti-SIRPβ1 antibody induces or increases respiratory burst in immune cells, such as neutrophils and/or monocytes, are described in Examples 5 and 6. For example, primary neutrophils are contacted with anti-SIRPβ1 antibody and the production of reactive oxygen species (ROS) is detected using a general oxidative stress indicator, such as fluorescent dye CM-H$_2$DCFDA. Alternatively, the assay may be carried out using anti-SIRPβ1 antibody immobilized on a solid support, such as a culture plate, or bound by a secondary anti-IgG antibody, or bound by Fc gamma receptor on an accessory cell.

In some embodiments, an anti-SIRPβ1 antibody is provided that induces or increases IL-8 expression in monocytes in vitro and/or in vivo. In some embodiments, an anti-SIRPβ1 antibody is provided that induces or increases IL-8 expression in monocytes in vitro. In some embodiments, an anti-SIRPβ1 antibody is provided that induces or increases IL-8 expression in monocytes in vivo. A nonlimiting exemplary in vitro assay for determining whether an anti-SIRPβ1 antibody induces or increases IL-8 expression in monocytes is described in Example 5. For example, primary monocytes may be stimulated with anti-SIRPβ1 antibody immobilized on a solid support, such as a culture plate, or bound by a secondary anti-IgG antibody, or bound by Fc gamma receptor on an accessory cell, for example, overnight. The supernatant may be collected to assay for IL-8 release. A nonlimiting exemplary assay to determine whether an anti-SIRPβ1 antibody induces or increases IL-8 expression in monocytes in vivo comprises administering the anti-SIRPβ1 antibody to human SIRPβ1 BAC transgenic C57BL/6 mice and obtaining one or more blood samples. Serum concentration of IL-8 may be determined using a commercial assay, such as the Duoset ELISA kit (R&D Systems).

In some embodiments, an anti-SIRPβ1 antibody is provided that induces or increases TNFα expression in macrophages and/or dendritic cells in vitro and/or in vivo. In some embodiments, an anti-SIRPβ1 antibody is provided that induces or increases TNFα expression in macrophages and/or dendritic cells in vitro. In some embodiments, an anti-SIRPβ1 antibody is provided that induces or increases TNFα expression in macrophages and/or dendritic cells in vivo. A nonlimiting exemplary in vitro assay for determining whether an anti-SIRPβ1 antibody induces or increases TNFα expression is described in Example 6. For example, monocyte-derived macrophages or dendritic cells may be stimulated with LPS in the presence of anti-SIRPβ1 antibody immobilized on a solid support, such as a culture plate, or bound by a secondary anti-IgG antibody, or bound by Fc gamma receptor on an accessory cell, for example, overnight. The supernatant may be collected to assay for TNFα release. A nonlimiting exemplary assay to determine whether an anti-SIRPβ1 antibody induces or increases TNFα expression in macrophages and/or dendritic cells in vivo comprises administering the anti-SIRPβ1 antibody to human SIRPβ1 BAC transgenic C57BL/6 mice along with LPS (such as 5 μg of LPS/mouse). Mice are then sacrificed, e.g., by C02 asphyxiation and peritoneal fluid is recovered and clarified by centrifugation. TNF-α concentration may be determined using a commercial assay, such as the Duoset ELISA kit (R&D Systems).

In some embodiments, an anti-SIRPβ1 antibody is provided that induces or increases neutrophil-mediated phagocytosis, for example, of tumor cells in vitro and/or in vivo. In some embodiments, an anti-SIRPβ1 antibody is provided that induces or increases neutrophil-mediated phagocytosis, for example, of tumor cells in vitro. In some embodiments, an anti-SIRPβ1 antibody is provided that induces or increases neutrophil-mediated phagocytosis, for example, of tumor cells in vivo. In some embodiments, an anti-SIRPβ1 antibody is provided that induces or increases neutrophil-mediated tumor cell clearance in vivo. A nonlimiting exemplary in vitro assay for determining whether an anti-SIRPβ1 antibody induces or increases neutrophil-mediated phagocytosis is described in Example 7. For example, primary neutrophils are contacted with anti-SIRPβ1 antibody immobilized on a solid support, such as a culture plate, or bound by a secondary anti-IgG antibody, or bound by Fc gamma receptor on an accessory cell. Cancer cells, such as Raji B cell lymphoma cells engineered to express luciferase, are co-cultured with the neutrophils and immobilized anti-SIRPβ1 antibody in the presence of opsonizing antibody, such as anti-CD20 antibody. Viable Raji cells are quantified by measuring luciferase activity. A reduction in viable Raji cells in the presence of anti-SIRPβ1 antibody compared to an IgG control antibody indicates that the anti-SIRPβ1 antibody induces or increases neutrophil-mediated phagocytosis. A nonlimiting exemplary assay to determine whether an anti-SIRPβ1 antibody induces or increases neutrophil-mediated tumor cell clearance in vivo comprises injecting intravenously GFP-expressing B16F10 melanoma cells into human SIRPβ1 BAC transgenic mice. Mice are then treated with the anti-SIRPβ1 antibody with an opsonizing anti-gp75 antibody. Peripheral blood is collected, red blood cells are lysed, and white blood cells resuspended in FACS buffer. Neutrophils are stained with anti-CD11b and anti-Ly6G antibodies and analyzed by flow cytometry for the acquisition of green fluorescence signal from ingested tumor cells. An increase in green fluorescence signal in the neutrophils compared to the same experiment with an isotype-matched control antibody indicates that anti-SIRPβ1 antibody induces or increases neutrophil-mediated phagocytosis.

A further nonlimiting exemplary assay to determine whether an anti-SIRPβ1 antibody induces or increases neutrophil-mediated tumor cell clearance in vivo uses a lung metastasis model, e.g., as follows. Fc receptor γ-chain deficient C57BL/6 mice, which lack expression of activating FcγRs, are injected intravenously with B16F10 melanoma cells. Bone marrow neutrophils isolated from human SIRPβ1 BAC transgenic mice are then injected intravenously with the anti-SIRPβ1 antibody in combination with an opsonizing anti-gp75 antibody. After a period of time, mice are euthanized and lungs are harvested and fixed. The number of metastatic tumor nodules with dark pigmentation are visually counted. A reduction in the number of metastatic tumor nodules compared to the same experiment with an isotype-matched control antibody indicates that the anti-SIRPβ1 antibody induces or increases neutrophil-mediated tumor cell clearance in vivo.

In some embodiments, an anti-SIRPβ1 antibody is provided that increases TREM2 expression on macrophages in vitro and/or in vivo. In some embodiments, an anti-SIRPβ1 antibody is provided that increases TREM2 expression on macrophages in vitro. In some embodiments, an anti-SIRPβ1 antibody is provided that increases TREM2 expression on macrophages in vivo. A nonlimiting exemplary in vitro assay for determining whether an anti-SIRPβ1 antibody increases TREM2 expression on macrophages is described in Example 16. For example, monocyte-derived macrophages differentiated in culture with M-CSF are incubated with anti-SIRPβ1 antibody immobilized on a solid support, such as a culture plate, or bound by a secondary anti-IgG antibody, or bound by Fc gamma receptor on an accessory cell. TREM2 expression on the macrophages is analyzed, e.g., by FACS analysis. A nonlimiting exemplary assay to determine whether an anti-SIRPβ1 antibody increases TREM2 expression on macrophages in vivo is as follows. Human SIRPβ1 BAC transgenic C57BL/6 mice are challenged with aged sterile thioglycolate broth injected into the peritoneum. Following challenge, mice are treated with the anti-SIRPβ1 antibody. Mice are then sacrificed, and peritoneal macrophages are harvested after euthanasia, e.g., by rinsing the peritoneal cavity with PBS. Macrophages are defined as CD11b+Ly6C−F4/80+ cells, and may be analyzed by FACS to determine TREM2 expression levels.

In some embodiments, an anti-SIRPβ1 antibody is provided that increases viability of macrophages in vitro and/or in vivo, alone and/or in combination with an agonist anti-TREM2 antibody. In some embodiments, an anti-SIRPβ1 antibody is provided that increases viability of macrophages in vitro, alone and/or in combination with an agonist anti-TREM2 antibody. In some embodiments, an anti-SIRPβ1 antibody is provided that increases viability of macrophages in vivo, alone and/or in combination with an agonist anti-TREM2 antibody. In some embodiments, an anti-SIRPβ1 antibody is provided that increases viability of dendritic cells in vitro and/or in vivo. In some embodiments, an anti-SIRPβ1 antibody is provided that increases viability of dendritic cells in vitro. In some embodiments, an anti-SIRPβ1 antibody is provided that increases viability of dendritic cells in vivo. Nonlimiting exemplary in vitro assays for determining whether an anti-SIRPβ1 antibody increases viability of macrophages in vitro, alone or in combination with an agonist anti-TREM2 antibody, are described in Examples 17, 18, and 19. For example, monocyte-derived macrophages differentiated in culture with M-CSF are incubated with anti-SIRPβ1 antibody immobilized on a solid support, such as a culture plate, or bound by a secondary anti-IgG antibody, or bound by Fc gamma receptor on an accessory cell, and with or without anti-TREM2 antibody. Cell viability is measured, for example, using Cell Titer Glo kit (Promega), a reagent that produces a luminescence signal relative to ATP concentration in the sample. A similar assay may be used to determine whether an anti-SIRPβ1 antibody increases the viability of bone marrow-derived macrophages or dendritic cells in vitro. For this assay, bone marrow cells are cultured with M-CSF to differentiate macrophages, or with GM-CSF to differentiate dendritic cells. The macrophages or dendritic cells are incubated with anti-SIRPβ1 antibody immobilized on a solid support, such as a culture plate, or bound by a secondary anti-IgG antibody, or bound by Fc gamma receptor on an accessory cell, and with or without anti-TREM2 antibody. As above, cell viability is measured, for example, using Cell Titer Glo kit (Promega), a reagent that produces a luminescence signal relative to ATP concentration in the sample. A nonlimiting exemplary assay to determine whether an anti-SIRPβ1 antibody increases viability of macrophages in vivo is as follows. Prolonged treatment with a blocking antibody to CSF1R depletes peritoneal and tissue resident F4/80+ macrophages due to the abrogation of M-CSF-mediated survival signal. For this assay, human SIRPβ1 BAC transgenic C57BL/6 mice are administered anti-CSF1R antibody along with the anti-SIRPβ1 antibody. Following treatment, mice are sacrificed, e.g., by C02 asphyxiation, and peripheral blood is collected by cardiac puncture. Peritoneal macrophages are collected by lavage with PBS. Macrophage populations are counted by FACS by gating on CD11b+ Ly6C−F4/80+ cells in blood and peritoneum.

III. Nucleic Acids, Vectors, and Host Cells

Anti-SIRPβ1 antibodies of the present disclosure may be produced using recombinant methods and compositions, e.g., as described in U.S. Pat. No. 4,816,567. In some embodiments, isolated nucleic acids having a nucleotide sequence encoding any of the anti-SIRPβ1 antibodies of the present disclosure are provided. Such nucleic acids may encode an amino acid sequence comprising the $V_L$ and/or an amino acid sequence comprising the $V_H$ of the anti-SIRPβ1 antibody (e.g., the light and/or heavy chains of the antibody). In some embodiments, one or more vectors (e.g., expression vectors) comprising such nucleic acids are provided. In some embodiments, a host cell comprising such nucleic acid is also provided. In some embodiments, the host cell comprises (e.g., has been transduced with): (1) a vector comprising a nucleic acid that encodes an amino acid sequence comprising the $V_L$ of the antibody and an amino acid sequence comprising the $V_H$ of the antibody, or (2) a first vector comprising a nucleic acid that encodes an amino acid sequence comprising the $V_L$ of the antibody and a second vector comprising a nucleic acid that encodes an amino acid sequence comprising the $V_H$ of the antibody. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells.

Methods of making an anti-SIRPβ1 antibody of the present disclosure are provided. In some embodiments, the method includes culturing a host cell of the present disclosure comprising a nucleic acid encoding the anti-SIRPβ1 antibody, under conditions suitable for expression of the antibody. In some embodiments, the antibody is subsequently recovered from the host cell (or host cell culture medium).

For recombinant production of an anti-SIRPβ1 antibody of the present disclosure, a nucleic acid encoding the anti-SIRPβ1 antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors comprising a nucleic acid sequence encoding any of the anti-SIRPβ1 antibodies of the present disclosure, or cell-surface expressed fragments or polypeptides thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones comprising the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Suitable host cells for cloning or expression of antibody-encoding vectors include prokaryotic or eukaryotic cells. For example, anti-SIRPβ1 antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523. After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross Nat. Biotech. 22:1409-1414 (2004); and Li et al. Nat. Biotech. 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. J Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MNMT 060562); TRI cells, as described, e.g., in Mather et al. Annals N. Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al. Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

IV. Pharmaceutical Compositions/Formulations

Provided herein are pharmaceutical compositions and/or pharmaceutical formulations comprising the anti-SIRPβ1 antibodies of the present disclosure and a pharmaceutically acceptable carrier.

In some embodiments, pharmaceutically acceptable carrier preferably are nontoxic to recipients at the dosages and concentrations employed. The antibodies described herein may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutically acceptable carriers can include, depending on the formulation desired, pharmaceutically-acceptable, non-toxic carriers of diluents, which are vehicles commonly used to formulate pharmaceutical compositions for animal or human administration. In certain embodiments, the pharmaceutical composition can comprise formulation materials for modifying, maintaining or preserving, for example, the pH, osmolarity, viscosity, clarity, color, isotonicity, odor, sterility, stability, rate of dissolution or release, adsorption or penetration of the composition.

In certain embodiments, pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Further examples of formulations that are suitable for various types of administration can be found in *Remington: The Science and Practice of Pharmacy, Pharmaceutical Press* 22nd ed. (2013). For a brief review of methods for drug delivery, see, Langer, Science 249:1527-1533 (1990).

Formulations suitable for parenteral administration include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-SIRPβ1 antibody of the present disclosure, in a biodegradable or bioerodible implant. The rate of release of the therapeutically active agent is controlled by the rate of transport through the polymeric matrix, and the biodegradation of the implant. Implants may be particles, sheets, patches, plaques, fibers, microcapsules and the like and may be of any size or shape compatible with the selected site of insertion. Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid.

V. Therapeutic Uses

As disclosed herein, anti-SIRPβ1 antibodies of the present disclosure may be used for preventing, reducing risk, or treating diseases and disorders. In various embodiments, the anti-SIRPβ1 antibodies provided herein have one or more activities selected from: agonizing SIRPβ1 activity on CD14-positive monocytes in vitro and/or in vivo; inducing respiratory burst in immune cells, such as neutrophils and/or monocytes in vitro and/or in vivo; inducing IL-8 expression in monocytes in vitro and/or in vivo; inducing TNFα expression in macrophages and/or dendritic cells in vitro and/or in vivo; inducing neutrophil-mediated phagocytosis, for example, of tumor cells in vitro and/or in vivo; increasing neutrophil-mediated tumor cell clearance in vivo; upregulating TREM2 expression on macrophages in vitro and/or in vivo; increasing viability of macrophages in vitro and/or in vivo, alone and/or in combination with an agonist anti-TREM2 antibody; and increasing viability of dendritic cells in vitro and/or in vivo.

In various embodiments, the anti-SIRPβ1 antibodies provided herein may be used for preventing, reducing risk, or treating dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and/or cancer. In some such embodiments, the anti-SIRPβ1 antibody is an agonist antibody.

In some embodiments, provided herein are methods of preventing, reducing risk, or treating an individual having dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, Taupathy disease, Nasu-Hakola disease, stroke, acute trauma, chronic trauma, lupus, acute and chronic colitis, wound healing, Crohn's disease, inflammatory bowel disease, ulcerative colitis, obesity, Malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and/or cancer, by administering to the individual a therapeutically effective amount of an anti-SIRPβ1 antibody of the present disclosure. In some such embodiments, the anti-SIRPβ1 antibody is an agonist of (e.g., induces or increases) SIRPβ1 activity.

As disclosed herein, anti-SIRPβ1 antibodies of the present disclosure may also be used for inducing and/or promoting innate immune cell survival. In some embodiments, the present disclosure provides methods of inducing or promoting innate immune cell survival in an individual in need thereof, by administering to the individual a therapeutically effective amount of an agonist anti-SIRPβ1 antibody of the present disclosure.

As disclosed herein, anti-SIRPβ1 antibodies of the present disclosure may also be used for inducing and/or promoting wound healing, such as after injury. In some embodiments, the wound healing may be colonic wound repair following injury. In some embodiments, the present disclosure provides methods of inducing or promoting wound healing in an individual in need thereof, by administering to the individual a therapeutically effective amount of an agonist anti-SIRPβ1 antibody of the present disclosure.

In some embodiments, a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

An antibody provided herein (and any additional therapeutic agent) can be administered by any suitable means, including parenteral, intrapulmonary, intranasal, intralesional administration, intracerebrospinal, intracranial, intraspinal, intrasynovial, intrathecal, oral, topical, or inhalation routes. Parenteral infusions include intramuscular, intravenous administration as a bolus or by continuous infusion over a period of time, intraarterial, intra-articular, intraperitoneal, or subcutaneous administration. In some embodiments, the administration is intravenous administration. In some embodiments, the administration is subcutaneous. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies provided herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or e.g., about six doses of the antibody). In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. An initial higher loading dose, followed by one or more lower doses may be administered. However, other dosage regimens may be useful. The progress of this therapy is easily monitored by conventional techniques and assays.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

In some embodiments, administering an anti-SIRPβ1 antibody of the present disclosure can prevent, reduce the risk, and/or treat dementia. In some embodiments, administering an anti-SIRPβ1 antibody may induce one or more SIRPβ1 activities in an individual having dementia.

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Cruts, M. & Van Broeckhoven, C., Trends Genet. 24:186-194 (2008); Neary, D., et al., Neurology 51:1546-1554 (1998); Ratnavalli, E., Brayne, C., Dawson, K. & Hodges, J. R., Neurology 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., Nature 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., Arch. Neurol. 64:1388-1394 (2007)). A majority of those FTD cases with Ub inclusions (FTD-U) were shown to carry mutations in the progranulin gene.

In some embodiments, administering an anti-SIRPβ1 antibody of the present disclosure can prevent, reduce the risk, and/or treat FTD. In some embodiments, administering an anti-SIRPβ1 antibody may induce one or more SIRPβ1 activities in an individual having FTD.

Alzheimer's Disease

Alzheimer's disease (AD) is the most common form of dementia. There is no cure for the disease, which worsens as it progresses, and eventually leads to death. Most often, AD is diagnosed in people over 65 years of age. However, the less-prevalent early-onset alzheimer's can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

In Some Embodiments, Administering an Anti-SIRPβ1 Antibody of the Present Disclosure can prevent, reduce the risk, and/or treat Alzheimer's disease. In some embodiments, administering an anti-SIRPβ1 antibody may induce one or more SIRPβ1 activities in an individual having Alzheimer's disease.

Nasu-Hakola Disease

Nasu-Hakola disease (NHD), which may alternatively be referred to as polycystic lipomembranous osteodysplasia with sclerosing leukoencephalopathy (PLOSL), is a rare inherited leukodystrophy characterized by progressive presenile dementia associated with recurrent bone fractures due to polycystic osseous lesions of the lower and upper extremities. NHD disease course is generally divided into four stages: latent, osseous, early neurologic, and late neurologic. After a normal development during childhood (latent stage), NHD starts manifesting during adolescence or young adulthood (typical age of onset 20-30 years) with pain in the hands, wrists, ankles, and feet. Patients then start suffering from recurrent bone fractures due to polycystic osseous and osteoporotic lesions in the limb bones (osseous stage). During the third or fourth decade of life (early neurologic stage), patients present with pronounced personality changes (e.g., euphoria, lack of concentration, loss of judgment, and social inhibitions) characteristic of a frontal lobe syndrome. Patients also typically suffer from progressive memory disturbances. Epileptic seizures are also frequently observed. Finally (late neurologic stage), patients progress to a profound dementia, are unable to speak and move, and usually die by the age of 50.

In some embodiments, administering an anti-SIRPβ1 antibody of the present disclosure can prevent, reduce the risk, and/or treat Nasu-Hakola disease (NHD). In some embodiments, administering an anti-SIRPβ1 antibody may induce one or more SIRP 1 activities in an individual having NHD.

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

In some embodiments, administering an anti-SIRPβ1 antibody of the present disclosure can prevent, reduce the risk, and/or treat Parkinson's disease. In some embodiments, administering an anti-SIRPβ1 antibody may induce one or more SIRPβ1 activities in an individual having Parkinson's disease.

Amyotrophic Lateral Sclerosis

As used herein, amyotrophic lateral sclerosis (ALS) or motor neuron disease or Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

It has been shown that progranulin play a role in ALS (Schymick, J C et al., (2007) J Neurol Neurosurg Psychiatry.; 78:754-6) and protects again the damage caused by ALS causing proteins such as TDP-43 (Laird, A S et al., (2010). PLoS ONE 5: e13368). It was also demonstrated that pro-NGF induces p75 mediated death of oligodendrocytes and corticospinal neurons following spinal cord injury (Beatty et al., Neuron (2002), 36, pp. 375-386; Giehl et al, Proc. Natl. Acad. Sci USA (2004), 101, pp 6226-30).

In some embodiments, administering an anti-SIRPβ1 antibody of the present disclosure can prevent, reduce the risk, and/or treat ALS. In some embodiments, administering an anti-SIRPβ1 antibody may induce one or more SIRPβ1 activities in an individual having ALS.

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

In some embodiments, administering an anti-SIRPβ1 antibody of the present disclosure can prevent, reduce the risk, and/or treat Huntington's disease (HD). In some embodiments, administering an anti-SIRPβ1 antibody may induce one or more SIRPβ1 activities in an individual having HD.

Taupathy Disease

Taupathy diseases, or Tauopathies, are a class of neurodegenerative disease caused by aggregation of the microtubule-associated protein tau within the brain. Alzheimer's disease (AD) is the most well-known Taupathy disease, and involves an accumulation of tau protein within neurons in the form of insoluble neurofibrillary tangles (NFTs). Other Taupathy diseases and disorders include progressive supranuclear palsy, dementia pugilistica (chromic traumatic encephalopathy), Frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, frontotemporal dementia, and frontotemporal lobar degeneration.

In some embodiments, administering an anti-SIRPβ1 antibody of the present disclosure can prevent, reduce the risk, and/or treat Taupathy disease. In some embodiments, administering an anti-SIRPβ1 antibody may induce one or more SIRPβ1 activities in an individual having Taupathy disease.

Multiple Sclerosis

Multiple sclerosis (MS) can also be referred to as disseminated sclerosis or encephalomyelitis disseminata. MS is an inflammatory disease in which the fatty myelin sheaths around the axons of the brain and spinal cord are damaged, leading to demyelination and scarring as well as a broad spectrum of signs and symptoms. MS affects the ability of nerve cells in the brain and spinal cord to communicate with each other effectively. Nerve cells communicate by sending electrical signals called action potentials down long fibers called axons, which are contained within an insulating substance called myelin. In MS, the body's own immune system attacks and damages the myelin. When myelin is lost, the axons can no longer effectively conduct signals. MS onset usually occurs in young adults, and is more common in women.

Symptoms of MS include, without limitation, changes in sensation, such as loss of sensitivity or tingling; pricking or numbness, such as hypoesthesia and paresthesia; muscle weakness; clonus; muscle spasms; difficulty in moving; difficulties with coordination and balance, such as ataxia; problems in speech, such as dysarthria, or in swallowing, such as dysphagia; visual problems, such as nystagmus, optic neuritis including phosphenes, and diplopia; fatigue; acute or chronic pain; and bladder and bowel difficulties; cognitive impairment of varying degrees; emotional symptoms of depression or unstable mood; Uhthoff s phenomenon, which is an exacerbation of extant symptoms due to an exposure to higher than usual ambient temperatures; and Lhermitte's sign, which is an electrical sensation that runs down the back when bending the neck.

In some embodiments, administering an anti-SIRPβ1 antibody of the present disclosure can prevent, reduce the risk, and/or treat multiple sclerosis. In some embodiments, administering an anti-SIRPβ1 antibody may induce one or more SIRPβ1 activities in an individual having multiple sclerosis.

Cancer

Yet further aspects of the present disclosure provide methods for preventing, reducing risk, or treating an individual having cancer, comprising administering to the individual a therapeutically effective amount of an isolated anti-SIRPβ1 antibody of the present disclosure. Any of the isolated antibodies of the present disclosure may be used in these methods. In some embodiments, the isolated antibody is an agonist antibody of the present disclosure.

The tumor microenvironment is known to contain a heterogeneous immune infiltrate, which includes T lymphocytes, macrophages and cells of myeloid/granulocytic lineage. In particular, the presence of M2-macrophages in tumors is associated with poor prognosis. Therapies that reduce the number of these cells in the tumor, such as CSF1R blocking agents, are showing beneficial effects in preclinical models and early stage clinical studies. A seminal preclinical study has also shown synergies between drugs that target tumor-associated macrophages (e.g., CSF1/CSF1R blocking antibodies) and checkpoint blocking antibodies that target T cells, indicating that manipulating both cell types shows efficacy in tumor models where individual therapies are poorly effective (Zhu Y; Cancer Res. 2014 Sep. 15; 74(18):5057-69). Without wishing to be bound by any particular theory, it is thought that inducing SIRPβ1 signaling in tumor associated macrophages and/or neutrophils may inhibit suppression of the immune response in the tumor microenvironment, resulting in a therapeutic anti-tumor immune response.

In certain embodiments, a cancer to be prevented or treated by the methods of the present disclosure includes, without limitation, squamous cell carcinoma (e.g., epithelial squamous cell carcinoma), lung cancer, small-cell lung cancer, non-small cell lung cancer, squamous non-small cell lung cancer (NSCLC), adenocarcinoma of the lung, squamous carcinoma of the lung, non-squamous NSCLC, glioma, cancer of the peritoneum, hepatocellular cancer, gastrointestinal cancer, gastric or stomach cancer including gastrointestinal cancer and gastrointestinal stromal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, myelodysplastic syndromes, colorectal neoplasms, solid tumors, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (M0), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), indolent lymphoma, large B cell diffuse lymphoma, B cell hematologic malignancy, e.g., B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytic lymphoma (LPL) with Waldenstrom's macroglobulinemia; myelomas, such as IgG myeloma, light chain myeloma, nonsecretory myeloma, smoldering myeloma (also called indolent myeloma), solitary plasmacytoma, and multiple myelomas, chronic lymphocytic leukemia (CLL), hairy cell lymphoma; hematopoietic tumors of myeloid lineage, tumors of mesenchymal origin, including fibrosarcoma and rhabdomyosarcoma; seminoma, teratocarcinoma, tumors of the central and peripheral nervous, including astrocytoma, schwannomas; tumors of mesenchymal origin, including fibrosarcoma, rhabdomyosarcoma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL heptasyllabic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. An anti-SIRPβ1 antibody of the present disclosure may also be used to treat metastatic cancer.

In some embodiments, the cancer is selected from sarcoma, bladder cancer, brain cancer, breast cancer, colon cancer, rectal cancer, endometrial cancer, kidney cancer, renal pelvis cancer, leukemia, lung cancer, small cell lung cancer, melanoma, lymphoma, pancreatic cancer, prostate cancer, ovarian cancer, and fibrosarcoma. In some embodiments, the cancer is triple-negative breast carcinoma. In some embodiments, the cancer may be an early stage cancer or a late stage cancer. In some embodiments, the cancer may be a primary tumor. In some embodiments, the cancer may be a metastatic tumor at a second site derived from any of the above types of cancer.

In some embodiments, the cancer is selected from glioblastoma multiforme; renal clear cell carcinoma; adrenocortical carcinoma; bladder urothelial carcinoma; diffuse large B-cell lymphoma; lung adenocarcinoma; pancreatic adenocarcinoma, renal cell cancer, Hodgkin's lymphoma, non-Hodgkin's lymphoma, indolent B cell lymphoma, aggressive B cell lymphoma, T cell lymphoma, acute lymphoblastic leukemia (ALL), acute myeloid leukemia (AML), chronic lymphocytic leukemia (CLL), chronic myeloid leukemia (CML), multiple myeloma, myelodysplastic syndromes, myeloproliferative neoplasms, breast invasive carcinoma, cervical squamous cell carcinoma, endocervical adenocarcinoma, cholangiocarcinoma, colon adenocarcinoma, diffuse large B-cell lymphoma, esophageal carcinoma, head and neck squamous cell carcinoma, kidney chromophobe, renal papillary cell carcinoma, lower grade glioma, hepatocellular carcinoma, lung squamous cell carcinoma, mesothelioma, ovarian serous cystadenocarcinoma, pancreatic adenocarcinoma, pheochromocytoma and paraganglioma, prostate adenocarcinoma, rectal adenocarcinoma, cutaneous melanoma, stomach adenocarcinoma, testicular germ cell tumors, thyroid carcinoma, thymoma, uterine corpus endometrial carcinoma, uterine carcinosarcoma, and uveal melanoma.

In some embodiments, the present disclosure provides methods of preventing, reducing risk, or treating an individual having cancer, by administering to the individual a therapeutically effective amount of an anti-SIRPβ1 antibody of the present disclosure.

In some embodiments, the present disclosure provides methods of preventing, reducing risk, or treating an individual having cancer, wherein the individual is refractory to checkpoint inhibitor therapy, by administering to the individual a therapeutically effective amount of an anti-SIRPβ1 antibody of the present disclosure.

In some embodiments, an anti-SIRPβ1 antibody of the present disclosure may be administered in conjunction with a therapeutic agent that acts as a checkpoint inhibitor. In some embodiments, the method further includes administering to the individual at least one antibody that specifically binds to an inhibitory immune checkpoint molecule, and/or another standard or investigational anti-cancer therapy. In some embodiments, the inhibitory checkpoint molecule is selected from PD1, PDL1, CD40, OX40, ICOS, CD28, CD137/4-1BB, CD27, GITR, CTLA4, PD-L2, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, and CD73. In typical embodiments, the therapeutic agent is an antibody to a checkpoint inhibitor selected from D1, PDL1, CD40, OX40, ICOS, CD28, CD137/4-1BB, CD27, GITR, CTLA4, PD-L2, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, or CD73. In some embodiments, the at least one antibody that specifically binds to an inhibitory checkpoint molecule is administered in combination with the anti-SIRPβ1 antibody of the present disclosure. In some embodiments, a combination of antibodies to directed against checkpoint inhibitors is administered in conjunction with an anti-SIRPβ1 antibody of the present invention.

In some embodiments, an anti-SIRPβ1 antibody of the present disclosure may be administered in conjunction with at least one agonistic antibody that specifically binds to a stimulatory checkpoint protein, e.g., an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, an agonist anti-CD30 antibody, an agonist anti-BTLA antibody, an agonist anti-HVEM antibody, an agonist anti-CD2 antibody, an agonist anti-CD5 antibody, and any combination thereof.

In some embodiments, the method further includes administering to the individual at least one antibody that specifically binds to an inhibitory immune checkpoint molecule, and/or another standard or investigational anti-cancer therapy. In some embodiments, the at least one antibody that specifically binds to an inhibitory checkpoint molecule is administered in combination with the anti-SIRPβ1 antibody of the present disclosure. In some embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, and any combination thereof. In some embodiments, the standard or investigational anti-cancer therapy is one or more therapies selected from radiotherapy, cytotoxic chemotherapy, targeted therapy, imatinib (Gleevec®), trastuzumab (Herceptin®), adoptive cell transfer (ACT), chimeric antigen receptor T cell transfer (CAR-T), vaccine therapy, and cytokine therapy. In some embodiments, the method further includes administering to the individual at least one antibody that specifically binds to an inhibitory cytokine. In some embodiments, the at least one antibody that specifically binds to an inhibitory cytokine is administered in combination with the anti-SIRPβ1 antibody of the present disclosure. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the method further includes administering to the individual at least one agonistic antibody that specifically binds to a stimulatory immune checkpoint protein. In some embodiments, the at least one agonistic antibody that specifically binds to a stimulatory checkpoint protein is administered in combination with the anti-SIRPβ1 antibody of the present disclosure. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof.

In some embodiments, an anti-SIRPβ1 antibody of the present invention is administered in combination with radiation therapy and/or a chemotherapeutic agent. Chemotherapeutic agents include, for example, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (methotrexate, pemetrexed, mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones, eribulin and navelbine; epipidophyllotoxins (etoposide, teniposide); DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); DNA methyltransferase inhibitors (azacytidine); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkylsulfonates (busulfan), nitrosoureas (carmustine (BCNU) and analogs, streptozocin), triazenes (dacarbazine (DTIC)); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein, pomalidomide) and growth factor inhibitors (vascular endothelial growth factor (VEGF) inhibitors, such as ziv-aflibercept; fibroblast growth factor (FGF) inhibitors); inhibitors of apoptosis protein (IAP) antagonists (birinapant); histone deacetylase (HDAC) inhibitors (vorinostat, romidepsin, chidamide, panobinostat, mocetinostat, abexinostat, belinostat, entinostat, resminostat, givinostat, quisinostat, SB939); proteasome inhibitors (ixazomib); angiotensin receptor blocker; nitric oxide donors; anti-sense oligonucleotides; antibodies (trastuzumab, panitumumab, pertuzumab, cetuximab, adalimumab, golimumab, infliximab, rituximab, ocrelizumab, ofatumumab, obinutuzumab, alemtuzumab, abciximab, atlizumab, daclizumab, denosumab, efalizumab, elotuzumab, rovelizumab, ruplizumab, ustekinumab, visilizumab, gemtuzumab ozogamicin, brentuximb vedotin); chimeric antigen receptors; cell cycle inhibitors (flavopiridol, roscovitine, bryostatin-1) and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); PARP inhibitors (niraparib, olaparib); focal adhesion kinase (FAK) inhibitors (defactinib (VS-6063), VS-4718, VS-6062, GSK2256098); growth factor signal transduction kinase inhibitors (cediranib, galunisertib, rociletinib, vandetanib, afatinib, EGF816, AZD4547); c-Met inhibitors (capmatinib, INC280); ALK inhibitors (ceritinib, crizotinib); mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors. In some embodiments, a chemotherapeutic agent is a B-Raf inhibitor, a MEK inhibitor, a VEGF inhibitor, a VEGFR inhibitor, a tyrosine kinase inhibitor, an anti-mitotic agent, or any combination thereof.

In some embodiments, an anti-SIRPβ1 antibody of the present disclosure is administered in combination with adoptive cell transfer (ACT) therapy, chimeric antigen receptor T cell transfer (CAR-T) therapy, vaccine therapy, and/or cytokine therapy.

In some embodiments, an anti-SIRPβ1 antibody of the present disclosure is administered in combination with at least one antibody that specifically binds to an inhibitory cytokine, e.g., an inhibitory cytokine such as an anti-CCL2 antibody, an anti-CSF-1 antibody, or an anti-IL-2 antibody.

In some embodiments, an anti-SIRPβ1 antibody of the present disclosure is administered in combination with at least one stimulatory cytokine. In some embodiments that may be combined with any of the preceding embodiments, the at least one stimulatory cytokine is selected from IFN-α4, IFN-β, IL-1β, TNF-α, IL-6, IL-8, CRP, IL-20 family members, LIF, IFN-γ, OSM, CNTF, GM-CSF, IL-11, IL-12, IL-15, IL-17, IL-18, IL-23, CXCL10, IL-33, MCP-1, MIP-1-beta, and any combination thereof.

VI. Diagnostic Uses

In some embodiments of any of the antibodies, any of the anti-SIRPβ1 antibodies provided herein is useful for detecting the presence of SIRPβ1 in a sample or an individual. The term "detecting" as used herein encompasses quantitative or qualitative detection. Provided herein are methods of using the antibodies of this disclosure for diagnostic purposes, such as the detection of SIRPβ1 in an individual or in tissue samples derived from an individual. In some embodiments, the individual is a human.

The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}$F and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

VII. Articles of Manufacture

Provided herein are articles of manufacture (e.g., kit) comprising an anti-SIRPβ1 antibody described herein. Article of manufacture may include one or more containers comprising an antibody described herein. Containers may be any suitable packaging including, but is not limited to, vials, bottles, jars, flexible packaging (e.g., sealed Mylar or plastic bags), and the like. The containers may be unit doses, bulk packages (e.g., multi-dose packages) or sub-unit doses.

In some embodiments, the kits may further include a second agent. In some embodiments, the second agent is a pharmaceutically-acceptable buffer or diluting agent including, but not limited to, such as bacteriostatic water for injection (BWFI), phosphate-buffered saline, Ringer's solution and dextrose solution. In some embodiments, the second agent is a pharmaceutically active agent. In some embodiments, the second agent is a pharmaceutically active agent described herein.

In some embodiments of any of the articles of manufacture, the article of manufactures further include instructions for use in accordance with the methods of this disclosure. The instructions generally include information as to dosage, dosing schedule, and route of administration for the intended treatment. In some embodiments, these instructions comprise a description of administration of the isolated antibody of the present disclosure (e.g., an anti-SIRPβ1 antibody described herein) to prevent, reduce risk, or treat an individual having a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer, according to any methods of this disclosure. In some embodiments, the instructions include instructions for use of the anti-SIRPβ1 antibody and the second agent (e.g., second pharmaceutically active agent).

The present disclosure will be more fully understood by reference to the following Examples. They should not, however, be construed as limiting the scope of the present disclosure. All citations throughout the disclosure are hereby expressly incorporated by reference.

EXAMPLES

The following examples are provided by way of illustration only and not by way of limitation. Those of skill in the art will readily recognize a variety of non-critical parameters that could be changed or modified to yield essentially similar results.

Example 1: Production, Identification, and Characterization of Agonist Anti-SIRPβ1 Antibodies The amino acid sequence of the human SIRPβ1 isoform 1 protein (SIRPβ1) is set forth below in SEQ ID NO: 1. Human SIRPβ1 contains a signal peptide located at amino residues 1-29 of SEQ ID NO: 1; an extracellular immunoglobulin-like variable-type (IgV) domain located at amino residues 30-136 of SEQ ID NO: 1; two immunoglobulin-like constant (IgC) domains located at amino acids 147-246 and 253-347 SEQ ID NO: 1; a transmembrane domain located at amino residues 372-392 of SEQ ID NO: 1; and an intracellular domain located at amino residues 393-398 of SEQ ID NO: 1.

```
Human SIRPβ1 amino acid sequence (SEQ ID NO: 1):
          10         20         30         40         50
  MPVPASWPHL PSPFLLMTLL LGRLTGVAGE DELQVIQPEK SVSVAAGESA 60         70         80         90        100
  TLRCAMTSLI PVGPIMWERG AGAGRELIYN QKEGHFPRVT TVSELTKRNN 110        120        130        140        150
  LDFSISISNI TPADAGTYYC VKFRKGSPDD VEFKSGAGTE LSVRAKPSAP 160        170        180        190        200
  VVSGPAVRAT PEHTVSFTCE SHGESPRDIT LKWFKNGNEL SDFQTNVDPA 210        220        230        240        250
  GDSVSYSIHS TARVVLTRGD VHSQVICEIA HITLQGDPLR GTANLSEAIR 260        270        280        290        300
  VPPTLEVTQQ PMRAENQANV TCQVSNFYPR GLQLTWLENG NVSRTETAST 310        320        330        340        350
  LIENKDGTYN WMSWLLVNTC AHRDDVVLTC QVEHDGQQAV SKSYALEISA 360        370        380        390
  HQKEHGSDIT HEAALAPTAP LLVALLLGPK LLLVVGVSAI YICWKQKA
```

The human SIRPβ1 amino acid sequence comprises a lysine residue (aa380) within the transmembrane domain that interacts with an aspartic acid in DAP12, a key adaptor protein that transduces signaling from SIRPβ1, as well as TREM1, TREM2, and other related IgV family members. A BLAST analysis of human SIRPβ1 identified multiple isoforms possibly derived from alternative splicing. Among these transcript variants, SIRPβ1 isoform 3 shares the most sequence identity to SIRPβ1 isoform 1 (FIG. 1A). Human SIRPβ1 is also related to human SIRPα. An alignment of the amino acid sequences of human SIRPβ1 and human SIRPα was generated by 2-way blast (FIG. 1B). The extracellular region of both receptors share 85% sequence identity. In contrast, human SIRPβ1 displays poorer homology to mouse SIRPβ1 (FIG. 2) suggesting that the SIRP gene loci in both species experience divergent selection pressure.

Antibodies that bind the extracellular domain of human SIRPβ1, particularly the extracellular IgV domain (amino acid residues 30-136 of SEQ ID NO: 1) can be generated using mouse hybridoma technology, phage display technology, and yeast-based platform technology. Antibodies are screened for their ability to bind cells that express SIRPβ1 and for their ability to activate SIRPβ1 signaling, activity, and function in cells and in a whole animal in vivo as described in Examples 2-20 below. For example, agonistic anti-SIRPβ1 antibodies can be produced that target the IgV domain (amino acid residues 30-136). By analogy to SIRPα, the IgV domain of SIRPβ1 is predicted bind to an unknown ligand(s), and through multimerization of receptor, lead to activation.

Production of His-Tagged and Fc-Conjugated Human SIRPα and Human SIRPβ1 IgV Domains For mammalian expression of human SIRPα and human SIRPβ1 IgV domain (also referred to as "domain 1") antigens (SEQ ID NOs: 387 and 388, respectively), synthetic genes based on cDNA were cloned into mammalian expression vectors, followed by transient transfection and expression in HEK293/T cells. Constructs included a heterologous signal peptide and C-terminal human IgG1 Fc and/or or His tag. Briefly, expression vectors containing the antigen of interest were transfected by complexing with a transfection reagent followed by exposure to HEK293/T cells for one hour followed by dilution of culture media to a final density of 4 million cells per mL. The cells were then cultured for 7 days with fresh feed media every 48 hours. After 7 days, the supernatant was collected following centrifugation and purification was performed using Ni-sepharose and, in some cases, an SEC column purification to reach >95% non-aggregated monomer content. SIRPα and SIRPβ1 monomer antigens were prepared by fragmenting a SIRPα/β1 Fc fusion antigen with modified hinge region (Lynaugh et al., MAbs. 2013 October; 5(5):641-45) with FabRICATOR (IdeS) protease (Genovis, Cat #A2-FR2-1000), followed by Protein A affinity purification to remove undigested Fc fusion protein and SEC to remove aggregated monomer.

Library Screening for Anti-SIRPβ1 Antibodies

Eight naïve (pre-immune) human synthetic yeast libraries each of ~$10^9$ diversity were designed, generated, and propagated as described previously (see, e.g.: Xu et al, 2013; WO2009036379; WO2010105256; WO2012009568; Xu et al., Protein Eng Des Sel. 2013 October; 26(10):663-70). Ten parallel selections were performed, using the eight naive libraries for human SIRPβ1-Fc fusion antigen selections and two pools of the eight libraries for human SIRPβ1 monomer selections. For the first two rounds of selection, a magnetic bead sorting technique utilizing the Miltenyi MACs system was performed, essentially as described (Siegel et al., J Immunol Methods. 2004 March; 286(1-2): 141-53). Briefly, yeast cells (~$10^9$ cells/library, total density ~$10^{10}$) were incubated with 3 ml of 10 nM biotinylated SIRPβ1-Fc fusion antigen or 100 nM biotinylated SIRPβ1 monomer antigen for 15 min at room temperature in FACS wash buffer PBS with 0.1% BSA. After washing once with 50 ml ice-cold wash buffer, the cell pellet was resuspended in 40 mL wash buffer, and 500 µL Streptavidin MicroBeads (Miltenyi Biotec, Bergisch Gladbach, Germany. Cat #130-048-101) were added to the yeast and incubated for 15 min at 4° C. Next, yeast cells were pelleted, resuspended in 5 mL wash buffer, and loaded onto a MACS LS column (Miltenyi Biotec, Bergisch Gladbach, Germany. Cat. #130-042-401). After the 5 mL was loaded, the column was washed 3 times with 3 ml FACS wash buffer. The column was then removed from the magnetic field, and the yeast were eluted with 5 mL of growth media and then grown overnight. The following four rounds of sorting were performed using flow cytometry.

For the first FACS selection round, approximately $1 \times 10^8$ yeast were pelleted, washed three times with wash buffer, and incubated with 10 nM biotinylated SIRPβ1-Fc fusion antigen or 100 nM biotinylated SIRPβ1 monomer antigen for 10 min at room temperature. Yeast were then washed twice and stained with goat anti-human F(ab')$_2$ kappa-FITC diluted 1:100 (Southern Biotech, Birmingham, Alabama, Cat #2062-02) and either streptavidin-Alexa Fluor 633 (Life Technologies, Grand Island, NY, Cat #S21375) diluted 1:500, or Extravidin-phycoerythrin (Sigma-Aldrich, St Louis, Cat #E4011) diluted 1:50, secondary reagents for 15 min at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences) and sort gates were determined to select only SIRPβ1 binding clones. In the following selection round approximately $2 \times 10^7$ yeast were prepared as above but incubation was with a polyspecific reactivity reagent to conduct a negative sort to decrease polyspecific binders (Xu et al., PEDS. 2013 October; 26(10):663-70), and binders to control protein, HIS-tagged human SIRPα monomer. The next round utilized labeling with 10 nM human SIRPβ1-Fc fusion antigens and 100 nM human SIRPβ1 monomer antigen. After the final round of sorting, yeast cells were plated and individual colonies were picked for characterization. The final round utilized labeling with 100 nM and 10 nM human SIRPβ1 monomer antigen.

Heavy chains from the second and fourth FACS sorting selection round outputs were used to prepare light chain diversification libraries used for additional selections. For these selections, the first selection round utilized Miltenyi MACs beads and labeling with 10 nM human SIRPβ1-Fc fusion antigen. Four rounds of FACS sorting followed. The first round used 100 nM human SIRPβ1 monomer antigen. The second FACS round was a negative sort to decrease binding to reagent binders, polyspecific binders, and binders to control protein human SIRPα HIS tagged monomer. The last two rounds utilized human SIRPβ1 monomer titration (100 nM, 10 nM, and 1 nM) to select highest affinity binders, 100 nM human SIRPα monomer, and competition with control AM4-5 antibody, which binds to SIRPβ1 IgV domain, to assess competitor representation in the enriched population. (See United Stated Patent Application Publication No. US2014/0242095.) After the final round of sorting, yeast cells were plated and individual colonies were picked for characterization.

Antibody IgG and Fab Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over CaptureSelect IgG-CH1 affinity matrix (LifeTechnologies, Cat #1943200250).

Octet® Binding Experiments

The affinities of the anti-SIRPβ1 antibodies were determined by measuring their dissociation constants ($K_D$) using a ForteBio Octet® Red384 system (ForteBio, Menlo Park, CA), performed generally as previously described (Estep et al., MAbs. 2013 March-April; 5(2):270-8). Briefly, Octet affinity measurements were performed by loading IgGs on-line onto AHQ sensors. Sensors were equilibrated off-line in assay buffer for 30 min and then monitored on-line for 60 seconds for baseline establishment. For avid binding measurement, sensors with loaded IgGs were exposed to 100 nM antigen (human SIRPα domain 1 (D1) Fc fusion or SIRPβ1 domain 1 (D1) Fc fusion) for 3 min, and then transferred to assay buffer for 3 min for off-rate measurement. Additional avid binding was determined by loading biotinylated SIRPβ1 monomer on SA sensors and exposing to 100 nM IgG in solution. Monovalent binding measurements were obtained by loading human SIRPα- or SIRPβ1-Fc fusion antigens onto AHQ sensor, followed by exposure to 100 nM anti-SIRPβ1 antibody Fab. Additional monovalent measurements were made by loading biotinylated human SIRPα or SIRPβ1 monomer to SA sensor followed by exposure to 100 nM Fab in solution. Kinetics data were fit using a 1:1 binding model in the data analysis software provided by ForteBio (ForteBio Data Analysis Software 7.0).

Epitope Binning

Epitope binning of the anti-SIRPβ1 antibodies was performed on a ForteBio Octet® Red384 system (ForteBio, Menlo Park, CA) using a standard sandwich format binning assay. Control anti-target IgG was loaded onto AHQ sensors and unoccupied Fc-binding sites on the sensor were blocked with a non-relevant human IgG1 antibody. The sensors were then exposed to 100 nM target antigen followed by a second anti-target antibody. Data was processed using ForteBio Data Analysis Software 7.0. Additional binding by the second antibody after antigen association indicates an unoccupied epitope (non-competitor), while no binding indicates epitope blocking (competitor). This process was iterated for two reference antibodies that bind the IgV domain of SIRPβ1: (i) AM4-5, which defines bin 1; and (ii) SB-17, which defines bin 2.

The final set of anti-SIRPβ1 antibodies were selected based on antigen binding affinities. Antibodies that were positive for binding to human SIRPβ1 were tested for cross-reactivity with human SIRPα. The bin category of each of the antibodies are listed below in Table 2. In Table 2, "ND" refers to antibodies for which the Bin category was not determined; "NB" refers to antibodies for which there was no binding to indicated antigen; "PF" refers to antibodies for which antigen binding kinetics showed poor fit to 1:1 binding model. No detectable binding to mouse SIRPβ1 D1-Fc, human SIRPα D1-Fc, or mouse SIRPα D1-Fc was observed for any of the anti-SIRPβ1 antibodies.

TABLE 2

Biochemical Characterization of anti-SIRPβ1 antibodies

| Clone Index (SB-#) | Bin Code (Human SIRPβ1) | Fab $K_D$ Human SIRPβ1-Fc (M) Monovalent | IgG $K_D$ Human SIRPβ1 D1-Fc (M) Avid |
|---|---|---|---|
| 1* | 2 | 9.79E-08 | 9.66E-10 |
| 2* | 2 | 2.66E-07 | 1.97E-09 |
| 3 | 2 | P.F. | P.F. |
| 4 | 2 | P.F | P.F. |
| 5 | 2 | P.F. | P.F. |
| 6 | 2 | 1.31E-07 | 1.30E-09 |
| 7 | 2 | P.F. | P.F. |
| 8* | 2 | 1.26E-07 | 2.72E-09 |
| 9 | 2 | P.F. | 3.66E-09 |
| 10 | 2 | P.F. | P.F. |
| 11 | 2 | 6.78E-07 | 3.69E-09 |
| 12 | 1 | N.B. | 4.94E-09 |
| 13 | 1 | P.F. | P.F. |
| 14 | 2 | P.F. | P.F. |
| 15 | 2 | 4.07E-07 | 3.45E-09 |
| 16 | 2 | N.B. | P.F. |
| 17 | 2 | 2.46E-07 | 3.32E-09 |
| 18 | 2 | P.F. | P.F. |
| 19 | 2 | N.B. | 7.41E-09 |
| 20 | 2 | P.F. | P.F. |
| 21 | 1 | N.B. | 5.86E-09 |
| 22 | 2 | N.B. | P.F. |
| 23 | 2 | P.F | P.F. |
| 24 | 1 | N.B. | P.F |
| 25 | 2 | N.B. | P.F. |
| 26 | 2 | N.B. | 6.17E-09 |
| 27 | 2 | P.F. | P.F. |
| 28 | 2 | P.F | 5.59E-09 |
| 29 | 2 | N.B. | 1.07E-08 |
| 30 | 2 | N.B. | 7.87E-09 |
| 31 | 2 | P.F. | 3.75E-09 |
| 32 | 1 | N.B. | 7.13E-09 |
| 33 | 2 | N.B. | 9.23E-09 |
| 34 | 1 | N.B. | P.F. |
| 35 | 2 | N.B. | 7.47E-09 |
| 36 | 2 | N.B. | P.F. |
| 37 | 2 | N.B. | 7.50E-09 |
| 38 | 2 | N.B. | 7.33E-09 |
| 39 | 1 | N.B. | 2.14E-08 |
| 40* | 1, 2 | 4.27E-07 | 9.64E-09 |
| 41 | 1, 2 | N.B. | 1.03E-08 |
| 42 | 1 | N.B. | 1.23E-08 |
| 43 | 1 | N.B. | 1.23E-08 |
| 44 | 1, 2 | N.B. | 1.89E-08 |
| 45 | 1 | N.B. | 1.39E-08 |
| 46 | 2 | N.B. | 2.00E-08 |
| 47 | 1, 2 | N.B. | 1.44E-08 |
| 48 | 1, 2 | N.B. | 2.77E-08 |
| 49 | 2 | 1.56E-07 | 4.39E-09 |
| 50 | 2 | P.F. | P.F. |

Antibody Heavy Chain and Light Chain Variable Domain Sequences

Using standard techniques, the amino acid sequences encoding the light chain variable domains and the heavy chain variable domains of the antibodies were determined. The EU or Kabat sequences of the antibodies are set forth in Tables 3-6, as follows. The EU or Kabat light chain HVR sequences of the antibodies are set forth in Table 3. The EU or Kabat heavy chain HVR sequences of the antibodies are set forth in Table 4. The EU or Kabat light chain framework (FR) sequences of the antibodies are set forth in Table 5. The EU or Kabat heavy chain framework (FR) sequences of the antibodies are set forth in Table 6.

TABLE 3

EU or Kabat light chain HVR sequences of anti-SIRPβ1 antibodies

| Ab ID | HVR L1 | SEQ ID NO | HVR L2 | SEQ ID NO | HVR L3 | SEQ ID NO |
|---|---|---|---|---|---|---|
| SB-1 | RASQSVSSSYLA | 383 | GASSRAT | 16 | QLLGSSPRT | 31 |
| SB-2 | RASQSVSSSYLA | 383 | GASSRAT | 16 | QQSSSHPFT | 32 |
| SB-3 | RASQSVSSYLA | 2 | DASNRAT | 17 | QQRLFHPPT | 33 |
| SB-4 | RASQSVSSSYLA | 383 | GASSRAT | 16 | QQYADAPIT | 34 |
| SB-5 | RASQSVSSYLA | 2 | DASNRAT | 17 | QQRLFHPPT | 33 |
| SB-6 | RASQSVSSSYLA | 383 | GASSRAT | 16 | QQSGHLPIT | 35 |
| SB-7 | KSSQSVLFSSNNKNYLA | 3 | WASTRES | 18 | QQHYIAPFT | 36 |
| SB-8 | RASQSVSSSYLA | 383 | GASNRAT | 19 | QQVYSSPYT | 37 |
| SB-9 | KSSQSVLFSSNNKNYLA | 3 | WASTRES | 18 | QQYHSVPPIT | 38 |
| SB-10 | RSSQSLLHSNGYNYLD | 4 | LGSNRAS | 20 | MQAIESPLT | 39 |
| SB-11 | RSSQSLLYSNGYNYLD | 5 | LGSNRAS | 20 | VQALQTPLT | 40 |
| SB-12 | RASQSVSSNLA | 6 | SASTRAT | 21 | QQLDNLPYT | 41 |
| SB-13 | RSSQSLLYSNGYNYLD | 5 | LGSNRAS | 20 | MQALRSPIT | 42 |
| SB-14 | RASQSVSSYLA | 2 | DSSNRAT | 22 | QQFSYYPIT | 43 |
| SB-15 | RASQSISSYLN | 7 | AASSLQS | 23 | QQAYSHPFT | 44 |

TABLE 3-continued

EU or Kabat light chain HVR sequences of anti-SIRPβ1 antibodies

| Ab ID | HVR L1 | SEQ ID NO | HVR L2 | SEQ ID NO | HVR L3 | SEQ ID NO |
|---|---|---|---|---|---|---|
| SB-16 | KSSQSVLFSSNNKNYLA | 3 | WASTRES | 18 | QQLFSTPFT | 45 |
| SB-17 | KSSQSVLFSSNNKNYLA | 3 | WASTRES | 18 | QQYDDPYT | 46 |
| SB-18 | RSSQSLLHSNGYNYLD | 4 | LGSNRAS | 20 | LQALQTPIT | 47 |
| SB-19 | RSSQSLLHSNGYNYLD | 4 | LGSNRAS | 20 | MQAIGVPPT | 48 |
| SB-20 | KSSQSVLYSSNNKNYLA | 8 | WASTRES | 18 | QQYYLSPFT | 49 |
| SB-21 | RSSQSLLHSNGYNYLD | 4 | LGSNRAS | 20 | MQTLRIPPT | 50 |
| SB-22 | RASQGISSWLA | 9 | AASNLQS | 24 | QQGNSYPIT | 51 |
| SB-23 | RASQSISSYLN | 7 | AASSLQS | 23 | QQAYPYPLT | 52 |
| SB-24 | RASQSVSSNLA | 6 | GASTRAT | 25 | QQLNIHPWT | 53 |
| SB-25 | RASQGISSWLA | 9 | AASSLQS | 23 | QQVNSFPWT | 54 |
| SB-26 | RSSQSLLHSNGYNYLD | 4 | LGSNRAS | 20 | MQARGLPT | 55 |
| SB-27 | KSSQSVLFSSNNKNYLA | 3 | WASTRES | 18 | QQAVSDPPT | 56 |
| SB-28 | RASQSVSSSYLA | 383 | GASSRAT | 16 | QQDGNFPLT | 57 |
| SB-29 | RSSQSLLHSNGYNYLD | 4 | LGSNRAS | 20 | MQARGSPIT | 58 |
| SB-30 | RASQSVSSSFLA | 10 | GASSRAT | 16 | QQFLSSPWT | 59 |
| SB-31 | RASQGISSWLA | 9 | AASSLQS | 23 | QQAVSHPFT | 60 |
| SB-32 | KSSQSVLYSSNNKNYLA | 8 | WASTRES | 18 | QQDFLTPIT | 61 |
| SB-33 | QASQDISNYLN | 11 | DASNLET | 26 | QQFAFLPLT | 62 |
| SB-34 | RASQSVSSNLA | 6 | GASTRAT | 25 | QQDNTFPYT | 63 |
| SB-35 | RSSQSLLHSNGYNYLD | 4 | LGSNRAS | 20 | MQTLQVPLT | 64 |
| SB-36 | RASQGISSWLA | 9 | AASSLQS | 23 | QQAFSHRT | 65 |
| SB-37 | RASQSVSSYLA | 2 | DASNRAT | 17 | QQRHTYPLT | 66 |
| SB-38 | RASQGISSWLA | 9 | AASSLQS | 23 | QQAVSYPIT | 67 |
| SB-39 | RASQSISSYLN | 7 | GASSLQS | 27 | QQSYDFPLT | 68 |
| SB-40 | RASQSVSSYLA | 2 | DSSNRAT | 22 | QQRDEHPPWT | 69 |
| SB-41 | QASQDITNYLN | 12 | DASNLET | 26 | QQADNFPYT | 70 |
| SB-42 | RASQSISSYLN | 7 | SASSLQS | 28 | QQGDSFPIT | 71 |
| SB-43 | RASQSVSSYLA | 2 | DASKRAT | 29 | QQRFDFPIT | 72 |
| SB-44 | RASQSIGSWLA | 13 | KASSLES | 30 | QEYGSYRT | 73 |
| SB-45 | RASQSVSSSFLA | 10 | GASSRAT | 16 | QQVSVPT | 74 |
| SB-46 | RASQSVRSSYLA | 14 | GASSRAT | 16 | QQLYSSPYT | 75 |
| SB-47 | QASQDISNYLN | 11 | DASNLET | 26 | QQADYFPIT | 76 |
| SB-48 | RASQGIDSWLA | 15 | AASSLQS | 23 | QQASNFPIT | 77 |
| SB-49 | QASQDITNYLN | 12 | DASNLET | 26 | QQYFHPPLT | 78 |
| SB-50 | KSSQSVLFSSNNKNYLA | 3 | WASTRES | 18 | QQFLHTPRT | 79 |

TABLE 4

EU or Kabat heavy chain HVR sequences of anti-SIRPβ1 antibodies

| Ab ID | HVR H1 | SEQ ID NO | HVR H2 | SEQ ID NO | HVR H3 | SEQ ID NO |
|---|---|---|---|---|---|---|
| SB-1 | SYAMS | 80 | TISGSGGSTYYADSVKG | 101 | DFTEVVGWLGMDV | 125 |
| SB-2 | SYGMN | 81 | VIWYDGSNKYYADSVKG | 102 | DQTAAAAIWGMDV | 126 |
| SB-3 | GYYMH | 82 | WINPSSGGTNYAQKFQG | 103 | EGIAATDAYFDL | 127 |
| SB-4 | SYGIS | 83 | WISAYNGNTNYAQKLQG | 104 | SGTHFGTYSYSNWFDP | 128 |
| SB-5 | GYYMH | 82 | WINPNSGGTNYAQKFQG | 105 | EGDEDWFDP | 129 |
| SB-6 | SYAMS | 80 | TISGSGGSTYYADSVKG | 101 | DFTEVVGWLGMDV | 125 |
| SB-7 | SYAIS | 84 | GIIPIFGTASYAQKFQG | 106 | ETRQDSAHYYGMDV | 130 |
| SB-8 | SGYYWG | 85 | SIYHSGSTYYNPSLKS | 107 | GGAMTPAGMDV | 131 |
| SB-9 | SYGIH | 86 | WISAYNGNTNYAQKLQG | 104 | DGLHYGDYIVYYGMDV | 132 |
| SB-10 | SYAIS | 84 | GIIPIFGTANYAQKFQG | 108 | GVPRGDLGMDV | 133 |
| SB-11 | NYAIS | 87 | GIIPIFGTANYAQKFQG | 108 | PVDSSSYSLGYYYGMDV | 134 |
| SB-12 | GYYMH | 82 | WINPNSGGTSYAQKFQG | 109 | DTYAYSYGMDV | 135 |
| SB-13 | SYYWS | 88 | SIYYSGSTNYNPSLKS | 110 | GDTSGGAYFDL | 136 |
| SB-14 | SYAIS | 84 | GIIPIFGTASYAQKFQG | 106 | DRGGVGFDY | 137 |
| SB-15 | SNSYYWG | 89 | SIYYSGSTYYNPSLKS | 111 | EVGAPPSYPFDI | 138 |
| SB-16 | SYAIS | 84 | SIIPIFGTANYAQKFQG | 112 | ANYYDSSGYSGLDL | 139 |
| SB-17 | SYGIS | 83 | WISAYNGNTNYAQKLQG | 104 | GPLLYGDYHVRYGMDV | 140 |
| SB-18 | SYAIS | 84 | GIIPIFGTANYAQKFQG | 108 | AKPRGDYGMDV | 141 |
| SB-19 | SYAIS | 84 | GIIPIFGTANYAQKFQG | 108 | DGGGGYAYEYFQH | 142 |
| SB-20 | SYAIS | 84 | SIIPIFGTANYAQKFQG | 112 | DGREYGGHYYGMDV | 143 |
| SB-21 | SNGIS | 90 | WISAYNGNTNYAQKLQG | 104 | VGNMDQEYFDL | 144 |
| SB-22 | SNYMS | 91 | VIYSDGSTYYADSVKG | 113 | PTRYGYDRLGMDV | 145 |
| SB-23 | SYAIS | 84 | GIAPIFGTANYAQKFQG | 114 | TTYRDYYMDV | 146 |
| SB-24 | SGYYWA | 92 | SIYHSGSTYYNPSLKS | 107 | DRSRGYPVYGMDV | 147 |
| SB-25 | SLAIS | 93 | GIIPIFGTANYAQKFQG | 108 | SGGDYSGYDYASGMDV | 148 |
| SB-26 | SYAIS | 84 | GIIPIFGTANYAQKFQG | 108 | DGSAGRQEHGMDV | 149 |
| SB-27 | SYAIS | 84 | GIIPIFGTANYAQKFQG | 108 | QDLGSSHWHFDL | 150 |
| SB-28 | SSSYYWG | 94 | SISYSGSTYYNPSLKS | 115 | DPRDYSSGSSGGGWGYFDL | 151 |
| SB-29 | SYAIS | 84 | SIIPIFGTANYAQKFQG | 112 | APYGSSSGYGYFDL | 152 |
| SB-30 | SGGYYWS | 95 | YIYYSGSTVYNPSLKS | 116 | EGPGYPSYFDP | 153 |
| SB-31 | SYYMH | 96 | IINPGGGSTSYAQKFQG | 117 | EGLYSSGWYIDV | 154 |
| SB-32 | SYYWS | 88 | YIYSSGSTNYNPSLKS | 118 | GDSSSGGLDL | 155 |
| SB-33 | SNYMS | 91 | VIYSGGSTYYADSVKG | 119 | GQYTGSLDV | 156 |
| SB-34 | GYYMH | 82 | WINPNSGGTKYAQKFQG | 120 | DTYYTPYGMDV | 157 |
| SB-35 | SYAIS | 84 | GIIPIFGTANYAQKFQG | 108 | GRPQSESYLLDY | 158 |
| SB-36 | SYYMH | 96 | IINPSGGSTSYAQKFQG | 121 | EGPEQLWYLDY | 159 |
| SB-37 | NYAIS | 87 | GIIPIFGTANYAQKFQG | 108 | SRWGASGYYYYMDV | 160 |

TABLE 4-continued

EU or Kabat heavy chain HVR sequences of anti-SIRPβ1 antibodies

| Ab ID | HVR H1 | SEQ ID NO | HVR H2 | SEQ ID NO | HVR H3 | SEQ ID NO |
|---|---|---|---|---|---|---|
| SB-38 | SYYMH | 96 | IINPSGGSTSYAQKFQG | 121 | ESGTDFGTISY | 161 |
| SB-39 | SGYYWA | 92 | SIYHSGSTYYNPSLKS | 107 | GGSNYGDYGRFDY | 162 |
| SB-40 | SYYMS | 97 | IINPSGGSTSYAQKFQG | 121 | DTGEYSYSPHGMDV | 163 |
| SB-41 | SSSYYWG | 94 | SIYYSGSTYYNPSLKS | 111 | VGQYPIYGMDV | 164 |
| SB-42 | SYGIS | 83 | WISAYNGNTNYAQKLQG | 104 | GPGHYYVAGMDV | 165 |
| SB-43 | SGYYWA | 92 | SIYHSGSTYYNPSLKS | 107 | DAPGYPMLGMDV | 166 |
| SB-44 | SNYMS | 91 | VIYSGGDTYYADSVKG | 122 | EGSSFWSGSAVSYYGMDV | 167 |
| SB-45 | SGYYWA | 92 | SIYHSGSTYYNPSLKS | 107 | DLSRGYAVSGMDV | 168 |
| SB-46 | SYAMS | 80 | AISGSGGSTYYADSVKG | 123 | ASPWELDV | 169 |
| SB-47 | SSSYAWG | 98 | SIYYSGSTYYNPSLKS | 111 | DLGHYDYWSGSRDYYYGMDV | 170 |
| SB-48 | SYGMH | 99 | VISYDGSNKYYADSVKG | 124 | DGTIAAAGWPPEYFQH | 171 |
| SB-49 | SSDYYWG | 100 | SIYYSGSTYYNPSLKS | 111 | GPTGYKDKWRYYYGMDV | 172 |
| SB-50 | SYAIS | 84 | GIIPIFGTANYAQKFQG | 108 | EGGGHASYHYYGMDV | 173 |

TABLE 5

EU or Kabat light chain Framework sequences of anti-SIRPβ1 antibodies

| Ab ID | VL FR1 | SEQ ID NO | VL FR2 | SEQ ID NO | VL F3 | SEQ ID NO | VL FR4 | SEQ ID NO |
|---|---|---|---|---|---|---|---|---|
| SB-1 | EIVMTQSPGTLSLSPGERATLSC | 174 | WYQQKPGQAPRLLIY | 186 | GIPDRFSGSGSGTDFTLTISRLEPEDFAVYYC | 192 | FGGGTKVEIK | 200 |
| SB-2 | EIVLTQSPGTLSLSPGERATLSC | 175 | WYQQKPGQAPRLLIY | 186 | GIPDRFSGSGSGTDFTLTISRLEPEDFAVYYC | 192 | FGGGTKVEIK | 200 |
| SB-3 | EIVMTQSPATLSLSPGERATLSC | 176 | WYQQKPGQAPRLLIY | 186 | GIPARFSGSGSGTDFTLTISSLEPEDFAVYYC | 193 | FGGGTKVEIK | 200 |
| SB-4 | EIVLTQSPGTLSLSPGERATLSC | 175 | WYQQKPGQAPRLLIY | 186 | GIPDRFSGSGSGTDFTLTISRLEPEDFAVYYC | 192 | FGGGTKVEIK | 200 |
| SB-5 | EIVLTQSPATLSLSPGERATITC | 177 | WYQQKPGQAPRLLIY | 186 | GIPARFSGSGSGTDFTLTISSLEPEDFAVYYC | 193 | FGGGTKVEIK | 200 |
| SB-6 | EIVLTQSPGTLSLSPGERATLSC | 175 | WYQQKPGQAPRLLIY | 186 | GIPDRFSGSGSGTDFTLTISRLEPEDFAVYYC | 192 | FGGGTKVEIK | 200 |
| SB-7 | DIVMTQSPDSLAVSLGERATINC | 178 | WYQQKPGQPPKLLIY | 187 | GVPDRFSGSGSGTDFTLTISSLQAEDVAVYYC | 194 | FGGGTKVEIK | 200 |
| SB-8 | EIVMTQSPGTLSLSPGERATLSC | 174 | WYQQKPGQAPRLLIY | 186 | GIPDRFSGSGSGTDFTLTISRLEPEDFAVYYC | 192 | FGGGTKVEIK | 200 |
| SB-9 | DIVMTQSPDSLAVSLGERATINC | 178 | WYQQKPGQPPKLLIY | 187 | GVPDRFSGSGSGTDFTLTISSLQAEDVAVYYC | 194 | FGGGTKVEIK | 200 |

TABLE 5-continued

EU or Kabat light chain Framework sequences of anti-SIRPβ1 antibodies

| Ab ID | VL FR1 | SEQ ID NO | VL FR2 | SEQ ID NO | VL F3 | SEQ ID NO | VL FR4 | SEQ ID NO |
|---|---|---|---|---|---|---|---|---|
| SB-10 | DIVMTQSPLSLPVTPGEPASISC | 179 | WYLQKPGQSPQLLIY | 188 | GVPDRFSGSGSGTDFTLKISRVEAEDVGVYYC | 195 | FGGGTKVEIK | 200 |
| SB-11 | DIVMTQSPLSLPVTPGEPASISC | 179 | WYLQKPGQSPQLLIY | 188 | GVPDRFSGSGSGTDFTLKISRVEAEDVGVYYC | 195 | FGGGTKVEIK | 200 |
| SB-12 | EIVMTQSPATLSVSPGERATLSC | 180 | WYQQKPGQAPRLLIY | 186 | GIPARFSGSGSGTEFTLTISSLQSEDFAVYYC | 196 | FGGGTKVEIK | 200 |
| SB-13 | DIVMTQSPLSLPVTPGEPASISC | 179 | WYLQKPGQSPQVLIY | 189 | GVPDRFSGSGSGTDFTLKISRVEAEDVGVYYC | 195 | FGGGTKVEIK | 200 |
| SB-14 | EIVMTQSPATLSLSPGERATLSC | 176 | WYQQKPGQAPRLLIY | 186 | GIPARFSGSGSGTDFTLTISSLEPEDFAVYYC | 193 | FGGGTKVEIK | 200 |
| SB-15 | DIQMTQSPSSLSASVGDRVTITC | 181 | WYQQKPGKAPKLLIY | 190 | GVPSRFSGSGSGTDFTLTISSLQPEDFATYYC | 197 | FGGGTKVEIK | 200 |
| SB-16 | DIVMTQSPDSLAVSLGERATINC | 178 | WYQQKPGQPPKLLIY | 187 | GVPDRFSGSGSGTDFTLTISSLQAEDVAVYYC | 194 | FGGGTKVEIK | 200 |
| SB-17 | DIVMTQSPDSLAVSLGERATINC | 178 | WYQQKPGQPPKLLIY | 187 | GVPDRFSGSGSGTDFTLTISSLQAEDVAVYYC | 194 | FGGGTKVEIK | 200 |
| SB-18 | EIVLTQSPATLSLSPGERATLSC | 182 | WYLQKPGQSPQLLIY | 188 | GVPDRFSGSGSGTDFTLKISRVEAEDVGVYYC | 195 | FGGGTKVEIK | 200 |
| SB-19 | DIVMTQSPLSLPVTPGEPASISC | 179 | WYLQKPGQSPQLLIY | 188 | GVPDRFSGSGSGTDFTLKISRVEAEDVGVYYC | 195 | FGGGTKVEIK | 200 |
| SB-20 | DIVMTQSPDSLAVSLGERATINC | 178 | WYQQKPGQPPKLLIY | 187 | GVPDRFSGSGSGTDFTLTISSLQAEDVAVYYC | 194 | FGGGTKVEIK | 200 |
| SB-21 | DIVMTQSPLSLPVTPGEPASISC | 179 | WYLQKPGQSPQLLIY | 188 | GVPDRFSGSGSGTDFTLKISRVEAEDVGVYYC | 195 | FGGGTKVEIK | 200 |
| SB-22 | DIQMTQSPSSVSASVGDRVTITC | 183 | WYQQKPGKAPKLLIY | 190 | GVPSRFSGSGSGTDFTLTISSLQPEDFATYYC | 197 | FGGGTKVEIK | 200 |
| SB-23 | DIQMTQSPSSLSASVGDRVTITC | 181 | WYQQKPGKAPKLLIY | 190 | GVPSRFSGSGSGTDFTLTISSLQPEDFATYYC | 197 | FGGGTKVEIK | 200 |
| SB-24 | EIVMTQSPATLSVSPGERATLSC | 180 | WYQQKPGQAPRLLIY | 186 | GIPARFSGSGSGTEFTLTISSLQSEDFAVYYC | 196 | FGGGTKVEIK | 200 |
| SB-25 | DIQMTQSPSSVSASVGDRVTITC | 183 | WYQQKPGKAPKLLIY | 190 | GVPSRFSGSGSGTDFTLTISSLQPEDFATYYC | 197 | FGGGTKVEIK | 200 |
| SB-26 | DIVMTQSPLSLPVTPGEPASISC | 179 | WYLQKPGQSPQLLIY | 188 | GVPDRFSGSGSGTDFTLKISRVEAEDVGVYYC | 195 | FGGGTKVEIK | 200 |
| SB-27 | DIVMTQSPDSLAVSLGERATINC | 178 | WYQQKPGQPPKLLIY | 187 | GVPDRFSGSGSGTDFTLTISSLQAEDVAVYYC | 194 | FGGGTKVEIK | 200 |

TABLE 5-continued

EU or Kabat light chain Framework sequences of anti-SIRPβ1 antibodies

| Ab ID | VL FR1 | SEQ ID NO | VL FR2 | SEQ ID NO | VL F3 | SEQ ID NO | VL FR4 | SEQ ID NO |
|---|---|---|---|---|---|---|---|---|
| SB-28 | EIVLTQSPGTLSLSPGERATLSC | 175 | WYQQKPGQAPRLLIY | 186 | GIPDRFSGSGSGTDFTLTISRLEPEDFAVYYC | 192 | FGGGTKVEIK | 200 |
| SB-29 | DIVMTQSPLSLPVTPGEPASISC | 179 | WYLQKPGQSPQLLIF | 191 | GVPDRFSGSGSGTDFTLKISRVEAEDVGVYYC | 195 | FGGGTKVEIK | 200 |
| SB-30 | EIVLTQSPGTLSLSPGERATLSC | 175 | WYQQKPGQAPRLLIY | 186 | GIPDRFSGSGSGTDFTLTISRLEPEDFAVYYC | 192 | FGGGTKVEIK | 200 |
| SB-31 | DIQMTQSPSSVSASVGDRVTITC | 183 | WYQQKPGKAPKLLIY | 190 | GVPSRFSGSGSGTDFTLTISSLQPEDFATYYC | 197 | FGGGTKVEIK | 200 |
| SB-32 | DIVMTQSPDSLAVSLGERATINC | 178 | WYQQKPGQPPKLLIY | 187 | GVPDRFSGSGSGTDFTLTISSLQAEDVAVYYC | 194 | FGGGTKVEIK | 200 |
| SB-33 | DIQMTQSPSSLSASVGDRVTITC | 181 | WYQQKPGKAPKLLIY | 190 | GVPSRFSGSGSGTDFTFTISSLQPEDIATYYC | 198 | FGGGTKVEIK | 200 |
| SB-34 | EIVMTQSPATLSVSPGERATLSC | 180 | WYQQKPGQAPRLLIY | 186 | GIPARFSGSGSGTEFTLTISSLQSEDFAVYYC | 196 | FGGGTKVEIK | 200 |
| SB-35 | DIVMTQSPLSLPVTPGEPASISC | 179 | WYLQKPGQSPQLLIY | 188 | GVPDRFSGSGSGTDFTLKISRVEAEDVGVYYC | 195 | FGGGTKVEIK | 200 |
| SB-36 | DIQMTQSPSSVSASVGDRVTITC | 183 | WYQQKPGKAPKLLIY | 190 | GVPSRFSGSGSGTDFTLTISSLQPEDFATYYC | 197 | FGGGTKVEIK | 200 |
| SB-37 | EIVLTQSPATLSLSPGERATLSC | 182 | WYQQKPGQAPRLLIY | 186 | GIPARFSGSGSGTDFTLTISSLEPEDFAVYYC | 193 | FGGGTKVEIK | 200 |
| SB-38 | DIQMTQSPSSVSASVGDRVTITC | 183 | WYQQKPGKAPKLLIY | 190 | GVPSRFSGSGSGTDFTLTISSLQPEDFATYYC | 197 | FGGGTKVEIK | 200 |
| SB-39 | DIQMTQSPSSLSASVGDRVTITC | 181 | WYQQKPGKAPKLLIY | 190 | GVPSRFSGSGSGTDFTLTISSLQPEDFATYYC | 197 | FGGGTKVEIK | 200 |
| SB-40 | EIVLTQSPATLSLSPGERATLSC | 182 | WYQQKPGQAPRLLIY | 186 | GIPARFSGSGSGTDFTLTISSLEPEDFAVYYC | 193 | FGGGTKVEIK | 200 |
| SB-41 | DIQMTQSPSSLSASVGDRVTITC | 181 | WYQQKPGKAPKLLIY | 190 | GVPSRFSGSGSGTDFTFTISSLQPEDIATYYC | 198 | FGGGTKVEIK | 200 |
| SB-42 | EIVMTQSPATLSVSPGERATITC | 184 | WYQQKPGKAPKLLIY | 190 | GVPSRFSGSGSGTDFTLTISSLQPEDFATYYC | 197 | FGGGTKVEIK | 200 |
| SB-43 | EIVLTQSPATLSLSPGERATLSC | 182 | WYQQKPGQAPRLLIY | 186 | GIPARFSGSGSGTDFTLTISSLEPEDFAVYYC | 193 | FGGGTKVEIK | 200 |
| SB-44 | DIQMTQSPSTLSASVGDRVTITC | 185 | WYQQKPGKAPKLLIY | 190 | GVPSRFSGSGSGTEFTLTISSLQPDDFATYYC | 199 | FGGGTKVEIK | 200 |
| SB-45 | EIVLTQSPGTLSLSPGERATLSC | 175 | WYQQKPGQAPRLLIY | 186 | GIPDRFSGSGSGTDFTLTISRLEPEDFAVYYC | 192 | FGGGTKVEIK | 200 |

TABLE 5-continued

EU or Kabat light chain Framework sequences of anti-SIRPβ1 antibodies

| Ab ID | VL FR1 | SEQ ID NO | VL FR2 | SEQ ID NO | VL F3 | SEQ ID NO | VL FR4 | SEQ ID NO |
|---|---|---|---|---|---|---|---|---|
| SB-46 | EIVLTQSPG TLSLSPGER ATLSC | 175 | WYQQKPGQ APRLLIY | 186 | GIPDRFSGSGSG TDFTLTISRLEP EDFAVYYC | 192 | FGGGTKVEIK | 200 |
| SB-47 | DIQMTQSP SSLSASVG DRVTITC | 181 | WYQQKPGK APKLLIY | 190 | GVPSRFSGSGS GTDFTFTISSLQ PEDIATYYC | 198 | FGGGTKVEIK | 200 |
| SB-48 | DIQMTQSP SSVSASVG DRVTITC | 183 | WYQQKPGK APKLLIY | 190 | GVPSRFSGSGS GTDFTLTISSLQ PEDFATYYC | 197 | FGGGTKVEIK | 200 |
| SB-49 | DIQMTQSP SSLSASVG DRVTITC | 181 | WYQQKPGK APKLLIY | 190 | GVPSRFSGSGS GTDFTFTISSLQ PEDIATYYC | 198 | FGGGTKVEIK | 200 |
| SB-50 | DIVMTQSP DSLAVSLG ERATINC | 178 | WYQQKPGQ PPKLLIY | 187 | GVPDRFSGSGS GTDFTLTISSLQ AEDVAVYYC | 194 | FGGGTKVEIK | 200 |

TABLE 6

EU or Kabat heavy chain Framework sequences of anti-SIRPβ1 antibodies

| Ab ID | VH FR1 | SEQ ID NO | VH FR2 | SEQ ID NO | VH F3 | SEQ ID NO | VH FR4 | SEQ ID NO |
|---|---|---|---|---|---|---|---|---|
| SB-1 | EVQLLESGGGL VQPGGSLRLSC AASGFTFS | 201 | WVRQAPGKG LEWVS | 210 | RFTISRDNSKNT LYLQMNSLRAE DTAVYYCAK | 215 | WGGGTTV TVSS | 222 |
| SB-2 | QVQLVESGGG VVQPGRSLRLS CAASGFTFS | 202 | WVRQAPGKG LEWVA | 211 | RFTISRDNSKNT LYLQMNSLRAE DTAVYYCAR | 216 | WGQGTTV TVSS | 222 |
| SB-3 | QVQLVQSGAE VKKPGASVKV SCKASGYTFT | 203 | WVRQAPGQG LEWMG | 212 | RVTMTRDTSIST AYMELSRLRSD DTAVYYCAR | 217 | WGRGTLV TVSS | 223 |
| SB-4 | QVQLVQSGAE VKKPGASVKV SCKASGYTFT | 203 | WVRQAPGQG LEWMG | 212 | RVTMTTDTSTST AYMELRSLRSD DTAVYYCAR | 218 | WGQGTLV TVSS | 224 |
| SB-5 | QVQLVQSGAE VKKPGASVKV SCKASGYTFT | 203 | WVRQAPGQG LEWMG | 212 | RVTMTRDTSIST AYMELSRLRSD DTAVYYCAR | 217 | WGQGTLV TVSS | 224 |
| SB-6 | EVQLLESGGGL VQPGGSLRLSC AASGFTFS | 201 | WVRQAPGKG LEWVS | 210 | RFTISRDNSKNT LYLQMNSLRAE DTAVYYCAK | 215 | WGQGTTV TVSS | 222 |
| SB-7 | QVQLVQSGAE VKKPGSSVKVS CKASGGTFS | 204 | WVRQAPGQG LEWMG | 212 | RVTITADESTST AYMELSSLRSED TAVYYCAR | 219 | WGQGTTV TVSS | 222 |
| SB-8 | QVQLQESGPGL VKPSETLSLTC AVSGYSIS | 205 | WIRQPPGKGL EWIG | 213 | RVTISVDTSKNQ FSLKLSSVTAAD TAVYYCAR | 220 | WGQGTTV TVSS | 222 |
| SB-9 | QVQLVQSGAE VKKPGASVKV SCKASGYTFT | 203 | WVRQAPGQG LEWMG | 212 | RVTMTTDTSTST AYMELRSLRSD DTAVYYCAR | 218 | WGQGTTV TVSS | 222 |
| SB-10 | QVQLVQSGAE VKKPGSSVKVS CKASGGTFS | 204 | WVRQAPGQG LEWMG | 212 | RVTITADESTST AYMELSSLRSED TAVYYCAR | 219 | WGQGTTV TVSS | 222 |
| SB-11 | QVQLVQSGAE VKKPGSSVKVS CKASGGTFS | 204 | WVRQAPGQG LEWMG | 212 | RVTITADESTST AYMELSSLRSED TAVYYCAR | 219 | WGKGTTV TVSS | 225 |

TABLE 6-continued

EU or Kabat heavy chain Framework sequences of anti-SIRPβ1 antibodies

| Ab ID | VH FR1 | SEQ ID NO | VH FR2 | SEQ ID NO | VH F3 | SEQ ID NO | VH FR4 | SEQ ID NO |
|---|---|---|---|---|---|---|---|---|
| SB-12 | QVQLVQSGAE VKKPGASVKV SCKASGYTFT | 203 | WVRQAPGQG LEWMG | 212 | RVTMTRDTSIST AYMELSRLRSD DTAVYYCAR | 217 | WGQGTTV TVSS | 222 |
| SB-13 | QVQLQESGPGL VKPSETLSLTC TVSGGSIS | 206 | WIRQPPGKGL EWIG | 213 | RVTISVDTSKNQ FSLKLSSVTAAD TAVYYCAR | 220 | WGRGTLV TVSS | 223 |
| SB-14 | QVQLVQSGAE VKKPGSSVKVS CKASGGTFS | 204 | WVRQAPGQG LEWMG | 212 | RVTITADESTST AYMELSSLRSED TAVYYCAR | 219 | WGQGTLV TVSS | 224 |
| SB-15 | QLQLQESGPGL VKPSETLSLTC TVSGGSIS | 207 | WIRQPPGKGL EWIG | 213 | RVTISVDTSKNQ FSLKLSSVTAAD TAVYYCAR | 220 | WGQGTM VTVSS | 226 |
| SB-16 | QVQLVQSGAE VKKPGSSVKVS CKASGGTFS | 204 | WVRQAPGQG LEWMG | 212 | RVTITADESTST AYMELSSLRSED TAVYYCAR | 219 | WGRGTLV TVSS | 223 |
| SB-17 | QVQLVQSGAE VKKPGASVKV SCKASGYTFT | 203 | WVRQAPGQG LEWMG | 212 | RVTMTTDTSTST AYMELRSLRSD DTAVYYCAR | 218 | WGQGTTV TVSS | 222 |
| SB-18 | QVQLVQSGAE VKKPGSSVKVS CKASGGTFS | 204 | WVRQAPGQG LEWMG | 212 | RVTITADESTST AYMELSSLRSED TAVYYCAR | 219 | WGQGTTV TVSS | 222 |
| SB-19 | QVQLVQSGAE VKKPGSSVKVS CKASGGTFS | 204 | WVRQAPGQG LEWMG | 212 | RVTITADESTST AYMELSSLRSED TAVYYCAR | 219 | WGQGTLV TVSS | 224 |
| SB-20 | QVQLVQSGAE VKKPGSSVKVS CKASGGTFS | 204 | WVRQAPGQG LEWMG | 212 | RVTITADESTST AYMELSSLRSED TAVYYCAR | 219 | WGQGTTV TVSS | 222 |
| SB-21 | QVQLVQSGAE VKKPGASVKV SCKASGYTFT | 203 | WVRQAPGQG LEWMG | 212 | RVTMTTDTSTST AYMELRSLRSD DTAVYYCAR | 218 | WGRGTLV TVSS | 223 |
| SB-22 | EVQLVESGGGL VQPGGSLRLSC AASGFTVS | 208 | WVRQAPGKG LEWVS | 210 | RFTISRDNSKNT LYLQMNSLRAE DTAVYYCAR | 216 | WGQGTTV TVSS | 222 |
| SB-23 | QVQLVQSGAE VKKPGSSVKVS CKASGGTFS | 204 | WVRQAPGQG LEWMG | 212 | RVTITADESTST AYMELSSLRSED TAVYYCAR | 219 | WGKGTTV TVSS | 225 |
| SB-24 | QVQLQESGPGL VKPSETLSLTC AVSGYSIS | 205 | WIRQPPGKGL EWIG | 213 | RVTISVDTSKNQ FSLKLSSVTAAD TAVYYCAR | 220 | WGQGTTV TVSS | 222 |
| SB-25 | QVQLVQSGAE VKKPGSSVKVS CKASGGTFS | 204 | WVRQAPGQG LEWMG | 212 | RVTITADESTST AYMELSSLRSED TAVYYCAR | 219 | WGQGTTV TVSS | 222 |
| SB-26 | QVQLVQSGAE VKKPGSSVKVS CKASGGTFS | 204 | WVRQAPGQG LEWMG | 212 | RVTITADESTST AYMELSSLRSED TAVYYCAR | 219 | WGQGTTV TVSS | 222 |
| SB-27 | QVQLVQSGAE VKKPGSSVKVS CKASGGTFS | 204 | WVRQAPGQG LEWMG | 212 | RVTITADESTST AYMELSSLRSED TAVYYCAR | 219 | WGRGTLV TVSS | 223 |
| SB-28 | QLQLQESGPGL VKPSETLSLTC TVSGGSIS | 207 | WIRQPPGKGL EWIG | 213 | RVTISVDTSKNQ FSLKLSSVTAAD TAVYYCAR | 220 | WGRGTLV TVSS | 223 |
| SB-29 | QVQLVQSGAE VKKPGSSVKVS CKASGGTFS | 204 | WVRQAPGQG LEWMG | 212 | RVTITADESTST AYMELSSLRSED TAVYYCAR | 219 | WGRGTLV TVSS | 223 |

TABLE 6-continued

EU or Kabat heavy chain Framework sequences of anti-SIRPβ1 antibodies

| Ab ID | VH FR1 | SEQ ID NO | VH FR2 | SEQ ID NO | VH F3 | SEQ ID NO | VH FR4 | SEQ ID NO |
|---|---|---|---|---|---|---|---|---|
| SB-30 | QVQLQESGPGL VKPSQTLSLTC TVSGGSIS | 209 | WIRQHPGKG LEWIG | 214 | RVTISVDTSKNQ FSLKLSSVTAAD TAVYYCAR | 220 | WGQGTLV TVSS | 224 |
| SB-31 | QVQLVQSGAE VKKPGASVKV SCKASGYTFT | 203 | WVRQAPGQG LEWMG | 212 | RVTMTRDTSTST VYMELSSLRSED TAVYYCAR | 221 | WGQGTLV TVSS | 224 |
| SB-32 | QVQLQESGPGL VKPSETLSLTC TVSGGSIS | 206 | WIRQPPGKGL EWIG | 213 | RVTISVDTSKNQ FSLKLSSVTAAD TAVYYCAR | 220 | WGRGTLV TVSS | 223 |
| SB-33 | EVQLVESGGGL VQPGGSLRLSC AASGFTVS | 208 | WVRQAPGKG LEWVS | 210 | RFTISRDNSKNT LYLQMNSLRAE DTAVYYCAR | 216 | WGQGTM VTVSS | 226 |
| SB-34 | QVQLVQSGAE VKKPGASVKV SCKASGYTFT | 203 | WVRQAPGQG LEWMG | 212 | RVTMTRDTSIST AYMELSRLRSD DTAVYYCAR | 217 | WGQGTTV TVSS | 222 |
| SB-35 | QVQLVQSGAE VKKPGSSVKVS CKASGGTFS | 204 | WVRQAPGQG LEWMG | 212 | RVTITADESTST AYMELSSLRSED TAVYYCAR | 219 | WGQGTLV TVSS | 224 |
| SB-36 | QVQLVQSGAE VKKPGASVKV SCKASGYTFT | 203 | WVRQAPGQG LEWMG | 212 | RVTMTRDTSTST VYMELSSLRSED TAVYYCAR | 221 | WGQGTLV TVSS | 224 |
| SB-37 | QVQLVQSGAE VKKPGSSVKVS CKASGGTFS | 204 | WVRQAPGQG LEWMG | 212 | RVTITADESTST AYMELSSLRSED TAVYYCAR | 219 | WGQGTM VTVSS | 226 |
| SB-38 | QVQLVQSGAE VKKPGASVKV SCKASGYTFT | 203 | WVRQAPGQG LEWMG | 212 | RVTMTRDTSTST VYMELSSLRSED TAVYYCAR | 221 | WGQGTLV TVSS | 224 |
| SB-39 | QVQLQESGPGL VKPSETLSLTC AVSGYSIS | 205 | WIRQPPGKGL EWIG | 213 | RVTISVDTSKNQ FSLKLSSVTAAD TAVYYCAR | 220 | WGQGTLV TVSS | 224 |
| SB-40 | QVQLVQSGAE VKKPGASVKV SCKASGYTFT | 203 | WVRQAPGQG LEWMG | 212 | RVTMTRDTSTST VYMELSSLRSED TAVYYCAR | 221 | WGQGTTV TVSS | 222 |
| SB-41 | QLQLQESGPGL VKPSETLSLTC TVSGGSIS | 207 | WIRQPPGKGL EWIG | 213 | RVTISVDTSKNQ FSLKLSSVTAAD TAVYYCAR | 220 | WGQGTTV TVSS | 222 |
| SB-42 | QVQLVQSGAE VKKPGASVKV SCKASGYTFT | 203 | WVRQAPGQG LEWMG | 212 | RVTMTTDTSTST AYMELRSLRSD DTAVYYCAR | 218 | WGQGTTV TVSS | 222 |
| SB-43 | QVQLQESGPGL VKPSETLSLTC AVSGYSIS | 205 | WIRQPPGKGL EWIG | 213 | RVTISVDTSKNQ FSLKLSSVTAAD TAVYYCAR | 220 | WGQGTTV SVSS | 227 |
| SB-44 | EVQLVESGGGL VQPGGSLRLSC AASGFTVS | 208 | WVRQAPGKG LEWVS | 210 | RFTISRDNSKNT LYLQMNSLRAE DTAVYYCAR | 216 | WGQGTTV TVSS | 222 |
| SB-45 | QVQLQESGPGL VKPSETLSLTC AVSGYSIS | 205 | WIRQPPGKGL EWIG | 213 | RVTISVDTSKNQ FSLKLSSVTAAD TAVYYCAR | 220 | WGQGTTV TVSS | 222 |
| SB-46 | EVQLLESGGGL VQPGGSLRLSC AASGFTFS | 201 | WVRQAPGKG LEWVS | 210 | RFTISRDNSKNT LYLQMNSLRAE DTAVYYCAR | 216 | WGQGTM VTVSS | 226 |
| SB-47 | QLQLQESGPGL VKPSETLSLTC TVSGGSIS | 207 | WIRQPPGKGL EWIG | 213 | RVTISVDTSKNQ FSLKLSSVTAAD TAVYYCAR | 220 | WGQGTTV TVSS | 222 |

TABLE 6-continued

EU or Kabat heavy chain Framework sequences of anti-SIRPβ1 antibodies

| Ab ID | VH FR1 | SEQ ID NO | VH FR2 | SEQ ID NO | VH F3 | SEQ ID NO | VH FR4 | SEQ ID NO |
|---|---|---|---|---|---|---|---|---|
| SB-48 | QVQLVESGGG VVQPGRSLRLS CAASGFTFS | 202 | WVRQAPGKG LEWVA | 211 | RFTISRDNSKNT LYLQMNSLRAE DTAVYYCAR | 216 | WGQGTLV TVSS | 224 |
| SB-49 | QLQLQESGPGL VKPSETLSLTC TVSGGSIS | 207 | WIRQPPGKGL EWIG | 213 | RVTISVDTSKNQ FSLKLSSVTAAD TAVYYCAR | 220 | WGQGTTV TVSS | 222 |
| SB-50 | QVQLVQSGAE VKKPGSSVKVS CKASGGTFS | 204 | WVRQAPGQG LEWMG | 212 | RVTITADESTST AYMELSSLRSED TAVYYCAR | 219 | WGQGTTV TVSS | 222 |

Characterization of SIRPβ1 Antibody Binding

Initial characterization of anti-SIRPβ1 antibodies involved determining their ability to bind cell lines expressing human or mouse SIRPβ11. Cells were harvested, plated at $10^6$/ml in a 96-well plate, washed, and incubated in 100 μl FACS buffer containing 1 μg/ml anti-SIRPβ1 antibody for 0.5 hour on ice. Cells were then washed twice and incubated in 100 μl FACS buffer containing 0.5 μg/ml PE-conjugated secondary antibody for 30 minutes on ice. Cells were washed twice in cold FACS buffer and acquired on a BD FACS Canto. Data analysis and calculation of mean fluorescence intensity (MFI) values or 00 positive cells was performed with FlowJo (TreeStar) software version 10.0.7.

Table 7 shows the mean fluorescence intensity (MFI) values of anti-SIRPβ1 antibodies binding to a Chinese hamster ovary (CHO) cell line expressing low levels of recombinant human SIRPβ1. The human IgG1 isotype control established the background fluorescence signal set to 1. Of the 50 anti-SIRPβ1 antibody clones tested, 32 clones bound to cells with an MFI ≥2-fold over background. As a negative control, the anti-SIRPβ1 antibodies were also screened for surface binding to CHO cells overexpressing recombinant mouse SIRPβ11. As expected, none of the test antibodies bound to mouse SIRPβ1. Given the high sequence similarity between receptors of the SIRP family, anti-SIRPβ1 antibodies were also screened for cross-reactivity to human and mouse SIR-Pa. In cell binding assays, none of the anti-SIRPβ1 antibodies bound cells overexpressing human or mouse SIRPα.

TABLE 7

Cell Binding Characterization of anti-SIRPβ1 antibodies

| Clone Index (SB-#) | Cell Binding Human SIRPβ FOB (Fold Over Background) | Cell Binding Human SIRPα FOB (Fold Over Background) | Cell Binding Mouse SIRPβ FOB (Fold Over Background) | Cell Binding Mouse SIRPα FOB (Fold Over Background) |
|---|---|---|---|---|
| 1* | 5.7 | 2.3 | 1.1 | 1.4 |
| 2* | 8.7 | 3.0 | 1.3 | 1.1 |
| 3 | 2.5 | 1.8 | 1.3 | 1.3 |
| 4 | 1.7 | 2.0 | 1.2 | 0.9 |
| 5 | 1.6 | 2.0 | 1.3 | 1.5 |
| 6 | 4.3 | 1.2 | 1.2 | 1.0 |
| 7 | 3.7 | 2.0 | 1.5 | 1.0 |
| 8* | 4.1 | 2.1 | 1.7 | 1.2 |
| 9 | 1.8 | 2.1 | 1.0 | 0.8 |
| 10 | 3.8 | 2.4 | 1.4 | 1.0 |
| 11 | 6.3 | 2.3 | 1.2 | 0.9 |
| 12 | 1.6 | 2.0 | 1.3 | 1.2 |
| 13 | 1.9 | 1.9 | 1.2 | 0.9 |
| 14 | 4.5 | 2.5 | 1.3 | 1.2 |
| 15 | 8.0 | 2.2 | 1.3 | 1.4 |
| 16 | 2.0 | 2.0 | 1.5 | 1.4 |
| 17 | 2.8 | 2.5 | 1.3 | 1.6 |
| 18 | 2.8 | 2.4 | 1.2 | 0.9 |
| 19 | 1.8 | 2.2 | 1.3 | 0.9 |
| 20 | 2.6 | 2.2 | 1.3 | 1.2 |
| 21 | 1.9 | 2.0 | 1.3 | 1.2 |
| 22 | 1.4 | 1.9 | 1.4 | 0.9 |
| 23 | 2.4 | 1.9 | 1.5 | 1.4 |
| 24 | 3.7 | 2.5 | 1.3 | 1.1 |
| 25 | 2.1 | 2.5 | 1.2 | 1.3 |
| 26 | 2.0 | 2.1 | 1.3 | 1.2 |
| 27 | 3.9 | 2.4 | 1.3 | 1.1 |
| 28 | 4.1 | 2.1 | 1.2 | 1.0 |
| 29 | 1.8 | 1.9 | 1.2 | 0.9 |
| 30 | 1.7 | 2.1 | 1.4 | 1.5 |
| 31 | 3.1 | 1.8 | 1.4 | 1.0 |
| 32 | 1.5 | 2.2 | 1.2 | 1.2 |
| 33 | 1.4 | 2.2 | 1.3 | 1.4 |
| 34 | 1.8 | 2.0 | 1.2 | 1.3 |
| 35 | 2.1 | 2.6 | 1.1 | 1.0 |
| 36 | 1.7 | 2.1 | 1.1 | 1.2 |
| 37 | 3.8 | 2.2 | 1.2 | 1.0 |
| 38 | 1.5 | 2.1 | 1.3 | 1.1 |
| 39 | 5.0 | 2.0 | 1.4 | 1.1 |
| 40* | 7.0 | 2.5 | 1.1 | 1.2 |
| 41 | 1.7 | 2.2 | 1.3 | 1.7 |
| 42 | 3.3 | 2.7 | 1.2 | 1.2 |
| 43 | 2.8 | 2.3 | 1.1 | 1.6 |
| 44 | 2.8 | 2.9 | 1.5 | 1.2 |
| 45 | 8.5 | 2.5 | 1.4 | 1.2 |
| 46 | 5.3 | 2.1 | 1.3 | 1.4 |
| 47 | 1.6 | 2.1 | 1.3 | 1.7 |
| 48 | 1.7 | 2.1 | 1.1 | 2.4 |
| 49 | 3.4 | 2.7 | 1.2 | 1.7 |
| 50 | 2.8 | 2.5 | 1.2 | 1.7 |

Additionally, anti-SIRPβ1 antibodies were also screened for antigen specificity by using a reporter cell line expressing the luciferase gene under the control of an NFAT (nuclear factor of activated T-cells) promoter. The cell line BW5147.G.1.4 (ATCC® TIB48™), derived from mouse thymus lymphoma T lymphocytes, was infected with Cignal Lenti NFAT-luciferase virus (Qiagen), resulting in BWZ/

Figure 3B:
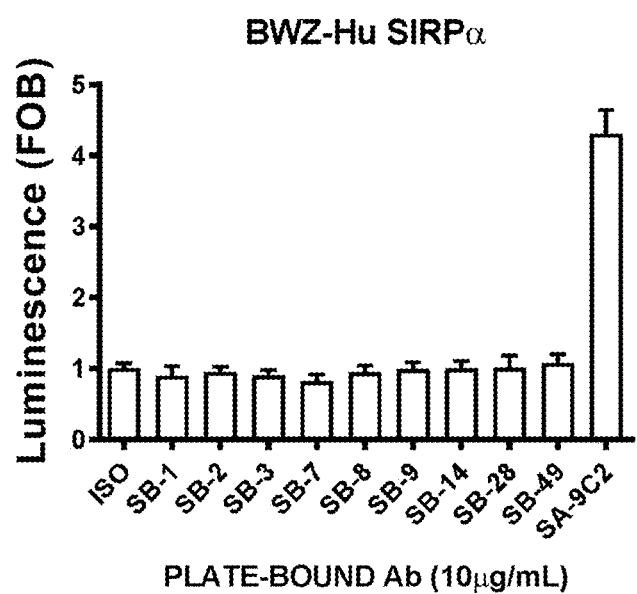

NFAT-luciferase reporter cells. Subsequently, cells were transduced with either a lentivirus expressing human SIRPα-DAP12 chimera, in which the intracellular ITIM motif of SIRPα was substituted with the intracellular ITAM motif of DAP12, or with two lentiviruses expressing human SIRPβ1 and human DAP12. Test antibodies, as well as the human IgG1 isotype control, were adsorbed onto a 96-well plate at 10 ug/mL. After washing, 105 NFAT-luciferase reporter cells expressing the huSIRPα/DAP12 chimera (BWZ-huSIRPα) or co-expressing huSIRPβ1 and DAP12 (BWZ-huSIRPβ1) were seeded onto plates and incubated overnight at 37 C. Luciferase activity was measured by adding OneGlo Reagent (Promega) to each well and incubating the samples for 3 min at room temperature on a plate shaker. The luminescence signal was quantified using a BioTek Synergy™ Microplate Reader using GEN5™ 2.04 software. As shown in FIG. 3A, 48 out of 50 anti-SIRPβ1 clones induced luciferase expression >5-fold over background in BWZ-huSIRPβ1 reporter cells. In contrast, anti-SIRPβ1 antibodies failed to induce luciferase expression when BWZ-huSIRPα reporter cells were added onto antibody-coated wells (FIG. 3B). In summary, only reporter cells expressing human SIRPβ1 induced luciferase expression in the presence of immobilized anti-SIRPβ1 antibodies, as measured by luminescence signal. These results establish that most anti-SIRPβ1 antibodies capable of binding membrane-bound antigen demonstrate specificity towards the target antigen without cross-reacting to other SIRP receptors.

Example 2: SIRPβ1 Expression Profile on Myeloid Cells

The SIRP family comprises several transmembrane glycoproteins primarily expressed within the myeloid cell compartment. The expression pattern of SIRPβ1 was verified on primary human cells isolated from healthy human donors. Human primary monocytes were isolated from heparinized human peripheral blood obtained from two healthy donors (Blood Centers of the Pacific) using RosetteSep Human Monocyte Enrichment Cocktail (STEMCELL Technologies), according to the manufacturer's protocol. Both SIRPβ1 and TREM1 are preferentially expressed on CD14-high monocytes. Monocytes were seeded in RPMI (Invitrogen) containing 10% Fetal Calf Serum (Hyclone) and 50 ng/ml M-CSF or GM-CSF (Peprotech) to induce differentiation of M2-like or M1-like macrophages, respectively. After 5-6 days, macrophages were harvested by scraping cells attached to plastic. Alternatively, monocytes were seeded in RPMI medium containing 10% Fetal Calf Serum (Hyclone) and 20 ng/ml IL-4 and GM-CSF (Peprotech) to induce differentiation of immature dendritic cells. After 6-7 days, dendritic cells were harvested by scraping cells attached to plastic.

Figure 4A:
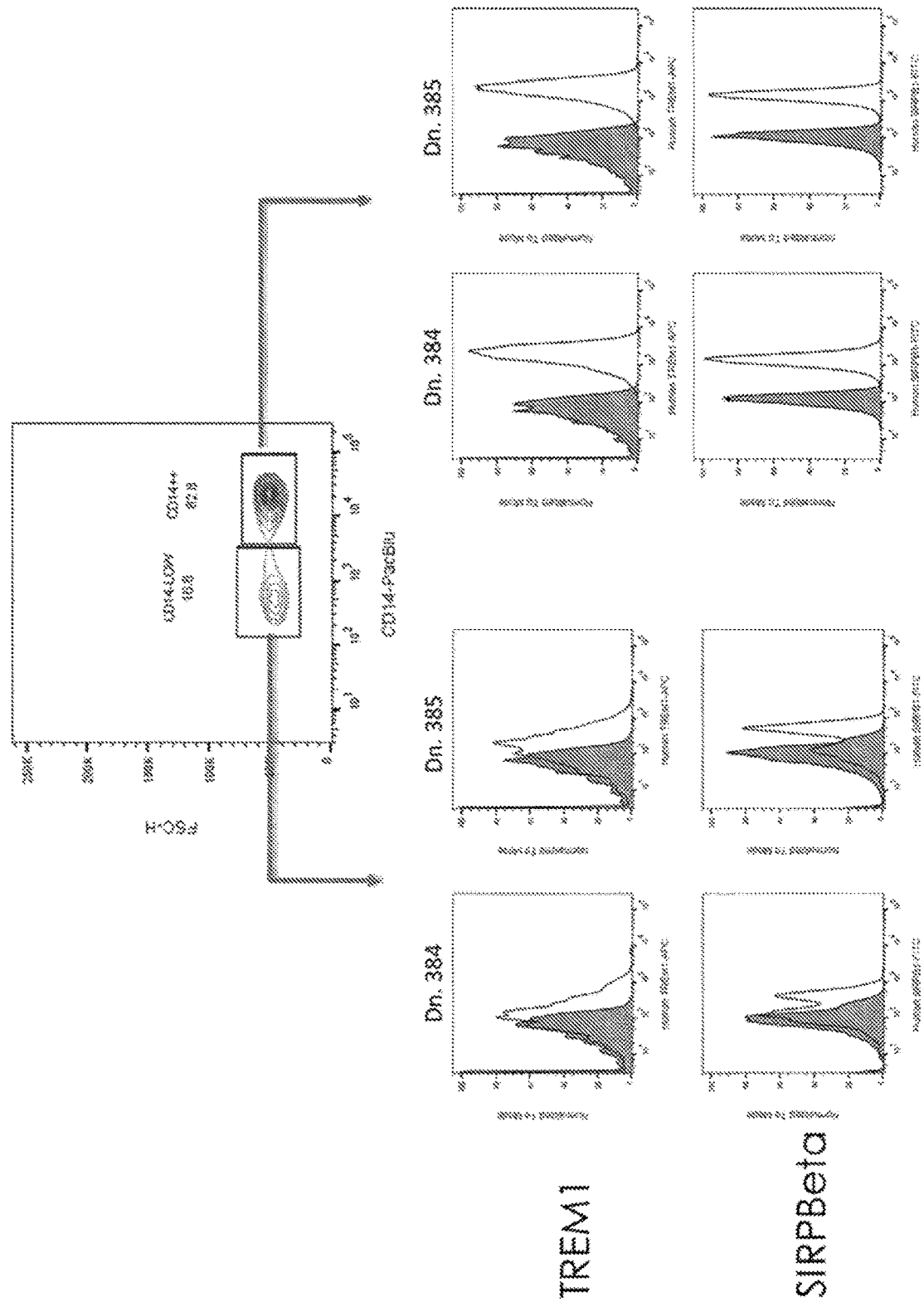
FIG. 4A shows the expression pattern of two DAP12-associated receptors, SIRPβ1 and TREM1, on human monocytes. Shaded histograms represent background fluorescence from isotype stained cells. Black outlined histograms represent receptor expression level with target-specific antibody stained cells.
Figure 4B:
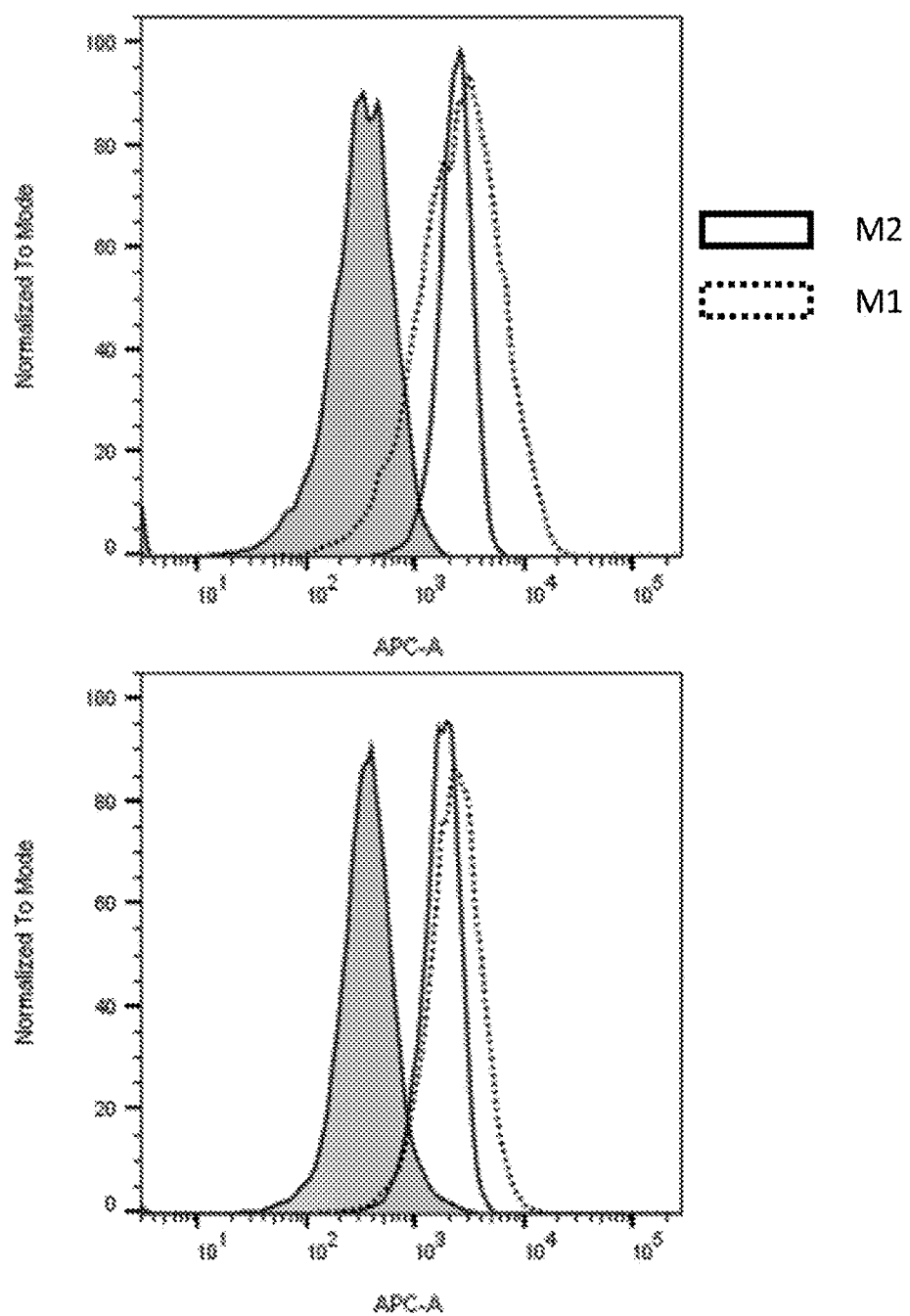
FIG. 4B shows the expression of SIRPβ1 on M1 and M2 polarized macrophages from 2 healthy donors. Shaded histograms represent background fluorescence from isotype stained cells. Black outlined histograms represent SIRPβ1 expression level on M2 macrophages, whereas dashed line histograms represent SIRPβ1 expression level on M1 macrophages.
Figure 4C:
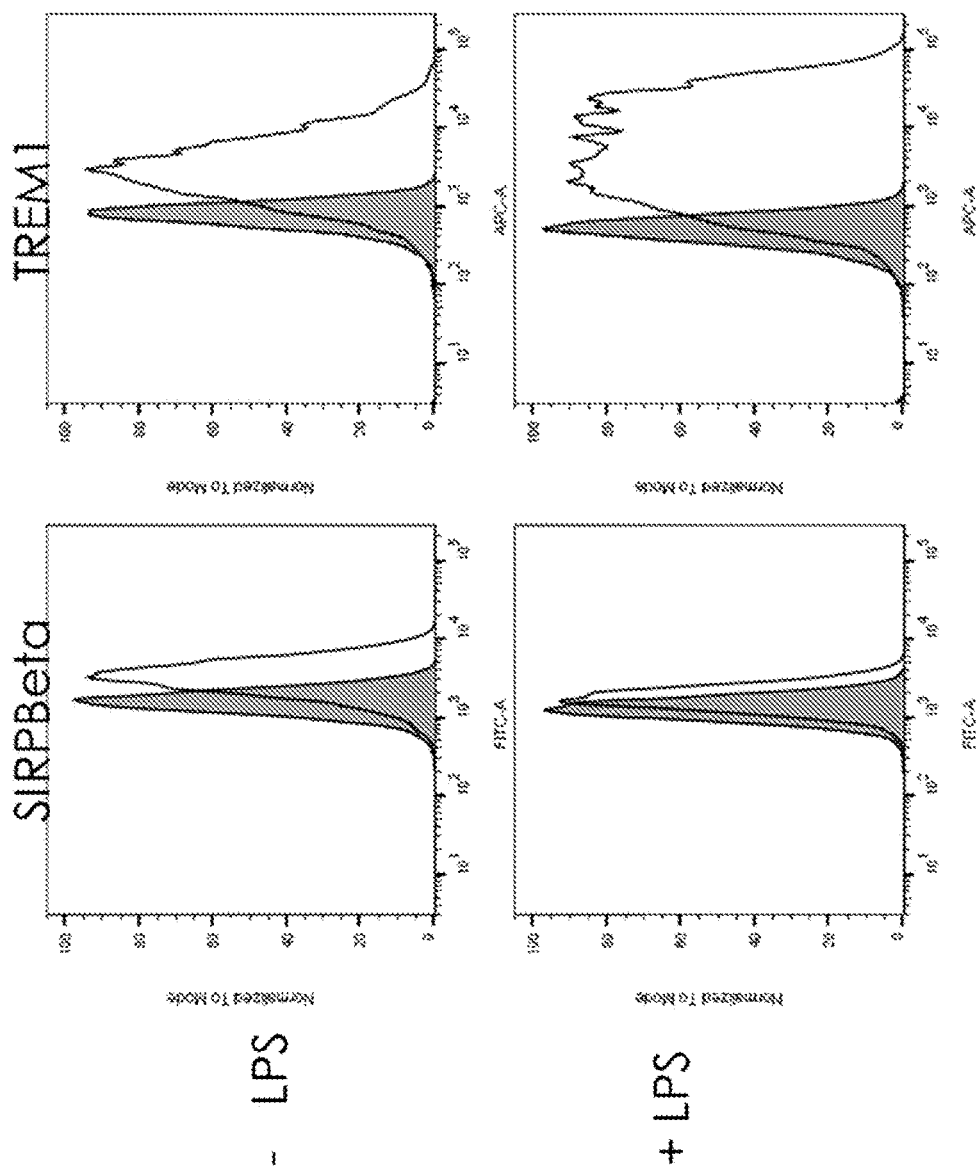
FIG. 4C shows the expression of SIRPβ1 and TREM1 on human monocyte-derived dendritic cells (DCs) with or without LPS stimulation. Shaded histograms represent background fluorescence from isotype stained cells. Black outlined histograms represent receptor expression level with target-specific antibody stained cells.
Figure 5A:
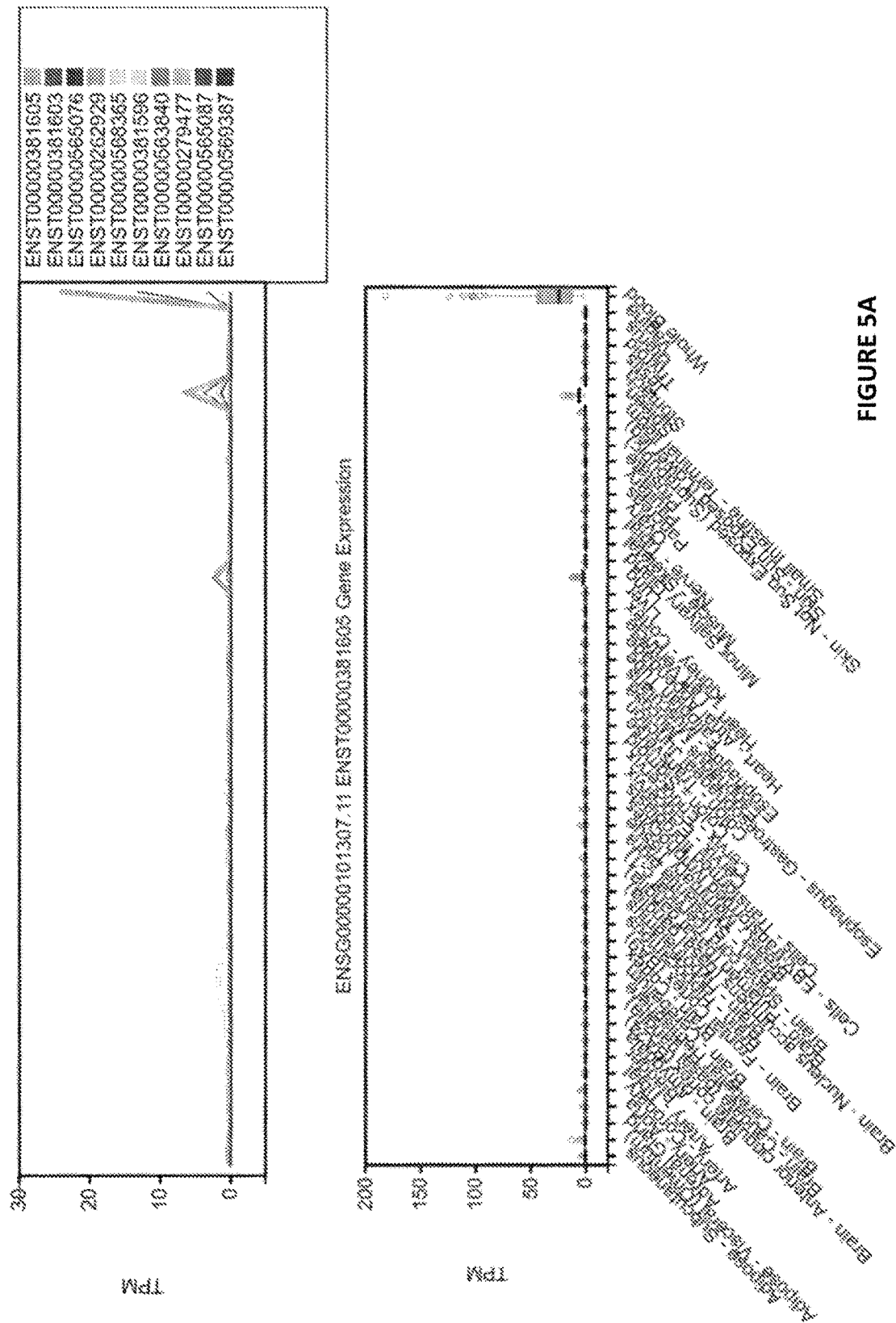
FIG. 5A profiles the RNA expression pattern of SIRPβ1 isoform 1 in various tissues from human donors.
Figure 5B:
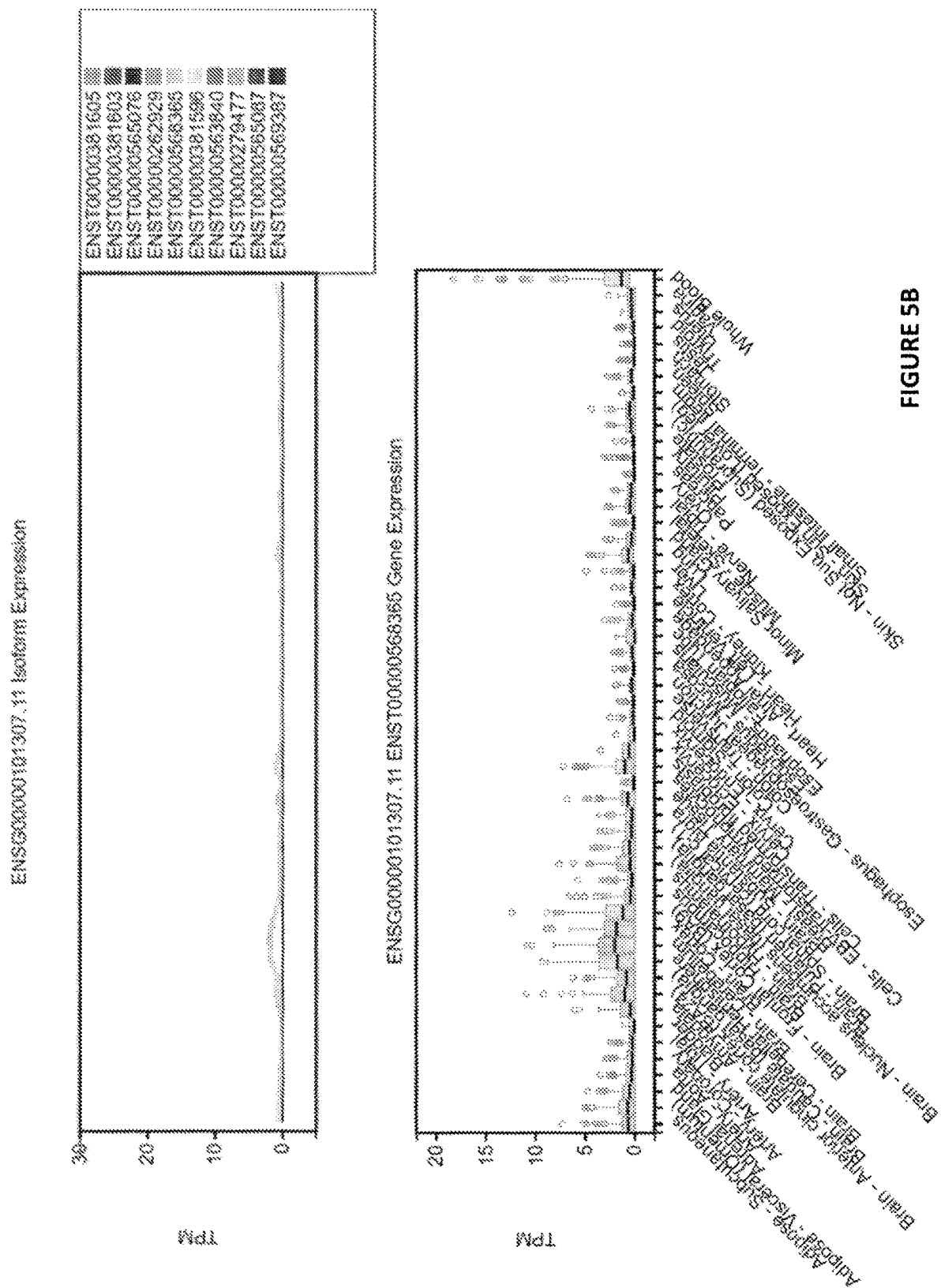
FIG. 5B profiles the RNA expression pattern of SIRPβ1 isoform 3 in various tissues from human donors. Peak expression for SIRPβ1 isoform 3 occurs in the brain with limited expression in peripheral tissues.

As shown in FIG. 4A, CD14 expression defines a subset of primary human monocytes. Classical and intermediate monocytes express high levels of CD14, whereas, non-classical monocytes lack CD14 expression. Like TREM1, SIRPβ1 is abundantly expressed in CD14+ monocytes. Monocytes isolated from peripheral blood as described above were cultured for 5 days with M-CSF or GM-CSF to generate M2 or M1 macrophages, respectively. SIRPβ1 expression decreases upon differentiation of primary monocytes into macrophages with M1-like macrophages expressing higher levels of the receptor relative to M2-like macrophages (FIG. 4B). Similarly, SIRPβ1 expression decreases upon differentiation of primary monocytes into immature dendritic cells. LPS-induced maturation of dendritic cells further downregulates SIRPβ1 expression, in contrast to the increased expression observed for TREM1 (FIG. 4C). Unlike TREM1, LPS treatment downregulates SIRPβ1 expression on DCs. Peak expression for SIRPβ1 occurs in blood, spleen, and lung. Surveying SIRPβ1 expression pattern from RNA-seq data sets from multiple tissue samples gathered from healthy donors confirms that SIRPβ1 transcript levels predominate in the blood, consistent with high expression of the receptor in circulating monocytes and neutrophils (FIG. 5A). However, RNA-seq data reveals that the expression pattern of SIRPβ1 isoform 3 transcript differs from that of SIRPβ1 isoform 1; SIRPβ1 isoform 3 is mostly expressed in the brain and not peripheral tissues (FIG. 5B). (Data were obtained from Genotype-Tissue Expression (GTEx) Consortium database.)

Example 3: SIRPβ1 Antibodies Induce Syk Phosphorylation

Spleen tyrosine kinase (Syk) is an intracellular signaling molecule that functions downstream of SIRPβ1 by phosphorylating several substrates, thereby facilitating the formation of a signaling complex leading to cellular activation and inflammatory processes. The ability of agonist SIRPβ1 antibodies to induce Syk activation is determined by culturing mouse monocytes and measuring the phosphorylation state of Syk protein in cell extracts. In these experiments, a secondary antibody is used to cross-link anti-SIRPβ1 antibodies on cells to induce intracellular signaling.

Bone marrow-derived monocytes (BMDM) from wild-type (WT) mice, from human SIRPβ1 BAC transgenic mice, and from mice that lack expression of functional Fc receptor common gamma chain gene (FcgR KO; REF: Takai T 1994. Cell 76(3):519-29) are starved for 4 hours in 1% serum RPMI and then removed from tissue culture dishes with PBS-EDTA, washed with PBS, and counted. The cells are coated with full-length SIRPβ1 antibodies or with huIgG1 isotype control for 15 minutes on ice. After washing with cold PBS, cells are incubated at 37° C. for the indicated period of time in the presence of goat anti-human IgG. After stimulation, cells are lysed with lysis buffer (1% v/v NP-40%, 50 Mm Tris-HCl (pH 8.0), 150 mM NaCl, 1 mM EDTA, 1.5 mM $MgCl_2$, 10% glycerol, plus protease and phosphatase inhibitors) followed by centrifugation at 16,000 g for 10 min at 4° C. to remove insoluble materials. Lysates are then immunoprecipitated with anti-Syk antibody (N-19 for BMDM or 4D10 for human DCs, Santa Cruz Biotechnology). Precipitated proteins are fractionated by SDS-PAGE, transferred to PVDF membranes and probed with anti-phosphotyrosine antibody (4G10, Millipore). To confirm that all substrates are adequately immunoprecipitated, immunoblots are reprobed with anti-Syk antibody (Abcam, for BMDM) or anti-Syk (Novus Biological, for human DCs). Visualization is performed with the enhanced chemiluminescence (ECL) system (GE healthcare), as described (e.g., Peng et al., (2010) Sci Signal., 3(122): ra38). These studies provide support that anti-SIRPβ1 antibodies of the present invention induce syk phosphorylation.

Example 4: SIRPβ1 Antibodies Induce Syk Phosphorylation when Clustered by Adjacent Cells that Expresses Fc Gamma Receptors Activation of spleen tyrosine kinase (Syk) is facilitated by crosslinking two or more SIRPβ1 receptors with antibodies, thereby facilitating the formation of a signaling complex leading to cellular activation and inflammatory processes. In vivo cross-linking is mediated by adjacent cells that express Fc receptors (FcR), such as B cells and other leukocytes (White AL Cancer Immunol Immunother (2013) 62:941-948; Wilson N S 2011, Cancer Cell 19, 101-113; Bartholomaeus P J Immunol 2014; 192:2091-2098). In these experiments, accessory cells expressing Fc gamma receptors (i.e., B cells) are used to cross-link anti-SIRPβ1 antibodies to induce intracellular signaling.

The ability of Fc receptors to induce activation of Syk through antibody clustering is determined by culturing mouse monocytes in the presence of cells expressing Fc receptors and measuring the phosphorylation state of Syk protein in cell extracts. Bone marrow-derived monocytes (BMDM) from wild-type (WT) mice and human SIRPβ1 BAC transgenic mice are starved for 4 hours in 1% serum RPMI and then removed from tissue culture dishes with PBS-EDTA, washed with PBS, and counted. The cells are coated with full-length SIRPβ1 antibodies, or huIgG1 isotype control for 15 minutes on ice. After washing with cold PBS, cells are incubated for 5 minutes at 37° C. with glutaraldehyde-fixed cells that express Fc receptors and that are previously prepared as follows. Briefly, Fc receptor expressing cells are either B cells isolated from mouse spleens using MACS microbeads (CD19+ B-cell isolation kit Miltenyi Biotec) according to the manufacturer's protocol, or alternatively, the P815 cell line that overexpresses FcR2b and FcR3. $2 \times 10^6$ cells/ml cells are fixed with 0.05% glutaraldehyde for 1 minute at room temperature, the reaction is stopped with 1 μM Glycine and cells are then washed extensively with PBS. After stimulation, cells are lysed with lysis buffer (1% v/v NP-40%, 50 Mm Tris-HCl (pH 8.0), 150 mM NaCl, 1 mM EDTA, 1.5 mM $MgCl_2$, 10% glycerol, plus protease and phosphatase inhibitors) followed by centrifugation at 16,000 g for 10 min at 4° C. to remove insoluble materials. Lysates are then immunoprecipitated with anti-Syk antibody (N-19 for BMDM or 4D10 for human DCs, Santa Cruz Biotechnology). Precipitated proteins are fractionated by SDS-PAGE, transferred to PVDF membranes and probed with anti-phosphotyrosine antibody (4G10, Millipore). To confirm that all substrates are adequately immunoprecipitated, immunoblots are reprobed with anti-Syk antibody (Abcam, for BMDM) or anti-Syk (Novus Biological, for human DCs). Visualization is performed with the enhanced chemiluminescence (ECL) system (GE healthcare), as described (e.g., Peng et al., (2010) Sci Signal., 3(122): ra38). These studies provide support that anti-SIRPβ1 antibodies of the present invention induce syk phosphorylation when clustered by adjacent cells expressing Fc gamma receptors.

Example 5: SIRPβ1 Antibodies Induce Respiratory Burst in Immune Cells

The agonistic function of SIRPβ1 antibodies of the present disclosure was evaluated in primary human innate immune cells (e.g., monocytes and neutrophils).

Anti-SIRPβ1 and isotype control antibodies were diluted in serum-free RPMI media and mixed with 100,000 neutrophils on 96-well plates at a concentration of 10 μg/ml. Primary neutrophils were isolated with EasySep™ Direct Human Neutrophil Isolation Kit (STEMCELL) according to the manufacturer's instructions from peripheral blood obtained the same day. To detect the production of reactive oxygen species (ROS), cells were labeled with 2 M of the fluorescent dye, CM-H2DCFDA. Cells were stimulated with soluble, full-length human IgG1 isotype control or the anti-SIRPβ1 antibodies SB-1, -2, -3, -4, -5, -6, -7, -8, -9, -11, -14, -15, -17, -27, -28, -31, -39, -40, -41, -45, -46, and -49. Following 1 hour of antibody-mediated stimulation in the presence of CM-H2DCFDA at 37° C., the relative fluorescence units in cells were measured at excitation wavelength 495 nm and emission wavelength 530 nm. Specific fluorescence index of stimulated cells was obtained by subtraction of background fluorescence of labeled cells incubated in medium alone and/or with isotype control antibody (hu-IgG1). Plates were read with a BioTek Synergy™ Microplate Reader using GEN5™ 2.04 software.

Figure 6A:
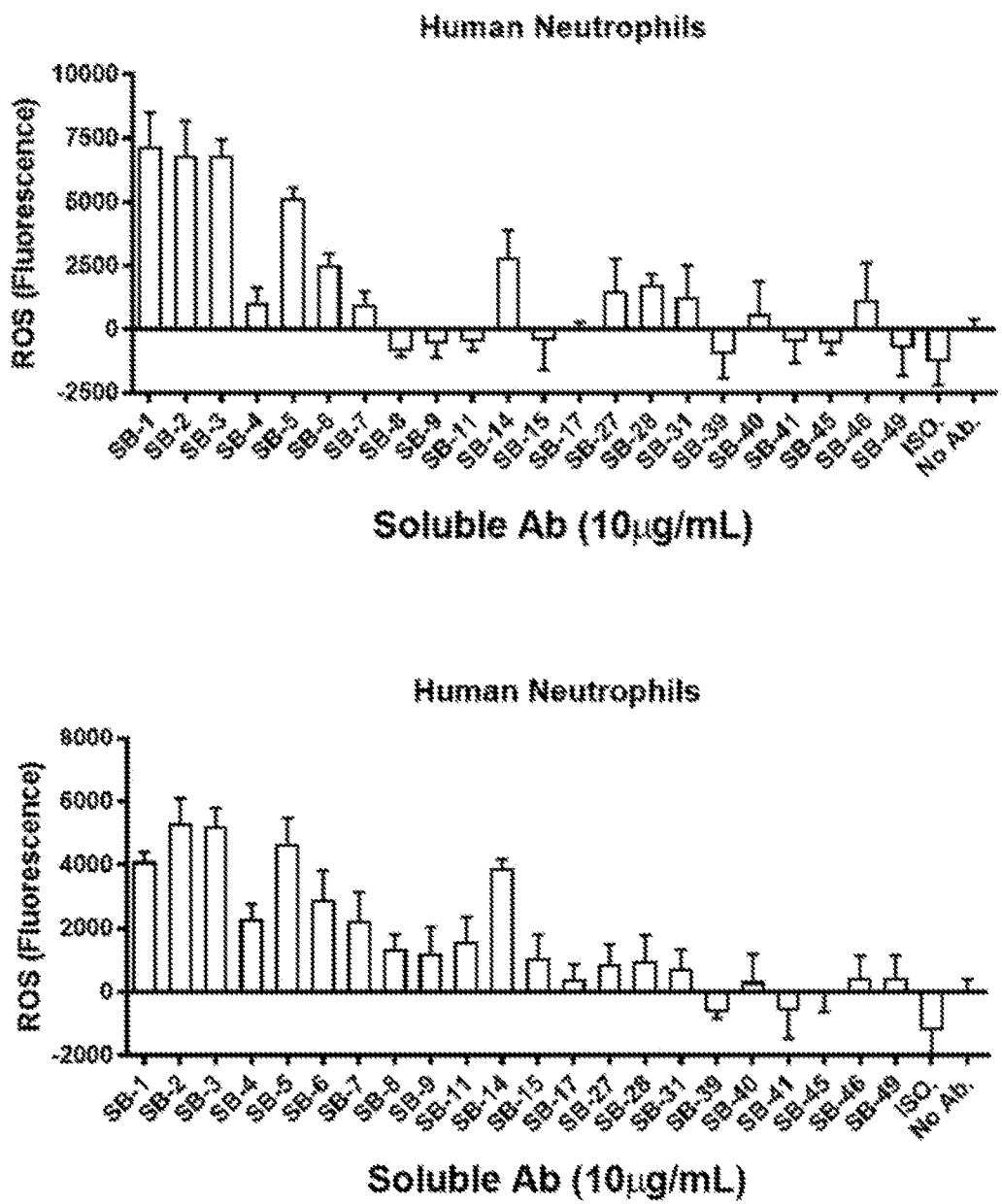
FIG. 6A shows SIRPβ1-mediated respiratory burst from primary human neutrophils obtained from two different donors.

In FIG. 6A, primary human neutrophils from 2 healthy donors were stimulated with 10 μg/mL of soluble full-length anti-SIRPβ1 antibodies or human IgG1 isotype control and labeled with 2 μM CM-H2DCFDA for 1 hour at 37° C. to monitor SIRPβ1-mediated ROS production. The SIRPβ1 antibodies SB-1, -2, -3, and -5 proved highly agonistic in solution. In contrast, the SIRPβ1 antibodies SB-15, -17, -27, -28, -31, -39, -40, -41, -45, -46, and -49 weakly activated SIRPβ1-mediated respiratory burst in solution.

Cells were left untreated or stimulated with soluble, full-length human IgG1 isotype control or the anti-SIRPβ1 antibodies SB-1, -2, -3, -4, -5, -6, -7, -8, -9, -11, -12, -13, -14, -15, -17, -23, -26, -27, -28, -31, -33, -34, -35, -36, -37, -39, -40, -41, -45, -46, and -49. In FIG. 6B, primary human monocytes were stimulated with 20 μg/mL of soluble full-length anti-SIRPβ1 antibodies or human IgG1 isotype control and labeled with 2 μM CM-H2DCFDA for 1 hour at 37° C. to monitor SIRPβ1-mediated ROS production and IL-8 production. The SIRPβ1 antibodies SB-2, -3, -4, -5, -6, -7, -28, and -49 proved highly agonistic in solution. In contrast, the SIRPβ1 antibodies SB-14, -15, -17, -27, -41, -45, and -46 weakly activated SIRPβ1-mediated respiratory burst while in solution. Additionally, primary monocytes were stimulated overnight at 37° C. with anti-SIRPβ1 antibodies adsorbed onto 96-well plates at 10 μg/mL. The supernatant fraction was subsequently collected and assayed for IL-8 release. The SIRPβ1 antibodies SB-1, -2, -3, -7, -8, -9, -14, 28, and -49 proved highly agonistic as plate-bound antibodies. In contrast, the SIRPβ1 antibodies SB-4, -12, -23, -26, -33, -34, -35, -36, and -37 weakly activated SIRPβ1-mediated cytokine release.

Example 6: SIRPβ1 Increases Secretion of Inflammatory Cytokines from Macrophages Published literature describe bone marrow-derived macrophages (BMDM) or primary peritoneal macrophage possessing altered TLR responses when deficient in DAP12. To determine whether SIRPβ1 antibodies of the present disclosure induce changes in inflammatory cytokine production, primary human monocyte-derived macrophages and dendritic cells are cultured with plate-bound test antibodies in combination with non-saturating levels of TLR stimulators and the level of cytokines are measured after 24h. To generate monocyte-derived macrophages and dendritic cells, human primary monocytes were isolated from heparinized human blood (Blood Centers of the Pacific) using RosetteSep Human Monocyte Enrichment Cocktail (STEMCELL Technologies), according to the manufacturer's protocol. Monocytes were seeded in RPMI (Invitrogen) containing 10% Fetal Calf Serum (Hyclone) and 50 ng/ml M-CSF to induce macrophage differentiation. After 5-6 days, macrophages were harvested by scraping cells attached to plastic. Alternatively, monocytes were seeded in RPMI medium containing 10% Fetal Calf Serum (Hyclone) and 20 ng/ml IL-4 and GM-CSF (Peprotech) to induce differentiation of immature dendritic cells. After 6-7 days, dendritic cells were harvested by scraping cells attached to plastic. Macrophages or dendritic cells are plated on 96-well plates coated with indicated antibody at $10^5$ cells/well and incubated for 24h at 37° C. Cells are co-stimulated with TLR4 agonist, LPS (*Salmonella abortus* equi).

As shown in FIG. 6C, monocyte-derived macrophages and dendritic cells were stimulated overnight at 37° C. with 0.5 ng/mL LPS in the presence of anti-SIRPβ1 antibodies (SB-1, -2, -3, -4, -5, -6, -7, -8, -9, -11, -12, -14, -15, -16, -17, -18, -19, -20, -21, -28, -32, -40, and -49) adsorbed onto 96-well plates at 10 μg/mL. The supernatant fraction was subsequently collected and assayed for TNFα release. As a negative control, DCs were stimulated with LPS in the presence of plate-bound anti-SIRPα antibody, SA-56-90, which suppresses TNFα release. In all experiments measuring respiratory burst, production of reactive oxygen species (ROS) was monitored by labeling cells with 2 μM of the fluorescent indicator, CM-H2DCFDA. The SIRPβ1 antibodies SB-1, -2, -6, -8, and -49 proved highly agonistic as plate-bound antibodies. In contrast, most remaining SIRPβ1 antibodies weakly activated SIRPβ1-mediated cytokine release. Similarly, plate-bound SB-1 and SB-40, but not SB-32, enhanced LPS-induced TNFα release from monocyte-derived dendritic cells. In contrast, LPS-induced TNFα release was decreased in dendritic cells stimulated with plate-bound anti-SIRPα antibody, SA-90, confirming that agonistic anti-SIRPβ1 antibodies activate cells, whereas, agonistic SIRPα antibodies inhibit cellular activity.

Example 7: Anti-Tumor Activity of SIRPβ1-Stimulated Neutrophils

Though neutrophils are efficient phagocytes for antibody- or complement-opsonized target cells, in the context of the tumor microenvironment, neutrophils generally contribute towards tumor progression, invasion, and angiogenesis. However, recent publications suggest that tumor-associated neutrophils, like other myeloid cells, retain the potential to polarize towards an anti-tumor phenotype. Since neutrophils express high levels of SIRPβ1, anti-SIRPβ1 antibodies were evaluated for their ability to induce neutrophil-mediated tumor cell clearance in vitro. Primary neutrophils were isolated with EasySep™ Direct Human Neutrophil Isolation Kit (STEMCELL) according to the manufacturer's instructions from peripheral blood of healthy donors obtained the same day. Isolated human neutrophils were then added onto 96-well plates previously coated with 10 μg/mL anti-SIRPβ1 antibodies or isotype control. Subsequently, Raji B cell lymphoma cells engineered to stably express luciferase were mixed with neutrophils in a 1:1 ratio with or without opsonizing antibody (anti-CD20 human IgG1). Co-cultured cells were incubated overnight at 37° C., and viable Raji cells were quantified by measuring luciferase activity following the addition of OneGlo reagent (Promega) and incubating samples at room temperature for 3 min on a plate shaker. The luminescence signal was detected with a BioTek Synergy™ Microplate Reader using GEN5™ 2.04 software.

Figure 7:
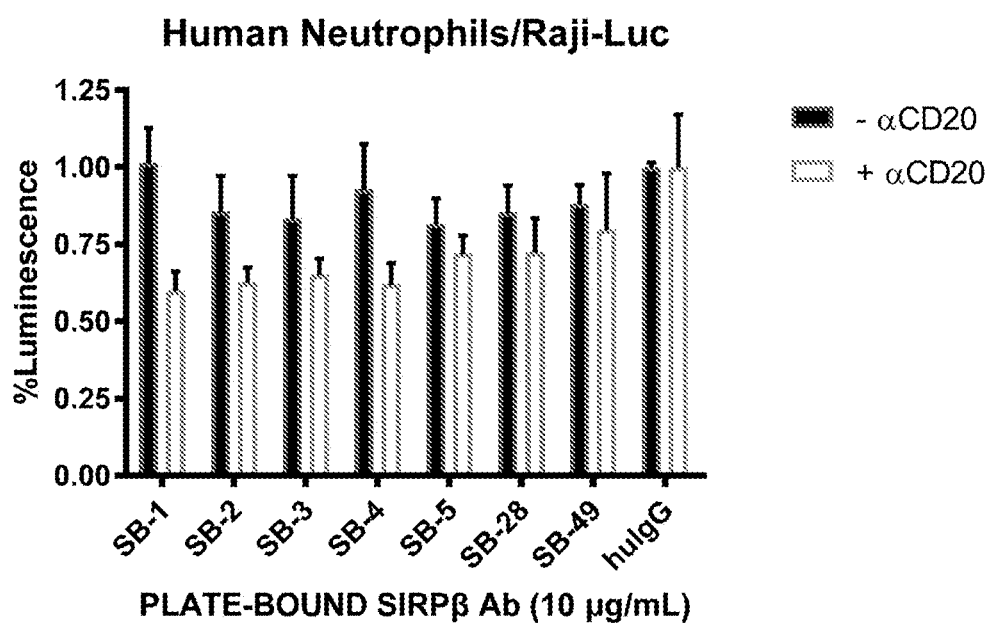
FIG. 7 shows the anti-tumor activity of primary human neutrophils stimulated with plate-bound anti-SIRPβ1 antibodies. Luminescence values are presented on a relative scale with the signal of Raji-Luc co-cultured with neutrophils in the absence of opsonizing antibody set to 1 on the y-axis.

As shown in FIG. 7, human neutrophils failed to eliminate Raji cells when co-cultured in the presence of immobilized isotype control antibody. The addition of anti-CD20 huIgG1 did not restore tumor cell clearance with unstimulated neutrophils. Similarly, neutrophils stimulated with immobilized anti-SIRPβ1 antibodies failed to significantly eliminate Raji cells. However, SIRPβ1-stimulated neutrophils cleared anti-CD20 opsonized Raji cells. The agonistic anti-SIRPβ1 antibodies SB-1, SB-2, SB-3, and SB-4 reduced luminescence signal from viable Raji cells ~50% compared to isotype control-treated neutrophils. The anti-SIRPβ1 antibodies SB-28 and SB-49 demonstrated weak activity against opsonized Raji cells. These results suggest that agonistic anti-SIRPβ1 antibodies enhance the anti-tumor properties of neutrophils.

Example 8: Affinity Maturation of Anti-SIRPβ1 Antibodies

Five anti-SIRPβ1 antibodies, SB-1, SB-2, SB-8, and SB-40 (termed "parent" antibodies), with various physical and functional attributes were affinity-matured. Briefly, diversified antibody libraries were created in yeast for each of the starting parent antibodies. The diversity was created by utilizing standard molecular cloning techniques to combine the parental heavy chain CDR-H3 and light chain (LC) with pre-existing genetic diversity in the CDR-H1 and CDR-H2 regions of the heavy chain (HC) (termed "H1/H2" optimization). This resulted in six libraries of roughly $10^5$ clones in size; 1:755-768 for selection of antibodies with improved affinity. Selection pressures used for screening the libraries included human SIRPα and SIRPβ1 antigen equilibrium titration, parental antibody Fab competition kinetics, and the use of polyspecificity reagent deselection (as described, for example, in WO 2014/179363; Xu et al., *Protein Eng Des Sel*, 26(10): 663-670). FACS flow cytometry was then employed to visualize and select antibodies, using standard techniques (see, e.g., Chao et al. *Nature Protocols*, 2006; 1:755-768). The desired population was then carried forward into additional selection rounds. After 6 rounds of enrichment, yeast cells were plated out in order to obtain single antibody isolates, which were then produced and characterized as described in Example 1. Seventeen affinity-improved antibodies from four of the five starting parental antibodies were thus obtained.

Antibody IgG and Fab Production and Purification

Yeast clones were grown to saturation and then induced for 48 h at 30° C. with shaking. After induction, yeast cells were pelleted and the supernatants were harvested for purification.

Immunoglobulins were purified using a Protein A column and eluted with acetic acid, pH 2.0. Fab fragments were generated by papain digestion and purified over CaptureSelect IgG-CH1 affinity matrix (LifeTechnologies).

Affinity Determination

The affinities of the anti-SIRPβ1 antibodies were determined by measuring $K_D$ values by ForteBio Octet® and Meso Scale Discovery (MSD) instrument. Octet® affinity measurements were performed at room temperature, generally as previously described (Estep et al, MAbs. 2013 March-April; 5(2):270-8). Briefly, Octet® affinity measurements were performed by loading IgGs on-line onto AHQ sensors. Sensors were equilibrated off-line in assay buffer for 30 min and then monitored on-line for 60 seconds for baseline establishment. For avid binding measurement, sensors with loaded IgGs were exposed to 100 nM antigen (human SIRPα or SIRPβ1 Fc fusion) for 3 min, and then transferred to assay buffer for 3 min for off-rate measurement. Additional avid binding was determined by loading biotinylated SIRPβ1 monomer on SA sensors and exposuring to 100 nM IgG in solution. Monovalent binding measurements were obtained by loading human SIRPβ1 Fc fusion antigens to AHQ sensor, followed by exposure to 100 nM anti-SIRPβ1 antibody Fab. Additional monovalent measurements were made by loading biotinylated human SIRPβ1 monomer to SA sensor followed by exposure to 100 nM Fab in solution. Kinetics data were fit using a 1:1 binding model in the data analysis software provided by ForteBio.

For MSD-SET $K_D$ measurements, solution equilibrium titrations (SET) were performed in PBS+0.1% IgG-Free BSA (PBSF) with recombinant human SIRPβ1, held constant at 100 μM and incubated with 3-to 5-fold serial dilutions of antibody starting at around 50 nM. Antibodies (20 nM in PBS) were coated onto standard bind MSD-ECL plates overnight at 4° C. or at room temperature for 30 min. Plates were then blocked with 1% BSA for 30 min with shaking at 700 rpm, followed by three washes with wash buffer (PBSF+0.05% Tween 20). SET samples were applied and incubated on the plates for 150s with shaking at 700 rpm followed by one wash. Antigen captured on a plate was detected with 250 ng/ml sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the $K_D$. To improve throughput, liquid handling robots were used throughout MSD-SET experiments, including SET sample preparation.

Cell binding affinity measurements were performed at 4° C. using BWZ reporter cells either expressing either human SIRPα or SIRPβ1. Briefly, cells were harvested, washed in PBS and incubated with increasing concentration of anti-SIRPβ1 antibodies or isotype control. Antibodies were diluted in FACS buffer (PBS+2% FBS). After incubation on ice for 30 min, cells were washed two times in FACS buffer and incubated with anti-human PE conjugated secondary antibody (BD Biosciences) for 30 min on ice. Cells were then washed twice in 200 ul FACS buffer, and subsequently analyzed on a FACS Canto screening instrument (BD). Apparent $K_D$ values were determined by non-linear curve fitting (modified OneSiteTotal, Graph Pad Prism).

Anti-SIRPβ1 Antibody Selection

Affinity-matured anti-SIRPβ1 antibody clones, which showed improved affinity compared to the respective parental antibody, were characterized further. After initial screening of all affinity-matured antibody clones, clones for each parental antibody were selected for further analysis.

Antibody Heavy Chain and Light Chain Variable Domain Sequences

Using standard techniques, the amino acid sequences encoding the light chain variable and the heavy chain variable domains of the affinity matured antibodies were determined. The Kabat light chain HVR sequences of the affinity matured antibodies are set forth in Table 8. The Kabat heavy chain HVR sequences of the antibodies are set forth in Table 9. The Kabat heavy chain framework (FR) sequences of the antibodies are set forth in Table 10. The Kabat light chain framework (FR) sequences of the antibodies are set forth in Table 11.

TABLE 8

Kabat light chain HVR sequences of affinity matured anti-SIRPβ1 antibodies

| Ab ID | HVR L1 | SEQ ID NO | HVR L2 | SEQ ID NO | HVR L3 | SEQ ID NO |
|---|---|---|---|---|---|---|
| SB-1 (p) | RASQSVSSSYLA | 383 | GASSRAT | 16 | QLLGSSPRT | 31 |
| SB-1-2 | RASQSVSSSYLA | 383 | GASSRAT | 16 | QLLGSSPRT | 31 |
| SB-1-3 | RASQSVSSSYLA | 383 | GASSRAT | 16 | QLLGSSPRT | 31 |
| SB-1-4 | RASQSVSSSYLA | 383 | GASSRAT | 16 | QLLGSSPRT | 31 |
| SB-1-5 | RASQSVSSSYLA | 383 | GASSRAT | 16 | QLLGSSPRT | 31 |
| SB-2 (p) | RASQSVSSSYLA | 383 | GASSRAT | 16 | QQSSSHPFT | 32 |
| SB-2-7 | RASQSVSSSYLA | 383 | GASSRAT | 16 | QQSSSHPFT | 32 |
| SB-2-8 | RASQSVSSSYLA | 383 | GASSRAT | 16 | QQSSSHPFT | 32 |
| SB-2-9 | RASQSVSSSYLA | 383 | GASSRAT | 16 | QQSSSHPFT | 32 |
| SB-2-10 | RASQSVSSSYLA | 383 | GASSRAT | 16 | QQSSSHPFT | 32 |
| SB-2-11 | RASQSVSSSYLA | 383 | GASSRAT | 16 | QQSSSHPFT | 32 |
| SB-8 (p) | RASQSVSSSYLA | 383 | GASNRAT | 19 | QQVYSSPYT | 37 |
| SB-8-13 | RASQSVSSSYLA | 383 | GASNRAT | 19 | QQVYSSPYT | 37 |
| SB-8-14 | RASQSVSSSYLA | 383 | GASNRAT | 19 | QQVYSSPYT | 37 |
| SB-8-15 | RASQSVSSSYLA | 383 | GASNRAT | 19 | QQVYSSPYT | 37 |
| SB-8-16 | RASQSVSSSYLA | 383 | GASNRAT | 19 | QQVYSSPYT | 37 |
| SB-40 (p) | RASQSVSSYLA | 2 | DSSNRAT | 22 | QQRDEHPPWT | 69 |
| SB-40-18 | RASQSVSSYLA | 2 | DSSNRAT | 22 | QQRDEHPPWT | 69 |

TABLE 8-continued

Kabat light chain HVR sequences of affinity matured anti-SIRPβ1 antibodies

| Ab ID | HVR L1 | SEQ ID NO | HVR L2 | SEQ ID NO | HVR L3 | SEQ ID NO |
|---|---|---|---|---|---|---|
| SB-40-19 | RASQSVSSYLA | 2 | DSSNRAT | 22 | QQRDEHPPWT | 69 |
| SB-40-20 | RASQSVSSYLA | 2 | DSSNRAT | 22 | QQRDEHPPWT | 69 |
| SB-40-21 | RASQSVSSYLA | 2 | DSSNRAT | 22 | QQRDEHPPWT | 69 |

(p) denotes parental antibody sequence

TABLE 9

Kabat heavy chain HVR sequences of affinity matured anti-SIRPβ1 antibodies

| Ab ID | HVR H1 | SEQ ID NO | HVR H2 | SEQ ID NO | HVR H3 | SEQ ID NO |
|---|---|---|---|---|---|---|
| SB-1 (p) | SYAMS | 80 | TISGSGGSTYYADSVKG | 101 | DFTEVVGWLGMDV | 125 |
| SB-1-2 | SFGMN | 228 | AITASGGSTFYADSVKG | 238 | DFTEVVGWLGMDV | 125 |
| SB-1-3 | AYGMN | 229 | AITSSGRSTYYADSVKG | 239 | DFTEVVGWLGMDV | 125 |
| SB-1-4 | AYGMN | 229 | AIRASGGATYYADSVKG | 240 | DFTEVVGWLGMDV | 125 |
| SB-1-5 | AYGMN | 229 | AISASGRSTFYADSVKG | 241 | DFTEVVGWLGMDV | 125 |
| SB-2 (p) | SYGMN | 81 | VIWYDGSNKYYADSVKG | 102 | DQTAAAAIWGMDV | 126 |
| SB-2-7 | RYGMH | 230 | AISGLAGPT-YADSVKG | 242 | DQTAAAAIWGMDV | 126 |
| SB-2-8 | DYGMH | 231 | AISAFAGST-YADSVKG | 243 | DQTAAAAIWGMDV | 126 |
| SB-2-9 | TYGMH | 232 | HIWYEGSNKVYADSVKG | 244 | DQTAAAAIWGMDV | 126 |
| SB-2-10 | SYGMH | 99 | AISGLAGQT-YADSVKG | 245 | DQTAAAAIWGMDV | 126 |
| SB-2-11 | RYGMH | 230 | AISGLAGPT-YADSVKG | 242 | DQTAAWGIWGMDV | 253 |
| SB-8 (p) | SGYYWG | 85 | SIYHSGSTYYNPSLKS | 107 | GGAMTPAGMDV | 131 |
| SB-8-13 | AHYYWG | 233 | SIFHSGHTYYNPSLKS | 246 | GGAMTPAGMDV | 131 |
| SB-8-14 | PHYYWG | 234 | SIYHSGHTYYNPSLKS | 247 | GGAMTPAGMDV | 131 |
| SB-8-15 | AHYYWG | 233 | SIYQSGHTYYNPSLKS | 248 | GGAMTPAGMDV | 131 |
| SB-8-16 | AHYYWG | 233 | SIFHSGHTYYNPSLKS | 246 | AGAMTPAGMDV | 254 |
| SB-40 (p) | SYYMS | 97 | IINPSGGSTSYAQKFQG | 121 | DTGEYSYSPHGMDV | 163 |
| SB-40-18 | SYYMA | 235 | WINPAVGATIYSQKFQG | 249 | DTGEYSYSPHGMDV | 163 |
| SB-40-19 | SYYMV | 236 | IINPSSGATNYAQKFQG | 250 | DTGEYSYSPHGMDV | 163 |
| SB-40-20 | SFYIS | 237 | IINPSSGHTNYAQKLQG | 251 | DTGEYSYSPHGMDV | 163 |
| SB-40-21 | SYYMV | 236 | IINPSSGDTNYAQKFQG | 252 | DTGEYSYSPHGMDV | 163 |

(p) denotes parental antibody sequence

TABLE 10

Kabat light chain FR sequences of affinity matured anti-SIRPβ1 antibodies

| Ab ID | VL FR1 | SEQ ID NO | VL FR2 | SEQ ID NO | VL F3 | SEQ ID NO | VL FR4 | SEQ ID NO |
|---|---|---|---|---|---|---|---|---|
| SB-1 (p) | EIVMTQSPGTLSLSPGERATLSC | 174 | WYQQKPGQAPRLLIY | 186 | GIPDRFSGSGSGTDFTLTISRLEPEDFAVYYC | 192 | FGGGTKVEIK | 200 |
| SB-1-2 | EIVMTQSPGTLSLSPGERATLSC | 174 | WYQQKPGQAPRLLIY | 186 | GIPDRFSGSGSGTDFTLTISRLEPEDFAVYYC | 192 | FGGGTKVEIK | 200 |
| SB-1-3 | EIVMTQSPGTLSLSPGERATLSC | 174 | WYQQKPGQAPRLLIY | 186 | GIPDRFSGSGSGTDFTLTISRLEPEDFAVYYC | 192 | FGGGTKVEIK | 200 |
| SB-1-4 | EIVMTQSPGTLSLSPGERATLSC | 174 | WYQQKPGQAPRLLIY | 186 | GIPDRFSGSGSGTDFTLTISRLEPEDFAVYYC | 192 | FGGGTKVEIK | 200 |
| SB-1-5 | EIVMTQSPGTLSLSPGERATLSC | 174 | WYQQKPGQAPRLLIY | 186 | GIPDRFSGSGSGTDFTLTISRLEPEDFAVYYC | 192 | FGGGTKVEIK | 200 |
| SB-2 (p) | EIVLTQSPGTLSLSPGERATLSC | 175 | WYQQKPGQAPRLLIY | 186 | GIPDRFSGSGSGTDFTLTISRLEPEDFAVYYC | 192 | FGGGTKVEIK | 200 |
| SB-2-7 | EVVLTQSPGTLSLSPGERATLSC | 255 | WYQQKPGQAPRLLIY | 186 | GIPDRFSGSGSGTDFTLTISRLEPEDFAVYYC | 192 | FGGGTKVEIK | 200 |
| SB-2-8 | EVVLTQSPGTLSLSPGERATLSC | 255 | WYQQKPGQAPRLLIY | 186 | GIPDRFSGSGSGTDFTLTISRLEPEDFAVYYC | 192 | FGGGTKVEIK | 200 |
| SB-2-9 | EVVLTQSPGTLSLSPGERATLSC | 255 | WYQQKPGQAPRLLIY | 186 | GIPDRFSGSGSGTDFTLTISRLEPEDFAVYYC | 192 | FGGGTKVEIK | 200 |
| SB-2-10 | EIVLTQSPGTLSLSPGERATLSC | 175 | WYQQKPGQAPRLLIY | 186 | GIPDRFSGSGSGTDFTLTISRLEPEDFAVYYC | 192 | FGGGTKVEIK | 200 |
| SB-2-11 | EIVLTQSPGTLSLSPGERATLSC | 175 | WYQQKPGQAPRLLIY | 186 | GIPDRFSGSGSGTDFTLTISRLEPEDFAVYYC | 192 | FGGGTKVEIK | 200 |
| SB-8 (p) | EIVMTQSPGTLSLSPGERATLSC | 174 | WYQQKPGQAPRLLIY | 186 | GIPDRFSGSGSGTDFTLTISRLEPEDFAVYYC | 192 | FGGGTKVEIK | 200 |
| SB-8-13 | EIVMTQSPGTLSLSPGERATLSC | 174 | WYQQKPGQAPRLLIY | 186 | GIPDRFSGSGSGTDFTLTISRLEPEDFAVYYC | 192 | FGGGTKVEIK | 200 |
| SB-8-14 | EIVMTQSPGTLSLSPGERATLSC | 174 | WYQQKPGQAPRLLIY | 186 | GIPDRFSGSGSGTDFTLTISRLEPEDFAVYYC | 192 | FGGGTKVEIK | 200 |
| SB-8-15 | EIVMTQSPGTLSLSPGERATLSC | 174 | WYQQKPGQAPRLLIY | 186 | GIPDRFSGSGSGTDFTLTISRLEPEDFAVYYC | 192 | FGGGTKVEIK | 200 |

TABLE 10-continued

Kabat light chain FR sequences of affinity matured anti-SIRPβ1 antibodies

| Ab ID | VL FR1 | SEQ ID NO | VL FR2 | SEQ ID NO | VL F3 | SEQ ID NO | VL FR4 | SEQ ID NO |
|---|---|---|---|---|---|---|---|---|
| SB-8-16 | EIVMTQSPGTLSLSPGERATLSC | 174 | WYQQKPGQAPRLLIY | 186 | GIPDRFSGSGSGTDFTLTISRLEPEDFAVYYC | 192 | FGGGTKVEIK | 200 |
| SB-40 (p) | EIVLTQSPATLSLSPGERATLSC | 182 | WYQQKPGQAPRLLIY | 186 | GIPARFSGSGSGTDFTLTISSLEPEDFAVYYC | 193 | FGGGTKVEIK | 200 |
| SB-40-18 | EIVLTQSPATLSLSPGERATLSC | 182 | WYQQKPGQAPRLLIY | 186 | GIPARFSGSGSGTDFTLTISSLEPEDFAVYYC | 193 | FGGGTKVEIK | 200 |
| SB-40-19 | EIVLTQSPATLSLSPGERATLSC | 182 | WYQQKPGQAPRLLIY | 186 | GIPARFSGSGSGTDFTLTISSLEPEDFAVYYC | 193 | FGGGTKVEIK | 200 |
| SB-40-20 | EIVLTQSPATLSLSPGERATLSC | 182 | WYQQKPGQAPRLLIY | 186 | GIPARFSGSGSGTDFTLTISSLEPEDFAVYYC | 193 | FGGGTKVEIK | 200 |
| SB-40-21 | EIVLTQSPATLSLSPGERATLSC | 182 | WYQQKPGQAPRLLIY | 186 | GIPARFSGSGSGTDFTLTISSLEPEDFAVYYC | 193 | FGGGTKVEIK | 200 |

(p) denotes parental antibody sequence

TABLE 11

Kabat heavy chain FR sequences of affinity matured anti-SIRPβ1 antibodies

| Ab ID | VH FR1 | SEQ ID NO | VH FR2 | SEQ ID NO | VH F3 | SEQ ID NO | VH FR4 | SEQ ID NO |
|---|---|---|---|---|---|---|---|---|
| SB-1 (p) | EVQLLESGGGLVQPGGSLRLSCAASGFTFS | 201 | WVRQAPGKGLEWVS | 210 | RFTISRDNSKNTLYLQMNSLRAEDTAVYYCAK | 215 | WGQGTTVTVSS | 222 |
| SB-1-2 | QVQLVESGGGVVQPGRSLRLSCAASGFTFG | 256 | WVRQAPGKGLEWVS | 210 | RFTISRDNSKNTLYLQMNSLRAEDTAVYYCAK | 215 | WGQGTTVTVSS | 222 |
| SB-1-3 | EVQLVESGGGLVKPGGSLRLSCAASGFTFS | 257 | WVRQAPGKGLEWVS | 210 | RFTISRDNSKNTLYLQMNSLRAEDTAVYYCAK | 215 | WGQGTTVTVSS | 222 |
| SB-1-4 | QVQLVESGGGVVQPGGSLRLSCAASGFTFS | 258 | WVRQAPGKGLEWVS | 210 | RFTISRDNSKNTLYLQMNSLRAEDTAVYYCAK | 215 | WGQGTTVTVSS | 222 |
| SB-1-5 | QVQLVESGGGVVQPGRSLRLSCAASGFTFS | 202 | WVRQAPGKGLEWVS | 210 | RFTISRDNSKNTLYLQMNSLRAEDTAVYYCAK | 215 | WGQGTTVTVSS | 222 |

TABLE 11-continued

Kabat heavy chain FR sequences of affinity matured anti-SIRPβ1 antibodies

| Ab ID | VH FR1 | SEQ ID NO | VH FR2 | SEQ ID NO | VH F3 | SEQ ID NO | VH FR4 | SEQ ID NO |
|---|---|---|---|---|---|---|---|---|
| SB-2 (p) | QVQLVESGGGVVQPGRSLRLSCAASGFTFS | 202 | WVRQAPGKGLEWVA | 211 | RFTISRDNSKNTLYLQMNSLRAEDTAVYYCAR | 216 | WGQGTTVTVSS | 222 |
| SB-2-7 | EVQLLESGGGLVQPGGSLRLSCAASGFTFA | 259 | WVRQAPGKGLEWVS | 210 | RFTISRDNSKNTLYLQMNSLRAEDTAVYYCAR | 216 | WGQGTTVTVSS | 222 |
| SB-2-8 | QVQLVESGGGVVQPGRSLRLSCAASGFTFL | 260 | WVRQAPGKGLEWVS | 210 | RFTISRDNSKNTLYLQMNSLRAEDTAVYYCAR | 216 | WGQGTTVTVSS | 222 |
| SB-2-9 | QVQLVESGGGVVQPGRSLRLSCAASGFTFK | 261 | WVRQAPGKGLEWVA | 211 | RFTISRDNSKNTLYLQMNSLRAEDTAVYYCAR | 216 | WGQGTTVTVSS | 222 |
| SB-2-10 | EVQLLESGGGLVQPGGSLRLSCAASGFTFG | 262 | WVRQAPGKGLEWVS | 210 | RFTISRDNSKNTLYLQMNSLRAEDTAVYYCAR | 216 | WGQGTTVTVSS | 222 |
| SB-2-11 | QVQLVESGGGLVQPGGSLRLSCAASGFTFA | 263 | WVRQAPGKGLEWVS | 210 | RFTISRDNSKNTLYLQMNSLRAEDTAVYYCAR | 216 | WGQGTTVTVSS | 222 |
| SB-8 (p) | QVQLQESGPGLVKPSETLSLTCAVSGYSIS | 205 | WIRQPPGKGLEWIG | 213 | RVTISVDTSKNQFSLKLSSVTAADTAVYYCAR | 220 | WGQGTTVTVSS | 222 |
| SB-8-13 | QVQLQESGPGLVKPSETLSLTCAVSGYSIS | 205 | WIRQPPGKGLEWIG | 213 | RVTISVDTSKNQFSLKLSSVTAADTAVYYCAR | 220 | WGQGTTVTVSS | 222 |
| SB-8-14 | QVQLQESGPGLVKPSETLSLTCAVSGYSIS | 205 | WIRQPPGKGLEWIG | 213 | RVTISVDTSKNQFSLKLSSVTAADTAVYYCAR | 220 | WGQGTTVTVSS | 222 |
| SB-8-15 | QVQLQESGPGLVKPSETLSLTCAVSGYSIS | 205 | WIRQPPGKGLEWIG | 213 | RVTISVDTSKNQFSLKLSSVTAADTAVYYCAR | 220 | WGQGTTVTVSS | 222 |
| SB-8-16 | QVQLQESGPGLVKPSETLSLTCAVSGYSIS | 205 | WIRQPPGKGLEWIG | 213 | RVTISVDTSKNQFSLKLSSVTAADTAVYYCAR | 220 | WGQGTTVTVSS | 222 |
| SB-40 (p) | QVQLVQSGAEVKKPGASVKVSCKASGYTFT | 203 | WVRQAPGQGLEWMG | 212 | RVTMTRDTSTSTVYMELSSLRSEDTAVYYCAR | 221 | WGQGTTVTVSS | 222 |

TABLE 11-continued

Kabat heavy chain FR sequences of affinity matured anti-SIRPβ1 antibodies

| Ab ID | VH FR1 | SEQ ID NO | VH FR2 | SEQ ID NO | VH F3 | SEQ ID NO | VH FR4 | SEQ ID NO |
|---|---|---|---|---|---|---|---|---|
| SB-40-18 | QVQLVQSGAEVKKPGASVKVSCKASGYTFT | 203 | WVRQAPGQRLEWMG | 264 | RVTITRDTSASTAYMELSSLRSEDTAVYYCAR | 265 | WGQGTTVTVSS | 222 |
| SB-40-19 | QVQLVQSGAEVKKPGASVKVSCKASGYTFT | 203 | WVRQAPGQGLEWMG | 212 | RVTMTTDTSTSTAYMELRSLRSDDTAVYYCAR | 218 | WGQGTTVTVSS | 222 |
| SB-40-20 | QVQLVQSGAEVKKPGASVKVSCKASGYTFT | 203 | WVRQAPGQGLEWMG | 212 | RVTMTTDTSTSTAYMELSSLRSEDTAVYYCAR | 266 | WGQGTTVTVSS | 222 |
| SB-40-21 | QVQLVQSGAEVKKPGASVKVSCKASGYTFT | 203 | WVRQAPGQGLEWMG | 212 | RVTMTRDTSISTAYMELSRLRSDDTAVYYCAR | 217 | WGQGTTVTVSS | 222 |

(p) denotes parental antibody sequence

Characterization of affinity-matured anti-SRPβ1 antibody binding

A final set of affinity matured anti-SIRPβ1 antibodies were selected based on antigen binding affinities. Antibodies that were positive for binding to human SIRPβ11 were tested for cross-reactivity to human SIRPα. The biochemical characteristics of each antibody are listed below in Table 12. In Table 12, "NB." refers to antibodies for which there is no binding to the indicated antigen; "P.F." refers to antibodies for which antigen binding kinetics show poor fit to 1:1 binding model, "N.M." refers to not measurable.

TABLE 12

Biochemical Characterization of affinity matured anti-SIRPβ1 antibodies

| Clone Index | Optimization Method | Fab $K_D$ Human SIRPβ Fc (M) Monovalent | IgG $K_D$ Mouse SIRPβ Fc (M) Avid | IgG $K_D$ Human SIRPα Fc (M) Avid | MSD Fab $K_D$ Human SIRPβ HIS (M) Monovalent |
|---|---|---|---|---|---|
| SB-1 | Parent | 1.72E-07 | N.B. | N.B. | N.M. |
| SB-1-2 | H1H2 | 3.78E-08 | N.B. | N.B. | N.M. |
| SB-1-3 | H1H2 | 4.54E-08 | N.B. | N.B. | N.M. |
| SB-1-4 | H1H2 | 4.33E-08 | N.B. | N.B. | N.M. |
| SB-1-5 | H1H2 | 8.24E-08 | N.B. | N.B. | N.M. |
| SB-2 | Parent | 9.77E-07 | N.B. | N.B. | N.M. |
| SB-2-7 | H1H2 | 6.21E-09 | N.B. | N.B. | N.M. |
| SB-2-8 | H1H2 | 5.02E-09 | N.B. | N.B. | N.M. |
| SB-2-9 | H1H2 | 1.92E-08 | N.B. | N.B. | N.M. |
| SB-2-10 | H1H2 | 1.23E-08 | N.B. | N.B. | N.M. |
| SB-2-11 | H3 | 4.40E-09 | N.B. | N.B. | N.M. |
| SB-8 | Parent | 1.51E-07 | N.B. | N.B. | N.M. |
| SB-8-13 | H1H2 | 2.85E-09 | N.B. | N.B. | 6.3E-11 |
| SB-8-14 | H1H2 | 3.25E-09 | N.B. | 1.83E-08 | 5.3E-11 |
| SB-8-15 | H1H2 | 3.73E-09 | N.B. | N.B. | 4.8E-11 |
| SB-8-16 | H3 | 2.32E-09 | N.B. | N.B. | 5.5E-11 |
| SB-40 | Parent | 9.18E-07 | N.B. | N.B. | N.M. |
| SB-40-18 | H1H2 | 1.81E-08 | N.B. | N.B. | N.M. |
| SB-40-19 | H1H2 | 4.48E-08 | N.B. | N.B. | N.M. |
| SB-40-20 | H1H2 | 9.41E-09 | N.B. | N.B. | N.M. |
| SB-40-21 | H1H2 | 4.04E-08 | N.B. | N.B. | N.M. |

Subsequent characterization of affinity matured anti-SIRPβ1 antibodies involved determining their ability to bind cell lines expressing human or mouse SIRPβ1. Cells were harvested, plated at $10^6$/ml in a 96-well plate, washed, and incubated in 100 μl FACS buffer containing 1 Hug/ml anti-SIRPβ1 antibody for 0.5 hour on ice. Cells were then washed twice and incubated in 100 ul FACS buffer containing 0.5 μg/ml PE-conjugated secondary antibody for 30 minutes on ice. Cells were washed twice in cold FACS buffer and acquired on a BD FACS Canto. Data analysis and calculation of mean fluorescence intensity (MFI) values or 00 positive cells was performed with FlowJo (TreeStar) software version 10.0.7.

Table 13 shows the mean fluorescence intensity (MFI) values of affinity matured anti-SIRPβ1 antibodies binding to the Chinese hamster ovary (CHO) cell line expressing low levels of human SIRPβ1. The human IgG1 isotype control established the background fluorescence signal set to 1. Of the 22 anti-SIRPβ 1 antibody clones tested, 17 clones bound to cells with an MFI ≥3-fold over background. As a negative control, the anti-SIRPβ1 antibodies were also screened for surface binding to CHO cells overexpressing mouse SIRPβ1 As expected, none of the test antibodies showed significant binding to mouse SIRPβ31, as clones were originally selected for binding the human antigen. Given the high sequence similarity between receptors of the SIRP family, anti-SIRPβ1 antibodies were also screened for cross-reactivity to human SIRPα. In cell binding assays, none of the anti-SIRPβ1 antibodies bound cells overexpressing human SIR-Pa.

TABLE 13

Cell Binding Characterization of affinity matured anti-SIRPβ1 antibodies

| Clone Index | Cell Binding Human SIRPβ FOB (Fold Over Background) | Cell Binding Human SIRPα FOB (Fold Over Background) | Cell Binding Mouse SIRPβ FOB (Fold Over Background) | EC50 (nM) |
|---|---|---|---|---|
| SB-1 | 2 | 1 | 1 | 0.072 |
| SB-1-2 | 4 | 1 | 1 | 0.059 |
| SB-1-3 | 4 | 0 | 2 | 0.062 |
| SB-1-4 | 3 | 1 | 1 | 0.073 |
| SB-1-5 | 3 | 1 | 2 | 0.038 |
| SB-2 | 2 | 1 | 1 | 0.235 |
| SB-2-7 | 5 | 1 | 1 | 0.132 |
| SB-2-8 | 5 | 1 | 1 | 0.174 |
| SB-2-9 | 4 | 1 | 2 | 0.469 |
| SB-2-10 | 4 | 1 | 2 | 0.234 |
| SB-2-11 | 6 | 0 | 2 | 0.220 |
| SB-8 | 2 | 1 | 2 | 0.441 |
| SB-8-13 | 7 | 1 | 2 | 0.253 |
| SB-8-14 | 7 | 1 | 1 | 0.304 |
| SB-8-15 | 7 | 1 | 1 | 0.737 |
| SB-8-16 | 9 | 1 | 2 | 0.147 |
| SB-40 | 2 | 1 | 1 | 0.707 |
| SB-40-18 | 4 | 1 | 2 | 0.320 |
| SB-40-19 | 3 | 1 | 2 | 0.713 |
| SB-40-20 | 3 | 1 | 2 | 0.405 |
| SB-40-21 | 5 | 1 | 2 | 0.715 |

Though the original four parental anti-SIRPβ1 antibodies did not demonstrate SIRPα cross-reactivity, Octet® analysis revealed that one of the progeny antibodies (SB-8-14) acquired avid binding to SIRPα despite the application of negative selection pressure during library screening. See Table 12 above. To determine if avid binding triggers SIRPα-dependent signaling, anti-SIRPβ1 antibodies were assessed for the ability to induce gene expression in human SIRPα and SIRPβ1 reporter cells. As described previously, test antibodies or two anti-SIRPα antibodies (clones SA-90, SA-94) were adsorbed onto 96-well plates at 10 μg/mL. After washing, $10^5$ BWZ-huSIRPα or BWZ-huSIRPβ1 NFAT-luciferase reporter cells were seeded onto wells and incubated overnight at 37° C. Luciferase activity was quantified by adding OneGlo reagent (Promega) to each well and incubating samples at room temperature for 3 min on a plate shaker. The luminescence signal was quantified using a BioTek Synergy™ Microplate Reader using GEN5™ 2.04 software. As shown in FIG. 8, both the parental anti-SIRPβ1 antibodies and their affinity improved progeny retained the ability to induce luciferase expression in the BWZ-huSIRPβ1 reporter cells. All affinity matured clones, including SB-8-14, failed to significantly induce luciferase expression when BWZ-huSIRPα reporter cells were added onto antibody-coated wells (FIG. 8). In contrast, both anti-SIRPα antibody clones induced luciferase expression in BWZ-huSIRPα and not in BWZ-huSIRPβ1 reporter cells (FIG. 8). These results establish that despite avid binding to soluble SIRPα of one of the affinity matured progeny antibodies disclosed herein, all anti-SIRPβ1 antibodies tested failed to functionally engage membrane-bound SIRPα. Instead, the anti-SIRPβ1 antibodies demonstrated functional specificity towards membrane-bound human SIRPβ1.

Example 9: Affinity Matured Anti-SIRPβ 1 Antibodies Increase Secretion of Inflammatory Cytokines from Dendritic Cells To determine whether affinity matured anti-SIRPβ 1 antibodies retain the ability to induce changes in inflammatory cytokine production, primary human monocyte-derived dendritic cells are cultured with plate-bound test antibodies in combination with non-saturating levels of TLR stimulators and the level of cytokines are measured after 24 hours. To generate monocyte-derived dendritic cells, human primary monocytes were isolated from heparinized human blood (Blood Centers of the Pacific) using RosetteSep Human Monocyte Enrichment Cocktail (STEMCELL Technologies), according to the manufacturer's protocol. Monocytes were seeded in RPMI (Invitrogen) containing 10% Fetal Calf Serum (Hyclone) and 20 ng/ml IL-4 and GM-CSF (Peprotech) to induce differentiation of immature dendritic cells. After 6-7 days, dendritic cells were harvested by scraping cells attached to plastic. Dendritic cells are plated on 96-well plates coated with indicated antibody at $10^5$ cells/well and incubated for 24h at 37° C. Cells are co-stimulated with TLR4 agonist, LPS (*Salmonella abortus equi*).

Figure 9:
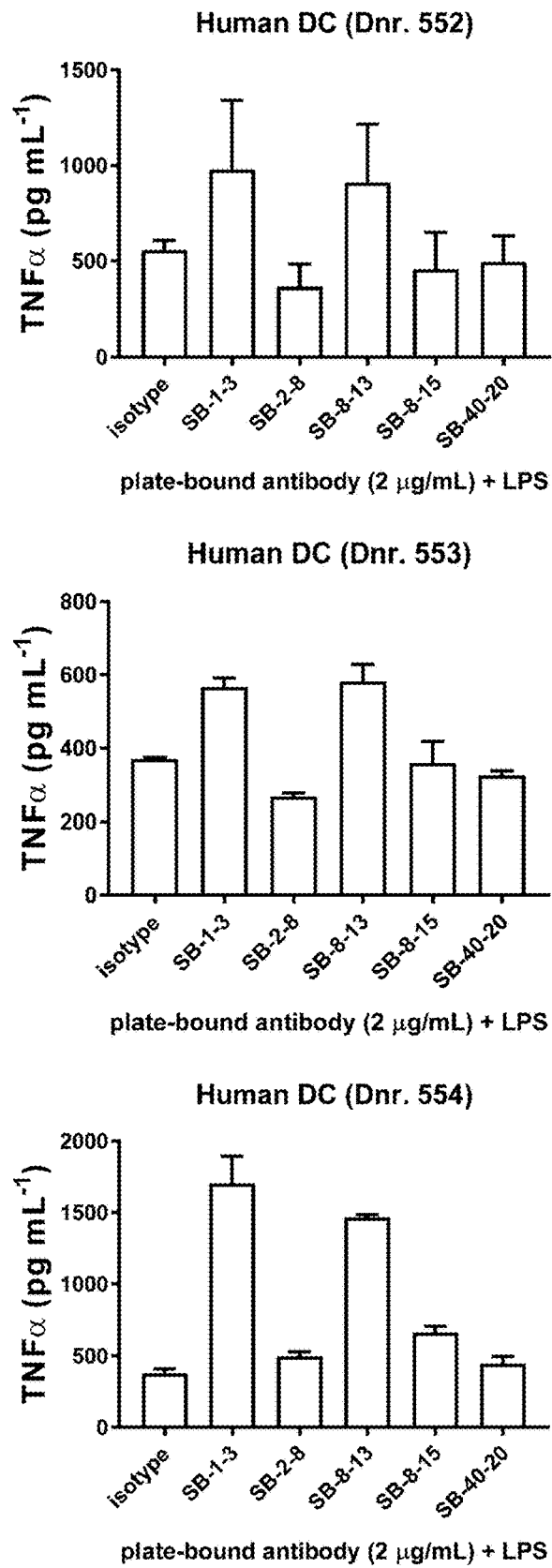
FIG. 9 shows SIRPβ1-mediated TNFα cytokine release from primary human dendritic cells (DCs).

In FIG. 9, monocyte-derived dendritic cells from 3 healthy donors were stimulated overnight at 37° C. with 0.5 ng/mL LPS in the presence of indicated affinity matured anti-SIRPβ1 antibodies adsorbed onto 96-well plates at 2 μg/mL. The supernatant fraction was subsequently collected and assayed for TNFα release. The SIRPβ1 antibodies SB-1-3, SB-2-8, and SB-8-13 proved highly agonistic as plate-bound antibodies. In contrast, remaining SIRPβ1 antibodies, SB-2-8, SB-8-15, and SB-40-20, weakly activated SIRPβ1-mediated cytokine release.

Example 10: Anti-SIRPβ1 Antibodies are Specific to Human SIRPβ1 Isoform 1

Among the multiple SIRPβ 1 isoforms catalogued, isoform 1 is the full-length version of the receptor primarily expressed in the periphery. Recombinant antigen based on the sequence of SIRPβ1 isoform 1 was used for selecting anti-SIRPβ1 antibodies from yeast library pools. To ascertain if the selected anti-SIRPβ1 antibodies cross-reacted with other isoforms of human SIRPβ1 or with cynomolgus SIRPβ1, recombinant antigens based on human SIRPβ1 isoform 3 sequence and cynomolgus SIRPβ1 isoform 1 sequence were produced by transient transfection in HEK293 cells. Purified, Fc-tagged recombinant proteins were adsorbed onto 96-well plates at 1 μg/mL overnight at 4° C. Plates were subsequently washed with PBS+0.05% Tween-20 and blocked with 1% BSA+PBS for 2 hours at room temperature. Antibodies diluted in blocking buffer at 1 μg/mL were added to wells, serially diluted, and allowed to bind antigen overnight at 4° C. The following day, the primary antibodies were removed and anti-human kappa light chain antibody conjugated to horseradish peroxidase diluted 1:10,000 in blocking buffer were added to wells and incubated for 1 hour at room temperature. Plates were washed with PBS+0.05% Tween-20 and 100 μL of TMB substrate solution was added to wells to generate a colorimetric signal proportional to amount of anti-SIRPβ1 antibody bound to antigen. Once the reaction reached an appropriate color intensity, 100 μL of Stop solution was added to quench the enzyme. Plates were read with a BioTek Synergy™ Microplate Reader using GEN5™ 2.04 software.

Figure 10A:
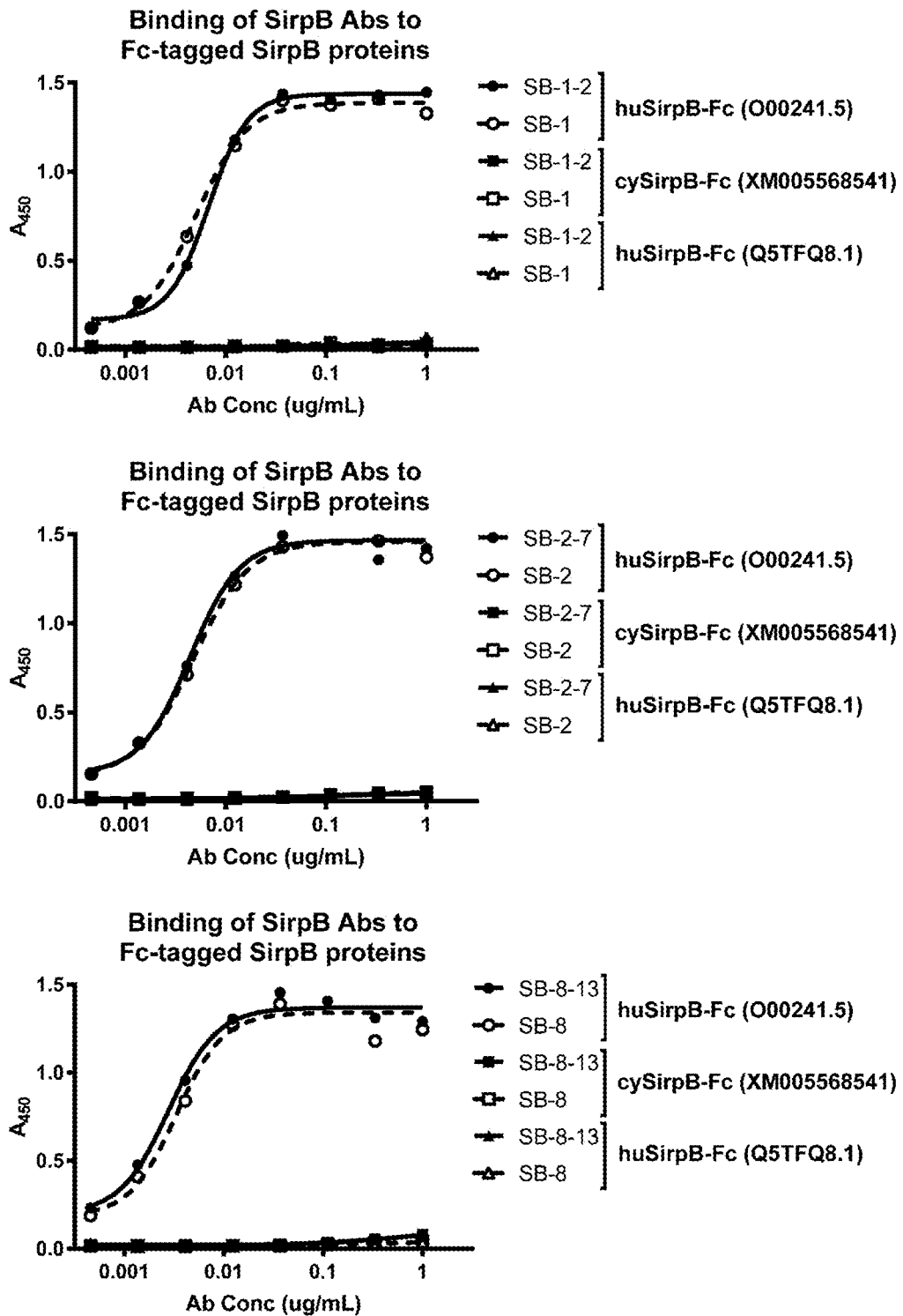
FIG. 10A-10B shows the cross-reactivity of anti-SIRPβ1 antibodies to multiple SIRPβ1 antigens. Soluble, human SIRPβ1-Fc isoform 1 (000241) or isoform 3 (Q5TFQ8) or cynomolgus SIRPβ1-Fc (XM005568541) were coated onto plates and incubated with increasing concentrations of parental and affinity matured forms of anti-SIRPβ1 antibodies SB-1, SB-1-2, SB-2, SB-2-7, SB-8, SB-8-13, SB-40, and SB-40-21. All anti-SIRPβ1 antibodies bound only to human SIRPβ1-Fc isoform 1 antigen.
Figure 10B:
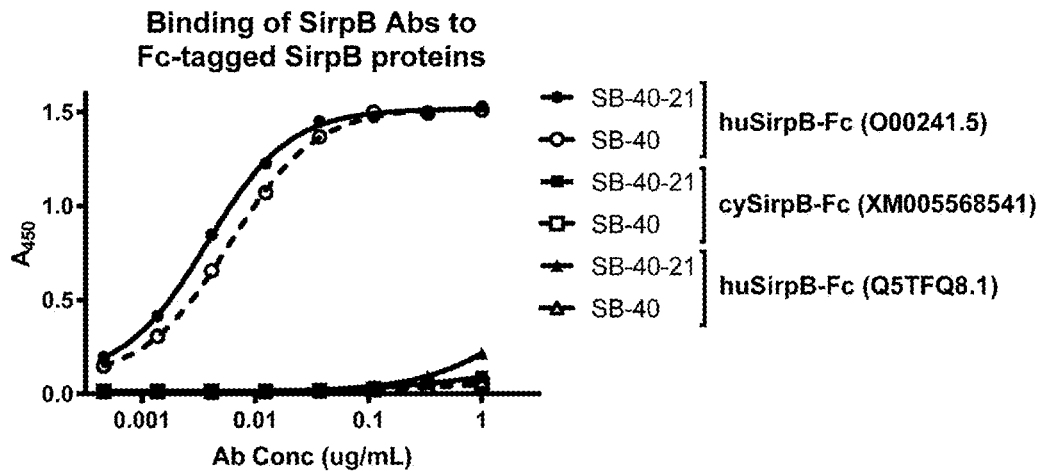

FIG. 10A-10B shows binding curves of anti-SIRPβ1 antibodies bound to indicated SIRPβ1 antigens based on ELISA data. Eight anti-SIRPβ1 antibodies (four parental antibodies and four corresponding affinity matured antibodies) were selected for analysis. EC50 values calculated from these binding curves demonstrated that all eight anti-SIRPβ1 antibodies recognized human SIRPβ1 isoform 1 with high affinity. For example, the EC50 values for SB-1 and SB-1-2 are 0.034 nM and 0.045 nM, respectively. The EC50 values for SB-2 and SB-2-7 are 0.032 nM and 0.029 nM, respectively. The EC50 values for SB-8 and SB-8-13 are 0.022 nM and 0.019 nM, respectively. The EC50 values for SB-40 and SB-40-21 are 0.040 nM and 0.025 nM, respectively. However, the anti-SIRPβ1 antibodies tested did not cross-react to either human SIRPβ1 isoform 3 or to cynomolgus SIRPβ1. These results demonstrate that the screening and selection platform yielded highly specific antibodies to human SIRPβ1 isoform 1 with no evidence of cross-reactivity towards human SIRPα, human SIRPβ1 isoform 3, murine SIRPβ1, or cynomolgus SIRPβ1.

Example 11: Analysis of the Effect of Anti-SIRPβ1 Antibodies in Increasing Recruitment of Immune Cells In Vivo The ability of anti-SIRPβ1 antibodies to modulate the recruitment of inflammatory cells (neutrophil granulocytes, monocytes, and macrophages) in the peritoneal cavity (PEC) of human SIRPβ1 BAC-transgenic mice after intraperitoneal (IP) administration of either antibody alone or in combination with LPS is evaluated as follows. Briefly, mice receive first an IP injection of 40 mg/kg anti-SIRPβ1 antibody or isotype control antibody mIgG1 (clone MOPC-21, Bioxcell). 14 hours later, mice receive an IP injection of 4 mg/kg LPS, or PBS as a control. 6 hours after LPS or PBS injection, cells are harvested from the PEC as described (see, e.g., Gawish R et al, 2014 *FASEB J*) and analyzed by FACS. For FACS analysis, PEC cells are incubated with anti-CD11b-Pacific Blue, anti-CD11c PeCy7, anti-MCH-II-APCCy7, anti-Gr1-FITC, anti-Ly6G-PE and a viability die (Life Technologies, Cat #L34957) for 1 hour on ice, then washed twice with cold FACS buffer. 4% PFA-fixed samples are then acquired. Data are acquired on a BD FACS CANTO II cytometer (Becton Dickinson) and analyzed with FlowJo software. These studies provide support that anti-SIRPβ1 antibodies of the present disclosure increase recruitment of immune cells in vivo.

Example 12: SIRPβ1 Expression in the Tumor Microenvironment

Groups of 3 human SIRPβ1 BAC-transgenic mice (females, 8 weeks old) are challenged subcutaneously with 1×10$^6$ MC38 or CT26 colon carcinoma cells, or EMT-6 murine mammary carcinoma cells, suspended in 100 µl PBS. Animals are anesthetized with isoflurane prior to implant. When the tumors reach a size of 700-1000 mm$^3$, tumors are explanted to analyze SIRPβ1 expression in the tumor microenvironment by FACS. As a comparison, the spleen of the tumor bearing mice or control spleen of naïve mice is also analyzed. For expression analysis by FACS, tumor and spleens are incubated in PBS containing 1 mg/ml collagenase and then processed through a cell strained to obtain a single cell suspension. Cells are then incubated with anti-CD45-PerCp-Cy7, anti-CD11b-PerCP-Cy5.5, anti-CD3-PC, anti-Gr1-FITC, anti-NK1.1-PE, anti-SIRPβ1-APC antibodies and a viability die (Life Technologies, Cat #L34957) for 30 min on ice, then washed twice with cold FACS buffer. 4% PFA-fixed samples are then acquired. Data are acquired on a BD FACS CANTO II cytometer (Becton Dickinson) and analyzed with FlowJo software. These studies provide support that myeloid cells or cells of myeloid lineage express SIRPβ1 in the tumor environment.

Example 13: Analysis of Tumor Growth in Human SIRPβ1 BAC Transgenic Mice

Groups of wild-type (WT, n=11) and human SIRPβ1 BAC transgenic mice (SIRPoltg, n=14) mice (sex and age-matched littermates, 10 weeks old (+/−2 weeks)) are challenged subcutaneously with 1×10$^6$ MC38 colon carcinoma tumor cells suspended in 100 µl PBS. Mice are then anesthetized with isoflurane prior to tumor implant. Following tumor implant, the mice are administered various concentrations of an anti-SIRPβ1 antibody of the present invention. Tumor growth is monitored with a caliper biweekly starting at day 5. The endpoint of the experiment is a tumor volume of 2000 mm$^3$ or 60 days. The effect of anti-SIRPβ1 antibody administration on reducing tumor growth or tumor size (expressed as volume, mm$^3$), as compared to that observed in control animals, is determined. These studies provide support that anti-SIRPβ1 antibodies of the present invention reduce tumor growth in vivo.

Example 14: Anti-SIRPβ1 Antibodies Induce the Expression of CD83 and CD86 on Human Dendritic Cells (DCs)

To evaluate the ability of anti-SIRPβ1 antibodies to modify expression of CD83 and CD86, both plate-bound and soluble antibodies are incubated with dendritic cells (DCs), and the expression of CD83, CD86, CCR7, and phosphorylated ERK are measured. Antibodies are plated overnight at 4° C. in 12 well plates at 2 or 10 µg/ml in PBS. Wells are washed 3× with PBS the next day. Primary human monocytes isolated from peripheral blood of healthy donors are added to antibody coated wells in RPMI media supplemented with 10% FBS and 20 ng/mL IL-4 and GM-CSF and incubated at 37° C., 5% CO$_2$ for 5 days. On day 5, immature human DCs are harvested and analyzed by FACS for CD86, CD83, CD1a, and HLA-DR, on a BD FACS Canto. Data analysis is performed with FlowJo (TreeStar) software version 10.0.7. Levels of CD83 and CD86 are evaluated for CD1a+/HLA−/DR+ cell populations. For intracellular ERK phosphorylation, cells are fixed with 1% formaldehyde, permeabilized with cytofix/cytoperm kit (BD), and intracellular Erk phopshorylation is determined with flow cytometry after staining with PE-ERK antibody (BD). These studies provide support that anti-SIRPβ1 antibodies of the present invention increase expression of CD83, CD86 and CCR7 in human dendritic cells. Additionally, these studies provide support that anti-SIRPβ1 antibodies of the present invention increase or induce ERK phosphorylation in human dendritic cells.

Example 15: Screening for Anti-SIRPβ1 and/or Anti-SIRPβ1 Bispecific Antibodies that Induce Phosphorylation of SIRPβ1, DAP12, SYK, ERK, and AKT, which Indicate Activation of the PI3K Pathway Primary human myeloid cells or murine myeloid cell lines engineered to express human SIRPβ1 (J774, RAW 264.7, BMM cells, or osteoclasts) are removed from tissue culture dishes with PBS-EDTA, washed with PBS, and counted. J774 ($40 \times 10^6$) or RAW 264.7 cells ($10 \times 10^6$ BMM or osteoclasts) are incubated with an anti-SIRPβ1 and/or an anti-SIRPβ1 bispecific antibody (such as an anti-SIRPβ1/TREM2 bispecific antibody) or with an isotype-matched control antibody at 1 μg/$10^6$ cells for 20 min on ice or under other conditions. Cells are lysed in ice-cold radioimmunoprecipitation assay (RIPA) buffer for 20 min followed by centrifugation at 16,000 g for 10 min at 4° C. to remove insoluble materials. The resulting supernatant is subjected to immunoprecipitation reactions with the indicated antibodies (DAP12, ERK, or AKT) and protein A- or protein G-agarose (Sigma). The beads are extensively washed with RIPA buffer and the proteins are separated by SDS-polyacrylamide gel electrophoresis (SDS-PAGE). The proteins are then transferred to nitrocellulose membranes by Western blotting, incubated with the appropriate antibodies (antibodies that specifically recognize the phosphorylated form of DAP12, ERK, or AKT), and visualized with the enhanced chemiluminescence (ECL) system (Pierce), as described (e.g., Peng et al., (2010) Sci Signal., 3(122): ra38). These studies provide support that anti-SIRPβ1 antibodies of the present invention induce phosphorylation of SIRPβ1, DAP12, SYK, ERK, and AKT. Additionally, these studies provide support that anti-SIRPβ1 antibodies of the present invention are effective at activating the PI3K pathway.

Example 16: Anti-SIRPβ1 Antibodies Upregulate TREM2 Expression on Human Macrophages SIRPβ1 and TREM2 are DAP12-associated receptors expressed on myeloid cells. To evaluate if SIRPβ1 modifies the expression of TREM2, macrophages were cultured on plate-bound antibodies and analyzed for cell surface levels of TREM2 by flow cytometry.

Antibodies (SB-1-3, SB-2-8, SB-8-13, SB-8-15, SB-40-20, and huIgG1 control) were adsorbed onto 96-well plates at 37° C. for 4 hours at 2 μg/mL in PBS. Wells were washed twice with PBS. Monocyte-derived human macrophages, differentiating in culture with M-CSF for 5-6 days, were harvested and plated at 100,000 cells per well. Macrophages were incubated overnight at 37° C., 5% $CO_2$. FACS analysis of TREM2 expression was performed on a BD FACS Canto II and data analysis was performed with FlowJo (TreeStar) software.

Figure 11A:
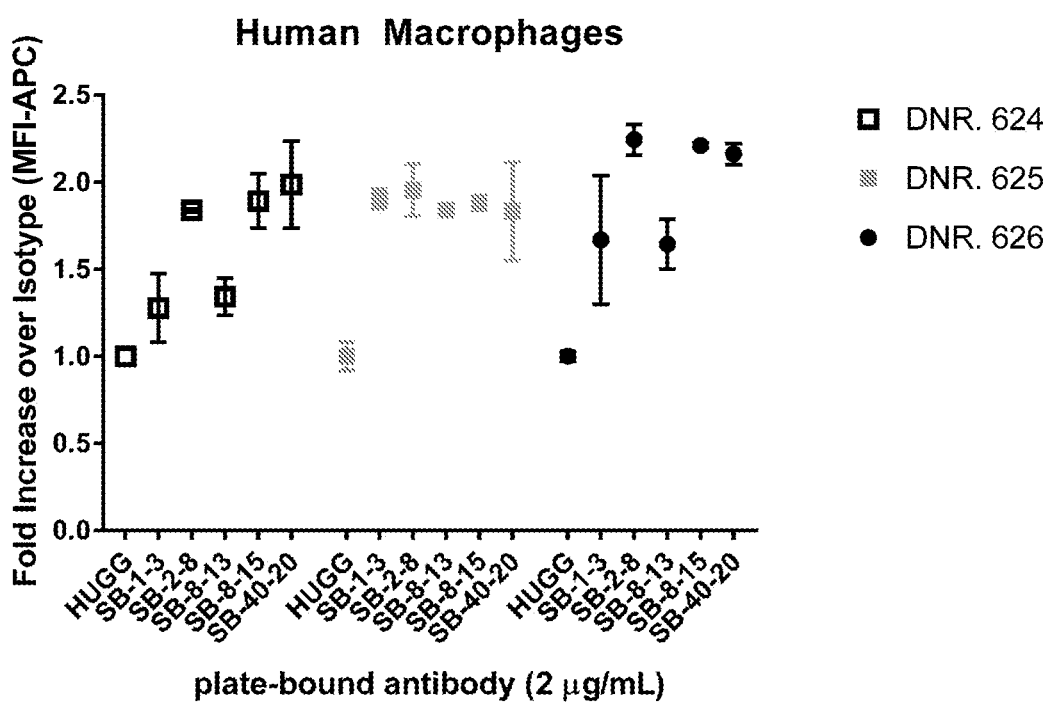
FIG. 11A shows the upregulation of TREM2 expression on monocyte-derived human macrophages from three different healthy donors by plate-bound, full-length anti-SIRPβ1 antibodies SB-1-3, SB-2-8, SB-8-13, SB-8-15, and SB-40-20. Baseline TREM2 expression was determined from cells incubated on human IgG1 isotype control antibody. TREM2 was detected with an anti-TREM2 antibody (clone ADI-22) conjugated with DyLight650 fluorophore.

As shown in FIG. 11A, Plate-bound anti-SIRPβ1 antibodies SB-2-8, SB-8-15, and SB-40-20 increased TREM2 expression approximately 2-fold relative to huIgG1 isotype control treated macrophages obtained from 3 healthy donors. In 2 out of 3 healthy donors (624 and 626), however, plate-bound anti-SIRPβ1 antibodies SB-1-3 and SB-8-13 only partially increased TREM2 expression relative to huIgG1 isotype control treated macrophages. In macrophages from a third healthy donor (625), plate-bound SB-1-3 and SB-8-13 increased TREM2 expression approximately 2-fold relative to huIgG1 isotype control. Based on these results, anti-SIRPβ1 antibodies SB-2-8, SB-8-15, and SB-40-20 function as agonists to induce cell surface TREM2 expression.

Example 17: Anti-SIRPβ1 Antibodies Increase Viability of Human Macrophages

Evidence in the literature suggests that TREM2 promotes macrophage/microglia viability. Since SIRPβ1 associates with DAP12 adaptor molecule and may influence TREM2 expression, anti-SIRPβ1 antibodies were evaluated for the ability to increase human macrophage viability.

Antibodies (SB-1-3, SB-2-8, SB-8-13, SB-8-15, SB-40-20, and huIgG1 control) were adsorbed onto 96-well plates at 37° C. for 4 hours at 2 μg/mL in PBS. Wells were washed twice with PBS. Monocyte-derived human macrophages, differentiating in culture with M-CSF for 5-6 days, were harvested and washed to remove residual M-CSF. Macrophages were resuspended in RPMI growth media supplemented with 10% FBS and 1% Penn/Strep at 500,000 cell per mL. Cells were diluted with equal volume of PBS and 100 μL containing 25,000 cells were added to each well. Macrophages were incubated at 37° C. for 2 days. Analysis of viability was performed using Cell Titer Glo kit (Promega), a reagent that produces a luminescence signal relative to ATP concentration in the sample. Plates were read with a Biotek Synergy Microplate Reader using GEN5 2.04 software.

Figure 11B:
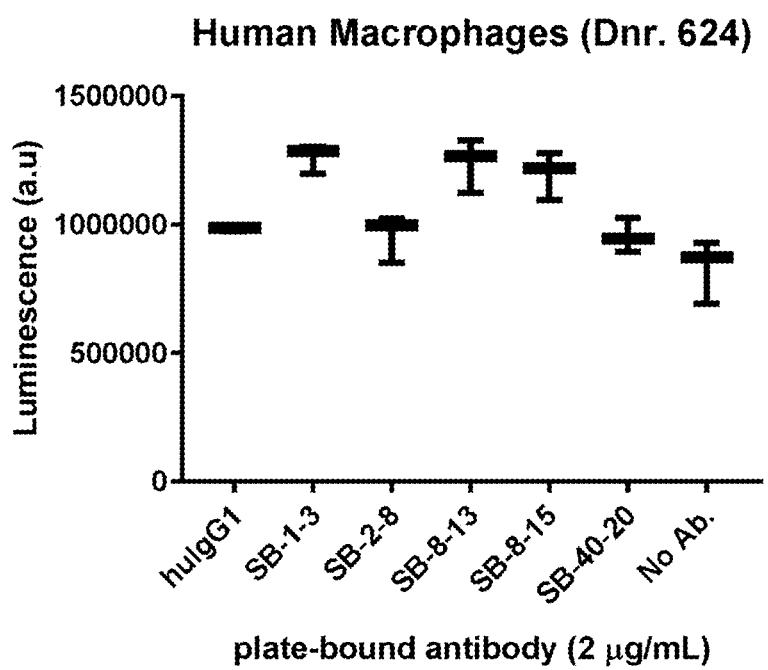
FIG. 11B shows the viability of monocyte-derived human macrophages cultured on plate-bound, full-length anti-SIRPβ1 antibodies SB-1-3, SB-2-8, SB-8-13, SB-8-15, and SB-40-20. Viable cells were quantified by measuring luminescence values following addition of Cell Titer Glo substrate. Cells cultured on human IgG1 isotype control or in the absence of plate-bound antibody (No Ab) established baseline viability of cells.

As shown in FIG. 11B, baseline luminescence was established with macrophages cultured on plate-bound, full-length huIgG1 isotype control. In comparison to macrophages seeded in the absence of antibody (No Ab), there is no significant change in macrophage viability with the isotype control. However, macrophages cultured on plate-bound, full-length anti-SIRPβ1 antibodies SB-1-3, SB-8-13, and SB-8-15 demonstrated a significant increase in viability relative to isotype control treated cells. Plate-bound, full-length anti-SIRPβ1 antibodies SB-2-8 and SB-40-20 failed to increase macrophage viability relative to the isotype control treated cells.

Given the differences in activity initially observed between the anti-SIRPβ1 antibodies, subsequent assays determined if antibody activity depended on concentration of adsorbed protein. Anti-SIRPβ1 antibodies SB-1-3 and SB-2-8 or the human IgG1 isotype control were coated onto 96-well plates at 37° C. for 4 hours starting at 10 μg/mL in PBS and serially diluted 3-fold. As described previously, macrophages were diluted with equal volume of PBS and 100 μL containing 25,000 cells were added to each well. Macrophages were incubated at 37° C. for 2 days. Analysis of viability was performed using Cell Titer Glo kit (Promega) and plates were read with a Biotek Synergy Microplate Reader using GEN5 2.04 software.

Figure 12:
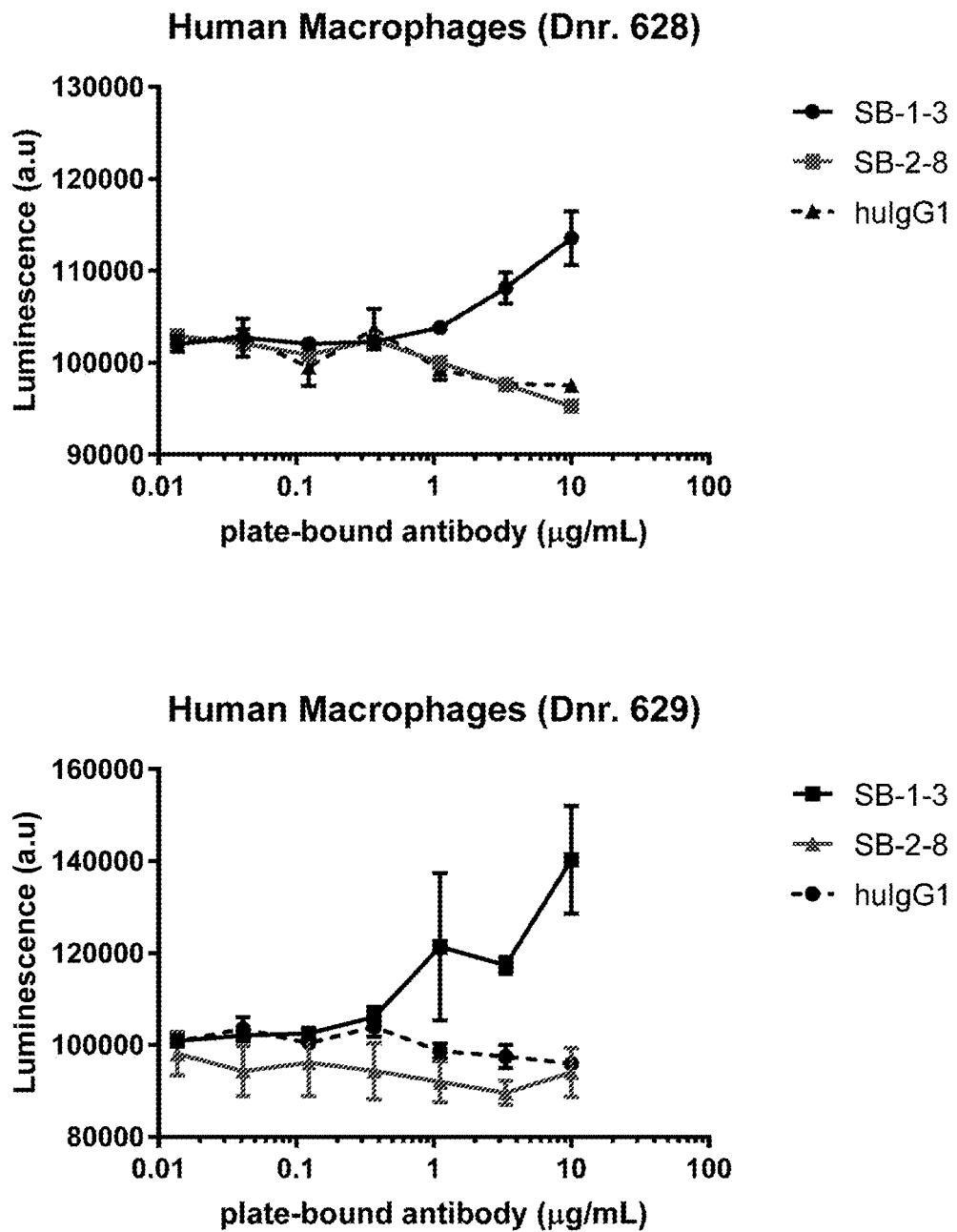
FIG. 12 shows the viability of monocyte-derived macrophages from two different healthy donors cultured on increasing concentrations of plate-bound, full-length anti-SIRPβ1 antibodies SB-1-3 and SB-2-8 or human IgG1 isotype control. Viable cells were quantified by measuring luminescence values following addition of Cell Titer Glo substrate.

As shown in FIG. 12, plate-bound, full-length anti-SIRPβ1 antibody SB-1-3 increased macrophage viability in a dose-dependent manner relative to isotype control treated cells. In contrast, plate-bound, full-length anti-SIRPβ1 antibody SB-2-8 failed to increase macrophage viability even at high concentrations of coated protein. Thus, anti-SIRPβ1 antibodies SB-1-3, SB-8-13, and SB-8-15 demonstrated agonistic activity in this assay.

Example 18: Additive and Synergistic Effect of Combination Treatment of Macrophages with Anti-SIRPβ1 and Anti-TREM2 Antibodies Agonistic anti-TREM2 antibodies have been shown to increase macrophage viability when added to cells in a soluble format. Viability assays were performed to determine if co-stimulating macrophages with anti-SIRPβ1 antibodies further enhances the agonist activity anti-TREM2 antibody.

Anti-SIRPβ1 antibodies SB-1-3 and SB-2-8 or the human IgG1 isotype control were coated onto 96-well plates at 37° C. for 4 hours at 10 μg/mL in PBS. As described previously, macrophages were diluted with equal volume of PBS and 100 gIL containing 25,000 cells were added to each well.

Where indicated, macrophages were also treated with 50 µg/mL of anti-TREM2 antibody. Macrophages were incubated at 37° C. for 2 days. Analysis of viability was performed using Cell Titer Glo kit (Promega) and plates were read with a Biotek Synergy Microplate Reader using GEN5 2.04 software.

Figure 13:
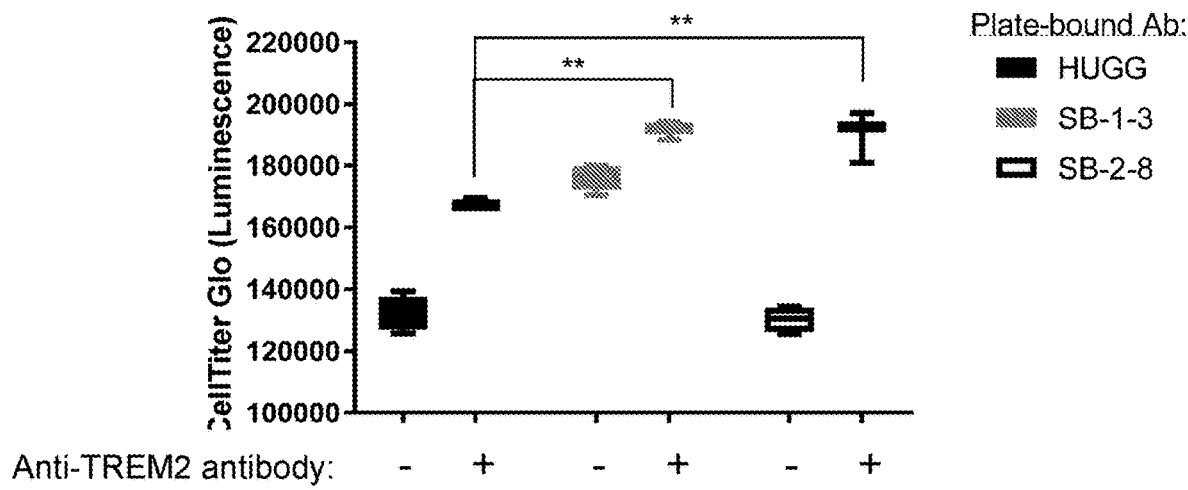
FIG. 13 shows anti-SIRPβ1 antibodies enhance the agonistic activity of anti-TREM2 antibody in a macrophage viability assay. Monocyte-derived macrophages were cultured on plate-bound, full-length SB-1-3, SB-2-8, or huIgG1 isotype control in the presence or absence of soluble anti-TREM2 antibody. Viable cells were quantified by measuring luminescence values following addition of Cell Titer Glo substrate.

As shown in FIG. 13, adding agonist anti-TREM2 antibody to cells cultured on human IgG1 isotype control significantly increased macrophage viability relative to cells cultured in the absence of agonist anti-TREM2 antibody, establishing the reproducibility of this assay. Furthermore, culturing macrophages on plate-bound, full-length anti-SIRPβ1 antibody SB-1-3 significantly increased viability relative to isotype treated cells, whereas anti-SIRPβ1 antibody SB-2-8 did not show that activity (FIG. 12). Co-stimulating macrophages with plate-bound anti-SIRPβ1 antibody SB-1-3 and soluble agonist anti-TREM2 antibody shows additivity by further enhancing macrophage viability. Interestingly, co-stimulating macrophages with plate-bound anti-SIRPβ1 antibody SB-2-8 and soluble anti-TREM2 antibody shows synergistic activity by increasing macrophage viability. Thus, anti-SIRPβ1 antibodies enhance the activity of agonistic anti-TREM2 antibodies.

Example 19: Anti-SIRPβ1 Antibodies Increase the Viability of Bone Marrow-Derived Macrophages Human SIRPβ1 BAC transgenic mice that recapitulate the expression of the human antigen in mouse myeloid cells were generated. Murine bone marrow cells from human SIRPβ1 transgenic mice were obtained by flushing tibia and femurs with PBS. Bone marrow cells were cultured in RPMI media supplemented with 50 ng/mL M-CSF to differentiate macrophages or 10 ng/mL GM-CSF to differentiate dendritic cells. Anti-SIRPβ1 antibodies were evaluated for their ability to increase murine myeloid cell viability.

Figure 14A:
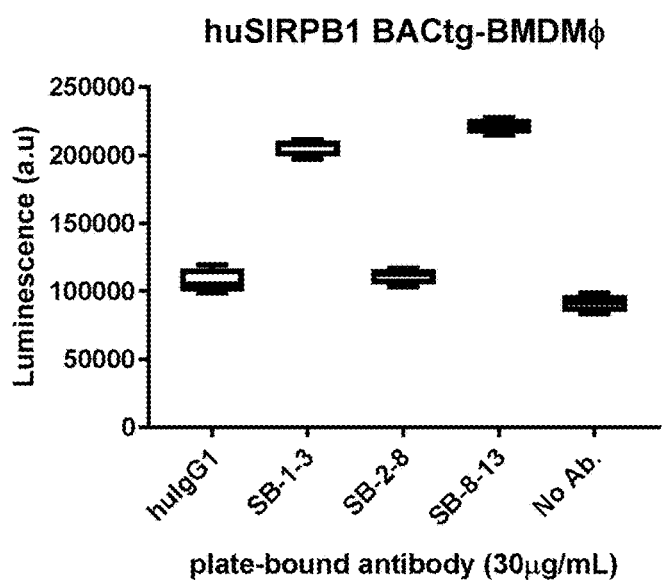
FIG. 14A shows the viability of bone marrow-derived macrophages obtained from human SIRPβ1 BAC transgenic mice cultured on plate-bound, full-length anti-SIRPβ1 antibodies SB-1-3, SB-2-8, and SB-8-13 or human IgG1 isotype control.
Figure 14B:
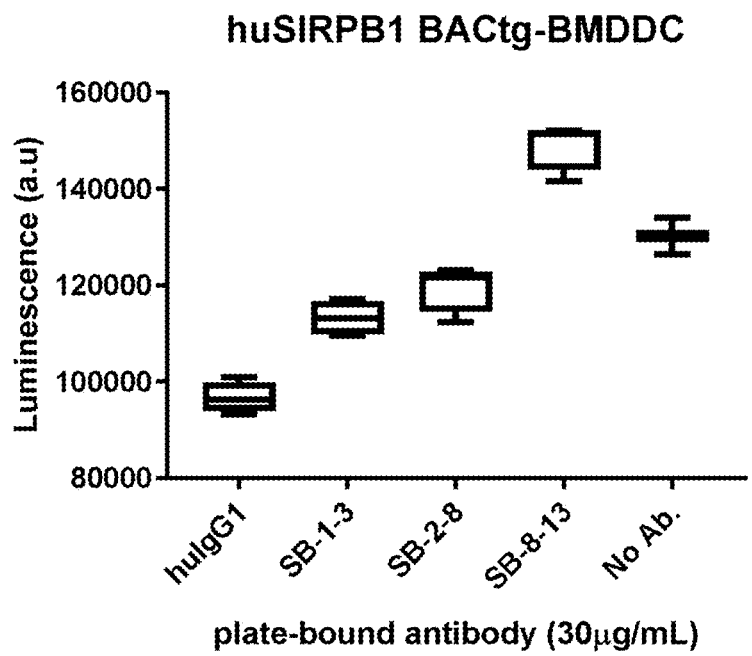
FIG. 14B shows the viability of bone marrow-derived dendritic cells obtained from human SIRPβ1 BAC transgenic mice cultured on plate-bound, full-length anti-SIRPβ1 antibodies SB-1-3, SB-2-8, and SB-8-13 or human IgG1 isotype control. Viable cells were quantified by measuring luminescence values following addition of Cell Titer Glo substrate. Cells cultured on human IgG1 isotype control or in the absence of plate-bound antibody (No Ab) established baseline viability of cells.

Anti-SIRPβ1 antibodies SB-1-3, SB-2-8, and SB-8-13 or the human IgG1 isotype control were coated onto 96-well plates at 37° C. for 4 hours at 10 µg/mL in PBS. Macrophages and dendritic cells were diluted with equal volume of PBS and 100 µL containing 25,000 cells were added to each well. Cells were incubated at 37° C. for 2 days. Analysis of viability was performed using Cell Titer Glo kit (Promega) and plates were read with a Biotek Synergy Microplate Reader using GEN5 2.04 software. As shown in FIG. 14A, consistent with human macrophages, culturing bone marrow-derived macrophages on plate-bound, full-length anti-SIRPβ1 antibodies SB-1-3 and SB-8-13 enhanced macrophage viability relative to isotype control treated cells. In contrast, anti-SIRPβ1 antibody SB-2-8 failed to increase macrophage viability. As shown in FIG. 14B, when dendritic cells (DC) were cultured on plate-bound antibodies, all anti-SIRPβ1 antibodies increased DC viability relative to isotype control treated cells. However, only anti-SIRPβ1 antibody SB-8-13 treated DC showed increased viability relative to untreated dendritic cells (No Ab.). Thus, anti-SIRPβ1 antibodies show agonistic activity with murine myeloid cells expressing human SIRPβ1.

Example 20: Cross-Reactivity of Affinity Matured Anti-SIRPβ1 Antibodies to Related SIRP Receptors A characteristic feature of proteins of the SIRP family is their extensive amino acid sequence conservation in the extracellular domain. For example, the extracellular region of SIRPβ1 shares ~90% sequence identity with SIRPα and ~77% sequence identity with SIRPγ. Antibodies developed against one SIRP protein family member often cross-react with multiple SIRP receptor family members.

Despite the homology in sequence/structure, the SIRP receptors exhibit different functional properties and expression patterns. For example, SIRPα contains a cytoplasmic ITIM motif to mediate immune suppression upon binding to CD47. In contrast, SIRPβ1, which lacks intracellular signaling motifs and does not bind CD47, associates with the ITAM-containing DAP12 adaptor protein to propagate activation signals. SIRPγ, unlike other SIRP receptors that are primarily expressed on myeloid cells, is expressed on lymphocytes and NK cells and serves to stabilize cell-cell adhesion during antigen presentation to T cells.

To determine antigen specificity of anti-SIRPβ1 antibodies of the present disclosure, cell-based affinity measurements were performed to ascertain the apparent affinities of affinity-matured anti-SIRPβ1 antibodies to cell surface-expressed antigen. BW5147.G.1.4 cells, an immortalized mouse T-cell line, were engineered to overexpress human SIRPβ1 (BWZ-huSIRPβ1) or human SIRPα (BWZ-huSIRPα). Jurkat cells, an immortalized human T cell line, endogenously express SIRPγ.

In these experiments, two antibodies previously described were used as positive controls: antibody 18D5 (an anti-SIRP antibody that cross-reacts with SIRPα and SIRPβ) and antibody KWAR23 (an anti-SIRP antibody that cross-reacts with SIRPα, SIRPβ, and SIRPγ). These antibodies were recombinantly produced on a human IgG4 backbone. A commercially available anti-SIRPγ antibody (clone LSB2.20; Biolegend, San Diego) conjugated with phycoerythrin (PE) fluorophore was used to verify SIRPγ expression on Jurkat cells. Serial dilutions of each of the anti-SIRPβ1 monoclonal antibodies and control antibodies were added to $10^5$ cells and allowed to achieve binding equilibrium at 4° C. After addition of fluorescently-labeled secondary antibody and brief washing steps, MFI values as a function of titrated antibody concentration were recorded via FACS analysis.

Figure 15A:
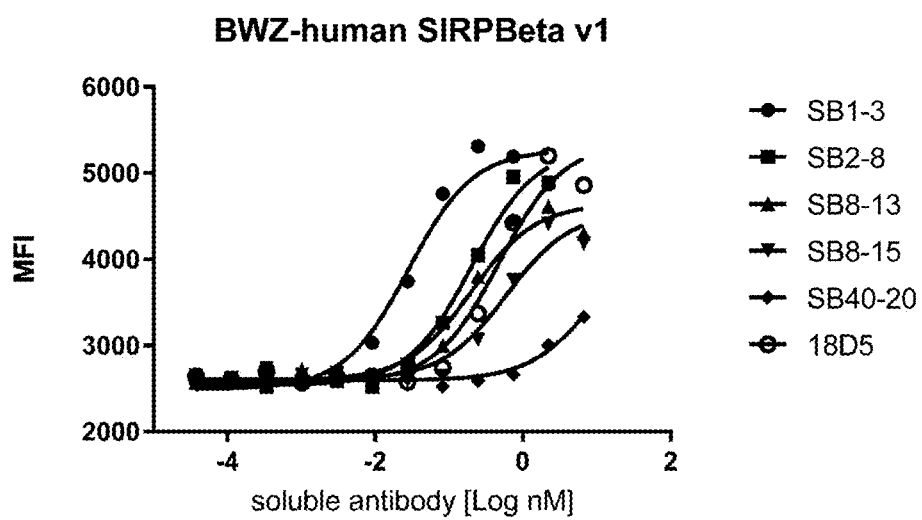
FIG. 15A-15C show cross-reactivity of anti-SIRP 1 antibodies to different receptors of the SIRP family.
Figure 15B:
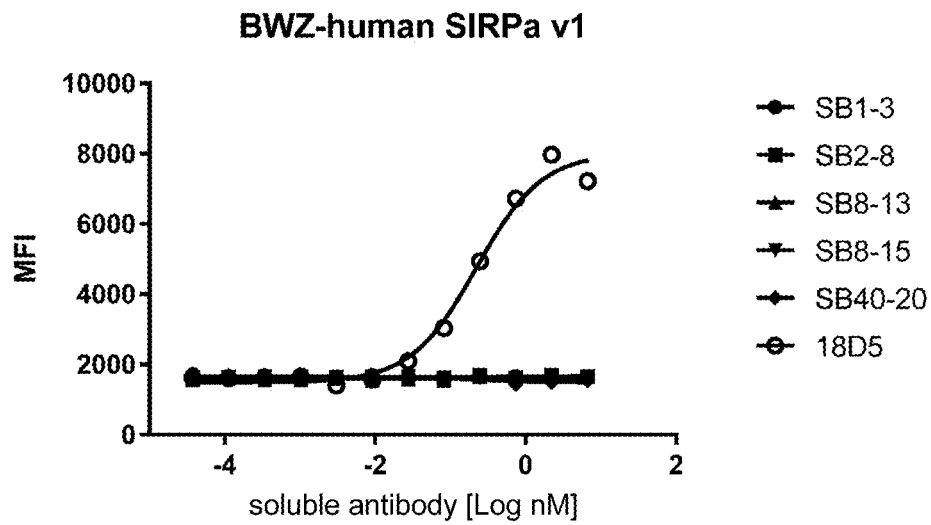
Figure 15C:
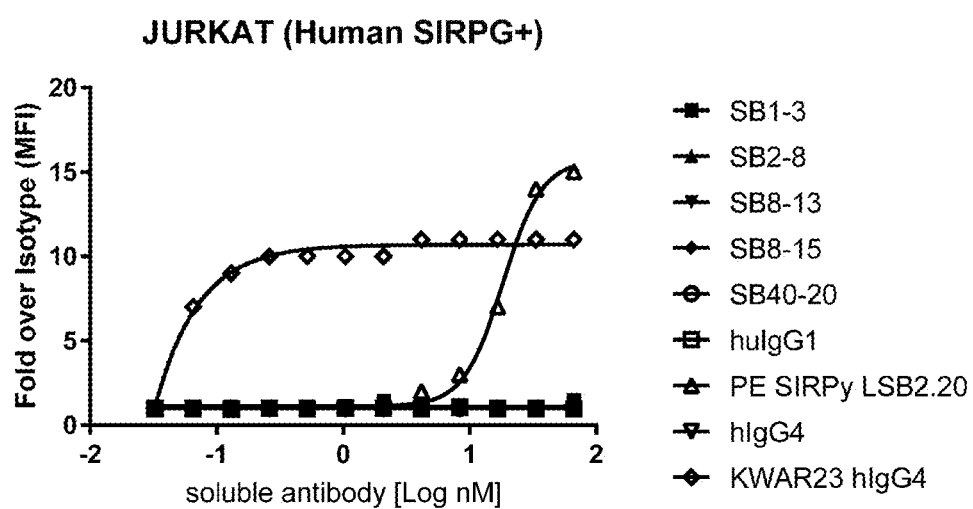

In Table 14 below, EC50 values assign relative affinity by adding increasing concentrations of antibody variants to cells overexpressing SIRPβ1. Receptor bound antibodies were detected by staining cells with anti-human IgG PE secondary antibody (Southern Biotech). Curves were fit using nonlinear regression analysis with Graphpad Prism 6 software. As shown in FIG. 15A, anti-SIRPβ1 antibodies bound BWZ-huSIRPR1 cells with distinct EC50 profiles. Anti-SIRPβ1 antibody SB1-3 showed the best apparent affinity relative to other anti-SIRPβ1 antibodies, as well as compared to that of the positive control antibody, 18D5. Anti-SIRPβ1 antibodies failed to bind cells expressing SIRPα (FIG. 15B) or SIRPγ (FIG. 15C) demonstrating that these antibodies are antigen-specific.

TABLE 14

EC50 values of antibodies binding BWZ-human SIRPβ1 cells

| | SB1-3 | SB2-8 | SB8-13 | SB8-15 | SB40-20 | 18D5 |
|---|---|---|---|---|---|---|
| $EC_{50}$ (nM) | 0.02837 | 0.2025 | 0.1993 | 0.5962 | 8.704 | 0.4769 |

CERTAIN SEQUENCES

SB-1: Light Chain Variable Region
(SEQ ID NO: 267)
EIVMTQSPGTLSLSPGERATLSCRASQSVSSSYLAWYQQKPGQAPRLLI
YGASSRATGIPDRESGSGSGTDFTLTISRLEPEDFAVYYCQLLGSSPRT
FGGGTKVEIK SB-1: Heavy Chain Variable Region
(SEQ ID NO: 268)
EVQLLESGGGLVQPGGSLRLSCAASGFTFSSYAMSWVRQAPGKGLEWVS
TISGSGGSTYYADSVKGRFTISRDNSKNTLYLQMNSLRAEDTAVYYCAK
DFTEVVGWLGMDVWGQGTTVTSS SB-2: Light Chain Variable Region
(SEQ ID NO: 269)
EIVLTQSPGTLSLSPGERATLSCRASQSVSSSYLAWYQQKPGQAPRLLI
YGASSRATGIPDRESGSGSGTDFTLTISRLEPEDFAVYYCQQSSSHPFT
FGGGTKVEIK SB-2: Heavy Chain Variable Region
(SEQ ID NO: 270)
QVQLVESGGGVVQPGRSLRLSCAASGFTFSSYGMNWVRQAPGKGLEWVA
VIWYDGSNKYYADSVKGRFTISRDNSKNTLYLQMNSLRAEDTAVYYCAR
DQTAAAAIWGMDVWGQGTTVTVSS SB-3: Light Chain Variable Region
(SEQ ID NO: 271)
EIVMTQSPATLSLSPGERATLSCRASQSVSSYLAWYQQKPGQAPRLLIY
DASNRATGIPARFSGSGSGTDFTLTISSLEPEDFAVYYCQQRLFHPPTF
GGGTKVEIK SB-3: Heavy Chain Variable Region
(SEQ ID NO: 272)
QVQLVQSGAEVKKPGASVKVSCKASGYTFTYYMHWVRQAPGQGLEWMG
WINPSSGGTNYAQKFQGRVTMTRDTSISTAYMELSRLRSDDTAVYYCAR
EGIAATDAYFDLWGRGTLVTVSS SB-4: Light Chain Variable Region
(SEQ ID NO: 273)
EIVLTQSPGTLSLSPGERATLSCRASQSVSSSYLAWYQQKPGQAPRLLI
YGASSRATGIPDRESGSGSGTDFTLTISRLEPEDFAVYYCQQYADAPIT
FGGGTKVEIK SB-4: Heavy Chain Variable Region
(SEQ ID NO: 274)
QVQLVQSGAEVKKPGASVKVSCKASGYTFTSYGISWVRQAPGQGLEWMG
WISAYNGNTNYAQKLQGRVTMTTDTSTSTAYMELRSLRSDDTAVYYCAR
SGTHFGTYSYSNWFDPWGQGTLVTVSS SB-5: Light Chain Variable Region
(SEQ ID NO: 275)
EIVLTQSPATLSLSPGERATITCRASQSVSSSYLAWYQQKPGQAPRLLI
YDASNRATGIPARFSGSGSGTDFTLTISSLEPEDFAVYYCQQRLFHPPTF
GGGTKVEIK SB-5: Heavy Chain Variable Region
(SEQ ID NO: 276)
QVQLVQSGAEVKKPGASVKVSCKASGYTFTGYYMHWVRQAPGQGLEWMG
WINPNSGGTNYAQKFQGRVTMTRDTSISTAYMELSRLRSDDTAVYYCAR
EGDEDWEDPWGQGTLVTVSS SB-6: Light Chain Variable Region
(SEQ ID NO: 277)
EIVLTQSPGTLSLSPGERATLSCRASQSVSSSYLAWYQQKPGQAPRLLI
YGASSRATGIPDRESGSGSGTDETLTISRLEPEDFAVYYCQQSGHLPIT
FGGGTKVEIK SB-6: Heavy Chain Variable Region
(SEQ ID NO: 268)
EVQLLESGGGLVQPGGSLRLSCAASGFTFSSYAMSWVRQAPGKGLEWVS
TISGSGGSTYYADSVKGRFTISRDNSKNTLYLQMNSLRAEDTAVYYCAK
DFTEVVGWLGMDVWGQGTTVTSS SB-7: Light Chain Variable Region
(SEQ ID NO: 278)
DIVMTQSPDSLAVSLGERATINCKSSQSVLFSSNNKNYLAWYQQKPGQP
PKLLIYWASTRESGVPDRFSGSGSGTDFTLTISSLQAEDVAVYYCQQHY
IAPFTFGGGTKVEIK SB-7: Heavy Chain Variable Region
(SEQ ID NO: 279)
QVQLVQSGAEVKKPGSSVKVSCKASGGTFSSYAISWVRQAPGQGLEWMG
GIIPIFGTASYAQKFQGRVTITADESTSTAYMELSSLRSEDTAVYYCAR
ETRQDSAHYYGMDVWGQGTTVTVSS SB-8: Light Chain Variable Region
(SEQ ID NO: 280)
EIVMTQSPGTLSLSPGERATLSCRASQSVSSSYLAWYQQKPGQAPRLLI
YGASNRATGIPDRESGSGSGTDFTLTISRLEPEDFAVYYCQQVYSSPYT
FGGGTKVEIK SB-8: Heavy Chain Variable Region
(SEQ ID NO: 281)
QVQLQESGPGLVKPSETLSLTCAVSGYSISSGYYWGWIRQPPGKGLEWI
GSIYHSGSTYYNPSLKSRVTISVDTSKNQFSLKLSSVTAADTAVYYCAR
GGAMTPAGMDVWGQGTTVTVSS SB-9: Light Chain Variable Region
(SEQ ID NO: 282)
DIVMTQSPDSLAVSLGERATINCKSSQSVLESSNNKNYLAWYQQKPGQP
PKLLIYWASTRESGVPDRFSGSGSGTDFTLTISSLQAEDVAVYYCQQYH
SVPPITFGGGTKVEIK SB-9: Heavy Chain Variable Region
(SEQ ID NO: 283)
QVQLVQSGAEVKKPGASVKVSCKASGYTFTSYGIHWVRQAPGQGLEWMG
WISAYNGNTYAQKFQGRVTMTTDTSTSTAYMELRSLRSDDTAVYYCAR
DGLHYGDYIVYYGMDVWGQGTTVTVSS SB-10: Light Chain Variable Region
(SEQ ID NO: 284)
DIVMTQSPLSLPVTPGEPASISCRSSQSLLHSNGYNYLDWYLQKPGQSP
QLLIYLGSNRASGVPDRESGSGSGTDFTLKISRVEAEDVGVYYCMQAIE
SPLTFGGGTKVEIK SB-10: Heavy Chain Variable Region
(SEQ ID NO: 285)
QVQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
GVPRGDLGMDVWGQGTTVTVSS SB-11: Light Chain Variable Region
(SEQ ID NO: 286)
DIVMTQSPLSLPVTPGEPASISCRSSQSLLYSNGYNYLDWYLQKPGQSP
QLLIYLGSNRASGVPDRESGSGSGTDFTLKISRVEAEDVGVYYCVQALQ
TPLTFGGGTKVEIK SB-11: Heavy Chain Variable Region
(SEQ ID NO: 287)
QVQLVQSGAEVKKPGSSVKVSCKASGGTFSNYAISWVRQAPGQGLEWMG
GIIPIFGTANYAQKFQGRVTITADESTSTAYMELSSLRSEDTAVYYCAR
PVDSSSYSLGYYYGMDVWGKGTTVTVSS SB-12: Light Chain Variable Region
(SEQ ID NO: 288)
EIVMTQSPATLSVSPGERATLSCRASQSVSSNLAWYQQKPGQAPRLLIY
SASTRATGIPARFSGSGSGTEFTLTISSLQSEDFAVYYCQQLDNLPYTF
GGGTKVEIK SB-12: Heavy Chain Variable Region
(SEQ ID NO: 289)
QVQLVQSGAEVKKPGASVKVSCKASGYTFTGYYMHWVRQAPGQGLEWMG
WINPNSGGTSYAQKFQGRVTMTRDTSISTAYMELSRLRSDDTAVYYCAR
DTYAYSYGMDVWGQGTTVTVSS SB-13: Light Chain Variable Region
(SEQ ID NO: 290)
DIVMTQSPLSLPVTPGEPASISCRSSQSLLYSNGYNYLDWYLQKPGQSP
QVLIYLGSNRASGVPDRESGSGSGTDFTLKISRVEAEDVGVYYCMQALR
SPITFGGGTKVEIK SB-13: Heavy Chain Variable Region
(SEQ ID NO: 291)
QVQLQESGPGLVKPSETLSLTCTVSGGSISSYYWSWIRQPPGKGLEWIG
SIYYSGSTNYNPSLKSRVTISVDTSKNQFSLKLSSVTAADTAVYYCARG
DTSGGAYFDLWGRGTLVTVSS

CERTAIN SEQUENCES

SB-14: Light Chain Variable Region
(SEQ ID NO: 292)
EIVMTQSPATLSLSPGERATLSCRASQSVSSYLAWYQQKPGQAPRLLIY
DSSNRATGIPARFSGSGSGTDFTLTISSLEPEDFAVYYCQQFSYYPITF
GGGTKVEIK SB-14: Heavy Chain Variable Region
(SEQ ID NO: 293)
QVQLVQSGAEVKKPGSSVKVSCKASGGTFSSYAISWVRQAPGQGLEWMG
GIIPIFGTASYAQKFQGRVTITADESTSTAYMELSSLRSEDTAVYYCAR
DRGGVGFDYWGQGTLVTVSS SB-15: Light Chain Variable Region
(SEQ ID NO: 294)
DIQMTQSPSSLSASVGDRVTITCRASQSISSYLNWYQQKPGKAPKLLIY
AASSLQSGVPSRESGSGSGTDFTLTISSLQPEDFATYYCQQAYSHPFTF
GGGTKVEIK SB-15: Heavy Chain Variable Region
(SEQ ID NO: 295)
QLQLQESGPGLVKPSETLSLTCTVSGGSISSNSYYWGWIRQPPGKGLEW
IGSIYYSGSTYYNPSLKSRVTISVDTSKNQFSLKLSSVTAADTAVYYCA
REVGAPPSYPFDIWGQGTMVTVSS SB-16: Light Chain Variable Region
(SEQ ID NO: 296)
DIVMTQSPDSLAVSLGERATINCKSSQSVLFSSNNKNYLAWYQQKPGQP
PKLLIYWASTRESGVPDRFSGSGSGTDFTLTISSLQAEDVAVYYCQQLF
STPFTFGGGTKVEIK SB-16: Heavy Chain Variable Region
(SEQ ID NO: 297)
QVQLVQSGAEVKKPGSSVKVSCKASGGTESSYAISWVRQAPGQGLEWMG
SIIPIFGTANYAQKFQGRVTITADESTSTAYMELSSLRSEDTAVYYCAR
ANYYDSSGYSGLDLWGRGTLVTVSS SB-17: Light Chain Variable Region
(SEQ ID NO: 298)
DIVMTQSPDSLAVSLGERATINCKSSQSVLESSNNKNYLAWYQQKPGQP
PKLLIYWASTRESGVPDRFSGSGSGTDFTLTISSLQAEDVAVYYCQQYY
DDPYTFGGGTKVEIK SB-17: Heavy Chain Variable Region
(SEQ ID NO: 299)
QVQLVQSGAEVKKPGASVKVSCKASGYTFTSYGISWVRQAPGQGLEWMG
WISAYNGNTNYAQKLQGRVTMTTDTSTSTAYMELRSLRSDDTAVYYCAR
GPLLYGDYHVRYGMDVWGQGTTVTVSS SB-18: Light Chain Variable Region
(SEQ ID NO: 300)
EIVLTQSPATLSLSPGERATLSCRSSQSLLHSNGYNYLDWYLQKPGQSP
QLLIYLGSNRASGVPDRFSGSGSGTDFTLKISRVEAEDVGVYYCLQALQ
TPITFGGGTKVEIK SB-18: Heavy Chain Variable Region
(SEQ ID NO: 301)
QVQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
AKPRGDYGMDVWGQGTTVTVSS SB-19: Light Chain Variable Region
(SEQ ID NO: 302)
DIVMTQSPLSLPVTPGEPASISCRSSQSLLHSNGYNYLDWYLQKPGQSP
QLLIYLGSNRASGVPDRESGSGSGTDFTLKISRVEAEDVGVYYCMQAIG
VPPTFGGGTKVEIK SB-19: Heavy Chain Variable Region
(SEQ ID NO: 303)
QVQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
DGGGGYAYEYFQHWGQGTLVTVSS SB-20: Light Chain Variable Region
(SEQ ID NO: 304)
DIVMTQSPDSLAVSLGERATINCKSSQSVLYSSNNKNYLAWYQQKPGQP
PKLLIYWASTRESGVPDRFSGSGSGTDFTLTISSLQAEDVAVYYCQQYY
LSPFTFGGGTKVEIK SB-20: Heavy Chain Variable Region
(SEQ ID NO: 305)
QVQLVQSGAEVKKPGSSVKVSCKASGGTFSSYAISWVRQAPGQGLEWMG
SIIPIFGTANYAQKFQGRVTITADESTSTAYMELSSLRSEDTAVYYCAR
DGREYGGHYYGMDVWGQGTTVTVSS SB-21: Light Chain Variable Region
(SEQ ID NO: 306)
DIVMTQSPLSLPVTPGEPASISCRSSQSLLHSNGYNYLDWYLQKPGQSP
QLLIYLGSNRASGVPDRFSGSGSGTDFTLKISRVEAEDVGVYYCMQTLR
IPPTFGGGTKVEIK SB-21: Heavy Chain Variable Region
(SEQ ID NO: 307)
QVQLVQSGAEVKKPGASVKVSCKASGYTFTSNGISWVRQAPGQGLEWMG
WISAYNGNTNYAQKLQGRVTMTTDTSTSTAYMELRSLRSDDTAVYYCAR
VGNMDQEYFDLWGRGTLVTVSS SB-22: Light Chain Variable Region
(SEQ ID NO: 308)
DIQMTQSPSSVSASVGDRVTITCRASQGISSWLAWYQQKPGKAPKLLIY
AASNLQSGVPSRESGSGSGTDFTLTISSLQPEDFATYYCQQGNSYPITF
GGGTKVEIK SB-22: Heavy Chain Variable Region
(SEQ ID NO: 309)
EVQLVESGGGLVQPGGSLRLSCAASGFTVSSNYMSWVRQAPGKGLEWVS
VIYSDGSTYYADSVKGRFTISRDNSKNTLYLQMNSLRAEDTAVYYCARP
TRYGYDRLGMDVWGQGTTVTVSS SB-23: Light Chain Variable Region
(SEQ ID NO: 310)
DIQMTQSPSSLSASVGDRVTITCRASQSISSYLNWYQQKPGKAPKLLIY
AASSLQSGVPSRESGSGSGTDFTLTISSLQPEDFATYYCQQAYPYPLTF
GGGTKVEIK SB-23: Heavy Chain Variable Region
(SEQ ID NO: 311)
QVQLVQSGAEVKKPGSSVKVSCKASGGTFSSYAISWVRQAPGQGLEWMG
GIAPIFGTANYAQKFQGRVTITADESTSTAYMELSSLRSEDTAVYYCAR
TTYRDYYMDVWGKGTTVTVSS SB-24: Light Chain Variable Region
(SEQ ID NO: 312)
EIVMTQSPATLSVSPGERATLSCRASQSVSSNLAWYQQKPGQAPRLLIY
GASTRATGIPARFSGSGSGTEFTLTISSLQSEDFAVYYCQQLNIHPWTF
GGGTKVEIK SB-24: Heavy Chain Variable Region
(SEQ ID NO: 313)
QVQLQESGPGLVKPSETLSLTCAVSGYSISSGYYWAWIRQPPGKGLEWI
GSIYHSGSTYYNPSLKSRVTISVDTSKNQFSLKLSSVTAADTAVYYCAR
DRSRGYPVYGMDVWGQGTTVTVSS SB-25: Light Chain Variable Region
(SEQ ID NO: 314)
DIQMTQSPSSVSASVGDRVTITCRASQGISSWLAWYQQKPGKAPKLLIY
AASSLQSGVPSRESGSGSGTDFTLTISSLQPEDFATYYCQQVNSFPWTF
GGGTKVEIK SB-25: Heavy Chain Variable Region
(SEQ ID NO: 315)
QVQLVQSGAEVKKPGSSVKVSCKASGGTFSSLAISWVRQAPGQGLEWMG
GIIPIFGTANYAQKFQGRVTITADESTSTAYMELSSLRSEDTAVYYCAR
SGGDYSGYDYASGMDVWGQGTTVTVSS SB-26: Light Chain Variable Region
(SEQ ID NO: 316)
DIVMTQSPLSLPVTPGEPASISCRSSQSLLHSNGYNYLDWYLQKPGQSP
QLLIYLGSNRASGVPDRESGSGSGTDFTLKISRVEAEDVGVYYCMQARG
LPTFGGGTKVEIK

CERTAIN SEQUENCES

SB-26: Heavy Chain Variable Region
(SEQ ID NO: 317)
QVQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
DGSAGRQEHGMDVWGQGTTVTSS SB-27: Light Chain Variable Region
(SEQ ID NO: 318)
DIVMTQSPDSLAVSLGERATINCKSSQSVLFSSNNKNYLAWYQQKPGQP
PKLLIYWASTRESGVPDRFSGSGSGTDFTLTISSLQAEDVAVYYCQQAV
SDPPTFGGGTKVEIK SB-27: Heavy Chain Variable Region
(SEQ ID NO: 319)
QVQLVQSGAEVKKPGSSVKVSCKASGGTESSYAISWVRQAPGQGLEWMG
GIIPIFGTANYAQKFQGRVTITADESTSTAYMELSSLRSEDTAVYYCAR
QDLGSSHWHEDLWGRGTLVTVSS SB-28: Light Chain Variable Region
(SEQ ID NO: 320)
EIVLTQSPGTLSLSPGERATLSCRASQSVSSSYLAWYQQKPGQAPRLLI
YGASSRATGIPDRESGSGSGTDFTLTISRLEPEDFAVYYCQQDGNFPLT
FGGGTKVEIK SB-28: Heavy Chain Variable Region
(SEQ ID NO: 321)
QLQLQESGPGLVKPSETLSLTCTVSGGSISSSSYYWGWIRQPPGKGLEW
IGSISYSGSTYYNPSLKSRVTISVDTSKNQFSLKLSSVTAADTAVYYCA
RDPRDYSSGSSGGGWGYFDLWGRGTLVTVSS SB-29: Light Chain Variable Region
(SEQ ID NO: 322)
DIVMTQSPLSLPVTPGEPASISCRSSQSLLHSNGYNYLDWYLQKPGQSP
QLLIFLGSNRASGVPDRFSGSGSGTDFTLKISRVEAEDVGVYYCMQARG
SPITFGGGTKVEIK SB-29: Heavy Chain Variable Region
(SEQ ID NO: 323)
QVQLVQSGAEVKKPGSSVKVSCKASGGTFSSYAISWVRQAPGQGLEWMG
SIIPIFGTANYAQKFQGRVTITADESTSTAYMELSSLRSEDTAVYYCAR
APYGSSSGYGYFDLWGRGTLVTVSS SB-30: Light Chain Variable Region
(SEQ ID NO: 324)
EIVLTQSPGTLSLSPGERATLSCRASQSVSSSFLAWYQQKPGQAPRLLI
YGASSRATGIPDRESGSGSGTDFTLTISRLEPEDFAVYYCQQFLSSPWT
FGGGTKVENQ SB-30: Heavy Chain Variable Region
(SEQ ID NO: 325)
QVQLQESGPGLVKPSQTLSLTCTVSGGSISSGGYYWSWIRQHPGKGLEW
IGYIYYSGSTVYNPSLKSRVTISVDTSKNQFSLKLSSVTAADTAVYYCA
REGPGYPSYFDPWGQGTLVTVSS SB-31: Light Chain Variable Region
(SEQ ID NO: 326)
DIQMTQSPSSVSASVGDRVTITCRASQGISSWLAWYQQKPGKAPKLLIY
AASSLQSGVPSRESGSGSGTDFTLTISSLQPEDFATYYCQQAVSHPFTF
GGGTKVEIK SB-31: Heavy Chain Variable Region
(SEQ ID NO: 327)
QVQLVQSGAEVKKPGASVKVSCKASGYTFTSYYMHWVRQAPGQGLEWMG
IINPGGGSTSYAQKFQGRVTMTRDTSTSTVYMELSSLRSEDTAVYYCAR
EGLYSSGWYIDVWGQGTLVTVSS SB-32: Light Chain Variable Region
(SEQ ID NO: 328)
DIVMTQSPDSLAVSLGERATINCKSSQSVLYSSNNKNYLAWYQQKPGQP
PKLLIYWASTRESGVPDRFSGSGSGTDFTLTISSLQAEDVAVYYCQQDE
LTPITFGGGTKVEIK SB-32: Heavy Chain Variable Region
(SEQ ID NO: 329)
QVQLQESGPGLVKPSETLSLTCTVSGGSISSYYWSWIRQPPGKGLEWIG
YIYSSGSTNYNPSLKSRVTISVDTSKNQFSLKLSSVTAADTAVYYCARG
DSSSGGLDLWGRGTLVTVSS SB-33: Light Chain Variable Region
(SEQ ID NO: 330)
DIQMTQSPSSLSASVGDRVTITCQASQDISNYLNWYQQKPGKAPKLLIY
DASNLETGVPSRFSGSGSGTDFTFTISSLQPEDIATYYCQQFAFLPLTF
GGGTKVENQ SB-33: Heavy Chain Variable Region
(SEQ ID NO: 331)
EVQLVESGGGLVQPGGSLRLSCAASGFTVSSNYMSWVRQAPGKGLEWVS
VIYSGGSTYYADSVKGRFTISRDNSKNTLYLQMNSLRAEDTAVYYCARG
QYTGSLDVWGQGTMVTVSS SB-34: Light Chain Variable Region
(SEQ ID NO: 332)
EIVMTQSPATLSVSPGERATLSCRASQSVSSNLAWYQQKPGQAPRLLIY
GASTRATGIPARFSGSGSGTEFTLTISSLQSEDFAVYYCQQDNTFPYTF
GGGTKVEIK SB-34: Heavy Chain Variable Region
(SEQ ID NO: 333)
QVQLVQSGAEVKKPGASVKVSCKASGYTFTGYYMHWVRQAPGQGLEWMG
WINPNSGGTKYAQKFQGRVTMTRDTSISTAYMELSRLRSDDTAVYYCAR
DTYYTPYGMDVWGQGTTVTVSS SB-35: Light Chain Variable Region
(SEQ ID NO: 334)
DIVMTQSPLSLPVTPGEPASISCRSSQSLLHSNGYNYLDWYLQKPGQSP
QLLIYLGSNRASGVPDRFSGSGSGTDFTLKISRVEAEDVGVYYCMQTLQ
VPLTFGGGTKVEIK SB-35: Heavy Chain Variable Region
(SEQ ID NO: 335)
QVQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
GRPQSESYLLDYWGQGTLVTVSS SB-36: Light Chain Variable Region
(SEQ ID NO: 336)
DIQMTQSPSSVSASVGDRVTITCRASQGISSWLAWYQQKPGKAPKLLIY
AASSLQSGVPSRFSGSGSGTDFTLTISSLQPEDFATYYCQQAFSHRTFG
GGTKVEIK SB-36: Heavy Chain Variable Region
(SEQ ID NO: 337)
QVQLVQSGAEVKKPGASVKVSCKASGYTFTSYYMHWVRQAPGQGLEWMG
IINPSGGSTSYAQKFQGRVTMTRDTSTSTVYMELSSLRSEDTAVYYCAR
EGPEQLWYLDYWGQGTLVTVSS SB-37: Light Chain Variable Region
(SEQ ID NO: 338)
EIVLTQSPATLSLSPGERATLSCRASQSVSSYLAWYQQKPGQAPRLLIY
DASNRATGIPARFSGSGSGTDFTLTISSLEPEDFAVYYCQQRHTYPLTF
GGGTKVEIK SB-37: Heavy Chain Variable Region
(SEQ ID NO: 339)
QVQLVQSGAEVKKPGSSVKVSCKASGGTFSNYAISWVRQAPGQGLEWMG
GIIPIFGTANYAQKFQGRVTITADESTSTAYMELSSLRSEDTAVYYCAR
SRWGASGYYYYMDVWGQGTMVTVSS SB-38: Light Chain Variable Region
(SEQ ID NO: 340)
DIQMTQSPSSVSASVGDRVTITCRASQGISSWLAWYQQKPGKAPKLLIY
AASSLQSGVPSRFSGSGSGTDFTLTISSLQPEDFATYYCQQAVSYPITF
GGGTKVEIK SB-38: Heavy Chain Variable Region
(SEQ ID NO: 341)
QVQLVQSGAEVKKPGASVKVSCKASGYTFTSYYMHWVRQAPGQGLEWMG
IINPSGGSTSYAQKFQGRVTMTRDTSTSTVYMELSSLRSEDTAVYYCAR
ESGTDFGTISYWGQGTLVTVSS

| CERTAIN SEQUENCES |
|---|
| SB-39: Light Chain Variable Region<br>(SEQ ID NO: 342)<br>DIQMTQSPSSLSASVGDRVTITCRASQSISSYLNWYQQKPGKAPKLLIY<br>GASSLQSGVPSRFSGSGSGTDFTLTISSLQPEDFATYYCQQSYDFPLTF<br>GGGTKVEIK |
| SB-39: Heavy Chain Variable Region<br>(SEQ ID NO: 343)<br>QVQLQESGPGLVKPSETLSLTCAVSGYSISSGYYWAWIRQPPGKGLEWI<br>GSIYHSGSTYYNPSLKSRVTISVDTSKNQFSLKLSSVTAADTAVYYCAR<br>GGSNYGDYGRFDYWGQGTLVTVSS |
| SB-40: Light Chain Variable Region<br>(SEQ ID NO: 344)<br>EIVLTQSPATLSLSPGERATLSCRASQSVSSYLAWYQQKPGQAPRLLIY<br>DSSNRATGIPARFSGSGSGTDFTLTISSLEPEDFAVYYCQQRDEHPPWT<br>FGGGTKVEIK |
| SB-40: Heavy Chain Variable Region<br>(SEQ ID NO: 345)<br>QVQLVQSGAEVKKPGASVKVSCKASGYTFTSYYMSWVRQAPGQGLEWMG<br>IINPSGGSTSYAQKFQGRVTMTRDTSTSTVYMELSSLRSEDTAVYYCAR<br>DTGEYSYSPHGMDVWGQGTTVTVSS |
| SB-41: Light Chain Variable Region<br>(SEQ ID NO: 346)<br>DIQMTQSPSSLSASVGDRVTITCQASQDITNYLNWYQQKPGKAPKLLIY<br>DASNLETGVPSRFSGSGSGTDFTFTISSLQPEDIATYYCQQADNFPYTF<br>GGGTKVEIK |
| SB-41: Heavy Chain Variable Region<br>(SEQ ID NO: 347)<br>QLQLQESGPGLVKPSETLSLTCTVSGGSISSSSYYWGWIRQPPGKGLEW<br>IGSIYYSGSTYYNPSLKSRVTISVDTSKNQFSLKLSSVTAADTAVYYCA<br>RVGQYPIYGMDVWGQGTTVTVSS |
| SB-42: Light Chain Variable Region<br>(SEQ ID NO: 348)<br>EIVMTQSPATLSVSPGERATITCRASQSISSYLNWYQQKPGKAPKLLIY<br>SASSLQSGVPSRESGSGSGTDFTLTISSLQPEDFATYYCQQGDSFPITF<br>GGGTKVEIK |
| SB-42: Heavy Chain Variable Region<br>(SEQ ID NO: 349)<br>QVQLVQSGAEVKKPGASVKVSCKASGYTFTSYGISWVRQAPGQGLEWMG<br>WISAYNGNTNYAQKLQGRVTMTTDTSTSTAYMELRSLRSDDTAVYYCAR<br>GPGHYYVAGMDVWGQGTTVTVSS |
| SB-43: Light Chain Variable Region<br>(SEQ ID NO: 350)<br>EIVLTQSPATLSLSPGERATLSCRASQSVSSYLAWYQQKPGQAPRLLIY<br>DASKRATGIPARFSGSGSGTDFTLTISSLEPEDFAVYYCQQRFDFPITF<br>GGGTKVEIK |
| SB-43: Heavy Chain Variable Region<br>(SEQ ID NO: 351)<br>QVQLQESGPGLVKPSETLSLTCAVSGYSISSGYYWAWIRQPPGKGLEWI<br>GSIYHSGSTYYNPSLKSRVTISVDTSKNQFSLKLSSVTAADTAVYYCAR<br>DAPGYPMLGMDVWGQGTTVSVSS |
| SB-44: Light Chain Variable Region<br>(SEQ ID NO: 352)<br>DIQMTQSPSTLSASVGDRVTITCRASQSIGSWLAWYQQKPGKAPKLLIY<br>KASSLESGVPSRESGSGSGTEFTLTISSLQPDDFATYYCQEYGSYRTFG<br>GGTKVEIK |
| SB-44: Heavy Chain Variable Region<br>(SEQ ID NO: 353)<br>EVQLVESGGGLVQPGGSLRLSCAASGFTVSSNYMSWVRQAPGKGLEWVS<br>VIYSGGDTYYADSVKGRFTISRDNSKNTLYLQMNSLRAEDTAVYYCARE<br>GSSFWSGSAVSYYGMDVWGQGTTVTVSS |
| SB-45: Light Chain Variable Region<br>(SEQ ID NO: 354)<br>VLTQSPGTLSLSPGERATLSCRASQSVSSSFLAWYQQKPGQAPRLLIYG<br>ASSRATGIPDRESGSGSGTDFTLTISRLEPEDFAVYYCQQVVSVPTFGG<br>GTKVEIK |
| SB-45: Heavy Chain Variable Region<br>(SEQ ID NO: 355)<br>QVQLQESGPGLVKPSETLSLTCAVSGYSISSGYYWAWIRQPPGKGLEWI<br>GSIYHSGSTYYNPSLKSRVTISVDTSKNQFSLKLSSVTAADTAVYYCAR<br>DLSRGYAVSGMDVWGQGTTVTVSS |
| SB-46: Light Chain Variable Region<br>(SEQ ID NO: 356)<br>EIVLTQSPGTLSLSPGERATLSCRASQSVRSSYLAWYQQKPGQAPRLLI<br>YGASSRATGIPDRESGSGSGTDFTLTISRLEPEDFAVYYCQQLYSSPYT<br>FGGGTKVEIK |
| SB-46: Heavy Chain Variable Region<br>(SEQ ID NO: 357)<br>EVQLLESGGGLVQPGGSLRLSCAASGFTFSSYAMSWVRQAPGKGLEWVS<br>AISGSGGSTYYADSVKGRFTISRDNSKNTLYLQMNSLRAEDTAVYYCAR<br>ASPWELDVWGQGTMVTVSS |
| SB-47: Light Chain Variable Region<br>(SEQ ID NO: 358)<br>DIQMTQSPSSLSASVGDRVTITCQASQDISNYLNWYQQKPGKAPKLLIY<br>DASNLETGVPSRESGSGSGTDFTFTISSLQPEDIATYYCQQADYFPITF<br>GGGTKVEIK |
| SB-47: Heavy Chain Variable Region<br>(SEQ ID NO: 359)<br>QLQLQESGPGLVKPSETLSLTCTVSGGSISSSSYAWGWIRQPPGKGLEW<br>IGSIYYSGSTYYNPSLKSRVTISVDTSKNQFSLKLSSVTAADTAVYYCA<br>RDLGHYDYWSGSRDYYYGMDVWGQGTTVTVSS |
| SB-48: Light Chain Variable Region<br>(SEQ ID NO: 360)<br>DIQMTQSPSVSASVGDRVTITCRASQGIDSWLAWYQQKPGKAPKLLIY<br>AASSLQSGVPSRFSGSGSGTDFTLTISSLQPEDFATYYCQQASNFPITF<br>GGGTKVEIK |
| SB-48: Heavy Chain Variable Region<br>(SEQ ID NO: 361)<br>QVQLVESGGGVVQPGRSLRLSCAASGFTFSSYGMHWVRQAPGKGLEWVA<br>VISYDGSNKYYADSVKGRFTISRDNSKNTLYLQMNSLRAEDTAVYYCAR<br>DGTIAAAGWPPEYFQHWGQGTLVTVSS |
| SB-49: Light Chain Variable Region<br>(SEQ ID NO: 362)<br>DIQMTQSPSSLSASVGDRVTITCQASQDITNYLNWYQQKPGKAPKLLIY<br>DASNLETGVPSRFSGSGSGTDFTFTISSLQPEDIATYYCQQYFHPPLTF<br>GGGTKVEIK |
| SB-49: Heavy Chain Variable Region<br>(SEQ ID NO: 363)<br>QLQLQESGPGLVKPSETLSLTCTVSGGSISSSDYYWGWIRQPPGKGLEW<br>IGSIYYSGSTYYNPSLKSRVTISVDTSKNQFSLKLSSVTAADTAVYYCA<br>RGPTGYKDKWRYYYGMDVWGQGTTVTVSS |
| SB-50: Light Chain Variable Region<br>(SEQ ID NO: 364)<br>DIVMTQSPDSLAVSLGERATINCKSSQSVLFSSNNKNYLAWYQQKPGQP<br>PKLLIYWASTRESGVPDRFSGSGSGTDFTLTISSLQAEDVAVYYCQQFL<br>HTPRTFGGGTKVEIK |
| SB-50: Heavy Chain Variable Region<br>(SEQ ID NO: 365)<br>QVQLVQSGAEVKKPGSSVKVSCKASGGTFSSYAISWVRQAPGQGLEWMG<br>GIIPIFGTANYAQKFQGRVTITADESTSTAYMELSSLRSEDTAVYYCAR<br>EGGGHASYHYYGMDVWGQGTTVTVSS |
| SB-1-2: Light Chain Variable Region<br>(SEQ ID NO: 267)<br>EIVMTQSPGTLSLSPGERATLSCRASQSVSSSYLAWYQQKPGQAPRLLI<br>YGASSRATGIPDRESGSGSGTDFTLTISRLEPEDFAVYYCQLLGSSPRT<br>FGGGTKVEIK |

CERTAIN SEQUENCES

SB-1-2: Heavy Chain Variable Region
(SEQ ID NO: 366)
QVQLVESGGGVVQPGRSLRLSCAASGFTFGSFGMNWVRQAPGKGLEWVS
AITASGGSTFYADSVKGRFTISRDNSKNTLYLQMNSLRAEDTAVYYCAK
DFTEVVGWLGMDVWGQGTTVTVSS SB-1-3: Light Chain Variable Region
(SEQ ID NO: 267)
EIVMTQSPGTLSLSPGERATLSCRASQSVSSSYLAWYQQKPGQAPRLLI
YGASSRATGIPDRESGSGSGTDFTLTISRLEPEDFAVYYCQLLGSSPRT
FGGGTKVEIK SB-1-3: Heavy Chain Variable Region
(SEQ ID NO: 367)
EVQLVESGGGLVKPGGSLRLSCAASGFTFSAYGMNWVRQAPGKGLEWVS
AITSSGRSTYYADSVKGRFTISRDNSKNTLYLQMNSLRAEDTAVYYCAK
DFTEVVGWLGMDVWGQGTTVTVSS SB-1-4: Light Chain Variable Region
(SEQ ID NO: 267)
EIVMTQSPGTLSLSPGERATLSCRASQSVSSSYLAWYQQKPGQAPRLLI
YGASSRATGIPDRESGSGSGTDFTLTISRLEPEDFAVYYCQLLGSSPRT
FGGGTKVEIK SB-1-4: Heavy Chain Variable Region
(SEQ ID NO: 368)
QVQLVESGGGVVQPGGSLRLSCAASGFTFSAYGMNWVRQAPGKGLEWVS
AIRASGGATYYADSVKGRFTISRDNSKNTLYLQMNSLRAEDTAVYYCAK
DFTEVVGWLGMDVWGQGTTVTVSS SB-1-5: Light Chain Variable Region
(SEQ ID NO: 267)
EIVMTQSPGTLSLSPGERATLSCRASQSVSSSYLAWYQQKPGQAPRLLI
YGASSRATGIPDRESGSGSGTDFTLTISRLEPEDFAVYYCQLLGSSPRT
FGGGTKVEIK SB-1-5: Heavy Chain Variable Region
(SEQ ID NO: 369)
QVQLVESGGGVVQPGRSLRLSCAASGFTFSAYGMNWVRQAPGKGLEWVS
AISASGRSTFYADSVKGRFTISRDNSKNTLYLQMNSLRAEDTAVYYCAK
DFTEVVGWLGMDVWGQGTTVTVSS SB-2-7: Light Chain Variable Region
(SEQ ID NO: 370)
EVVLTQSPGTLSLSPGERATLSCRASQSVSSSYLAWYQQKPGQAPRLLI
YGASSRATGIPDRESGSGSGTDFTLTISRLEPEDFAVYYCQQSSSHPFT
FGGGTKVEIK SB-2-7: Heavy Chain Variable Region
(SEQ ID NO: 371)
EVQLLESGGGLVQPGGSLRLSCAASGFTFARYGMHWVRQAPGKGLEWVS
AISGLAGPTYADSVKGRFTISRDNSKNTLYLQMNSLRAEDTAVYYCARD
QTAAAAIWGMDVWGQGTTVTVSS SB-2-8: Light Chain Variable Region
(SEQ ID NO: 370)
EVVLTQSPGTLSLSPGERATLSCRASQSVSSSYLAWYQQKPGQAPRLLI
YGASSRATGIPDRESGSGSGTDFTLTISRLEPEDFAVYYCQQSSSHPFT
FGGGTKVEIK SB-2-8: Heavy Chain Variable Region
(SEQ ID NO: 372)
QVQLVESGGGVVQPGRSLRLSCAASGFTFLDYGMHWVRQAPGKGLEWVS
AISAFAGSTYADSVKGRFTISRDNSKNTLYLQMNSLRAEDTAVYYCARD
QTAAAAIWGMDVWGQGTTVTVSS SB-2-9: Light Chain Variable Region
(SEQ ID NO: 370)
EVVLTQSPGTLSLSPGERATLSCRASQSVSSSYLAWYQQKPGQAPRLLI
YGASSRATGIPDRESGSGSGTDFTLTISRLEPEDFAVYYCQQSSSHPFT
FGGGTKVEIK SB-2-9: Heavy Chain Variable Region
(SEQ ID NO: 373)
QVQLVESGGGVVQPGRSLRLSCAASGFTFKTYGMHWVRQAPGKGLEWVA
HIWYEGSNKVYADSVKGRFTISRDNSKNTLYLQMNSLRAEDTAVYYCAR
DQTAAAAIWGMDVWGQGTTVTVSS SB-2-10: Light Chain Variable Region
(SEQ ID NO: 269)
EIVLTQSPGTLSLSPGERATLSCRASQSVSSSYLAWYQQKPGQAPRLLI
YGASSRATGIPDRESGSGSGTDFTLTISRLEPEDFAVYYCQQSSSHPFT
FGGGTKVEIK SB-2-10: Heavy Chain Variable Region
(SEQ ID NO: 374)
EVQLLESGGGLVQPGGSLRLSCAASGFTFGSYGMHWVRQAPGKGLEWVS
AISGLAGQTYADSVKGRFTISRDNSKNTLYLQMNSLRAEDTAVYYCARD
QTAAAAIWGMDVWGQGTTVTVSS SB-2-11: Light Chain Variable Region
(SEQ ID NO: 269)
EIVLTQSPGTLSLSPGERATLSCRASQSVSSSYLAWYQQKPGQAPRLLI
YGASSRATGIPDRESGSGSGTDFTLTISRLEPEDFAVYYCQQSSSHPFT
FGGGTKVEIK SB-2-11: Heavy Chain Variable Region
(SEQ ID NO: 375)
QVQLVESGGGLVQPGGSLRLSCAASGFTFARYGMHWVRQAPGKGLEWVS
AISGLAGPTYADSVKGRFTISRDNSKNTLYLQMNSLRAEDTAVYYCARD
QTAAWGIWGMDVWGQGTTVTVSS SB-8-13: Light Chain Variable Region
(SEQ ID NO: 280)
EIVMTQSPGTLSLSPGERATLSCRASQSVSSSYLAWYQQKPGQAPRLLI
YGASNRATGIPDRESGSGSGTDFTLTISRLEPEDFAVYYCQQVYSSPYT
FGGGTKVEIK SB-8-13: Heavy Chain Variable Region
(SEQ ID NO: 376)
QVQLQESGPGLVKPSETLSLTCAVSGYSISAHYYWGWIRQPPGKGLEWI
GSIFHSGHTYYNPSLKSRVTISVDTSKNQFSLKLSSVTAADTAVYYCAR
GGAMTPAGMDVWGQGTTVTVSS SB-8-14: Light Chain Variable Region
(SEQ ID NO: 280)
EIVMTQSPGTLSLSPGERATLSCRASQSVSSSYLAWYQQKPGQAPRLLI
YGASNRATGIPDRESGSGSGTDETLTISRLEPEDFAVYYCQQVYSSPYT
FGGGTKVEIK SB-8-14: Heavy Chain Variable Region
(SEQ ID NO: 377)
QVQLQESGPGLVKPSETLSLTCAVSGYSISPHYYWGWIRQPPGKGLEWI
GSIYHSGHTYYNPSLKSRVTISVDTSKNQFSLKLSSVTAADTAVYYCAR
GGAMTPAGMDVWGQGTTVTVSS SB-8-15: Light Chain Variable Region
(SEQ ID NO: 280)
EIVMTQSPGTLSLSPGERATLSCRASQSVSSSYLAWYQQKPGQAPRLLI
YGASNRATGIPDRESGSGSGTDFTLTISRLEPEDFAVYYCQQVYSSPYT
FGGGTKVEIK SB-8-15: Heavy Chain Variable Region
(SEQ ID NO: 377)
QVQLQESGPGLVKPSETLSLTCAVSGYSISPHYYWGWIRQPPGKGLEWI
GSIYHSGHTYYNPSLKSRVTISVDTSKNQFSLKLSSVTAADTAVYYCAR
GGAMTPAGMDVWGQGTTVTVSS SB-8-16: Light Chain Variable Region
(SEQ ID NO: 280)
EIVMTQSPGTLSLSPGERATLSCRASQSVSSSYLAWYQQKPGQAPRLLI
YGASNRATGIPDRESGSGSGTDFTLTISRLEPEDFAVYYCQQVYSSPYT
FGGGTKVEIK SB-8-16: Heavy Chain Variable Region
(SEQ ID NO: 378)
QVQLQESGPGLVKPSETLSLTCAVSGYSISAHYYWGWIRQPPGKGLEWI
GSIFHSGHTYYNPSLKSRVTISVDTSKNQFSLKLSSVTAADTAVYYCAR
AGAMTPAGMDVWGQGTTVTVSS

CERTAIN SEQUENCES

SB-40-18: Light Chain Variable Region
(SEQ ID NO: 344)
EIVLTQSPATLSLSPGERATLSCRASQSVSSYLAWYQQKPGQAPRLLIY
DSSNRATGIPARFSGSGSGTDFTLTISSLEPEDFAVYYCQQRDEHPPWT
FGGGTKVEIK SB-40-18: Heavy Chain Variable Region
(SEQ ID NO: 379)
QVQLVQSGAEVKKPGASVKVSCKASGYTFTSYYMAWVRQAPGQRLEWMG
WINPAVGATIYSQKFQGRVTITRDTSASTAYMELSSLRSEDTAVYYCAR
DTGEYSYSPHGMDVWGQGTTVTVSS SB-40-19: Light Chain Variable Region
(SEQ ID NO: 344)
EIVLTQSPATLSLSPGERATLSCRASQSVSSYLAWYQQKPGQAPRLLIY
DSSNRATGIPARFSGSGSGTDFTLTISSLEPEDFAVYYCQQRDEHPPWT
FGGGTKVEIK SB-40-19: Heavy Chain Variable Region
(SEQ ID NO: 380)
QVQLVQSGAEVKKPGASVKVSCKASGYTFTSYYMVWVRQAPGQGLEWMG
IINPSSGATNYAQKFQGRVTMTTDTSTSTAYMELSRLRSDDTAVYYCAR
DTGEYSYSPHGMDVWGQGTTVTVSS SB-40-20: Light Chain Variable Region
(SEQ ID NO: 344)
EIVLTQSPATLSLSPGERATLSCRASQSVSSYLAWYQQKPGQAPRLLIY
DSSNRATGIPARFSGSGSGTDFTLTISSLEPEDFAVYYCQQRDEHPPWT
FGGGTKVEIK SB-40-20: Heavy Chain Variable Region
(SEQ ID NO: 381)
QVQLVQSGAEVKKPGASVKVSCKASGYTFTSFYISWVRQAPGQGLEWMG
IINPSSGHTNYAQKLQGRVTMTTDTSTSTAYMELSSLRSEDTAVYYCAR
DTGEYSYSPHGMDVWGQGTTVTVSS SB-40-21: Light Chain Variable Region
(SEQ ID NO: 344)
EIVLTQSPATLSLSPGERATLSCRASQSVSSYLAWYQQKPGQAPRLLIY
DSSNRATGIPARESGSGSGTDFTLTISSLEPEDFAVYYCQQRDEHPPWT
FGGGTKVEIK SB-40-21: Heavy Chain Variable Region
(SEQ ID NO: 382)
QVQLVQSGAEVKKPGASVKVSCKASGYTFTSYYMVWVRQAPGQGLEWMG
IINPSSGDTNYAQKFQGRVTMTRDTSISTAYMELSRLRSDDTAVYYCAR
DTGEYSYSPHGMDVWGQGTTVTVSS SIRPa domain 1 (IgV domain)
(SEQ ID NO: 387)
EELQVIQPDKSVLVAAGETATLRCTATSLIPVGPIQWERGAGPGRELIY
NQKEGHFPRVTTVSDLTKRNNMDFSIRIGNITPADAGTYYCVKFRKGSP
DDVEFKSGAGTELSVRAKPS SIRPß1 domain 1 (IgV domain)
(SEQ ID NO: 388)
EDELQVIQPEKSVSVAAGESATLRCAMTSLIPVGPIMWERGAGAGRELI
YNQKEGHFPRVTTVSELTKRNNLDFSISISNITPADAGTYYCVKFRKGS
PDDVEFKSGAGTELSVRAKPS

---

What is claimed is:

1. An isolated antibody that binds to human SIRPβ1, wherein the antibody comprises a heavy chain variable region comprising HVR-H1, HVR-H2, and HVR-H3 and a light chain variable region comprising HVR-L1, HVR-L2, and HVR-L3 wherein:
   a) HVR-L1 comprises the amino acid sequence of SEQ ID NO: 383, HVR-L2 comprises the amino acid sequence of SEQ ID NO: 16, HVR-L3 comprises the amino acid sequence of SEQ ID NO: 31, HVR-H1 comprises the amino acid sequence of SEQ ID NO: 80, HVR-H2 comprises the amino acid sequence of SEQ ID NO: 101, and HVR-H3 comprises the amino acid sequence of SEQ ID NO: 125;
   b) HVR-L1 comprises the amino acid sequence of SEQ ID NO: 383, HVR-L2 comprises the amino acid sequence of SEQ ID NO: 16, HVR-L3 comprises the amino acid sequence of SEQ ID NO: 31, HVR-H1 comprises the amino acid sequence of SEQ ID NO: 228, HVR-H2 comprises the amino acid sequence of SEQ ID NO: 238, and HVR-H3 comprises the amino acid sequence of SEQ ID NO: 125;
   c) HVR-L1 comprises the amino acid sequence of SEQ ID NO: 383, HVR-L2 comprises the amino acid sequence of SEQ ID NO: 16, HVR-L3 comprises the amino acid sequence of SEQ ID NO: 31, HVR-H1 comprises the amino acid sequence of SEQ ID NO: 229, HVR-H2 comprises the amino acid sequence of SEQ ID NO: 239, and HVR-H3 comprises the amino acid sequence of SEQ ID NO: 125;
   d) HVR-L1 comprises the amino acid sequence of SEQ ID NO: 383, HVR-L2 comprises the amino acid sequence of SEQ ID NO: 16, HVR-L3 comprises the amino acid sequence of SEQ ID NO: 31, HVR-H1 comprises the amino acid sequence of SEQ ID NO: 229, HVR-H2 comprises the amino acid sequence of SEQ ID NO: 240, and HVR-H3 comprises the amino acid sequence of SEQ ID NO: 125;
   e) HVR-L1 comprises the amino acid sequence of SEQ ID NO: 383, HVR-L2 comprises the amino acid sequence of SEQ ID NO: 16, HVR-L3 comprises the amino acid sequence of SEQ ID NO: 31, HVR-H1 comprises the amino acid sequence of SEQ ID NO: 229, HVR-H2 comprises the amino acid sequence of SEQ ID NO: 241, and HVR-H3 comprises the amino acid sequence of SEQ ID NO: 125;
   f) HVR-L1 comprises the amino acid sequence of SEQ ID NO: 383, HVR-L2 comprises the amino acid sequence of SEQ ID NO: 16, HVR-L3 comprises the amino acid sequence of SEQ ID NO: 32, HVR-H1 comprises the amino acid sequence of SEQ ID NO: 81, HVR-H2 comprises the amino acid sequence of SEQ ID NO: 102, and HVR-H3 comprises the amino acid sequence of SEQ ID NO: 126;
   g) HVR-L1 comprises the amino acid sequence of SEQ ID NO: 383, HVR-L2 comprises the amino acid sequence of SEQ ID NO: 16, HVR-L3 comprises the amino acid sequence of SEQ ID NO: 32, HVR-H1 comprises the amino acid sequence of SEQ ID NO: 230, HVR-H2 comprises the amino acid sequence of SEQ ID NO: 242, and HVR-H3 comprises the amino acid sequence of SEQ ID NO: 126;
   h) HVR-L1 comprises the amino acid sequence of SEQ ID NO: 383, HVR-L2 comprises the amino acid sequence of SEQ ID NO: 16, HVR-L3 comprises the amino acid sequence of SEQ ID NO: 32, HVR-H1 comprises the amino acid sequence of SEQ ID NO: 231, HVR-H2 comprises the amino acid sequence of SEQ ID NO: 243, and HVR-H3 comprises the amino acid sequence of SEQ ID NO: 126;
   i) HVR-L1 comprises the amino acid sequence of SEQ ID NO: 383, HVR-L2 comprises the amino acid sequence of SEQ ID NO: 16, HVR-L3 comprises the amino acid sequence of SEQ ID NO: 32, HVR-H1 comprises the amino acid sequence of SEQ ID NO: 232, HVR-H2 comprises the amino acid sequence of SEQ ID NO: 244, and HVR-H3 comprises the amino acid sequence of SEQ ID NO: 126;

j) HVR-L1 comprises the amino acid sequence of SEQ ID NO: 383, HVR-L2 comprises the amino acid sequence of SEQ ID NO: 16, HVR-L3 comprises the amino acid sequence of SEQ ID NO: 32, HVR-H1 comprises the amino acid sequence of SEQ ID NO: 99, HVR-H2 comprises the amino acid sequence of SEQ ID NO: 245, and HVR-H3 comprises the amino acid sequence of SEQ ID NO: 126;

k) HVR-L1 comprises the amino acid sequence of SEQ ID NO: 383, HVR-L2 comprises the amino acid sequence of SEQ ID NO: 16, HVR-L3 comprises the amino acid sequence of SEQ ID NO: 32, HVR-H1 comprises the amino acid sequence of SEQ ID NO: 230, HVR-H2 comprises the amino acid sequence of SEQ ID NO: 242, and HVR-H3 comprises the amino acid sequence of SEQ ID NO: 253;

l. HVR-L1 comprises the amino acid sequence of SEQ ID NO: 383, HVR-L2 comprises the amino acid sequence of SEQ ID NO: 19, HVR-L3 comprises the amino acid sequence of SEQ ID NO: 37, HVR-H1 comprises the amino acid sequence of SEQ ID NO: 85, HVR-H2 comprises the amino acid sequence of SEQ ID NO: 107, and HVR-H3 comprises the amino acid sequence of SEQ ID NO: 131;

m) HVR-L1 comprises the amino acid sequence of SEQ ID NO: 383, HVR-L2 comprises the amino acid sequence of SEQ ID NO: 19, HVR-L3 comprises the amino acid sequence of SEQ ID NO: 37, HVR-H1 comprises the amino acid sequence of SEQ ID NO: 233, HVR-H2 comprises the amino acid sequence of SEQ ID NO: 246, and HVR-H3 comprises the amino acid sequence of SEQ ID NO: 131;

n) HVR-L1 comprises the amino acid sequence of SEQ ID NO: 383, HVR-L2 comprises the amino acid sequence of SEQ ID NO: 19, HVR-L3 comprises the amino acid sequence of SEQ ID NO: 37, HVR-H1 comprises the amino acid sequence of SEQ ID NO: 234; HVR-H2 comprises the amino acid sequence of SEQ ID NO: 247, and HVR-H3 comprises the amino acid sequence of SEQ ID NO: 131;

o) HVR-L1 comprises the amino acid sequence of SEQ ID NO: 383, HVR-L2 comprises the amino acid sequence of SEQ ID NO: 19, HVR-L3 comprises the amino acid sequence of SEQ ID NO: 37, HVR-H1 comprises the amino acid sequence of SEQ ID NO: 233, HVR-H2 comprises the amino acid sequence of SEQ ID NO: 248, and HVR-H3 comprises the amino acid sequence of SEQ ID NO: 131;

p) HVR-L1 comprises the amino acid sequence of SEQ ID NO: 383, HVR-L2 comprises the amino acid sequence of SEQ ID NO: 19, HVR-L3 comprises the amino acid sequence of SEQ ID NO: 37, HVR-H1 comprises the amino acid sequence of SEQ ID NO: 233, HVR-H2 comprises the amino acid sequence of SEQ ID NO: 246, and HVR-H3 comprises the amino acid sequence of SEQ ID NO: 254;

q) HVR-L1 comprises the amino acid sequence of SEQ ID NO: 2, HVR-L2 comprises the amino acid sequence of SEQ ID NO: 22, HVR-L3 comprises the amino acid sequence of SEQ ID NO: 69, HVR-H1 comprises the amino acid sequence of SEQ ID NO: 97, HVR-H2 comprises the amino acid sequence of SEQ ID NO: 121, and HVR-H3 comprises the amino acid sequence of SEQ ID NO: 163;

r) HVR-L1 comprises the amino acid sequence of SEQ ID NO: 2, HVR-L2 comprises the amino acid sequence of SEQ ID NO: 22, HVR-L3 comprises the amino acid sequence of SEQ ID NO: 69, HVR-H1 comprises the amino acid sequence of SEQ ID NO: 235, HVR-H2 comprises the amino acid sequence of SEQ ID NO: 249, and HVR-H3 comprises the amino acid sequence of SEQ ID NO: 163;

s) HVR-L1 comprises the amino acid sequence of SEQ ID NO: 2, HVR-L2 comprises the amino acid sequence of SEQ ID NO: 22, HVR-L3 comprises the amino acid sequence of SEQ ID NO: 69, HVR-H1 comprises the amino acid sequence of SEQ ID NO: 236, HVR-H2 comprises the amino acid sequence of SEQ ID NO: 250, and HVR-H3 comprises the amino acid sequence of SEQ ID NO: 163;

t) HVR-L1 comprises the amino acid sequence of SEQ ID NO: 2, HVR-L2 comprises the amino acid sequence of SEQ ID NO: 22, HVR-L3 comprises the amino acid sequence of SEQ ID NO: 69, HVR-H1 comprises the amino acid sequence of SEQ ID NO: 237, HVR-H2 comprises the amino acid sequence of SEQ ID NO: 251, and HVR-H3 comprises the amino acid sequence of SEQ ID NO: 163;

u) HVR-L1 comprises the amino acid sequence of SEQ ID NO: 2, HVR-L2 comprises the amino acid sequence of SEQ ID NO: 22, HVR-L3 comprises the amino acid sequence of SEQ ID NO: 69, HVR-H1 comprises the amino acid sequence of SEQ ID NO: 236, HVR-H2 comprises the amino acid sequence of SEQ ID NO: 252, and HVR-H3 comprises the amino acid sequence of SEQ ID NO: 163;

v) HVR-L1 comprises the amino acid sequence of SEQ ID NO: 2, HVR-L2 comprises the amino acid sequence of SEQ ID NO: 17, HVR-L3 comprises the amino acid sequence of SEQ ID NO: 33, HVR-H1 comprises the amino acid sequence of SEQ ID NO: 82, HVR-H2 comprises the amino acid sequence of SEQ ID NO: 103, and HVR-H3 comprises the amino acid sequence of SEQ ID NO: 127;

w) HVR-L1 comprises the amino acid sequence of SEQ ID NO: 383, HVR-L2 comprises the amino acid sequence of SEQ ID NO: 16, HVR-L3 comprises the amino acid sequence of SEQ ID NO: 34, HVR-H1 comprises the amino acid sequence of SEQ ID NO: 83, HVR-H2 comprises the amino acid sequence of SEQ ID NO: 104, and HVR-H3 comprises the amino acid sequence of SEQ ID NO: 128;

x) HVR-L1 comprises the amino acid sequence of SEQ ID NO: 2, HVR-L2 comprises the amino acid sequence of SEQ ID NO: 17, HVR-L3 comprises the amino acid sequence of SEQ ID NO: 33, HVR-H1 comprises the amino acid sequence of SEQ ID NO: 82, HVR-H2 comprises the amino acid sequence of SEQ ID NO: 105, and HVR-H3 comprises the amino acid sequence of SEQ ID NO: 129;

y) HVR-L1 comprises the amino acid sequence of SEQ ID NO: 383, HVR-L2 comprises the amino acid sequence of SEQ ID NO: 16, HVR-L3 comprises the amino acid sequence of SEQ ID NO: 35, HVR-H1 comprises the amino acid sequence of SEQ ID NO: 80; HVR-H2 comprises the amino acid sequence of SEQ ID NO: 101, and HVR-H3 comprises the amino acid sequence of SEQ ID NO: 125;

z) HVR-L1 comprises the amino acid sequence of SEQ ID NO: 3, HVR-L2 comprises the amino acid sequence of SEQ ID NO: 18, HVR-L3 comprises the amino acid sequence of SEQ ID NO: 36, HVR-H1 comprises the amino acid sequence of SEQ ID NO: 84, HVR-H2 comprises the amino acid sequence of SEQ ID NO: 106, and HVR-H3 comprises the amino acid sequence of SEQ ID NO: 130;

aa) HVR-L1 comprises the amino acid sequence of SEQ ID NO: 3, HVR-L2 comprises the amino acid sequence of SEQ ID NO: 18, HVR-L3 comprises the amino acid sequence of SEQ ID NO: 38, HVR-H1 comprises the amino acid sequence of SEQ ID NO: 86, HVR-H2 comprises the amino acid sequence of SEQ ID NO: 104, and HVR-H3 comprises the amino acid sequence of SEQ ID NO: 132;

bb) HVR-L1 comprises the amino acid sequence of SEQ ID NO: 4, HVR-L2 comprises the amino acid sequence of SEQ ID NO: 20, HVR-L3 comprises the amino acid sequence of SEQ ID NO: 39, HVR-H1 comprises the amino acid sequence of SEQ ID NO: 84, HVR-H2 comprises the amino acid sequence of SEQ ID NO: 108, and HVR-H3 comprises the amino acid sequence of SEQ ID NO: 133;

cc) HVR-L1 comprises the amino acid sequence of SEQ ID NO: 5, HVR-L2 comprises the amino acid sequence of SEQ ID NO: 20, HVR-L3 comprises the amino acid sequence of SEQ ID NO: 40, HVR-H1 comprises the amino acid sequence of SEQ ID NO: 87, HVR-H2 comprises the amino acid sequence of SEQ ID NO: 108, and HVR-H3 comprises the amino acid sequence of SEQ ID NO: 134;

dd) HVR-L1 comprises the amino acid sequence of SEQ ID NO: 6, HVR-L2 comprises the amino acid sequence of SEQ ID NO: 21, HVR-L3 comprises the amino acid sequence of SEQ ID NO: 41, HVR-H1 comprises the amino acid sequence of SEQ ID NO: 82, HVR-H2 comprises the amino acid sequence of SEQ ID NO: 109, and HVR-H3 comprises the amino acid sequence of SEQ ID NO: 135;

ee) HVR-L1 comprises the amino acid sequence of SEQ ID NO: 5, HVR-L2 comprises the amino acid sequence of SEQ ID NO: 20, HVR-L3 comprises the amino acid sequence of SEQ ID NO: 42, HVR-H1 comprises the amino acid sequence of SEQ ID NO: 88, HVR-H2 comprises the amino acid sequence of SEQ ID NO: 110, and HVR-H3 comprises the amino acid sequence of SEQ ID NO: 136;

ff) HVR-L1 comprises the amino acid sequence of SEQ ID NO: 2, HVR-L2 comprises the amino acid sequence of SEQ ID NO: 22, HVR-L3 comprises the amino acid sequence of SEQ ID NO: 43, HVR-H1 comprises the amino acid sequence of SEQ ID NO: 84, HVR-H2 comprises the amino acid sequence of SEQ ID NO: 106, and HVR-H3 comprises the amino acid sequence of SEQ ID NO: 137;

gg) HVR-L1 comprises the amino acid sequence of SEQ ID NO: 7, HVR-L2 comprises the amino acid sequence of SEQ ID NO: 23, HVR-L3 comprises the amino acid sequence of SEQ ID NO: 44, HVR-H1 comprises the amino acid sequence of SEQ ID NO: 89, HVR-H2 comprises the amino acid sequence of SEQ ID NO: 111, and HVR-H3 comprises the amino acid sequence of SEQ ID NO: 138;

hh) HVR-L1 comprises the amino acid sequence of SEQ ID NO: 3, HVR-L2 comprises the amino acid sequence of SEQ ID NO: 18, HVR-L3 comprises the amino acid sequence of SEQ ID NO: 45, HVR-H1 comprises the amino acid sequence of SEQ ID NO: 84, HVR-H2 comprises the amino acid sequence of SEQ ID NO: 112, and HVR-H3 comprises the amino acid sequence of SEQ ID NO: 139;

ii) HVR-L1 comprises the amino acid sequence of SEQ ID NO: 3, HVR-L2 comprises the amino acid sequence of SEQ ID NO: 18, HVR-L3 comprises the amino acid sequence of SEQ ID NO: 46, HVR-H1 comprises the amino acid sequence of SEQ ID NO: 83, HVR-H2 comprises the amino acid sequence of SEQ ID NO: 104, and HVR-H3 comprises the amino acid sequence of SEQ ID NO: 140;

jj) HVR-L1 comprises the amino acid sequence of SEQ ID NO: 4, HVR-L2 comprises the amino acid sequence of SEQ ID NO: 20, HVR-L3 comprises the amino acid sequence of SEQ ID NO: 47, HVR-H1 comprises the amino acid sequence of SEQ ID NO: 84, HVR-H2 comprises the amino acid sequence of SEQ ID NO: 108, and HVR-H3 comprises the amino acid sequence of SEQ ID NO: 141;

kk) HVR-L1 comprises the amino acid sequence of SEQ ID NO: 4, HVR-L2 comprises the amino acid sequence of SEQ ID NO: 20, HVR-L3 comprises the amino acid sequence of SEQ ID NO: 48, HVR-H1 comprises the amino acid sequence of SEQ ID NO: 84, HVR-H2 comprises the amino acid sequence of SEQ ID NO: 108, and HVR-H3 comprises the amino acid sequence of SEQ ID NO: 142;

ll) HVR-L1 comprises the amino acid sequence of SEQ ID NO: 8, HVR-L2 comprises the amino acid sequence of SEQ ID NO: 18, HVR-L3 comprises the amino acid sequence of SEQ ID NO: 49, HVR-H1 comprises the amino acid sequence of SEQ ID NO: 84, HVR-H2 comprises the amino acid sequence of SEQ ID NO: 112, and HVR-H3 comprises the amino acid sequence of SEQ ID NO: 143;

mm) HVR-L1 comprises the amino acid sequence of SEQ ID NO: 4, HVR-L2 comprises the amino acid sequence of SEQ ID NO: 20, HVR-L3 comprises the amino acid sequence of SEQ ID NO: 50, HVR-H1 comprises the amino acid sequence of SEQ ID NO: 90, HVR-H2 comprises the amino acid sequence of SEQ ID NO: 104, and HVR-H3 comprises the amino acid sequence of SEQ ID NO: 144;

nn) HVR-L1 comprises the amino acid sequence of SEQ ID NO: 9, HVR-L2 comprises the amino acid sequence of SEQ ID NO: 24, HVR-L3 comprises the amino acid sequence of SEQ ID NO: 51, HVR-H1 comprises the amino acid sequence of SEQ ID NO: 91, HVR-H2 comprises the amino acid sequence of SEQ ID NO: 113, and HVR-H3 comprises the amino acid sequence of SEQ ID NO: 145;

oo) HVR-L1 comprises the amino acid sequence of SEQ ID NO: 7, HVR-L2 comprises the amino acid sequence of SEQ ID NO: 23, HVR-L3 comprises the amino acid sequence of SEQ ID NO: 52, HVR-H1 comprises the amino acid sequence of SEQ ID NO: 84, HVR-H2 comprises the amino acid sequence of SEQ ID NO: 114, and HVR-H3 comprises the amino acid sequence of SEQ ID NO: 146;

pp) HVR-L1 comprises the amino acid sequence of SEQ ID NO: 6, HVR-L2 comprises the amino acid sequence of SEQ ID NO: 25, HVR-L3 comprises the amino acid sequence of SEQ ID NO: 53, HVR-H1 comprises the amino acid sequence of SEQ ID NO: 92, HVR-H2 comprises the amino acid sequence of SEQ ID NO: 107, and HVR-H3 comprises the amino acid sequence of SEQ ID NO: 147;

qq) HVR-L1 comprises the amino acid sequence of SEQ ID NO: 9, HVR-L2 comprises the amino acid sequence of SEQ ID NO: 23, HVR-L3 comprises the amino acid sequence of SEQ ID NO: 54, HVR-H1 comprises the amino acid sequence of SEQ ID NO: 93, HVR-H2 comprises the amino acid sequence of SEQ ID NO: 108, and HVR-H3 comprises the amino acid sequence of SEQ ID NO: 148;

rr) HVR-L1 comprises the amino acid sequence of SEQ ID NO: 4, HVR-L2 comprises the amino acid sequence of SEQ ID NO: 20, HVR-L3 comprises the amino acid sequence of SEQ ID NO: 55, HVR-H1 comprises the amino acid sequence of SEQ ID NO: 84, HVR-H2 comprises the amino acid sequence of SEQ ID NO: 108, and HVR-H3 comprises the amino acid sequence of SEQ ID NO: 149;

ss) HVR-L1 comprises the amino acid sequence of SEQ ID NO: 3, HVR-L2 comprises the amino acid sequence of SEQ ID NO: 18, HVR-L3 comprises the amino acid sequence of SEQ ID NO: 56, HVR-H1 comprises the amino acid sequence of SEQ ID NO: 84, HVR-H2 comprises the amino acid sequence of SEQ ID NO: 108, and HVR-H3 comprises the amino acid sequence of SEQ ID NO: 150;

tt) HVR-L1 comprises the amino acid sequence of SEQ ID NO: 383, HVR-L2 comprises the amino acid sequence of SEQ ID NO: 16, HVR-L3 comprises the amino acid sequence of SEQ ID NO: 57, HVR-H1 comprises the amino acid sequence of SEQ ID NO: 94, HVR-H2 comprises the amino acid sequence of SEQ ID NO: 115, and HVR-H3 comprises the amino acid sequence of SEQ ID NO: 151;

uu) HVR-L1 comprises the amino acid sequence of SEQ ID NO: 4, HVR-L2 comprises the amino acid sequence of SEQ ID NO: 20, HVR-L3 comprises the amino acid sequence of SEQ ID NO: 58, HVR-H1 comprises the amino acid sequence of SEQ ID NO: 84, HVR-H2 comprises the amino acid sequence of SEQ ID NO: 112, and HVR-H3 comprises the amino acid sequence of SEQ ID NO: 152;

vv) HVR-L1 comprises the amino acid sequence of SEQ ID NO: 10, HVR-L2 comprises the amino acid sequence of SEQ ID NO: 16, HVR-L3 comprises the amino acid sequence of SEQ ID NO: 59, HVR-H1 comprises the amino acid sequence of SEQ ID NO: 95, HVR-H2 comprises the amino acid sequence of SEQ ID NO: 116, and HVR-H3 comprises the amino acid sequence of SEQ ID NO: 153;

ww) HVR-L1 comprises the amino acid sequence of SEQ ID NO: 9, HVR-L2 comprises the amino acid sequence of SEQ ID NO: 23, HVR-L3 comprises the amino acid sequence of SEQ ID NO: 60, HVR-H1 comprises the amino acid sequence of SEQ ID NO: 96, HVR-H2 comprises the amino acid sequence of SEQ ID NO: 117, and HVR-H3 comprises the amino acid sequence of SEQ ID NO: 154;

xx) HVR-L1 comprises the amino acid sequence of SEQ ID NO: 8, HVR-L2 comprises the amino acid sequence of SEQ ID NO: 18, HVR-L3 comprises the amino acid sequence of SEQ ID NO: 61, HVR-H1 comprises the amino acid sequence of SEQ ID NO: 88, HVR-H2 comprises the amino acid sequence of SEQ ID NO: 118, and HVR-H3 comprises the amino acid sequence of SEQ ID NO: 155;

yy) HVR-L1 comprises the amino acid sequence of SEQ ID NO: 11, HVR-L2 comprises the amino acid sequence of SEQ ID NO: 26, HVR-L3 comprises the amino acid sequence of SEQ ID NO: 62, HVR-H1 comprises the amino acid sequence of SEQ ID NO: 91, HVR-H2 comprises the amino acid sequence of SEQ ID NO: 119, and HVR-H3 comprises the amino acid sequence of SEQ ID NO: 156;

zz) HVR-L1 comprises the amino acid sequence of SEQ ID NO: 6, HVR-L2 comprises the amino acid sequence of SEQ ID NO: 25, HVR-L3 comprises the amino acid sequence of SEQ ID NO: 63, HVR-H1 comprises the amino acid sequence of SEQ ID NO: 82, HVR-H2 comprises the amino acid sequence of SEQ ID NO: 120, and HVR-H3 comprises the amino acid sequence of SEQ ID NO: 157;

aaa) HVR-L1 comprises the amino acid sequence of SEQ ID NO: 4, HVR-L2 comprises the amino acid sequence of SEQ ID NO: 20, HVR-L3 comprises the amino acid sequence of SEQ ID NO: 64, HVR-H1 comprises the amino acid sequence of SEQ ID NO: 84, HVR-H2 comprises the amino acid sequence of SEQ ID NO: 108, and HVR-H3 comprises the amino acid sequence of SEQ ID NO: 158;

bbb) HVR-L1 comprises the amino acid sequence of SEQ ID NO: 9, HVR-L2 comprises the amino acid sequence of SEQ ID NO: 23, HVR-L3 comprises the amino acid sequence of SEQ ID NO: 65, HVR-H1 comprises the amino acid sequence of SEQ ID NO: 96, HVR-H2 comprises the amino acid sequence of SEQ ID NO: 121, and HVR-H3 comprises the amino acid sequence of SEQ ID NO: 159;

ccc) HVR-L1 comprises the amino acid sequence of SEQ ID NO: 2, HVR-L2 comprises the amino acid sequence of SEQ ID NO: 17, HVR-L3 comprises the amino acid sequence of SEQ ID NO: 66, HVR-H1 comprises the amino acid sequence of SEQ ID NO: 87, HVR-H2 comprises the amino acid sequence of SEQ ID NO: 108, and HVR-H3 comprises the amino acid sequence of SEQ ID NO: 160;

ddd) HVR-L1 comprises the amino acid sequence of SEQ ID NO: 9, HVR-L2 comprises the amino acid sequence of SEQ ID NO: 23, HVR-L3 comprises the amino acid sequence of SEQ ID NO: 67, HVR-H1 comprises the amino acid sequence of SEQ ID NO: 96, HVR-H2 comprises the amino acid sequence of SEQ ID NO: 121, and HVR-H3 comprises the amino acid sequence of SEQ ID NO: 161;

eee) HVR-L1 comprises the amino acid sequence of SEQ ID NO: 7, HVR-L2 comprises the amino acid sequence of SEQ ID NO: 27, HVR-L3 comprises the amino acid sequence of SEQ ID NO: 68, HVR-H1 comprises the amino acid sequence of SEQ ID NO: 92, HVR-H2 comprises the amino acid sequence of SEQ ID NO: 107, and HVR-H3 comprises the amino acid sequence of SEQ ID NO: 162;

fff) HVR-L1 comprises the amino acid sequence of SEQ ID NO: 12, HVR-L2 comprises the amino acid sequence of SEQ ID NO: 26, HVR-L3 comprises the amino acid sequence of SEQ ID NO: 70, HVR-H1 comprises the amino acid sequence of SEQ ID NO: 94, HVR-H2 comprises the amino acid sequence of SEQ ID NO: 111, and HVR-H3 comprises the amino acid sequence of SEQ ID NO: 164;

ggg) HVR-L1 comprises the amino acid sequence of SEQ ID NO: 7, HVR-L2 comprises the amino acid sequence of SEQ ID NO: 28, HVR-L3 comprises the amino acid sequence of SEQ ID NO: 71, HVR-H1 comprises the amino acid sequence of SEQ ID NO: 83, HVR-H2 comprises the amino acid sequence of SEQ ID NO: 104, and HVR-H3 comprises the amino acid sequence of SEQ ID NO: 165;

hhh) HVR-L1 comprises the amino acid sequence of SEQ ID NO: 2, HVR-L2 comprises the amino acid sequence of SEQ ID NO: 29, HVR-L3 comprises the amino acid sequence of SEQ ID NO: 72, HVR-H1 comprises the amino acid sequence of SEQ ID NO: 92, HVR-H2 comprises the amino acid sequence of SEQ ID NO: 107, and HVR-H3 comprises the amino acid sequence of SEQ ID NO: 166;

iii) HVR-L1 comprises the amino acid sequence of SEQ ID NO: 13, HVR-L2 comprises the amino acid sequence of SEQ ID NO: 30, HVR-L3 comprises the amino acid sequence of SEQ ID NO: 73, HVR-H1 comprises the amino acid sequence of SEQ ID NO: 91, HVR-H2 comprises the amino acid sequence of SEQ ID NO: 122, and HVR-H3 comprises the amino acid sequence of SEQ ID NO: 167;

jjj) HVR-L1 comprises the amino acid sequence of SEQ ID NO: 10, HVR-L2 comprises the amino acid sequence of SEQ ID NO: 16, HVR-L3 comprises the amino acid sequence of SEQ ID NO: 74, HVR-H1 comprises the amino acid sequence of SEQ ID NO: 92, HVR-H2 comprises the amino acid sequence of SEQ ID NO: 107, and HVR-H3 comprises the amino acid sequence of SEQ ID NO: 168;

kkk) HVR-L1 comprises the amino acid sequence of SEQ ID NO: 14, HVR-L2 comprises the amino acid sequence of SEQ ID NO: 16, HVR-L3 comprises the amino acid sequence of SEQ ID NO: 75, HVR-H1 comprises the amino acid sequence of SEQ ID NO: 80, HVR-H2 comprises the amino acid sequence of SEQ ID NO: 123, and HVR-H3 comprises the amino acid sequence of SEQ ID NO: 169;

lll) HVR-L1 comprises the amino acid sequence of SEQ ID NO: 11, HVR-L2 comprises the amino acid sequence of SEQ ID NO: 26, HVR-L3 comprises the amino acid sequence of SEQ ID NO: 76, HVR-H1 comprises the amino acid sequence of SEQ ID NO: 98, HVR-H2 comprises the amino acid sequence of SEQ ID NO: 111, and HVR-H3 comprises the amino acid sequence of SEQ ID NO: 170;

mmm) HVR-L1 comprises the amino acid sequence of SEQ ID NO: 15, HVR-L2 comprises the amino acid sequence of SEQ ID NO: 23, HVR-L3 comprises the amino acid sequence of SEQ ID NO: 77, HVR-H1 comprises the amino acid sequence of SEQ ID NO: 99, HVR-H2 comprises the amino acid sequence of SEQ ID NO: 124, and HVR-H3 comprises the amino acid sequence of SEQ ID NO: 171;

nnn) HVR-L1 comprises the amino acid sequence of SEQ ID NO: 12, HVR-L2 comprises the amino acid sequence of SEQ ID NO: 26, HVR-L3 comprises the amino acid sequence of SEQ ID NO: 78, HVR-H1 comprises the amino acid sequence of SEQ ID NO: 100, HVR-H2 comprises the amino acid sequence of SEQ ID NO: 111, and HVR-H3 comprises the amino acid sequence of SEQ ID NO: 172; or ooo) HVR-L1 comprises the amino acid sequence of SEQ ID NO: 3, HVR-L2 comprises the amino acid sequence of SEQ ID NO: 18, HVR-L3 comprises the amino acid sequence of SEQ ID NO: 79, HVR-H1 comprises the amino acid sequence of SEQ ID NO: 84, HVR-H2 comprises the amino acid sequence of SEQ ID NO: 108, and HVR-H3 comprises the amino acid sequence of SEQ ID NO: 173.

2. The antibody of claim 1, wherein the heavy chain variable region comprises one, two, three or four framework regions selected from VL FR2, VL FR3, and VL FR4, wherein the antibody comprises;

a) the antibody of claim 1a, and VL FR1 comprising the amino acid sequence of SEQ ID NO: 174, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

b) the antibody of claim 1b, and VL FR1 comprising the amino acid sequence of SEQ ID NO: 174, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

c) the antibody of claim 1c, and VL FR1 comprising the amino acid sequence of SEQ ID NO: 174, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

d) the antibody of claim 1d, and VL FR1 comprising the amino acid sequence of SEQ ID NO: 174, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

e) the antibody of claim 1e, and VL FR1 comprising the amino acid sequence of SEQ ID NO: 174, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

f) the antibody of claim 1f, and VL FR1 comprising the amino acid sequence of SEQ ID NO: 175, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

g) the antibody of claim 1g, and VL FR1 comprising the amino acid sequence of SEQ ID NO: 255, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

h) the antibody of claim 1h, and VL FR1 comprising the amino acid sequence of SEQ ID NO: 255, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

i) the antibody of claim 1i, and VL FR1 comprising the amino acid sequence of SEQ ID NO: 255, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

j) the antibody of claim 1j, and VL FR1 comprising the amino acid sequence of SEQ ID NO: 175, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

k) the antibody of claim 1k, and VL FR1 comprising the amino acid sequence of SEQ ID NO: 175, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

l) the antibody of claim 1l, and VL FR1 comprising the amino acid sequence of SEQ ID NO: 174, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

m) the antibody of claim 1m, and VL FR1 comprising the amino acid sequence of SEQ ID NO: 174, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

n) the antibody of claim 1n, and VL FR1 comprising the amino acid sequence of SEQ ID NO: 174, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

o) the antibody of claim 1o, and VL FR1 comprising the amino acid sequence of SEQ ID NO: 174, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

p) the antibody of claim 1p, and VL FR1 comprising the amino acid sequence of SEQ ID NO: 174, VL FR2 comprising the amino acid sequence of SEQ ID NO: 186, VL FR3 comprising the amino acid sequence of SEQ ID NO: 192; and/or VL FR4 comprising the amino acid sequence of SEQ ID NO: 200;

q) the antibody of claim 1q, and VL FR1 comprising the amino acid sequence of SEQ ID NO: 182, VL FR2 comprising the amino acid sequence of SEQ ID NO: 186, VL FR3 comprising the amino acid sequence of SEQ ID NO: 193; and/or VL FR4 comprising the amino acid sequence of SEQ ID NO: 200;

r) the antibody of claim 1r, and VL FR1 comprising the amino acid sequence of SEQ ID NO: 182, VL FR2 comprising the amino acid sequence of SEQ ID NO: 186, VL FR3 comprising the amino acid sequence of SEQ ID NO: 193; and/or VL FR4 comprising the amino acid sequence of SEQ ID NO: 200;

s) the antibody of claim 1s, and VL FR1 comprising the amino acid sequence of SEQ ID NO: 182, VL FR2 comprising the amino acid sequence of SEQ ID NO: 186, VL FR3 comprising the amino acid sequence of SEQ ID NO: 193; and/or VL FR4 comprising the amino acid sequence of SEQ ID NO: 200;

t) the antibody of claim 1t, and VL FR1 comprising the amino acid sequence of SEQ ID NO: 182, VL FR2 comprising the amino acid sequence of SEQ ID NO: 186, VL FR3 comprising the amino acid sequence of SEQ ID NO: 193; and/or VL FR4 comprising the amino acid sequence of SEQ ID NO: 200;

u) the antibody of claim 1u, and VL FR1 comprising the amino acid sequence of SEQ ID NO: 182, VL FR2 comprising the amino acid sequence of SEQ ID NO: 186, VL FR3 comprising the amino acid sequence of SEQ ID NO: 193; and/or VL FR4 comprising the amino acid sequence of SEQ ID NO: 200;

v) the antibody of claim 1v, and VL FR1 comprising the amino acid sequence of SEQ ID NO: 176, VL FR2 comprising the amino acid sequence of SEQ ID NO: 186, VL FR3 comprising the amino acid sequence of SEQ ID NO: 193, and/or VL FR4 comprising the amino acid sequence of SEQ ID NO: 200;

w) the antibody of claim 1w, and VL FR1 comprising the amino acid sequence of SEQ ID NO: 175, VL FR2 comprising the amino acid sequence of SEQ ID NO: 186, VL FR3 comprising the amino acid sequence of SEQ ID NO: 192, and/or VL FR4 comprising the amino acid sequence of SEQ ID NO: 200;

x) the antibody of claim 1x, and VL FR1 comprising the amino acid sequence of SEQ ID NO: 177, VL FR2 comprising the amino acid sequence of SEQ ID NO: 186, VL FR3 comprising the amino acid sequence of SEQ ID NO: 193, and/or VL FR4 comprising the amino acid sequence of SEQ ID NO: 200;

y) the antibody of claim 1y, and VL FR1 comprising the amino acid sequence of SEQ ID NO: 175, VL FR2 comprising the amino acid sequence of SEQ ID NO: 186, VL FR3 comprising the amino acid sequence of SEQ ID NO: 192, and/or VL FR4 comprising the amino acid sequence of SEQ ID NO: 200;

z) the antibody of claim 1z, and VL FR1 comprising the amino acid sequence of SEQ ID NO: 178, VL FR2 comprising the amino acid sequence of SEQ ID NO: 187, VL FR3 comprising the amino acid sequence of SEQ ID NO: 194, and/or VL FR4 comprising the amino acid sequence of SEQ ID NO: 200;

aa) the antibody of claim 1aa, and VL FR1 comprising the amino acid sequence of SEQ ID NO: 178, VL FR2 comprising the amino acid sequence of SEQ ID NO: 187, VL FR3 comprising the amino acid sequence of SEQ ID NO: 194, and/or VL FR4 comprising the amino acid sequence of SEQ ID NO: 200;

bb) the antibody of claim 1bb, and VL FR1 comprising the amino acid sequence of SEQ ID NO: 179, VL FR2 comprising the amino acid sequence of SEQ ID NO: 188, VL FR3 comprising the amino acid sequence of SEQ ID NO: 195, and/or VL FR4 comprising the amino acid sequence of SEQ ID NO: 200;

cc) the antibody of claim 1cc, and VL FR1 comprising the amino acid sequence of SEQ ID NO: 179, VL FR2 comprising the amino acid sequence of SEQ ID NO: 188, VL FR3 comprising the amino acid sequence of SEQ ID NO: 195, and/or VL FR4 comprising the amino acid sequence of SEQ ID NO: 200;

dd) the antibody of claim 1dd, and VL FR1 comprising the amino acid sequence of SEQ ID NO: 180, VL FR2 comprising the amino acid sequence of SEQ ID NO: 186, VL FR3 comprising the amino acid sequence of SEQ ID NO: 196, and/or VL FR4 comprising the amino acid sequence of SEQ ID NO: 200;

ee) the antibody of claim 1ee, and VL FR1 comprising the amino acid sequence of SEQ ID NO: 179, VL FR2 comprising the amino acid sequence of SEQ ID NO: 189, VL FR3 comprising the amino acid sequence of SEQ ID NO: 195, and/or VL FR4 comprising the amino acid sequence of SEQ ID NO: 200;

ff) the antibody of claim 1ff, and VL FR1 comprising the amino acid sequence of SEQ ID NO: 176, VL FR2 comprising the amino acid sequence of SEQ ID NO: 186, VL FR3 comprising the amino acid sequence of SEQ ID NO: 193, and/or VL FR4 comprising the amino acid sequence of SEQ ID NO: 200;

gg) the antibody of claim 1gg, and VL FR1 comprising the amino acid sequence of SEQ ID NO: 181, VL FR2 comprising the amino acid sequence of SEQ ID NO: 190, VL FR3 comprising the amino acid sequence of SEQ ID NO: 197, and/or VL FR4 comprising the amino acid sequence of SEQ ID NO: 200;

hh) the antibody of claim 1hh, and VL FR1 comprising the amino acid sequence of SEQ ID NO: 178, VL FR2 comprising the amino acid sequence of SEQ ID NO: 187, VL FR3 comprising the amino acid sequence of SEQ ID NO: 194, and/or VL FR4 comprising the amino acid sequence of SEQ ID NO: 200;

ii) (ii) the antibody of claim 1ii, and VL FR1 comprising the amino acid sequence of SEQ ID NO: 178, VL FR2 comprising the amino acid sequence of SEQ ID NO: 187, VL FR3 comprising the amino acid sequence of SEQ ID NO: 194, and/or VL FR4 comprising the amino acid sequence of SEQ ID NO: 200;

jj) the antibody of claim 1jj, and VL FR1 comprising the amino acid sequence of SEQ ID NO: 182, VL FR2 comprising the amino acid sequence of SEQ ID NO: 188, VL FR3 comprising the amino acid sequence of SEQ ID NO: 195, and/or VL FR4 comprising the amino acid sequence of SEQ ID NO: 200;

kk) the antibody of claim 1kk, and VL FR1 comprising the amino acid sequence of SEQ ID NO: 179, VL FR2 comprising the amino acid sequence of SEQ ID NO: 188, VL FR3 comprising the amino acid sequence of SEQ ID NO: 195, and/or VL FR4 comprising the amino acid sequence of SEQ ID NO: 200;

ll) the antibody of claim 1ll, and VL FR1 comprising the amino acid sequence of SEQ ID NO: 178, VL FR2 comprising the amino acid sequence of SEQ ID NO: 187, VL FR3 comprising the amino acid sequence of SEQ ID NO: 194, and/or VL FR4 comprising the amino acid sequence of SEQ ID NO: 200;

mm) the antibody of claim 1mm, and VL FR1 comprising the amino acid sequence of SEQ ID NO: 179, VL FR2 comprising the amino acid sequence of SEQ ID NO: 188, VL FR3 comprising the amino acid sequence of SEQ ID NO: 195, and/or VL FR4 comprising the amino acid sequence of SEQ ID NO: 200;

nn) the antibody of claim 1nn, and VL FR1 comprising the amino acid sequence of SEQ ID NO: 183, VL FR2 comprising the amino acid sequence of SEQ ID NO: 190, VL FR3 comprising the amino acid sequence of SEQ ID NO: 197, and/or VL FR4 comprising the amino acid sequence of SEQ ID NO: 200;

oo) the antibody of claim 1oo, and VL FR1 comprising the amino acid sequence of SEQ ID NO: 181, VL FR2 comprising the amino acid sequence of SEQ ID NO: 190, VL FR3 comprising the amino acid sequence of SEQ ID NO: 197, and/or VL FR4 comprising the amino acid sequence of SEQ ID NO: 200;

pp) the antibody of claim 1pp, and VL FR1 comprising the amino acid sequence of SEQ ID NO: 180, VL FR2 comprising the amino acid sequence of SEQ ID NO: 186, VL FR3 comprising the amino acid sequence of SEQ ID NO: 196, and/or VL FR4 comprising the amino acid sequence of SEQ ID NO: 200;

qq) the antibody of claim 1qq, and VL FR1 comprising the amino acid sequence of SEQ ID NO: 183, VL FR2 comprising the amino acid sequence of SEQ ID NO: 190, VL FR3 comprising the amino acid sequence of SEQ ID NO: 197, and/or VL FR4 comprising the amino acid sequence of SEQ ID NO: 200;

rr) the antibody of claim 1rr, and VL FR1 comprising the amino acid sequence of SEQ ID NO: 179, VL FR2 comprising the amino acid sequence of SEQ ID NO: 188, VL FR3 comprising the amino acid sequence of SEQ ID NO: 195, and/or VL FR4 comprising the amino acid sequence of SEQ ID NO: 200;

ss) the antibody of claim 1ss, and VL FR1 comprising the amino acid sequence of SEQ ID NO: 178, VL FR2 comprising the amino acid sequence of SEQ ID NO: 187, VL FR3 comprising the amino acid sequence of SEQ ID NO: 194, and/or VL FR4 comprising the amino acid sequence of SEQ ID NO: 200;

tt) the antibody of claim 1tt, and VL FR1 comprising the amino acid sequence of SEQ ID NO: 175, VL FR2 comprising the amino acid sequence of SEQ ID NO: 186, VL FR3 comprising the amino acid sequence of SEQ ID NO: 192, and/or VL FR4 comprising the amino acid sequence of SEQ ID NO: 200;

uu) the antibody of claim 1uu, and VL FR1 comprising the amino acid sequence of SEQ ID NO: 179, VL FR2 comprising the amino acid sequence of SEQ ID NO: 191, VL FR3 comprising the amino acid sequence of SEQ ID NO: 195, and/or VL FR4 comprising the amino acid sequence of SEQ ID NO: 200;

vv) the antibody of claim 1vv, and VL FR1 comprising the amino acid sequence of SEQ ID NO: 175, VL FR2 comprising the amino acid sequence of SEQ ID NO: 186, VL FR3 comprising the amino acid sequence of SEQ ID NO: 192, and/or VL FR4 comprising the amino acid sequence of SEQ ID NO: 200;

ww) the antibody of claim 1ww, and VL FR1 comprising the amino acid sequence of SEQ ID NO: 183, VL FR2 comprising the amino acid sequence of SEQ ID NO: 190, VL FR3 comprising the amino acid sequence of SEQ ID NO: 197, and/or VL FR4 comprising the amino acid sequence of SEQ ID NO: 200;

xx) the antibody of claim 1xx, and VL FR1 comprising the amino acid sequence of SEQ ID NO: 178, VL FR2 comprising the amino acid sequence of SEQ ID NO: 187, VL FR3 comprising the amino acid sequence of SEQ ID NO: 194, and/or VL FR4 comprising the amino acid sequence of SEQ ID NO: 200;

yy) the antibody of claim 1yy, and VL FR1 comprising the amino acid sequence of SEQ ID NO: 181, VL FR2 comprising the amino acid sequence of SEQ ID NO: 190, VL FR3 comprising the amino acid sequence of SEQ ID NO: 198, and/or VL FR4 comprising the amino acid sequence of SEQ ID NO: 200;

zz) the antibody of claim 1zz, and VL FR1 comprising the amino acid sequence of SEQ ID NO: 180, VL FR2 comprising the amino acid sequence of SEQ ID NO: 186, VL FR3 comprising the amino acid sequence of SEQ ID NO: 196, and/or VL FR4 comprising the amino acid sequence of SEQ ID NO: 200;

aaa) the antibody of claim 1aaa, and VL FR1 comprising the amino acid sequence of SEQ ID NO: 179, VL FR2 comprising the amino acid sequence of SEQ ID NO: 188, VL FR3 comprising the amino acid sequence of SEQ ID NO: 195, and/or VL FR4 comprising the amino acid sequence of SEQ ID NO: 200;

bbb) the antibody of claim 1bbb, and VL FR1 comprising the amino acid sequence of SEQ ID NO: 183, VL FR2 comprising the amino acid sequence of SEQ ID NO: 190, VL FR3 comprising the amino acid sequence of SEQ ID NO: 197, and/or VL FR4 comprising the amino acid sequence of SEQ ID NO: 200;

ccc) the antibody of claim 1ccc, and VL FR1 comprising the amino acid sequence of SEQ ID NO: 182, VL FR2 comprising the amino acid sequence of SEQ ID NO: 186, VL FR3 comprising the amino acid sequence of SEQ ID NO: 193, and/or VL FR4 comprising the amino acid sequence of SEQ ID NO: 200;

ddd) the antibody of claim 1ddd, and VL FR1 comprising the amino acid sequence of SEQ ID NO: 183, VL FR2 comprising the amino acid sequence of SEQ ID NO: 190, VL FR3 comprising the amino acid sequence of SEQ ID NO: 197, and/or VL FR4 comprising the amino acid sequence of SEQ ID NO: 200;

eee) the antibody of claim 1eee, and VL FR1 comprising the amino acid sequence of SEQ ID NO: 181, VL FR2 comprising the amino acid sequence of SEQ ID NO: 190, VL FR3 comprising the amino acid sequence of SEQ ID NO: 197, and/or VL FR4 comprising the amino acid sequence of SEQ ID NO: 200;

fff) the antibody of claim 1fff, and VL FR1 comprising the amino acid sequence of SEQ ID NO: 181, VL FR2 comprising the amino acid sequence of SEQ ID NO: 190, VL FR3 comprising the amino acid sequence of SEQ ID NO: 198, and/or VL FR4 comprising the amino acid sequence of SEQ ID NO: 200;

ggg) the antibody of claim 1ggg, and VL FR1 comprising the amino acid sequence of SEQ ID NO: 184, VL FR2 comprising the amino acid sequence of SEQ ID NO: 190, VL FR3 comprising the amino acid sequence of SEQ ID NO: 197, and/or VL FR4 comprising the amino acid sequence of SEQ ID NO: 200;

hhh) the antibody of claim 1hhh, and VL FR1 comprising the amino acid sequence of SEQ ID NO: 182, VL FR2 comprising the amino acid sequence of SEQ ID NO: 186, VL FR3 comprising the amino acid sequence of SEQ ID NO: 193, and/or VL FR4 comprising the amino acid sequence of SEQ ID NO: 200;

iii) the antibody of claim 1iii, and VL FR1 comprising the amino acid sequence of SEQ ID NO: 185, VL FR2 comprising the amino acid sequence of SEQ ID NO: 190, VL FR3 comprising the amino acid sequence of SEQ ID NO: 199, and/or VL FR4 comprising the amino acid sequence of SEQ ID NO: 200;

jjj) the antibody of claim 1jjj, and VL FR1 comprising the amino acid sequence of SEQ ID NO: 175, VL FR2 comprising the amino acid sequence of SEQ ID NO: 186, VL FR3 comprising the amino acid sequence of SEQ ID NO: 192, and/or VL FR4 comprising the amino acid sequence of SEQ ID NO: 200;

kkk) the antibody of claim 1kkk, and VL FR1 comprising the amino acid sequence of SEQ ID NO: 175, VL FR2 comprising the amino acid sequence of SEQ ID NO: 186, VL FR3 comprising the amino acid sequence of SEQ ID NO: 192, and/or VL FR4 comprising the amino acid sequence of SEQ ID NO: 200;

lll) the antibody of claim 1lll, and VL FR1 comprising the amino acid sequence of SEQ ID NO: 181, VL FR2 comprising the amino acid sequence of SEQ ID NO: 190, VL FR3 comprising the amino acid sequence of SEQ ID NO: 198, and/or VL FR4 comprising the amino acid sequence of SEQ ID NO: 200;

mmm) the antibody of claim 1mmm, and VL FR1 comprising the amino acid sequence of SEQ ID NO: 183, VL FR2 comprising the amino acid sequence of SEQ ID NO: 190, VL FR3 comprising the amino acid sequence of SEQ ID NO: 197, and/or VL FR4 comprising the amino acid sequence of SEQ ID NO: 200;

nnn) the antibody of claim 1nnn, and VL FR1 comprising the amino acid sequence of SEQ ID NO: 181, VL FR2 comprising the amino acid sequence of SEQ ID NO: 190, VL FR3 comprising the amino acid sequence of SEQ ID NO: 198, and/or VL FR4 comprising the amino acid sequence of SEQ ID NO: 200; or ooo) the antibody of claim 1ooo, and VL FR1 comprising the amino acid sequence of SEQ ID NO: 178, VL FR2 comprising the amino acid sequence of SEQ ID NO: 187, VL FR3 comprising the amino acid sequence of SEQ ID NO: 194, and/or VL FR4 comprising the amino acid sequence of SEQ ID NO: 200.

3. The antibody of claim 1, wherein the heavy chain variable region comprises one, two, three or four framework regions selected from VH FR1, VH FR2, VH FR3, and VH FR4, wherein the antibody comprises:

a) the antibody of claim 1a, and VH FR1 comprising the amino acid sequence of SEQ ID NO: 201, VH FR2 comprising the amino acid sequence of SEQ ID NO: 210, VH FR3 comprising the amino acid sequence of SEQ ID NO: 215; and/or VH FR4 comprising the amino acid sequence of SEQ ID NO: 222;

b) the antibody of claim 1b, and VH FR1 comprising the amino acid sequence of SEQ ID NO: 256, VH FR2 comprising the amino acid sequence of SEQ ID NO: 210, VH FR3 comprising the amino acid sequence of SEQ ID NO: 215; and/or VH FR4 comprising the amino acid sequence of SEQ ID NO: 222;

c) the antibody of claim 1c, and VH FR1 comprising the amino acid sequence of SEQ ID NO: 257, VH FR2 comprising the amino acid sequence of SEQ ID NO: 210, VH FR3 comprising the amino acid sequence of SEQ ID NO: 215; and/or VH FR4 comprising the amino acid sequence of SEQ ID NO: 222;

d) the antibody of claim 1d, and VH FR1 comprising the amino acid sequence of SEQ ID NO: 258, VH FR2 comprising the amino acid sequence of SEQ ID NO: 210, VH FR3 comprising the amino acid sequence of SEQ ID NO: 215; and/or VH FR4 comprising the amino acid sequence of SEQ ID NO: 222;

e) the antibody of claim 1e, and VH FR1 comprising the amino acid sequence of SEQ ID NO: 202, VH FR2 comprising the amino acid sequence of SEQ ID NO: 210, VH FR3 comprising the amino acid sequence of SEQ ID NO: 215; and/or VH FR4 comprising the amino acid sequence of SEQ ID NO: 222;

f) the antibody of claim 1f, and VH FR1 comprising the amino acid sequence of SEQ ID NO: 202, VH FR2 comprising the amino acid sequence of SEQ ID NO: 211, VH FR3 comprising the amino acid sequence of SEQ ID NO: 216; and/or VH FR4 comprising the amino acid sequence of SEQ ID NO: 222;

g) the antibody of claim 1g, and VH FR1 comprising the amino acid sequence of SEQ ID NO: 259, VH FR2 comprising the amino acid sequence of SEQ ID NO: 210, VH FR3 comprising the amino acid sequence of SEQ ID NO: 216; and/or VH FR4 comprising the amino acid sequence of SEQ ID NO: 222;

h) the antibody of claim 1h, and VH FR1 comprising the amino acid sequence of SEQ ID NO: 260, VH FR2 comprising the amino acid sequence of SEQ ID NO: 210, VH FR3 comprising the amino acid sequence of SEQ ID NO: 216; and/or VH FR4 comprising the amino acid sequence of SEQ ID NO: 222;

i) the antibody of claim 1i, and VH FR1 comprising the amino acid sequence of SEQ ID NO: 261, VH FR2 comprising the amino acid sequence of SEQ ID NO:

211, VH FR3 comprising the amino acid sequence of SEQ ID NO: 216; and/or VH FR4 comprising the amino acid sequence of SEQ ID NO: 222;

j) the antibody of claim 1j, and VH FR1 comprising the amino acid sequence of SEQ ID NO: 262, VH FR2 comprising the amino acid sequence of SEQ ID NO: 210, VH FR3 comprising the amino acid sequence of SEQ ID NO: 216; and/or VH FR4 comprising the amino acid sequence of SEQ ID NO: 222;

k) the antibody of claim 1k, and VH FR1 comprising the amino acid sequence of SEQ ID NO: 263, VH FR2 comprising the amino acid sequence of SEQ ID NO: 210, VH FR3 comprising the amino acid sequence of SEQ ID NO: 216; and/or VH FR4 comprising the amino acid sequence of SEQ ID NO: 222;

l) the antibody of claim 1l, and VH FR1 comprising the amino acid sequence of SEQ ID NO: 205, VH FR2 comprising the amino acid sequence of SEQ ID NO: 213, VH FR3 comprising the amino acid sequence of SEQ ID NO: 220; and/or VH FR4 comprising the amino acid sequence of SEQ ID NO: 222;

m) the antibody of claim 1m, and VH FR1 comprising the amino acid sequence of SEQ ID NO: 205, VH FR2 comprising the amino acid sequence of SEQ ID NO: 213, VH FR3 comprising the amino acid sequence of SEQ ID NO: 220; and/or VH FR4 comprising the amino acid sequence of SEQ ID NO: 222;

n) the antibody of claim 1n, and VH FR1 comprising the amino acid sequence of SEQ ID NO: 205, VH FR2 comprising the amino acid sequence of SEQ ID NO: 213, VH FR3 comprising the amino acid sequence of SEQ ID NO: 220; and/or VH FR4 comprising the amino acid sequence of SEQ ID NO: 222;

o) the antibody of claim 1o, and VH FR1 comprising the amino acid sequence of SEQ ID NO: 205, VH FR2 comprising the amino acid sequence of SEQ ID NO: 213, VH FR3 comprising the amino acid sequence of SEQ ID NO: 220; and/or VH FR4 comprising the amino acid sequence of SEQ ID NO: 222;

p) the antibody of claim 1p, and VH FR1 comprising the amino acid sequence of SEQ ID NO: 205, VH FR2 comprising the amino acid sequence of SEQ ID NO: 213, VH FR3 comprising the amino acid sequence of SEQ ID NO: 220; and/or VH FR4 comprising the amino acid sequence of SEQ ID NO: 222;

q) the antibody of claim 1q, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 221; and/or VH FR4 comprising the amino acid sequence of SEQ ID NO: 222;

r) the antibody of claim 1r, and VH FR1 comprising the amino acid sequence of SEQ ID NO: 203, VH FR2 comprising the amino acid sequence of SEQ ID NO: 264, VH FR3 comprising the amino acid sequence of SEQ ID NO: 265; and/or VH FR4 comprising the amino acid sequence of SEQ ID NO: 222;

s) the antibody of claim 1s, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 218; and/or VH FR4 comprising the amino acid sequence of SEQ ID NO: 222;

t) the antibody of claim 1t, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 266; and/or VH FR4 comprising the amino acid sequence of SEQ ID NO: 222;

u) the antibody of claim 1u, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 217; and/or VH FR4 comprising the amino acid sequence of SEQ ID NO: 222;

v) the antibody of claim 1v, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 217, and/or VL FR4 comprising the amino acid sequence of SEQ ID NO: 223;

w) the antibody of claim 1w, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 218, and/or VL FR4 comprising the amino acid sequence of SEQ ID NO: 224;

x) the antibody of claim 1x, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 217, and/or VL FR4 comprising the amino acid sequence of SEQ ID NO: 224;

y) the antibody of claim 1y, and VH FR1 comprising the amino acid sequence of SEQ ID NO: 201, VH FR2 comprising the amino acid sequence of SEQ ID NO: 210, VH FR3 comprising the amino acid sequence of SEQ ID NO: 215, and/or VL FR4 comprising the amino acid sequence of SEQ ID NO: 222;

z) the antibody of claim 1z, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 222;

aa) the antibody of claim 1aa, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 218, and/or VL FR4 comprising the amino acid sequence of SEQ ID NO: 222;

bb) the antibody of claim 1bb, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 222;

cc) the antibody of claim 1cc, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 225;

dd) the antibody of claim 1dd, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 217, and/or VL FR4 comprising the amino acid sequence of SEQ ID NO: 222;

ee) the antibody of claim 1ee, and VH FR1 comprising the amino acid sequence of SEQ ID NO: 206, VH FR2 comprising the amino acid sequence of SEQ ID NO: 213, VH FR3 comprising the amino acid sequence of SEQ ID NO: 220, and/or VL FR4 comprising the amino acid sequence of SEQ ID NO: 223;

ff) the antibody of claim 1ff, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 224;

gg) the antibody of claim 1gg, and VH FR1 comprising the amino acid sequence of SEQ ID NO: 207, VH FR2 comprising the amino acid sequence of SEQ ID NO: 213, VH FR3 comprising the amino acid sequence of SEQ ID NO: 220, and/or VL FR4 comprising the amino acid sequence of SEQ ID NO: 226;

hh) the antibody of claim 1hh, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 223;

ii) the antibody of claim 1ii, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 218, and/or VL FR4 comprising the amino acid sequence of SEQ ID NO: 222;

jj) the antibody of claim 1jj, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 222;

kk) the antibody of claim 1kk, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 224;

ll) the antibody of claim 1ll, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 222;

mm) the antibody of claim 1mm, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 218, and/or VL FR4 comprising the amino acid sequence of SEQ ID NO: 223;

nn) the antibody of claim 1nn, and VH FR1 comprising the amino acid sequence of SEQ ID NO: 208, VH FR2 comprising the amino acid sequence of SEQ ID NO: 210, VH FR3 comprising the amino acid sequence of SEQ ID NO: 216, and/or VL FR4 comprising the amino acid sequence of SEQ ID NO: 222;

oo) the antibody of claim 1oo, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 225;

pp) the antibody of claim 1pp, and VH FR1 comprising the amino acid sequence of SEQ ID NO: 205, VH FR2 comprising the amino acid sequence of SEQ ID NO: 213, VH FR3 comprising the amino acid sequence of SEQ ID NO: 220, and/or VL FR4 comprising the amino acid sequence of SEQ ID NO: 222;

qq) the antibody of claim 1qq, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 222;

rr) the antibody of claim 1rr, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 222;

ss) the antibody of claim 1ss, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 223;

tt) the antibody of claim 1tt, and VH FR1 comprising the amino acid sequence of SEQ ID NO: 207, VH FR2 comprising the amino acid sequence of SEQ ID NO: 213, VH FR3 comprising the amino acid sequence of SEQ ID NO: 220, and/or VL FR4 comprising the amino acid sequence of SEQ ID NO: 223;

uu) the antibody of claim 1uu, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 223;

vv) the antibody of claim 1vv, and VH FR1 comprising the amino acid sequence of SEQ ID NO: 209, VH FR2 comprising the amino acid sequence of SEQ ID NO: 214, VH FR3 comprising the amino acid sequence of SEQ ID NO: 220, and/or VL FR4 comprising the amino acid sequence of SEQ ID NO: 224;

ww) the antibody of claim 1ww, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 221, and/or VL FR4 comprising the amino acid sequence of SEQ ID NO: 224;

xx) the antibody of claim 1xx, and VH FR1 comprising the amino acid sequence of SEQ ID NO: 206, VH FR2 comprising the amino acid sequence of SEQ ID NO: 213, VH FR3 comprising the amino acid sequence of SEQ ID NO: 220, and/or VL FR4 comprising the amino acid sequence of SEQ ID NO: 223;

yy) the antibody of claim 1yy, and VH FR1 comprising the amino acid sequence of SEQ ID NO: 208, VH FR2 comprising the amino acid sequence of SEQ ID NO: 210, VH FR3 comprising the amino acid sequence of SEQ ID NO: 216, and/or VL FR4 comprising the amino acid sequence of SEQ ID NO: 226;

zz) the antibody of claim 1zz, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 217, and/or VL FR4 comprising the amino acid sequence of SEQ ID NO: 222;

aaa) the antibody of claim 1aaa, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 224;

bbb) the antibody of claim 1bbb, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 221, and/or VL FR4 comprising the amino acid sequence of SEQ ID NO: 224;

ccc) the antibody of claim 1ccc, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 226;

ddd) the antibody of claim 1ddd, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 221, and/or VL FR4 comprising the amino acid sequence of SEQ ID NO: 224;

eee) the antibody of claim 1eee, and VH FR1 comprising the amino acid sequence of SEQ ID NO: 205, VH FR2 comprising the amino acid sequence of SEQ ID NO: 213, VH FR3 comprising the amino acid sequence of SEQ ID NO: 220, and/or VL FR4 comprising the amino acid sequence of SEQ ID NO: 224;

fff) the antibody of claim 1fff, and VH FR1 comprising the amino acid sequence of SEQ ID NO: 207, VH FR2 comprising the amino acid sequence of SEQ ID NO: 213, VH FR3 comprising the amino acid sequence of SEQ ID NO: 220, and/or VL FR4 comprising the amino acid sequence of SEQ ID NO: 222;

ggg) the antibody of claim 1ggg, and VH FR1 comprising the amino acid sequence of SEQ ID NO: 203, VH FR2 comprising the amino acid sequence of SEQ ID NO: 212, VH FR3 comprising the amino acid sequence of SEQ ID NO: 218, and/or VL FR4 comprising the amino acid sequence of SEQ ID NO: 222;

hhh) the antibody of claim 1hhh, and VH FR1 comprising the amino acid sequence of SEQ ID NO: 205, VH FR2 comprising the amino acid sequence of SEQ ID NO: 213, VH FR3 comprising the amino acid sequence of SEQ ID NO: 220, and/or VL FR4 comprising the amino acid sequence of SEQ ID NO: 227;

iii) the antibody of claim 1iii, and VH FR1 comprising the amino acid sequence of SEQ ID NO: 208, VH FR2 comprising the amino acid sequence of SEQ ID NO: 210, VH FR3 comprising the amino acid sequence of SEQ ID NO: 216, and/or VL FR4 comprising the amino acid sequence of SEQ ID NO: 222;

jjj) the antibody of claim 1jjj, and VH FR1 comprising the amino acid sequence of SEQ ID NO: 205, VH FR2 comprising the amino acid sequence of SEQ ID NO: 213, VH FR3 comprising the amino acid sequence of SEQ ID NO: 220, and/or VL FR4 comprising the amino acid sequence of SEQ ID NO: 222;

kkk) the antibody of claim 1kkk, and VH FR1 comprising the amino acid sequence of SEQ ID NO: 201, VH FR2 comprising the amino acid sequence of SEQ ID NO: 210, VH FR3 comprising the amino acid sequence of SEQ ID NO: 216, and/or VL FR4 comprising the amino acid sequence of SEQ ID NO: 226;

lll) the antibody of claim 1lll, and VH FR1 comprising the amino acid sequence of SEQ ID NO: 207, VH FR2 comprising the amino acid sequence of SEQ ID NO: 213, VH FR3 comprising the amino acid sequence of SEQ ID NO: 220, and/or VL FR4 comprising the amino acid sequence of SEQ ID NO: 222;

mmm) the antibody of claim 1mmm, and VH FR1 comprising the amino acid sequence of SEQ ID NO: 202, VH FR2 comprising the amino acid sequence of SEQ ID NO: 211, VH FR3 comprising the amino acid sequence of SEQ ID NO: 216, and/or VL FR4 comprising the amino acid sequence of SEQ ID NO: 224;

nnn) the antibody of claim 1nnn, and VH FR1 comprising the amino acid sequence of SEQ ID NO: 207, VH FR2 comprising the amino acid sequence of SEQ ID NO: 213, VH FR3 comprising the amino acid sequence of SEQ ID NO: 220, and/or VL FR4 comprising the amino acid sequence of SEQ ID NO: 222: or ooo) the antibody of claim 1ooo, and VH FR1 comprising the amino acid sequence of SEQ ID NO: 204, VH FR2 comprising the amino acid sequence of SEQ ID NO: 212, VH FR3 comprising the amino acid sequence of SEQ ID NO: 219, and/or VL FR4 comprising the amino acid sequence of SEQ ID NO: 222.

4. The antibody of claim 1, wherein the antibody comprises:

a) the antibody of claim 1a, comprising a light chain variable region amino acid sequence that is at least 90%, at least 95%, at least 97%, or at least 99%, or 100% identical to the amino acid sequence of SEQ ID NO: 267;

b) the antibody of claim 1b, comprising a light chain variable region amino acid sequence that is at least 90%, at least 95%, at least 97%, or at least 99%, or 100% identical to the amino acid sequence of SEQ ID NO: 267;

c) the antibody of claim 1c, comprising a light chain variable region amino acid sequence that is at least 90%, at least 95%, at least 97%, or at least 99%, or 100% identical to the amino acid sequence of SEQ ID NO: 267;

d) the antibody of claim 1d, comprising a light chain variable region amino acid sequence that is at least 90%, at least 95%, at least 97%, or at least 99%, or 100% identical to the amino acid sequence of SEQ ID NO: 267;

e) the antibody of claim 1e, comprising a light chain variable region amino acid sequence that is at least 90%, at least 95%, at least 97%, or at least 99%, or 100% identical to the amino acid sequence of SEQ ID NO: 267;

f) the antibody of claim 1f, comprising a light chain variable region amino acid sequence that is at least 90%, at least 95%, at least 97%, or at least 99%, or 100% identical to the amino acid sequence of SEQ ID NO: 269;

g) the antibody of claim 1g, comprising a light chain variable region amino acid sequence that is at least 90%, at least 95%, at least 97%, or at least 99%, or 100% identical to the amino acid sequence of SEQ ID NO: 370;

h) the antibody of claim 1h, comprising a light chain variable region amino acid sequence that is at least 90%, at least 95%, at least 97%, or at least 99%, or 100% identical to the amino acid sequence of SEQ ID NO: 370;

i) the antibody of claim 1i, comprising a light chain variable region amino acid sequence that is at least 90%, at least 95%, at least 97%, or at least 99%, or 100% identical to the amino acid sequence of SEQ ID NO: 370;

j) the antibody of claim 1j, comprising a light chain variable region amino acid sequence that is at least 90%, at least 95%, at least 97%, or at least 99%, or 100% identical to the amino acid sequence of SEQ ID NO: 269;

k) the antibody of claim 1k, comprising a light chain variable region amino acid sequence that is at least 90%, at least 95%, at least 97%, or at least 99%, or 100% identical to the amino acid sequence of SEQ ID NO: 269;

l) the antibody of claim 1l, comprising a light chain variable region amino acid sequence that is at least 90%, at least 95%, at least 97%, or at least 99%, or 100% identical to the amino acid sequence of SEQ ID NO: 280;

m) the antibody of claim 1m, comprising a light chain variable region amino acid sequence that is at least 90%, at least 95%, at least 97%, or at least 99%, or 100% identical to the amino acid sequence of SEQ ID NO: 280;

n) the antibody of claim 1n, comprising a light chain variable region amino acid sequence that is at least 90%, at least 95%, at least 97%, or at least 99%, or 100% identical to the amino acid sequence of SEQ ID NO: 280;

o) the antibody of claim 1o, comprising a light chain variable region amino acid sequence that is at least 90%, at least 95%, at least 97%, or at least 99%, or 100% identical to the amino acid sequence of SEQ ID NO: 280;

p) the antibody of claim 1p, comprising a light chain variable region amino acid sequence that is at least 90%, at least 95%, at least 97%, or at least 99%, or 100% identical to the amino acid sequence of SEQ ID NO: 280;

q) the antibody of claim 1q, comprising a light chain variable region amino acid sequence that is at least 90%, at least 95%, at least 97%, or at least 99%, or 100% identical to the amino acid sequence of SEQ ID NO: 344;

r) the antibody of claim 1r, comprising a light chain variable region amino acid sequence that is at least 90%, at least 95%, at least 97%, or at least 99%, or 100% identical to the amino acid sequence of SEQ ID NO: 344;

s) the antibody of claim 1s, comprising a light chain variable region amino acid sequence that is at least 90%, at least 95%, at least 97%, or at least 99%, or 100% identical to the amino acid sequence of SEQ ID NO: 344;

t) the antibody of claim 1t, comprising a light chain variable region amino acid sequence that is at least 90%, at least 95%, at least 97%, or at least 99%, or 100% identical to the amino acid sequence of SEQ ID NO: 344;

u) the antibody of claim 1u, comprising a light chain variable region amino acid sequence that is at least 90%, at least 95%, at least 97%, or at least 99%, or 100% identical to the amino acid sequence of SEQ ID NO: 344;

v) the antibody of claim 1v, comprising a light chain variable region amino acid sequence that is at least 90%, at least 95%, at least 97%, or at least 99%, or 100% identical to the amino acid sequence of SEQ ID NO: 271;

w) the antibody of claim 1w, comprising a light chain variable region amino acid sequence that is at least 90%, at least 95%, at least 97%, or at least 99%, or 100% identical to the amino acid sequence of SEQ ID NO: 273;

x) the antibody of claim 1x, comprising a light chain variable region amino acid sequence that is at least 90%, at least 95%, at least 97%, or at least 99%, or 100% identical to the amino acid sequence of SEQ ID NO: 275;

y) the antibody of claim 1y, comprising a light chain variable region amino acid sequence that is at least 90%, at least 95%, at least 97%, or at least 99%, or 100% identical to the amino acid sequence of SEQ ID NO: 277;

z) the antibody of claim 1z, comprising a light chain variable region amino acid sequence that is at least 90%, at least 95%, at least 97%, or at least 99%, or 100% identical to the amino acid sequence of SEQ ID NO: 278;

aa) the antibody of claim 1aa, comprising a light chain variable region amino acid sequence that is at least 90%, at least 95%, at least 97%, or at least 99%, or 100% identical to the amino acid sequence of SEQ ID NO: 282;

bb) the antibody of claim 1bb, comprising a light chain variable region amino acid sequence that is at least 90%, at least 95%, at least 97%, or at least 99%, or 100% identical to the amino acid sequence of SEQ ID NO: 284;

cc) the antibody of claim 1cc, comprising a light chain variable region amino acid sequence that is at least 90%, at least 95%, at least 97%, or at least 99%, or 100% identical to the amino acid sequence of SEQ ID NO: 286;

dd) the antibody of claim 1dd, comprising a light chain variable region amino acid sequence that is at least 90%, at least 95%, at least 97%, or at least 99%, or 100% identical to the amino acid sequence of SEQ ID NO: 288;

ee) the antibody of claim 1ee, comprising a light chain variable region amino acid sequence that is at least 90%, at least 95%, at least 97%, or at least 99%, or 100% identical to the amino acid sequence of SEQ ID NO: 290;

ff) the antibody of claim 1ff, comprising a light chain variable region amino acid sequence that is at least 90%, at least 95%, at least 97%, or at least 99%, or 100% identical to the amino acid sequence of SEQ ID NO: 292;

gg) the antibody of claim 1gg, comprising a light chain variable region amino acid sequence that is at least 90%, at least 95%, at least 97%, or at least 99%, or 100% identical to the amino acid sequence of SEQ ID NO: 294;

hh) the antibody of claim 1hh, comprising a light chain variable region amino acid sequence that is at least 90%, at least 95%, at least 97%, or at least 99%, or 100% identical to the amino acid sequence of SEQ ID NO: 296;

ii) the antibody of claim 1ii, comprising a light chain variable region amino acid sequence that is at least 90%, at least 95%, at least 97%, or at least 99%, or 100% identical to the amino acid sequence of SEQ ID NO: 298;

jj) the antibody of claim 1jj, comprising a light chain variable region amino acid sequence that is at least 90%, at least 95%, at least 97%, or at least 99%, or 100% identical to the amino acid sequence of SEQ ID NO: 300;

kk) the antibody of claim 1kk, comprising a light chain variable region amino acid sequence that is at least 90%, at least 95%, at least 97%, or at least 99%, or 100% identical to the amino acid sequence of SEQ ID NO: 302;

ll) the antibody of claim 1ll, comprising a light chain variable region amino acid sequence that is at least 90%, at least 95%, at least 97%, or at least 99%, or 100% identical to the amino acid sequence of SEQ ID NO: 304;

mm) the antibody of claim 1mm, comprising a light chain variable region amino acid sequence that is at least 90%, at least 95%, at least 97%, or at least 99%, or 100% identical to the amino acid sequence of SEQ ID NO: 306;

nn) the antibody of claim 1nn, comprising a light chain variable region amino acid sequence that is at least 90%, at least 95%, at least 97%, or at least 99%, or 100% identical to the amino acid sequence of SEQ ID NO: 308;

oo) the antibody of claim 1oo, comprising a light chain variable region amino acid sequence that is at least 90%, at least 95%, at least 97%, or at least 99%, or 100% identical to the amino acid sequence of SEQ ID NO: 310;

pp) the antibody of claim 1pp, comprising a light chain variable region amino acid sequence that is at least 90%, at least 95%, at least 97%, or at least 99%, or 100% identical to the amino acid sequence of SEQ ID NO: 312;

qq) the antibody of claim 1qq, comprising a light chain variable region amino acid sequence that is at least 90%, at least 95%, at least 97%, or at least 99%, or 100% identical to the amino acid sequence of SEQ ID NO: 314;

rr) the antibody of claim 1rr, comprising a light chain variable region amino acid sequence that is at least 90%, at least 95%, at least 97%, or at least 99%, or 100% identical to the amino acid sequence of SEQ ID NO: 316;

ss) the antibody of claim 1ss, comprising a light chain variable region amino acid sequence that is at least 90%, at least 95%, at least 97%, or at least 99%, or 100% identical to the amino acid sequence of SEQ ID NO: 318;

tt) the antibody of claim 1tt, comprising a light chain variable region amino acid sequence that is at least 90%, at least 95%, at least 97%, or at least 99%, or 100% identical to the amino acid sequence of SEQ ID NO: 320;

uu) the antibody of claim 1uu, comprising a light chain variable region amino acid sequence that is at least 90%, at least 95%, at least 97%, or at least 99%, or 100% identical to the amino acid sequence of SEQ ID NO: 322;

vv) the antibody of claim 1vv, comprising a light chain variable region amino acid sequence that is at least 90%, at least 95%, at least 97%, or at least 99%, or 100% identical to the amino acid sequence of SEQ ID NO: 324;

ww) the antibody of claim 1ww, comprising a light chain variable region amino acid sequence that is at least 90%, at least 95%, at least 97%, or at least 99%, or 100% identical to the amino acid sequence of SEQ ID NO: 326;

xx) the antibody of claim 1xx, comprising a light chain variable region amino acid sequence that is at least 90%, at least 95%, at least 97%, or at least 99%, or 100% identical to the amino acid sequence of SEQ ID NO: 328;

yy) the antibody of claim 1yy, comprising a light chain variable region amino acid sequence that is at least 90%, at least 95%, at least 97%, or at least 99%, or 100% identical to the amino acid sequence of SEQ ID NO: 330;

zz) the antibody of claim 1zz, comprising a light chain variable region amino acid sequence that is at least 90%, at least 95%, at least 97%, or at least 99%, or 100% identical to the amino acid sequence of SEQ ID NO: 332;

aaa) the antibody of claim 1aaa, comprising a light chain variable region amino acid sequence that is at least 90%, at least 95%, at least 97%, or at least 99%, or 100% identical to the amino acid sequence of SEQ ID NO: 334;

bbb) the antibody of claim 1bbb, comprising a light chain variable region amino acid sequence that is at least 90%, at least 95%, at least 97%, or at least 99%, or 100% identical to the amino acid sequence of SEQ ID NO: 336;

ccc) the antibody of claim 1ccc, comprising a light chain variable region amino acid sequence that is at least 90%, at least 95%, at least 97%, or at least 99%, or 100% identical to the amino acid sequence of SEQ ID NO: 338;

ddd) the antibody of claim 1ddd, comprising a light chain variable region amino acid sequence that is at least 90%, at least 95%, at least 97%, or at least 99%, or 100% identical to the amino acid sequence of SEQ ID NO: 340;

eee) the antibody of claim 1eee, comprising a light chain variable region amino acid sequence that is at least 90%, at least 95%, at least 97%, or at least 99%, or 100% identical to the amino acid sequence of SEQ ID NO: 342;

fff) the antibody of claim 1fff, comprising a light chain variable region amino acid sequence that is at least 90%, at least 95%, at least 97%, or at least 99%, or 100% identical to the amino acid sequence of SEQ ID NO: 346;

ggg) the antibody of claim 1ggg, comprising a light chain variable region amino acid sequence that is at least 90%, at least 95%, at least 97%, or at least 99%, or 100% identical to the amino acid sequence of SEQ ID NO: 348;

hhh) the antibody of claim 1hhh, comprising a light chain variable region amino acid sequence that is at least 90%, at least 95%, at least 97%, or at least 99%, or 100% identical to the amino acid sequence of SEQ ID NO: 350;

iii) the antibody of claim 1iii comprising a light chain variable region amino acid sequence that is at least 90%, at least 95%, at least 97%, or at least 99%, or 100% identical to the amino acid sequence of SEQ ID NO: 352;

jjj) the antibody of claim 1jjj, comprising a light chain variable region amino acid sequence that is at least kkk) the antibody of claim 1kkk, comprising a light chain variable region amino acid sequence that is at least 90%, at least 95%, at least 97%, or at least 99%, or 100% identical to the amino acid sequence of SEQ ID NO: 356;

lll) the antibody of claim 1lll, comprising a light chain variable region amino acid sequence that is at least 90%, at least 95%, at least 97%, or at least 99%, or 100% identical to the amino acid sequence of SEQ ID NO: 358;

mmm) the antibody of claim 1mmm, comprising a light chain variable region amino acid sequence that is at least 90%, at least 95%, at least 97%, or at least 99%, or 100% identical to the amino acid sequence of SEQ ID NO: 360;

nnn) the antibody of claim 1nnn, comprising a light chain variable region amino acid sequence that is at least 90%, at least 95%, at least 97%, or at least 99%, or 100% identical to the amino acid sequence of SEQ ID NO: 362; or ooo) the antibody of claim 1ooo, comprising a light chain variable region amino acid sequence that is at least 90%, at least 95%, at least 97%, or at least 99%, or 100% identical to the amino acid sequence of SEQ ID NO: 364.

5. The antibody of claim 1, wherein the antibody comprises:

a) the antibody of claim 1a, comprising a heavy chain variable region amino acid sequence that is at least 90%, at least 95%, at least 97%, or at least 99%, or 100% identical to the amino acid sequence of SEQ ID NO: 268;

b) the antibody of claim 1b, comprising a heavy chain variable region amino acid sequence that is at least 90%, at least 95%, at least 97%, or at least 99%, or 100% identical to the amino acid sequence of SEQ ID NO: 366;

c) the antibody of claim 1c, comprising a heavy chain variable region amino acid sequence that is at least 90%, at least 95%, at least 97%, or at least 99%, or 100% identical to the amino acid sequence of SEQ ID NO: 367;

d) the antibody of claim 1d, comprising a heavy chain variable region amino acid sequence that is at least 90%, at least 95%, at least 97%, or at least 99%, or 100% identical to the amino acid sequence of SEQ ID NO: 368;

e) the antibody of claim 1e, comprising a heavy chain variable region amino acid sequence that is at least 90%, at least 95%, at least 97%, or at least 99%, or 100% identical to the amino acid sequence of SEQ ID NO: 369;

f) the antibody of claim 1f, comprising a heavy chain variable region amino acid sequence that is at least 90%, at least 95%, at least 97%, or at least 99%, or 100% identical to the amino acid sequence of SEQ ID NO: 270;

g) the antibody of claim 1g, comprising a heavy chain variable region amino acid sequence that is at least 90%, at least 95%, at least 97%, or at least 99%, or 100% identical to the amino acid sequence of SEQ ID NO: 371;

h) the antibody of claim 1h, comprising a heavy chain variable region amino acid sequence that is at least 90%, at least 95%, at least 97%, or at least 99%, or 100% identical to the amino acid sequence of SEQ ID NO: 372;

i) the antibody of claim 1i, comprising a heavy chain variable region amino acid sequence that is at least 90%, at least 95%, at least 97%, or at least 99%, or 100% identical to the amino acid sequence of SEQ ID NO: 373;

j) the antibody of claim 1j, comprising a heavy chain variable region amino acid sequence that is at least 90%, at least 95%, at least 97%, or at least 99%, or 100% identical to the amino acid sequence of SEQ ID NO: 374;

k) the antibody of claim 1k, comprising a heavy chain variable region amino acid sequence that is at least 90%, at least 95%, at least 97%, or at least 99%, or 100% identical to the amino acid sequence of SEQ ID NO: 375;

l) the antibody of claim 1l, comprising a heavy chain variable region amino acid sequence that is at least 90%, at least 95%, at least 97%, or at least 99%, or 100% identical to the amino acid sequence of SEQ ID NO: 281;

m) the antibody of claim 1m, comprising a heavy chain variable region amino acid sequence that is at least 90%, at least 95%, at least 97%, or at least 99%, or 100% identical to the amino acid sequence of SEQ ID NO: 376;

n) the antibody of claim 1n, comprising a heavy chain variable region amino acid sequence that is at least 90%, at least 95%, at least 97%, or at least 99%, or 100% identical to the amino acid sequence of SEQ ID NO: 377;

o) the antibody of claim 1o, comprising a heavy chain variable region amino acid sequence that is at least 90%, at least 95%, at least 97%, or at least 99%, or 100% identical to the amino acid sequence of SEQ ID NO: 377;

p) the antibody of claim 1p, comprising a heavy chain variable region amino acid sequence that is at least 90%, at least 95%, at least 97%, or at least 99%, or 100% identical to the amino acid sequence of SEQ ID NO: 378;

q) the antibody of claim 1q, comprising a heavy chain variable region amino acid sequence that is at least 90%, at least 95%, at least 97%, or at least 99%, or 100% identical to the amino acid sequence of SEQ ID NO: 345;

r) the antibody of claim 1r, comprising a heavy chain variable region amino acid sequence that is at least 90%, at least 95%, at least 97%, or at least 99%, or 100% identical to the amino acid sequence of SEQ ID NO: 379;

s) the antibody of claim 1s, comprising a heavy chain variable region amino acid sequence that is at least 90%, at least 95%, at least 97%, or at least 99%, or 100% identical to the amino acid sequence of SEQ ID NO: 380;

t) the antibody of claim 1t, comprising a heavy chain variable region amino acid sequence that is at least 90%, at least 95%, at least 97%, or at least 99%, or 100% identical to the amino acid sequence of SEQ ID NO: 381;

u) the antibody of claim 1u, comprising a heavy chain variable region amino acid sequence that is at least v) the antibody of claim 1v, comprising a heavy chain variable region amino acid sequence that is at least 90%, at least 95%, at least 97%, or at least 99%, or 100% identical to the amino acid sequence of SEQ ID NO: 272;

w) the antibody of claim 1w, comprising a heavy chain variable region amino acid sequence that is at least 90%, at least 95%, at least 97%, or at least 99%, or 100% identical to the amino acid sequence of SEQ ID NO: 274;

x) the antibody of claim 1x, comprising a heavy chain variable region amino acid sequence that is at least 90%, at least 95%, at least 97%, or at least 99%, or 100% identical to the amino acid sequence of SEQ ID NO: 276;

y) the antibody of claim 1y, comprising a heavy chain variable region amino acid sequence that is at least 90%, at least 95%, at least 97%, or at least 99%, or 100% identical to the amino acid sequence of SEQ ID NO: 268;

z) the antibody of claim 1z, comprising a heavy chain variable region amino acid sequence that is at least 90%, at least 95%, at least 97%, or at least 99%, or 100% identical to the amino acid sequence of SEQ ID NO: 279;

aa) the antibody of claim 1aa, comprising a heavy chain variable region amino acid sequence that is at least 90%, at least 95%, at least 97%, or at least 99%, or 100% identical to the amino acid sequence of SEQ ID NO: 283;

bb) the antibody of claim 1bb, comprising a heavy chain variable region amino acid sequence that is at least 90%, at least 95%, at least 97%, or at least 99%, or 100% identical to the amino acid sequence of SEQ ID NO: 285;

cc) the antibody of claim 1cc, comprising a heavy chain variable region amino acid sequence that is at least 90%, at least 95%, at least 97%, or at least 99%, or 100% identical to the amino acid sequence of SEQ ID NO: 287;

dd) the antibody of claim 1dd, comprising a heavy chain variable region amino acid sequence that is at least 90%, at least 95%, at least 97%, or at least 99%, or 100% identical to the amino acid sequence of SEQ ID NO: 289;

ee) the antibody of claim 1ee, comprising a heavy chain variable region amino acid sequence that is at least 90%, at least 95%, at least 97%, or at least 99%, or 100% identical to the amino acid sequence of SEQ ID NO: 291;

ff) the antibody of claim 1ff, comprising a heavy chain variable region amino acid sequence that is at least 90%, at least 95%, at least 97%, or at least 99%, or 100% identical to the amino acid sequence of SEQ ID NO: 293;

gg) the antibody of claim 1gg, comprising a heavy chain variable region amino acid sequence that is at least 90%, at least 95%, at least 97%, or at least 99%, or 100% identical to the amino acid sequence of SEQ ID NO: 295;

hh) the antibody of claim 1hh, comprising a heavy chain variable region amino acid sequence that is at least 90%, at least 95%, at least 97%, or at least 99%, or 100% identical to the amino acid sequence of SEQ ID NO: 297;

ii) the antibody of claim 1ii, comprising a heavy chain variable region amino acid sequence that is at least 90%, at least 95%, at least 97%, or at least 99%, or 100% identical to the amino acid sequence of SEQ ID NO: 299;

jj) the antibody of claim 1jj, comprising a heavy chain variable region amino acid sequence that is at least 90%, at least 95%, at least 97%, or at least 99%, or 100% identical to the amino acid sequence of SEQ ID NO: 301;

kk) the antibody of claim 1kk, comprising a heavy chain variable region amino acid sequence that is at least 90%, at least 95%, at least 97%, or at least 99%, or 100% identical to the amino acid sequence of SEQ ID NO: 303;

ll) the antibody of claim 1ll, comprising a heavy chain variable region amino acid sequence that is at least 90%, at least 95%, at least 97%, or at least 99%, or 100% identical to the amino acid sequence of SEQ ID NO: 305;

mm) the antibody of claim 1mm, comprising a heavy chain variable region amino acid sequence that is at least 90%, at least 95%, at least 97%, or at least 99%, or 100% identical to the amino acid sequence of SEQ ID NO: 307;

nn) the antibody of claim 1nn, comprising a heavy chain variable region amino acid sequence that is at least 90%, at least 95%, at least 97%, or at least 99%, or 100% identical to the amino acid sequence of SEQ ID NO: 309;

oo) the antibody of claim 1oo, comprising a heavy chain variable region amino acid sequence that is at least 90%, at least 95%, at least 97%, or at least 99%, or 100% identical to the amino acid sequence of SEQ ID NO: 311;

pp) the antibody of claim 1pp, comprising a heavy chain variable region amino acid sequence that is at least 90%, at least 95%, at least 97%, or at least 99%, or 100% identical to the amino acid sequence of SEQ ID NO: 313;

qq) the antibody of claim 1qq, comprising a heavy chain variable region amino acid sequence that is at least 90%, at least 95%, at least 97%, or at least 99%, or 100% identical to the amino acid sequence of SEQ ID NO: 315;

rr) the antibody of claim 1rr, comprising a heavy chain variable region amino acid sequence that is at least 90%, at least 95%, at least 97%, or at least 99%, or 100% identical to the amino acid sequence of SEQ ID NO: 317;

ss) the antibody of claim 1ss, comprising a heavy chain variable region amino acid sequence that is at least 90%, at least 95%, at least 97%, or at least 99%, or 100% identical to the amino acid sequence of SEQ ID NO: 319;

tt) the antibody of claim 1tt, comprising a heavy chain variable region amino acid sequence that is at least 90%, at least 95%, at least 97%, or at least 99%, or 100% identical to the amino acid sequence of SEQ ID NO: 321;

uu) the antibody of claim 1uu, comprising a heavy chain variable region amino acid sequence that is at least 90%, at least 95%, at least 97%, or at least 99%, or 100% identical to the amino acid sequence of SEQ ID NO: 323;
vv) the antibody of claim 1vv, comprising a heavy chain variable region amino acid sequence that is at least 90%, at least 95%, at least 97%, or at least 99%, or 100% identical to the amino acid sequence of SEQ ID NO: 325;
ww) the antibody of claim 1ww, comprising a heavy chain variable region amino acid sequence that is at least 90%, at least 95%, at least 97%, or at least 99%, or 100% identical to the amino acid sequence of SEQ ID NO: 327;
xx) the antibody of claim 1xx, comprising a heavy chain variable region amino acid sequence that is at least 90%, at least 95%, at least 97%, or at least 99%, or 100% identical to the amino acid sequence of SEQ ID NO: 329;
yy) the antibody of claim 1yy, comprising a heavy chain variable region amino acid sequence that is at least 90%, at least 95%, at least 97%, or at least 99%, or 100% identical to the amino acid sequence of SEQ ID NO: 331;
zz) the antibody of claim 1zz, comprising a heavy chain variable region amino acid sequence that is at least 90%, at least 95%, at least 97%, or at least 99%, or 100% identical to the amino acid sequence of SEQ ID NO: 333;
aaa) the antibody of claim 1aaa, comprising a heavy chain variable region amino acid sequence that is at least 90%, at least 95%, at least 97%, or at least 99%, or 100% identical to the amino acid sequence of SEQ ID NO: 335;
bbb) the antibody of claim 1bbb, comprising a heavy chain variable region amino acid sequence that is at least 90%, at least 95%, at least 97%, or at least 99%, or 100% identical to the amino acid sequence of SEQ ID NO: 337;
ccc) the antibody of claim 1ccc, comprising a heavy chain variable region amino acid sequence that is at least 90%, at least 95%, at least 97%, or at least 99%, or 100% identical to the amino acid sequence of SEQ ID NO: 339;
ddd) the antibody of claim 1ddd, comprising a heavy chain variable region amino acid sequence that is at least 90%, at least 95%, at least 97%, or at least 99%, or 100% identical to the amino acid sequence of SEQ ID NO: 341;
eee) the antibody of claim 1eee, comprising a heavy chain variable region amino acid sequence that is at least 90%, at least 95%, at least 97%, or at least 99%, or 100% identical to the amino acid sequence of SEQ ID NO: 343;
fff) the antibody of claim 1fff, comprising a heavy chain variable region amino acid sequence that is at least 90%, at least 95%, at least 97%, or at least 99%, or 100% identical to the amino acid sequence of SEQ ID NO: 347;
ggg) the antibody of claim 1ggg, comprising a heavy chain variable region amino acid sequence that is at least 90%, at least 95%, at least 97%, or at least 99%, or 100% identical to the amino acid sequence of SEQ ID NO: 349;
hhh) the antibody of claim 1hhh, comprising a heavy chain variable region amino acid sequence that is at least 90%, at least 95%, at least 97%, or at least 99%, or 100% identical to the amino acid sequence of SEQ ID NO: 351;
iii) the antibody of claim 1iii, comprising a heavy chain variable region amino acid sequence that is at least 90%, at least 95%, at least 97%, or at least 99%, or 100% identical to the amino acid sequence of SEQ ID NO: 353;
jjj) the antibody of claim 1jjj, comprising a heavy chain variable region amino acid sequence that is at least 90%, at least 95%, at least 97%, or at least 99%, or 100% identical to the amino acid sequence of SEQ ID NO: 355;
kkk) the antibody of claim 1kkk, comprising a heavy chain variable region amino acid sequence that is at least 90%, at least 95%, at least 97%, or at least 99%, or 100% identical to the amino acid sequence of SEQ ID NO: 357;
lll) the antibody of claim 1lll, comprising a heavy chain variable region amino acid sequence that is at least 90%, at least 95%, at least 97%, or at least 99%, or 100% identical to the amino acid sequence of SEQ ID NO: 359;
mmm) the antibody of claim 1mmm, comprising a heavy chain variable region amino acid sequence that is at least 90%, at least 95%, at least 97%, or at least 99%, or 100% identical to the amino acid sequence of SEQ ID NO: 361;
nnn) the antibody of claim 1nnn, comprising a heavy chain variable region amino acid sequence that is at least 90%, at least 95%, at least 97%, or at least 99%, or 100% identical to the amino acid sequence of SEQ ID NO: 363; or
ooo) the antibody of claim 1ooo, comprising a heavy chain variable region amino acid sequence that is at least 90%, at least 95%, at least 97%, or at least 99%, or 100% identical to the amino acid sequence of SEQ ID NO: 365.

6. The antibody of claim 1, wherein the antibody comprises:
a) the antibody of claim 1a, comprising a heavy chain variable region amino acid sequence that is at least 90%, at least 95%, at least 97%, or at least 99%, or 100% identical to the amino acid sequence of SEQ ID NO: 268 and a light chain variable region amino acid sequence that is at least 90%, at least 95%, at least 97%, or at least 99%, or 100% identical to the amino acid sequence of SEQ ID NO: 267;
b) the antibody of claim 1b, comprising a heavy chain variable region amino acid sequence that is at least 90%, at least 95%, at least 97%, or at least 99%, or 100% identical to the amino acid sequence of SEQ ID NO: 366 and a light chain variable region amino acid sequence that is at least 90%, at least 95%, at least 97%, or at least 99%, or 100% identical to the amino acid sequence of SEQ ID NO: 267;
c) the antibody of claim 1c, comprising a heavy chain variable region amino acid sequence that is at least 90%, at least 95%, at least 97%, or at least 99%, or 100% identical to the amino acid sequence of SEQ ID NO: 367 and a light chain variable region amino acid sequence that is at least 90%, at least 95%, at least 97%, or at least 99%, or 100% identical to the amino acid sequence of SEQ ID NO: 267;
d) the antibody of claim 1d, comprising a heavy chain variable region amino acid sequence that is at least 90%, at least 95%, at least 97%, or at least 99%, or 100% identical to the amino acid sequence of SEQ ID NO: 368 and a light chain variable region amino acid sequence that is at least 90%, at least 95%, at least 97%, or at least 99%, or 100% identical to the amino acid sequence of SEQ ID NO: 267;

e) the antibody of claim 1e, comprising a heavy chain variable region amino acid sequence that is at least 90%, at least 95%, at least 97%, or at least 99%, or 100% identical to the amino acid sequence of SEQ ID NO: 369 and a light chain variable region amino acid sequence that is at least 90%, at least 95%, at least 97%, or at least 99%, or 100% identical to the amino acid sequence of SEQ ID NO: 267;

f) the antibody of claim 1f, comprising a heavy chain variable region amino acid sequence that is at least 90%, at least 95%, at least 97%, or at least 99%, or 100% identical to the amino acid sequence of SEQ ID NO: 270 and a light chain variable region amino acid sequence that is at least 90%, at least 95%, at least 97%, or at least 99%, or 100% identical to the amino acid sequence of SEQ ID NO: 269;

g) the antibody of claim 1g, comprising a heavy chain variable region amino acid sequence that is at least 90%, at least 95%, at least 97%, or at least 99%, or 100% identical to the amino acid sequence of SEQ ID NO: 371 and a light chain variable region amino acid sequence that is at least 90%, at least 95%, at least 97%, or at least 99%, or 100% identical to the amino acid sequence of SEQ ID NO: 370;

h) the antibody of claim 1h, comprising a heavy chain variable region amino acid sequence that is at least 90%, at least 95%, at least 97%, or at least 99%, or 100% identical to the amino acid sequence of SEQ ID NO: 372 and a light chain variable region amino acid sequence that is at least 90%, at least 95%, at least 97%, or at least 99%, or 100% identical to the amino acid sequence of SEQ ID NO: 370;

i) the antibody of claim 1i, comprising a heavy chain variable region amino acid sequence that is at least 90%, at least 95%, at least 97%, or at least 99%, or 100% identical to the amino acid sequence of SEQ ID NO: 373 and a light chain variable region amino acid sequence that is at least 90%, at least 95%, at least 97%, or at least 99%, or 100% identical to the amino acid sequence of SEQ ID NO: 370;

j) the antibody of claim 1j, comprising a heavy chain variable region amino acid sequence that is at least 90%, at least 95%, at least 97%, or at least 99%, or 100% identical to the amino acid sequence of SEQ ID NO: 374 and a light chain variable region amino acid sequence that is at least 90%, at least 95%, at least 97%, or at least 99%, or 100% identical to the amino acid sequence of SEQ ID NO: 269;

k) the antibody of claim 1k, comprising a heavy chain variable region amino acid sequence that is at least 90%, at least 95%, at least 97%, or at least 99%, or 100% identical to the amino acid sequence of SEQ ID NO: 375 and a light chain variable region amino acid sequence that is at least 90%, at least 95%, at least 97%, or at least 99%, or 100% identical to the amino acid sequence of SEQ ID NO: 269;

l) the antibody of claim 1l, comprising a heavy chain variable region amino acid sequence that is at least 90%, at least 95%, at least 97%, or at least 99%, or 100% identical to the amino acid sequence of SEQ ID NO: 281 and a light chain variable region amino acid sequence that is at least 90%, at least 95%, at least 97%, or at least 99%, or 100% identical to the amino acid sequence of SEQ ID NO: 280;

m) the antibody of claim 1m, comprising a heavy chain variable region amino acid sequence that is at least 90%, at least 95%, at least 97%, or at least 99%, or 100% identical to the amino acid sequence of SEQ ID NO: 376 and a light chain variable region amino acid sequence that is at least 90%, at least 95%, at least 97%, or at least 99%, or 100% identical to the amino acid sequence of SEQ ID NO: 280;

n) the antibody of claim 1n, comprising a heavy chain variable region amino acid sequence that is at least 90%, at least 95%, at least 97%, or at least 99%, or 100% identical to the amino acid sequence of SEQ ID NO: 377 and a light chain variable region amino acid sequence that is at least 90%, at least 95%, at least 97%, or at least 99%, or 100% identical to the amino acid sequence of SEQ ID NO: 280;

o) the antibody of claim 1o, comprising a heavy chain variable region amino acid sequence that is at least 90%, at least 95%, at least 97%, or at least 99%, or 100% identical to the amino acid sequence of SEQ ID NO: 377 and a light chain variable region amino acid sequence that is at least 90%, at least 95%, at least 97%, or at least 99%, or 100% identical to the amino acid sequence of SEQ ID NO: 280;

p) the antibody of claim 1p, comprising a heavy chain variable region amino acid sequence that is at least 90%, at least 95%, at least 97%, or at least 99%, or 100% identical to the amino acid sequence of SEQ ID NO: 378 and a light chain variable region amino acid sequence that is at least 90%, at least 95%, at least 97%, or at least 99%, or 100% identical to the amino acid sequence of SEQ ID NO: 280;

q) the antibody of claim 1q, comprising a heavy chain variable region amino acid sequence that is at least 90%, at least 95%, at least 97%, or at least 99%, or 100% identical to the amino acid sequence of SEQ ID NO: 345 and a light chain variable region amino acid sequence that is at least 90%, at least 95%, at least 97%, or at least 99%, or 100% identical to the amino acid sequence of SEQ ID NO: 344;

r) the antibody of claim 1r, comprising a heavy chain variable region amino acid sequence that is at least 90%, at least 95%, at least 97%, or at least 99%, or 100% identical to the amino acid sequence of SEQ ID NO: 379 and a light chain variable region amino acid sequence that is at least 90%, at least 95%, at least 97%, or at least 99%, or 100% identical to the amino acid sequence of SEQ ID NO: 344;

s) the antibody of claim 1s, comprising a heavy chain variable region amino acid sequence that is at least 90%, at least 95%, at least 97%, or at least 99%, or 100% identical to the amino acid sequence of SEQ ID NO: 380 and a light chain variable region amino acid sequence that is at least 90%, at least 95%, at least 97%, or at least 99%, or 100% identical to the amino acid sequence of SEQ ID NO: 344;

t) the antibody of claim 1t, comprising a heavy chain variable region amino acid sequence that is at least 90%, at least 95%, at least 97%, or at least 99%, or 100% identical to the amino acid sequence of SEQ ID NO: 381 and a light chain variable region amino acid sequence that is at least 90%, at least 95%, at least 97%, or at least 99%, or 100% identical to the amino acid sequence of SEQ ID NO: 344;

u) the antibody of claim 1u, comprising a heavy chain variable region amino acid sequence that is at least 90%, at least 95%, at least 97%, or at least 99%, or 100% identical to the amino acid sequence of SEQ ID NO: 382 and a light chain variable region amino acid sequence that is at least 90%, at least 95%, at least 97%, or at least 99%, or 100% identical to the amino acid sequence of SEQ ID NO: 344;

v) the antibody of claim 1v, comprising a light chain variable region amino acid sequence that is at least 90%, at least 95%, at least 97%, or at least 99%, or 100% identical to the amino acid sequence of SEQ ID NO: 271, and a heavy chain variable region amino acid sequence that is at least 90%, at least 95%, at least 97%, or at least 99%, or 100% identical to the amino acid sequence of SEQ ID NO: 272;

w) the antibody of claim 1w, comprising a light chain variable region amino acid sequence that is at least 90%, at least 95%, at least 97%, or at least 99%, or 100% identical to the amino acid sequence of SEQ ID NO: 273, and a heavy chain variable region amino acid sequence that is at least 90%, at least 95%, at least 97%, or at least 99%, or 100% identical to the amino acid sequence of SEQ ID NO: 274;

x) the antibody of claim 1x, comprising a light chain variable region amino acid sequence that is at least 90%, at least 95%, at least 97%, or at least 99%, or 100% identical to the amino acid sequence of SEQ ID NO: 275, and a heavy chain variable region amino acid sequence that is at least 90%, at least 95%, at least 97%, or at least 99%, or 100% identical to the amino acid sequence of SEQ ID NO: 276;

y) the antibody of claim 1y, comprising a light chain variable region amino acid sequence that is at least 90%, at least 95%, at least 97%, or at least 99%, or 100% identical to the amino acid sequence of SEQ ID NO: 277, and a heavy chain variable region amino acid sequence that is at least 90%, at least 95%, at least 97%, or at least 99%, or 100% identical to the amino acid sequence of SEQ ID NO: 268;

z) the antibody of claim 1z, comprising a light chain variable region amino acid sequence that is at least 90%, at least 95%, at least 97%, or at least 99%, or 100% identical to the amino acid sequence of SEQ ID NO: 278, and a heavy chain variable region amino acid sequence that is at least 90%, at least 95%, at least 97%, or at least 99%, or 100% identical to the amino acid sequence of SEQ ID NO: 279;

aa) the antibody of claim 1aa, comprising a light chain variable region amino acid sequence that is at least 90%, at least 95%, at least 97%, or at least 99%, or 100% identical to the amino acid sequence of SEQ ID NO: 282; and a heavy chain variable region amino acid sequence that is at least 90%, at least 95%, at least 97%, or at least 99%, or 100% identical to the amino acid sequence of SEQ ID NO: 283;

bb) the antibody of claim 1bb, comprising a light chain variable region amino acid sequence that is at least 90%, at least 95%, at least 97%, or at least 99%, or 100% identical to the amino acid sequence of SEQ ID NO: 284, and a heavy chain variable region amino acid sequence that is at least 90%, at least 95%, at least 97%, or at least 99%, or 100% identical to the amino acid sequence of SEQ ID NO: 285;

cc) the antibody of claim 1cc, comprising a light chain variable region amino acid sequence that is at least 90%, at least 95%, at least 97%, or at least 99%, or 100% identical to the amino acid sequence of SEQ ID NO: 286, and a heavy chain variable region amino acid sequence that is at least 90%, at least 95%, at least 97%, or at least 99%, or 100% identical to the amino acid sequence of SEQ ID NO: 287;

dd) the antibody of claim 1dd, comprising a light chain variable region amino acid sequence that is at least 90%, at least 95%, at least 97%, or at least 99%, or 100% identical to the amino acid sequence of SEQ ID NO: 288, and a heavy chain variable region amino acid sequence that is at least 90%, at least 95%, at least 97%, or at least 99%, or 100% identical to the amino acid sequence of SEQ ID NO: 289;

ee) the antibody of claim 1ee, comprising a light chain variable region amino acid sequence that is at least 90%, at least 95%, at least 97%, or at least 99%, or 100% identical to the amino acid sequence of SEQ ID NO: 290, and a heavy chain variable region amino acid sequence that is at least 90%, at least 95%, at least 97%, or at least 99%, or 100% identical to the amino acid sequence of SEQ ID NO: 291;

ff) the antibody of claim 1ff, comprising a light chain variable region amino acid sequence that is at least 90%, at least 95%, at least 97%, or at least 99%, or 100% identical to the amino acid sequence of SEQ ID NO: 292, and a heavy chain variable region amino acid sequence that is at least 90%, at least 95%, at least 97%, or at least 99%, or 100% identical to the amino acid sequence of SEQ ID NO: 293;

gg) the antibody of claim 1gg, comprising a light chain variable region amino acid sequence that is at least 90%, at least 95%, at least 97%, or at least 99%, or 100% identical to the amino acid sequence of SEQ ID NO: 294, and a heavy chain variable region amino acid sequence that is at least 90%, at least 95%, at least 97%, or at least 99%, or 100% identical to the amino acid sequence of SEQ ID NO: 295;

hh) the antibody of claim 1hh, comprising a light chain variable region amino acid sequence that is at least 90%, at least 95%, at least 97%, or at least 99%, or 100% identical to the amino acid sequence of SEQ ID NO: 296, and a heavy chain variable region amino acid sequence that is at least 90%, at least 95%, at least 97%, or at least 99%, or 100% identical to the amino acid sequence of SEQ ID NO: 297;

ii) the antibody of claim 1ii, comprising a light chain variable region amino acid sequence that is at least 90%, at least 95%, at least 97%, or at least 99%, or 100% identical to the amino acid sequence of SEQ ID NO: 298, and a heavy chain variable region amino acid sequence that is at least 90%, at least 95%, at least 97%, or at least 99%, or 100% identical to the amino acid sequence of SEQ ID NO: 299;

jj) the antibody of claim 1jj, comprising a light chain variable region amino acid sequence that is at least 90%, at least 95%, at least 97%, or at least 99%, or 100% identical to the amino acid sequence of SEQ ID NO: 300, and a heavy chain variable region amino acid sequence that is at least 90%, at least 95%, at least 97%, or at least 99%, or 100% identical to the amino acid sequence of SEQ ID NO: 301;

kk) the antibody of claim 1kk, comprising a light chain variable region amino acid sequence that is at least 90%, at least 95%, at least 97%, or at least 99%, or 100% identical to the amino acid sequence of SEQ ID NO: 302, and a heavy chain variable region amino acid sequence that is at least 90%, at least 95%, at least 97%, ll) the antibody of claim 1ll, comprising a light chain variable region amino acid sequence that is at least 90%, at least 95%, at least 97%, or at least 99%, or 100% identical to the amino acid sequence of SEQ ID NO: 304; and a heavy chain variable region amino acid sequence that is at least 90%, at least 95%, at least 97%, or at least 99%, or 100% identical to the amino acid sequence of SEQ ID NO: 305;

mm) the antibody of claim 1mm, comprising a light chain variable region amino acid sequence that is at least 90%, at least 95%, at least 97%, or at least 99%, or 100% identical to the amino acid sequence of SEQ ID NO: 306, and a heavy chain variable region amino acid sequence that is at least 90%, at least 95%, at least 97%, or at least 99%, or 100% identical to the amino acid sequence of SEQ ID NO: 307;

nn) the antibody of claim 1nn, comprising a light chain variable region amino acid sequence that is at least 90%, at least 95%, at least 97%, or at least 99%, or 100% identical to the amino acid sequence of SEQ ID NO: 308, and a heavy chain variable region amino acid sequence that is at least 90%, at least 95%, at least 97%, or at least 99%, or 100% identical to the amino acid sequence of SEQ ID NO: 309;

oo) the antibody of claim 1oo, comprising a light chain variable region amino acid sequence that is at least 90%, at least 95%, at least 97%, or at least 99%, or 100% identical to the amino acid sequence of SEQ ID NO: 310, and a heavy chain variable region amino acid sequence that is at least 90%, at least 95%, at least 97%, or at least 99%, or 100% identical to the amino acid sequence of SEQ ID NO: 311;

pp) the antibody of claim 1pp, comprising a light chain variable region amino acid sequence that is at least 90%, at least 95%, at least 97%, or at least 99%, or 100% identical to the amino acid sequence of SEQ ID NO: 312, and a heavy chain variable region amino acid sequence that is at least 90%, at least 95%, at least 97%, or at least 99%, or 100% identical to the amino acid sequence of SEQ ID NO: 313;

qq) the antibody of claim 1qq, comprising a light chain variable region amino acid sequence that is at least 90%, at least 95%, at least 97%, or at least 99%, or 100% identical to the amino acid sequence of SEQ ID NO: 314, and a heavy chain variable region amino acid sequence that is at least 90%, at least 95%, at least 97%, or at least 99%, or 100% identical to the amino acid sequence of SEQ ID NO: 315;

rr) the antibody of claim 1rr, comprising a light chain variable region amino acid sequence that is at least 90%, at least 95%, at least 97%, or at least 99%, or 100% identical to the amino acid sequence of SEQ ID NO: 316, and a heavy chain variable region amino acid sequence that is at least 90%, at least 95%, at least 97%, or at least 99%, or 100% identical to the amino acid sequence of SEQ ID NO: 317;

ss) the antibody of claim 1ss, comprising a light chain variable region amino acid sequence that is at least 90%, at least 95%, at least 97%, or at least 99%, or 100% identical to the amino acid sequence of SEQ ID NO: 318, and a heavy chain variable region amino acid sequence that is at least 90%, at least 95%, at least 97%, or at least 99%, or 100% identical to the amino acid sequence of SEQ ID NO: 319;

tt) the antibody of claim 1tt, comprising a light chain variable region amino acid sequence that is at least 90%, at least 95%, at least 97%, or at least 99%, or 100% identical to the amino acid sequence of SEQ ID NO: 320, and a heavy chain variable region amino acid sequence that is at least 90%, at least 95%, at least 97%, or at least 99%, or 100% identical to the amino acid sequence of SEQ ID NO: 321;

uu) the antibody of claim 1uu, comprising a light chain variable region amino acid sequence that is at least 90%, at least 95%, at least 97%, or at least 99%, or 100% identical to the amino acid sequence of SEQ ID NO: 322, and a heavy chain variable region amino acid sequence that is at least 90%, at least 95%, at least 97%, or at least 99%, or 100% identical to the amino acid sequence of SEQ ID NO: 323;

vv) the antibody of claim 1vv, comprising a light chain variable region amino acid sequence that is at least 90%, at least 95%, at least 97%, or at least 99%, or 100% identical to the amino acid sequence of SEQ ID NO: 324, and a heavy chain variable region amino acid sequence that is at least 90%, at least 95%, at least 97%, or at least 99%, or 100% identical to the amino acid sequence of SEQ ID NO: 325;

ww) the antibody of claim 1ww, comprising a light chain variable region amino acid sequence that is at least 90%, at least 95%, at least 97%, or at least 99%, or 100% identical to the amino acid sequence of SEQ ID NO: 326, and a heavy chain variable region amino acid sequence that is at least 90%, at least 95%, at least 97%, or at least 99%, or 100% identical to the amino acid sequence of SEQ ID NO: 327;

xx) the antibody of claim 1xx, comprising a light chain variable region amino acid sequence that is at least 90%, at least 95%, at least 97%, or at least 99%, or 100% identical to the amino acid sequence of SEQ ID NO: 328, and a heavy chain variable region amino acid sequence that is at least 90%, at least 95%, at least 97%, or at least 99%, or 100% identical to the amino acid sequence of SEQ ID NO: 329;

yy) the antibody of claim 1yy, comprising a light chain variable region amino acid sequence that is at least 90%, at least 95%, at least 97%, or at least 99%, or 100% identical to the amino acid sequence of SEQ ID NO: 330, and a heavy chain variable region amino acid sequence that is at least 90%, at least 95%, at least 97%, or at least 99%, or 100% identical to the amino acid sequence of SEQ ID NO: 331;

zz) the antibody of claim 1zz, comprising a light chain variable region amino acid sequence that is at least 90%, at least 95%, at least 97%, or at least 99%, or 100% identical to the amino acid sequence of SEQ ID NO: 332, and a heavy chain variable region amino acid sequence that is at least 90%, at least 95%, at least 97%, or at least 99%, or 100% identical to the amino acid sequence of SEQ ID NO: 333;

aaa) the antibody of claim 1aaa, comprising a light chain variable region amino acid sequence that is at least 90%, at least 95%, at least 97%, or at least 99%, or 100% identical to the amino acid sequence of SEQ ID NO: 334, and a heavy chain variable region amino acid sequence that is at least 90%, at least 95%, at least 97%, or at least 99%, or 100% identical to the amino acid sequence of SEQ ID NO: 335;

bbb) the antibody of claim 1bbb, comprising a light chain variable region amino acid sequence that is at least 90%, at least 95%, at least 97%, or at least 99%, or 100% identical to the amino acid sequence of SEQ ID NO: 336, and a heavy chain variable region amino acid sequence that is at least 90%, at least 95%, at least 97%, or at least 99%, or 100% identical to the amino acid sequence of SEQ ID NO: 337;

ccc) the antibody of claim 1ccc, comprising a light chain variable region amino acid sequence that is at least 90%, at least 95%, at least 97%, or at least 99%, or 100% identical to the amino acid sequence of SEQ ID NO: 338, and a heavy chain variable region amino acid sequence that is at least 90%, at least 95%, at least 97%, or at least 99%, or 100% identical to the amino acid sequence of SEQ ID NO: 339;

ddd) the antibody of claim 1ddd, comprising a light chain variable region amino acid sequence that is at least 90%, at least 95%, at least 97%, or at least 99%, or 100% identical to the amino acid sequence of SEQ ID NO: 340, and a heavy chain variable region amino acid sequence that is at least 90%, at least 95%, at least 97%, or at least 99%, or 100% identical to the amino acid sequence of SEQ ID NO: 341;

eee) the antibody of claim 1eee, comprising a light chain variable region amino acid sequence that is at least 90%, at least 95%, at least 97%, or at least 99%, or 100% identical to the amino acid sequence of SEQ ID NO: 342, and a heavy chain variable region amino acid sequence that is at least 90%, at least 95%, at least 97%, or at least 99%, or 100% identical to the amino acid sequence of SEQ ID NO: 343;

fff) the antibody of claim 1fff, comprising a light chain variable region amino acid sequence that is at least 90%, at least 95%, at least 97%, or at least 99%, or 100% identical to the amino acid sequence of SEQ ID NO: 346; and a heavy chain variable region amino acid sequence that is at least 90%, at least 95%, at least 97%, or at least 99%, or 100% identical to the amino acid sequence of SEQ ID NO: 347;

ggg) the antibody of claim 1ggg, comprising a light chain variable region amino acid sequence that is at least 90%, at least 95%, at least 97%, or at least 99%, or 100% identical to the amino acid sequence of SEQ ID NO: 348, and a heavy chain variable region amino acid sequence that is at least 90%, at least 95%, at least 97%, or at least 99%, or 100% identical to the amino acid sequence of SEQ ID NO: 349;

hhh) the antibody of claim 1hhh, comprising a light chain variable region amino acid sequence that is at least 90%, at least 95%, at least 97%, or at least 99%, or 100% identical to the amino acid sequence of SEQ ID NO: 350, and a heavy chain variable region amino acid sequence that is at least 90%, at least 95%, at least 97%, or at least 99%, or 100% identical to the amino acid sequence of SEQ ID NO: 351;

iii) the antibody of claim 1iii, comprising a light chain variable region amino acid sequence that is at least 90%, at least 95%, at least 97%, or at least 99%, or 100% identical to the amino acid sequence of SEQ ID NO: 352, and a heavy chain variable region amino acid sequence that is at least 90%, at least 95%, at least 97%, or at least 99%, or 100% identical to the amino acid sequence of SEQ ID NO: 353;

jjj) the antibody of claim 1jjj, comprising a light chain variable region amino acid sequence that is at least 90%, at least 95%, at least 97%, or at least 99%, or 100% identical to the amino acid sequence of SEQ ID NO: 354, and a heavy chain variable region amino acid sequence that is at least 90%, at least 95%, at least 97%, or at least 99%, or 100% identical to the amino acid sequence of SEQ ID NO: 355;

kkk) the antibody of claim 1kkk, comprising a light chain variable region amino acid sequence that is at least 90%, at least 95%, at least 97%, or at least 99%, or 100% identical to the amino acid sequence of SEQ ID NO: 356, and a heavy chain variable region amino acid sequence that is at least 90%, at least 95%, at least 97%, or at least 99%, or 100% identical to the amino acid sequence of SEQ ID NO: 357;

lll) the antibody of claim 1lll, comprising a light chain variable region amino acid sequence that is at least 90%, at least 95%, at least 97%, or at least 99%, or 100% identical to the amino acid sequence of SEQ ID NO: 358, and a heavy chain variable region amino acid sequence that is at least 90%, at least 95%, at least 97%, or at least 99%, or 100% identical to the amino acid sequence of SEQ ID NO: 359;

mmm) the antibody of claim 1mmm, comprising a light chain variable region amino acid sequence that is at least 90%, at least 95%, at least 97%, or at least 99%, or 100% identical to the amino acid sequence of SEQ ID NO: 360, and a heavy chain variable region amino acid sequence that is at least 90%, at least 95%, at least 97%, or at least 99%, or 100% identical to the amino acid sequence of SEQ ID NO: 361;

nnn) the antibody of claim 1nnn, comprising a light chain variable region amino acid sequence that is at least 90%, at least 95%, at least 97%, or at least 99%, or 100% identical to the amino acid sequence of SEQ ID NO: 362; or, and a heavy chain variable region amino acid sequence that is at least 90%, at least 95%, at least 97%, or at least 99%, or 100% identical to the amino acid sequence of SEQ ID NO: 363; or ooo) the antibody of claim 1ooo, comprising a light chain variable region amino acid sequence that is at least 90%, at least 95%, at least 97%, or at least 99%, or 100% identical to the amino acid sequence of SEQ ID NO: 364, and a heavy chain variable region amino acid sequence that is at least 90%, at least 95%, at least 97%, or at least 99%, or 100% identical to the amino acid sequence of SEQ ID NO: 365.

7. The antibody of claim 1, wherein the antibody comprises
   a) the antibody of claim 1a, comprising a light chain variable region comprising the amino acid sequence of SEQ ID NO: 267;
   b) the antibody of claim 1b, comprising a light chain variable region comprising the amino acid sequence of SEQ ID NO: 267;
   c) the antibody of claim 1c, comprising a light chain variable region comprising the amino acid sequence of SEQ ID NO: 267;
   d) the antibody of claim 1d, comprising a light chain variable region comprising the amino acid sequence of SEQ ID NO: 267;
   e) the antibody of claim 1e, comprising a light chain variable region comprising the amino acid sequence of SEQ ID NO: 267;
   f) the antibody of claim 1f, comprising a light chain variable region comprising the amino acid sequence of SEQ ID NO: 269;
   g) the antibody of claim 1g, comprising a light chain variable region comprising the amino acid sequence of SEQ ID NO: 370;

h) the antibody of claim 1h, comprising a light chain variable region comprising the amino acid sequence of SEQ ID NO: 370;
i) the antibody of claim 1i, comprising a light chain variable region comprising the amino acid sequence of SEQ ID NO: 370;
j) the antibody of claim 1j, comprising a light chain variable region comprising the amino acid sequence of SEQ ID NO: 269;
k) the antibody of claim 1k, comprising a light chain variable region comprising the amino acid sequence of SEQ ID NO: 269;
l) the antibody of claim 1l, comprising a light chain variable region comprising the amino acid sequence of SEQ ID NO: 280;
m) the antibody of claim 1m, comprising a light chain variable region comprising the amino acid sequence of SEQ ID NO: 280;
n) the antibody of claim 1n, comprising a light chain variable region comprising the amino acid sequence of SEQ ID NO: 280;
o) the antibody of claim 1o, comprising a light chain variable region comprising the amino acid sequence of SEQ ID NO: 280;
p) the antibody of claim 1p, comprising a light chain variable region comprising the amino acid sequence of SEQ ID NO: 280;
q) the antibody of claim 1q, comprising a light chain variable region comprising the amino acid sequence of SEQ ID NO: 344;
r) the antibody of claim 1r, comprising a light chain variable region comprising the amino acid sequence of SEQ ID NO: 344;
s) the antibody of claim 1r, comprising a light chain variable region comprising the amino acid sequence of SEQ ID NO: 344;
t) the antibody of claim 1t, comprising a light chain variable region comprising the amino acid sequence of SEQ ID NO: 344;
u) the antibody of claim 1u, comprising a light chain variable region comprising the amino acid sequence of SEQ ID NO: 344;
v) the antibody of claim 1v, comprising a light chain variable region comprising the amino acid sequence of SEQ ID NO: 271;
w) the antibody of claim 1w, comprising a light chain variable region comprising the amino acid sequence of SEQ ID NO: 273;
x) the antibody of claim 1x, comprising a light chain variable region comprising the amino acid sequence of SEQ ID NO: 275;
y) the antibody of claim 1y, comprising a light chain variable region comprising the amino acid sequence of SEQ ID NO: 277;
z) the antibody of claim 1z, comprising a light chain variable region comprising the amino acid sequence of SEQ ID NO: 278;
aa) the antibody of claim 1aa, comprising a light chain variable region comprising the amino acid sequence of SEQ ID NO: 282;
bb) the antibody of claim 1bb, comprising a light chain variable region comprising the amino acid sequence of SEQ ID NO: 284;
cc) the antibody of claim 1cc, comprising a light chain variable region comprising the amino acid sequence of SEQ ID NO: 286;
dd) the antibody of claim 1dd, comprising a light chain variable region comprising the amino acid sequence of SEQ ID NO: 288;
ff) the antibody of claim 1ff, comprising a light chain variable region comprising the amino acid sequence of SEQ ID NO: 292;
gg) the antibody of claim 1gg, comprising a light chain variable region comprising the amino acid sequence of SEQ ID NO: 294;
hh) the antibody of claim 1hh, comprising a light chain variable region comprising the amino acid sequence of SEQ ID NO: 296;
ii) the antibody of claim 1ii, comprising a light chain variable region comprising the amino acid sequence of SEQ ID NO: 298;
jj) the antibody of claim 1jj, comprising a light chain variable region comprising the amino acid sequence of SEQ ID NO: 300;
kk) the antibody of claim 1kk, comprising a light chain variable region comprising the amino acid sequence of SEQ ID NO: 302;
ll) the antibody of claim 1ll, comprising a light chain variable region comprising the amino acid sequence of SEQ ID NO: 304;
mm) the antibody of claim 1mm, comprising a light chain variable region comprising the amino acid sequence of SEQ ID NO: 306;
nn) the antibody of claim 1nn, comprising a light chain variable region comprising the amino acid sequence of SEQ ID NO: 308;
oo) the antibody of claim 1oo, comprising a light chain variable region comprising the amino acid sequence of SEQ ID NO: 310;
pp) the antibody of claim 1pp, comprising a light chain variable region comprising the amino acid sequence of SEQ ID NO: 312;
qq) the antibody of claim 1qq, comprising a light chain variable region comprising the amino acid sequence of SEQ ID NO: 314;
rr) the antibody of claim 1rr, comprising a light chain variable region comprising the amino acid sequence of SEQ ID NO: 316;
ss) the antibody of claim 1ss, comprising a light chain variable region comprising the amino acid sequence of SEQ ID NO: 318;
tt) the antibody of claim 1tt, comprising a light chain variable region comprising the amino acid sequence of SEQ ID NO: 320;
uu) the antibody of claim 1uu, comprising a light chain variable region comprising the amino acid sequence of SEQ ID NO: 322;
vv) the antibody of claim 1vv, comprising a light chain variable region comprising the amino acid sequence of SEQ ID NO: 324;
ww) the antibody of claim 1ww, comprising a light chain variable region comprising the amino acid sequence of SEQ ID NO: 326;
xx) the antibody of claim 1xx, comprising a light chain variable region comprising the amino acid sequence of SEQ ID NO: 328;
yy) the antibody of claim 1yy, comprising a light chain variable region comprising the amino acid sequence of SEQ ID NO: 330;

zz) the antibody of claim 1zz, comprising a light chain variable region comprising the amino acid sequence of SEQ ID NO: 332;
aaa) the antibody of claim 1aaa, comprising a light chain variable region comprising the amino acid sequence of SEQ ID NO: 334;
bbb) the antibody of claim 1bbb, comprising a light chain variable region comprising the amino acid sequence of SEQ ID NO: 336;
ccc) the antibody of claim 1ccc, comprising a light chain variable region comprising the amino acid sequence of SEQ ID NO: 338;
ddd) the antibody of claim 1ddd, comprising a light chain variable region comprising the amino acid sequence of SEQ ID NO: 340;
eee) the antibody of claim 1eee, comprising a light chain variable region comprising the amino acid sequence of SEQ ID NO: 342;
fff) the antibody of claim 1fff, comprising a light chain variable region comprising the amino acid sequence of SEQ ID NO: 346;
ggg) the antibody of claim 1ggg, comprising a light chain variable region comprising the amino acid sequence of SEQ ID NO: 348;
hhh) the antibody of claim 1hhh, comprising a light chain variable region comprising the amino acid sequence of SEQ ID NO: 350;
iii) the antibody of claim 1iii, comprising a light chain variable region comprising the amino acid sequence of SEQ ID NO: 352;
jjj) the antibody of claim 1jjj, comprising a light chain variable region comprising the amino acid sequence of SEQ ID NO: 354;
kkk) the antibody of claim 1kkk, comprising a light chain variable region comprising the amino acid sequence of SEQ ID NO: 356;
lll) the antibody of claim 1lll, comprising a light chain variable region comprising the amino acid sequence of SEQ ID NO: 358;
mmm) the antibody of claim 1mmm, comprising a light chain variable region comprising the amino acid sequence of SEQ ID NO: 360;
nnn) the antibody of claim 1nnn, comprising a light chain variable region comprising the amino acid sequence of SEQ ID NO: 362; or
ooo) the antibody of claim 1ooo, comprising a light chain variable region comprising the amino acid sequence of SEQ ID NO: 364.

8. The antibody of claim 1, wherein the antibody comprises
a) the antibody of claim 1a, comprising a heavy chain variable region comprising the amino acid sequence of SEQ ID NO: 268;
b) the antibody of claim 1b, comprising a heavy chain variable region comprising the amino acid sequence of SEQ ID NO: 366;
c) the antibody of claim 1c, comprising a heavy chain variable region comprising the amino acid sequence of SEQ ID NO: 367;
d) the antibody of claim 1d, comprising a heavy chain variable region comprising the amino acid sequence of SEQ ID NO: 368;
e) the antibody of claim 1e, comprising a heavy chain variable region comprising the amino acid sequence of SEQ ID NO: 369;
f) the antibody of claim 1f, comprising a heavy chain variable region comprising the amino acid sequence of SEQ ID NO: 270;
g) the antibody of claim 1g, comprising a heavy chain variable region comprising the amino acid sequence of SEQ ID NO: 371;
h) the antibody of claim 1h, comprising a heavy chain variable region comprising the amino acid sequence of SEQ ID NO: 372;
i) the antibody of claim 1i, comprising a heavy chain variable region comprising the amino acid sequence of SEQ ID NO: 373;
j) the antibody of claim 1j, comprising a heavy chain variable region comprising the amino acid sequence of SEQ ID NO: 374;
k) the antibody of claim 1k, comprising a heavy chain variable region comprising the amino acid sequence of SEQ ID NO: 375;
l) the antibody of claim 1l, comprising a heavy chain variable region comprising the amino acid sequence of SEQ ID NO: 281;
m) the antibody of claim 1m, comprising a heavy chain variable region comprising the amino acid sequence of SEQ ID NO: 376;
n) the antibody of claim 1n, comprising a heavy chain variable region comprising the amino acid sequence of SEQ ID NO: 377;
o) the antibody of claim 1o, comprising a heavy chain variable region comprising the amino acid sequence of SEQ ID NO: 377;
p) the antibody of claim 1p, comprising a heavy chain variable region comprising the amino acid sequence of SEQ ID NO: 378;
q) the antibody of claim 1q, comprising a heavy chain variable region comprising the amino acid sequence of SEQ ID NO: 345;
r) the antibody of claim 1r, comprising a heavy chain variable region comprising the amino acid sequence of SEQ ID NO: 379;
s) the antibody of claim 1s, comprising a heavy chain variable region comprising the amino acid sequence of SEQ ID NO: 380;
t) the antibody of claim 1t, comprising a heavy chain variable region comprising the amino acid sequence of SEQ TD NO: 381;
u) the antibody of claim 1u, comprising a heavy chain variable region comprising the amino acid sequence of SEQ ID NO: 382;
v) the antibody of claim 1v, comprising a heavy chain variable region comprising the amino acid sequence of SEQ ID NO: 272;
w) the antibody of claim 1w, comprising a heavy chain variable region comprising the amino acid sequence of SEQ ID NO: 274;
x) the antibody of claim 1x, comprising a heavy chain variable region comprising the amino acid sequence of SEQ ID NO: 276;
y) the antibody of claim 1y comprising a heavy chain variable region comprising the amino acid sequence of SEQ ID NO: 268;
z) the antibody of claim 1z, comprising a heavy chain variable region comprising the amino acid sequence of SEQ ID NO: 279;
aa) the antibody of claim 1aa, comprising a heavy chain variable region comprising the amino acid sequence of SEQ ID NO: 283;

bb) the antibody of claim 1bb, comprising a heavy chain variable region comprising the amino acid sequence of SEQ ID NO: 285;
cc) the antibody of claim 1cc, comprising a heavy chain variable region comprising the amino acid sequence of SEQ ID NO: 287;
dd) the antibody of claim 1dd, comprising a heavy chain variable region comprising the amino acid sequence of SEQ ID NO: 289;
ee) the antibody of claim 1ee, comprising a heavy chain variable region comprising the amino acid sequence of SEQ ID NO: 291;
ff) the antibody of claim 1ff, comprising a heavy chain variable region comprising the amino acid sequence of SEQ ID NO: 293;
gg) the antibody of claim 1gg, comprising a heavy chain variable region comprising the amino acid sequence of SEQ ID NO: 295;
hh) the antibody of claim 1hh, comprising a heavy chain variable region comprising the amino acid sequence of SEQ ID NO: 297;
ii) the antibody of claim 1ii, comprising a heavy chain variable region comprising the amino acid sequence of SEQ ID NO: 299;
jj) the antibody of claim 1jj, comprising a heavy chain variable region comprising the amino acid sequence of SEQ ID NO: 301;
kk) the antibody of claim 1kk, comprising a heavy chain variable region comprising the amino acid sequence of SEQ ID NO: 303;
ll) the antibody of claim 1ll, comprising a heavy chain variable region comprising the amino acid sequence of SEQ ID NO: 305;
mm) the antibody of claim 1mm, comprising a heavy chain variable region comprising the amino acid sequence of SEQ ID NO: 307;
nn) the antibody of claim 1nn, comprising a heavy chain variable region comprising the amino acid sequence of SEQ ID NO: 309;
oo) the antibody of claim 1oo, comprising a heavy chain variable region comprising the amino acid sequence of SEQ ID NO: 311;
pp) the antibody of claim 1pp, comprising a heavy chain variable region comprising the amino acid sequence of SEQ ID NO: 313;
qq) the antibody of claim 1qq, comprising a heavy chain variable region comprising the amino acid sequence of SEQ ID NO: 315;
rr) the antibody of claim 1rr, comprising a heavy chain variable region comprising the amino acid sequence of SEQ ID NO: 317;
ss) the antibody of claim 1ss, comprising a heavy chain variable region comprising the amino acid sequence of SEQ ID NO: 319;
tt) the antibody of claim 1tt, comprising a heavy chain variable region comprising the amino acid sequence of SEQ ID NO: 321;
uu) the antibody of claim 1uu, comprising a heavy chain variable region comprising the amino acid sequence of SEQ ID NO: 323;
vv) the antibody of claim 1vv, comprising a heavy chain variable region comprising the amino acid sequence of SEQ ID NO: 325;
ww) the antibody of claim 1ww, comprising a heavy chain variable region comprising the amino acid sequence of SEQ ID NO: 327;
xx) the antibody of claim 1xx, comprising a heavy chain variable region comprising the amino acid sequence of SEQ ID NO: 329;
yy) the antibody of claim 1yy, comprising a heavy chain variable region comprising the amino acid sequence of SEQ ID NO: 331;
zz) the antibody of claim 1zz, comprising a heavy chain variable region comprising the amino acid sequence of SEQ ID NO: 333;
aaa) the antibody of claim 1aaa, comprising a heavy chain variable region comprising the amino acid sequence of SEQ ID NO: 335;
bbb) the antibody of claim 1bbb, comprising a heavy chain variable region comprising the amino acid sequence of SEQ ID NO: 337;
ccc) the antibody of claim 1ccc, comprising a heavy chain variable region comprising the amino acid sequence of SEQ ID NO: 339;
ddd) the antibody of claim 1ddd, comprising a heavy chain variable region comprising the amino acid sequence of SEQ ID NO: 341;
eee) the antibody of claim 1eee, comprising a heavy chain variable region comprising the amino acid sequence of SEQ ID NO: 343;
fff) the antibody of claim 1fff, comprising a heavy chain variable region comprising the amino acid sequence of SEQ ID NO: 347;
ggg) the antibody of claim 1ggg, comprising a heavy chain variable region comprising the amino acid sequence of SEQ ID NO: 349;
hhh) the antibody of claim 1hhh, comprising a heavy chain variable region comprising the amino acid sequence of SEQ ID NO: 351;
iii) the antibody of claim 1iii, comprising a heavy chain variable region comprising the amino acid sequence of SEQ ID NO: 353;
jjj) the antibody of claim 1jjj, comprising a heavy chain variable region comprising the amino acid sequence of SEQ ID NO: 355;
kkk) the antibody of claim 1kkk, comprising a heavy chain variable region comprising the amino acid sequence of SEQ ID NO: 357;
lll) the antibody of claim 1lll, comprising a heavy chain variable region comprising the amino acid sequence of SEQ ID NO: 359;
mmm) the antibody of claim 1mmm, comprising a heavy chain variable region comprising the amino acid sequence of SEQ ID NO: 361;
nnn) the antibody of claim 1nnn, comprising a heavy chain variable region comprising the amino acid sequence of SEQ ID NO: 363; or
ooo) the antibody of claim 1ooo, comprising a heavy chain variable region comprising the amino acid sequence of SEQ ID NO: 365.

9. The antibody of claim 1, wherein the antibody comprises
a) the antibody of claim 1a, comprising a heavy chain variable region comprising the amino acid sequence of SEQ ID NO: 268 and a light chain variable region comprising the amino acid sequence of SEQ ID NO: 267;
b) the antibody of claim 1b, comprising a heavy chain variable region comprising the amino acid sequence of SEQ ID NO: 366 and a light chain variable region comprising the amino acid sequence of SEQ ID NO: 267;

c) the antibody of claim 1c, comprising a heavy chain variable region comprising the amino acid sequence of SEQ ID NO: 367 and a light chain variable region comprising the amino acid sequence of SEQ ID NO: 267;

d) the antibody of claim 1d, comprising a heavy chain variable region comprising the amino acid sequence of SEQ ID NO: 368 and a light chain variable region comprising the amino acid sequence of SEQ ID NO: 267;

e) the antibody of claim 1e, comprising a heavy chain variable region comprising the amino acid sequence of SEQ ID NO: 369 and a light chain variable region comprising the amino acid sequence of SEQ ID NO: 267;

f) the antibody of claim 1f, comprising a heavy chain variable region comprising the amino acid sequence of SEQ ID NO: 270 and a light chain variable region comprising the amino acid sequence of SEQ ID NO: 269;

g) the antibody of claim 1g, comprising a heavy chain variable region comprising the amino acid sequence of SEQ ID NO: 371 and a light chain variable region comprising the amino acid sequence of SEQ ID NO: 370;

h) the antibody of claim 1h, comprising a heavy chain variable region comprising the amino acid sequence of SEQ ID NO: 372 and a light chain variable region comprising the amino acid sequence of SEQ ID NO: 370;

i) the antibody of claim 1i, comprising a heavy chain variable region comprising the amino acid sequence of SEQ ID NO: 373 and a light chain variable region comprising the amino acid sequence of SEQ ID NO: 370;

j) the antibody of claim 1j, comprising a heavy chain variable region comprising the amino acid sequence of SEQ ID NO: 374 and a light chain variable region comprising the amino acid sequence of SEQ ID NO: 269;

k) the antibody of claim 1k, comprising a heavy chain variable region comprising the amino acid sequence of SEQ ID NO: 375 and a light chain variable region comprising the amino acid sequence of SEQ ID NO: 269;

l) the antibody of claim 1l, comprising a heavy chain variable region comprising the amino acid sequence of SEQ ID NO: 281 and a light chain variable region comprising the amino acid sequence of SEQ ID NO: 280;

m) the antibody of claim 1m, comprising a heavy chain variable region comprising the amino acid sequence of SEQ ID NO: 376 and a light chain variable region comprising the amino acid sequence of SEQ ID NO: 280;

n) the antibody of claim 1n, comprising a heavy chain variable region comprising the amino acid sequence of SEQ ID NO: 377 and a light chain variable region comprising the amino acid sequence of SEQ ID NO: 280;

o) the antibody of claim 1o, comprising a heavy chain variable region comprising the amino acid sequence of SEQ ID NO: 377 and a light chain variable region comprising the amino acid sequence of SEQ ID NO: 280;

p) the antibody of claim 1p, comprising a heavy chain variable region comprising the amino acid sequence of SEQ ID NO: 378 and a light chain variable region comprising the amino acid sequence of SEQ ID NO: 280;

q) the antibody of claim 1q, comprising a heavy chain variable region comprising the amino acid sequence of SEQ ID NO: 345 and a light chain variable region comprising the amino acid sequence of SEQ ID NO: 344;

r) the antibody of claim 1r, comprising a heavy chain variable region comprising the amino acid sequence of SEQ ID NO: 379 and a light chain variable region comprising the amino acid sequence of SEQ ID NO: 344;

s) the antibody of claim 1s, comprising a heavy chain variable region comprising the amino acid sequence of SEQ ID NO: 380 and a light chain variable region comprising the amino acid sequence of SEQ ID NO: 344;

t) the antibody of claim 1t, comprising a heavy chain variable region comprising the amino acid sequence of SEQ ID NO: 381 and a light chain variable region comprising the amino acid sequence of SEQ ID NO: 344;

u) the antibody of claim 1u, comprising a heavy chain variable region comprising the amino acid sequence of SEQ ID NO: 382 and a light chain variable region comprising the amino acid sequence of SEQ ID NO: 344;

v) the antibody of claim 1v, comprising a light chain variable region comprising the amino acid sequence of SEQ ID NO: 271, and a heavy chain variable region comprising the amino acid sequence of SEQ ID NO: 272;

w) the antibody of claim 1w, comprising a light chain variable region comprising the amino acid sequence of SEQ ID NO: 273, and a heavy chain variable region comprising the amino acid sequence of SEQ ID NO: 274;

x) the antibody of claim 1x, comprising a light chain variable region comprising the amino acid sequence of SEQ ID NO: 275, and a heavy chain variable region comprising the amino acid sequence of SEQ ID NO: 276;

y) the antibody of claim 1y, comprising a light chain variable region comprising the amino acid sequence of SEQ ID NO: 277, and a heavy chain variable region comprising the amino acid sequence of SEQ ID NO: 268;

z) the antibody of claim 1z, comprising a light chain variable region comprising the amino acid sequence of SEQ ID NO: 278, and a heavy chain variable region comprising the amino acid sequence of SEQ ID NO: 279;

aa) the antibody of claim 1aa, comprising a light chain variable region comprising the amino acid sequence of SEQ ID NO: 282, and a heavy chain variable region comprising the amino acid sequence of SEQ ID NO: 283;

bb) the antibody of claim 1bb, comprising a light chain variable region comprising the amino acid sequence of SEQ ID NO: 284, and a heavy chain variable region comprising the amino acid sequence of SEQ ID NO: 285;

cc) the antibody of claim 1cc, comprising a light chain variable region comprising the amino acid sequence of SEQ ID NO: 286, and a heavy chain variable region comprising the amino acid sequence of SEQ ID NO: 287;
dd) the antibody of claim 1dd, comprising a light chain variable region comprising the amino acid sequence of SEQ ID NO: 288, and a heavy chain variable region comprising the amino acid sequence of SEQ ID NO: 289;
ee) the antibody of claim 1ee, comprising a light chain variable region comprising the amino acid sequence of SEQ ID NO: 290, and a heavy chain variable region comprising the amino acid sequence of SEQ ID NO: 291;
ff) the antibody of claim 1ff, comprising a light chain variable region comprising the amino acid sequence of SEQ ID NO: 292, and a heavy chain variable region comprising the amino acid sequence of SEQ ID NO: 293;
gg) the antibody of claim 1gg, comprising a light chain variable region comprising the amino acid sequence of SEQ ID NO: 294, and a heavy chain variable region comprising the amino acid sequence of SEQ ID NO: 295;
hh) the antibody of claim 1hh, comprising a light chain variable region comprising the amino acid sequence of SEQ ID NO: 296, and a heavy chain variable region comprising the amino acid sequence of SEQ ID NO: 297;
ii) the antibody of claim 1ii, comprising a light chain variable region comprising the amino acid sequence of SEQ ID NO: 298, and a heavy chain variable region comprising the amino acid sequence of SEQ ID NO: 299;
jj) the antibody of claim 1jj, comprising a light chain variable region comprising the amino acid sequence of SEQ ID NO: 300, and a heavy chain variable region comprising the amino acid sequence of SEQ ID NO: 301;
kk) the antibody of claim 1kk, comprising a light chain variable region comprising the amino acid sequence of SEQ ID NO: 302, and a heavy chain variable region comprising the amino acid sequence of SEQ ID NO: 303;
ll) the antibody of claim 1ll, comprising a light chain variable region comprising the amino acid sequence of SEQ ID NO: 304, and a heavy chain variable region comprising the amino acid sequence of SEQ ID NO: 305;
mm) the antibody of claim 1mm, comprising a light chain variable region comprising the amino acid sequence of SEQ ID NO: 306, and a heavy chain variable region comprising the amino acid sequence of SEQ ID NO: 307;
nn) the antibody of claim 1nn, comprising a light chain variable region comprising the amino acid sequence of SEQ ID NO: 308, and a heavy chain variable region comprising the amino acid sequence of SEQ ID NO: 309;
oo) the antibody of claim 1oo, comprising a light chain variable region comprising the amino acid sequence of SEQ ID NO: 310, and a heavy chain variable region comprising the amino acid sequence of SEQ ID NO: 311;
pp) the antibody of claim 1pp, comprising a light chain variable region comprising the amino acid sequence of SEQ ID NO: 312, and a heavy chain variable region comprising the amino acid sequence of SEQ ID NO: 313;
qq) the antibody of claim 1qq, comprising a light chain variable region comprising the amino acid sequence of SEQ ID NO: 314, and a heavy chain variable region comprising the amino acid sequence of SEQ ID NO: 315;
rr) the antibody of claim 1rr, comprising a light chain variable region comprising the amino acid sequence of SEQ ID NO: 316, and a heavy chain variable region comprising the amino acid sequence of SEQ ID NO: 317;
ss) the antibody of claim 1ss, comprising a light chain variable region comprising the amino acid sequence of SEQ ID NO: 318, and a heavy chain variable region comprising the amino acid sequence of SEQ ID NO: 319;
tt) the antibody of claim 1tt, comprising a light chain variable region comprising the amino acid sequence of SEQ ID NO: 320, and a heavy chain variable region comprising the amino acid sequence of SEQ ID NO: 321;
uu) the antibody of claim 1uu, comprising a light chain variable region comprising the amino acid sequence of SEQ ID NO: 322, and a heavy chain variable region comprising the amino acid sequence of SEQ ID NO: 323;
vv) the antibody of claim 1vv, comprising a light chain variable region comprising the amino acid sequence of SEQ ID NO: 324, and a heavy chain variable region comprising the amino acid sequence of SEQ ID NO: 325;
ww) the antibody of claim 1ww, comprising a light chain variable region comprising the amino acid sequence of SEQ ID NO: 326, and a heavy chain variable region comprising the amino acid sequence of SEQ ID NO: 327;
xx) the antibody of claim 1xx, comprising a light chain variable region comprising the amino acid sequence of SEQ ID NO: 328, and a heavy chain variable region comprising the amino acid sequence of SEQ ID NO: 329;
yy) the antibody of claim 1yy, comprising a light chain variable region comprising the amino acid sequence of SEQ ID NO: 330, and a heavy chain variable region comprising the amino acid sequence of SEQ ID NO: 331;
zz) the antibody of claim 1zz, comprising a light chain variable region comprising the amino acid sequence of SEQ ID NO: 332, and a heavy chain variable region comprising the amino acid sequence of SEQ ID NO: 333;
aaa) the antibody of claim 1aaa, comprising a light chain variable region comprising the amino acid sequence of SEQ ID NO: 334, and a heavy chain variable region comprising the amino acid sequence of SEQ ID NO: 335;
bbb) the antibody of claim 1bbb, comprising a light chain variable region comprising the amino acid sequence of SEQ ID NO: 336, and a heavy chain variable region comprising the amino acid sequence of SEQ ID NO: 337;
ccc) the antibody of claim 1ccc, comprising a light chain variable region comprising the amino acid sequence of SEQ ID NO: 338, and a heavy chain variable region comprising the amino acid sequence of SEQ ID NO: 339;
ddd) the antibody of claim 1ddd, comprising a light chain variable region comprising the amino acid sequence of SEQ ID NO: 340, and a heavy chain variable region comprising the amino acid sequence of SEQ ID NO: 341;
eee) the antibody of claim 1eee, comprising a light chain variable region comprising the amino acid sequence of SEQ ID NO: 342, and a heavy chain variable region comprising the amino acid sequence of SEQ ID NO: 343;
fff) the antibody of claim 1fff, comprising a light chain variable region comprising the amino acid sequence of SEQ ID NO: 346, and a heavy chain variable region comprising the amino acid sequence of SEQ ID NO: 347;
ggg) the antibody of claim 1ggg, comprising a light chain variable region comprising the amino acid sequence of SEQ ID NO: 348, and a heavy chain variable region comprising the amino acid sequence of SEQ ID NO: 349;
hhh) the antibody of claim 1hhh, comprising a light chain variable region comprising the amino acid sequence of SEQ ID NO: 350, and a heavy chain variable region comprising the amino acid sequence of SEQ ID NO: 351;
iii) the antibody of claim 1iii, comprising a light chain variable region comprising the amino acid sequence of SEQ ID NO: 352, and a heavy chain variable region comprising the amino acid sequence of SEQ ID NO: 353;
jjj) the antibody of claim 1jjj, comprising a light chain variable region comprising the amino acid sequence of SEQ ID NO: 354, and a heavy chain variable region comprising the amino acid sequence of SEQ ID NO: 355;
kkk) the antibody of claim 1kkk, comprising a light chain variable region comprising the amino acid sequence of SEQ ID NO: 356, and a heavy chain variable region comprising the amino acid sequence of SEQ ID NO: 357;
lll) the antibody of claim 1lll, comprising a light chain variable region comprising the amino acid sequence of SEQ ID NO: 358, and a heavy chain variable region comprising the amino acid sequence of SEQ ID NO: 359;
mmm) the antibody of claim 1mmm, comprising a light chain variable region comprising the amino acid sequence of SEQ ID NO: 360, and a heavy chain variable region comprising the amino acid sequence of SEQ ID NO: 361;
nnn) the antibody of claim 1nnn, comprising a light chain variable region comprising the amino acid sequence of SEQ ID NO: 362, and a heavy chain variable region comprising the amino acid sequence of SEQ ID NO: 363; or
ooo) the antibody of claim 1ooo, comprising a light chain variable region comprising the amino acid sequence of SEQ ID NO: 364, and a heavy chain variable region comprising the amino acid sequence of SEQ ID NO: 365.

10. The antibody of claim 1, wherein the antibody is a monoclonal antibody.

11. The antibody of claim 1, wherein the antibody is of the IgG class, the IgM class, or the IgA class.

12. The antibody of claim 11, wherein the antibody is of the IgG class and has an IgG1, IgG2, or IgG4 isotype.

13. The antibody of claim 12, wherein the antibody has an IgG1 isotype, optionally wherein the antibody comprises a E430G substitution and a P331S substitution according to EU numbering.

14. The antibody of claim 1, wherein the antibody is an antibody fragment, optionally a Fab, Fab', Fab'-SH, F(ab')$_2$, Fv or scFv fragment.

15. The antibody of claim 1, wherein the antibody has an affinity ($K_D$) for human SIRPβ1 isoform 1 of 0.1 nM to 50 nM.

16. The antibody of claim 1, wherein the antibody recognizes a first and a second antigen, wherein the first antigen is SIRPβ1 and the second antigen is;
(a) an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), and diphtheria toxin receptor;
(b) a disease-causing agent selected from the group consisting of disease-causing peptides or proteins or disease-causing nucleic acids, wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides;
(c) ligands and/or proteins expressed on immune cells, wherein the ligands and/or proteins selected from the group consisting of CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; and
(d) a protein, lipid, polysaccharide, or glycolipid expressed on one or more tumor cells.

17. An isolated nucleic acid comprising a nucleic acid sequence encoding the antibody of claim 1.

18. A vector comprising the nucleic acid of claim 17.

19. An isolated host cell that expresses the antibody of claim 1.

20. A method of producing an antibody that binds to human SIRPβ1, comprising culturing the cell of claim 19 so that the antibody is produced, and optionally recovering the antibody produced by the cell.

21. A pharmaceutical composition comprising the antibody of claim 1 and a pharmaceutically acceptable carrier.

22. A method of treating cancer, comprising administering to an individual in need thereof a therapeutically effective amount of the antibody of claim 1.

23. A method of treating a neurodegenerative disease or disorder, comprising administering to an individual in need thereof a therapeutically effective amount of the antibody of claim 1.

* * * * *